United States Patent
Wu et al.

(10) Patent No.: US 10,889,591 B2
(45) Date of Patent: Jan. 12, 2021

(54) PDE9 INHIBITOR AND USE THEREOF

(71) Applicant: Nanjing TransThera Biosciences Co. Ltd., Nanjing (CN)

(72) Inventors: Frank Wu, Nanjing (CN); Lin Li, Nanjing (CN); Xiaoju Yang, Nanjing (CN)

(73) Assignee: Nanjing TransThera Biosciences Co. Ltd., Nanjing (CN)

( * ) Notice: Subject to any disclaimer, the term of this patent is extended or adjusted under 35 U.S.C. 154(b) by 18 days.

(21) Appl. No.: 16/702,711

(22) Filed: Dec. 4, 2019

(65) Prior Publication Data
US 2020/0115384 A1    Apr. 16, 2020

Related U.S. Application Data

(63) Continuation of application No. PCT/CN2018/107461, filed on Sep. 26, 2018.

(30) Foreign Application Priority Data

| Sep. 28, 2017 | (CN) | .......................... | 2017 1 0900197 |
| Mar. 13, 2018 | (CN) | .......................... | 2018 1 0203538 |
| Aug. 2, 2018 | (CN) | .......................... | 2018 1 0871998 |

(51) Int. Cl.
C07D 491/107 (2006.01)
C07D 471/04 (2006.01)
C07D 519/00 (2006.01)

(52) U.S. Cl.
CPC ....... *C07D 491/107* (2013.01); *C07D 471/04* (2013.01); *C07D 519/00* (2013.01)

(58) Field of Classification Search
CPC . C07D 491/107; C07D 471/04; C07D 519/00
See application file for complete search history.

(56) References Cited

U.S. PATENT DOCUMENTS

| 5,817,670 A | 10/1998 | Takayama et al. |
| 6,740,662 B1 | 5/2004 | Iwata et al. |
| 9,133,164 B2 * | 9/2015 | Gaweco ............... C07D 215/56 |

FOREIGN PATENT DOCUMENTS

| CN | 1156455 A | 8/1997 |
| CN | 1382141 A | 11/2002 |
| WO | 2009/124119 A2 | 10/2009 |
| WO | 2017/019723 A1 | 2/2017 |
| WO | 2017/019724 A1 | 2/2017 |
| WO | 2017/019726 A1 | 2/2017 |

OTHER PUBLICATIONS

STN Registration No. 1643380-13-5, 1, 6-Naphthyridine-3-carbonitrile, 1,2-dihydro-5-methyl-2-oxo-4-phenyl-7-propyl. 4 pages, Jan. 16, 2015.
International Search Report for Application No. PCT/CN2018/107461, dated Dec. 29, 2018, 6 pages.

* cited by examiner

*Primary Examiner* — D Margaret M Seaman
(74) *Attorney, Agent, or Firm* — McCarter & English, LLP; Steven G. Davis; Wei Song

(57) ABSTRACT

The present invention falls within the technical field of medicine, and in particular relates to PDE9 inhibitor compounds as shown in formula (I) or pharmaceutically acceptable salts or stereoisomers thereof, and also relates to pharmaceutical preparations and pharmaceutical compositions of the compounds and the uses thereof. $X_1$, $X_2$, $X_3$, $X_4$, $R_1$, $R_2$, ring A, L and m are as defined in the description. The compounds can be used to prepare drugs for treating or preventing related diseases mediated by PDE9.

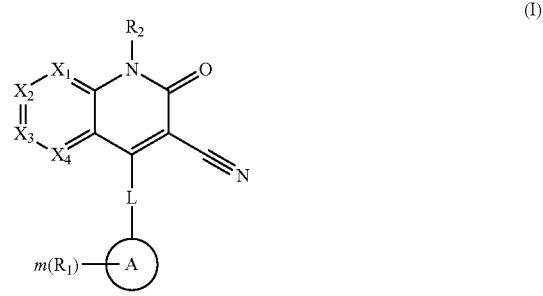

(I)

8 Claims, No Drawings

PDE9 INHIBITOR AND USE THEREOF

CROSS-REFERENCE TO RELATED APPLICATIONS

This application is a continuation application of International Application No. PCT/CN2018/107461, filed on Sep. 26, 2018, which claims, under 35 U.S.C. 365, the priority of the Chinese patent application No. 201710900197.8, titled "PDE9 INHIBITOR AND USE THEREOF", filed before the China National Intellectual Property Administration on Sep. 28, 2017; the Chinese patent application No. 201810203538.0, titled "PDE9 INHIBITOR AND USE THEREOF", filed before the China National Intellectual Property Administration on Mar. 13, 2018; and the Chinese patent application No. 201810871998.0, titled "PDE9 INHIBITOR AND USE THEREOF", filed before the China National Intellectual Property Administration on Aug. 2, 2018. The entire contents of each of the aforementioned applications are incorporated herein by reference.

TECHNICAL FIELD

The present invention belongs to the technical field of medicine, and relates to a phosphodiesterase 9 inhibitor represented by formula (I), or a pharmaceutically acceptable salt thereof, a stereoisomer thereof and use thereof.

BACKGROUND

Phosphodiesterases (PDEs) are a class of proteases that selectively degrade the important second messenger cGMP (cyclic guanosine monophosphate) and cAMP (cyclic adenosine monophosphate) in the body, thereby participating in important physiological processes in the body. PDEs can be divided into 11 members (PDE1-PDE11) based on their sequence homology of genes and selectivity for cGMP or cAMP. Among them, PDE9A is an important member of the PDE family, which is widely expressed in the testis, brain, small intestine, skeletal muscle, heart, lung, thymus and pancreas. With the deepening research in recent years, many literature reports and clinical data have proved that PDE9A inhibitors are used to treat diseases related to cognitive impairment caused by central nervous system disorders, such as Alzheimer's disease and schizophrenia, and brain neurodegenerative process disease.

Both nucleotides cAMP and cGMP are important second messengers that play a central role in cell signaling process. They primarily activate protein kinases: the one activated by cAMP is called protein kinase A (PKA); and the one activated by cGMP is called protein kinase G (PKG). The activated PKA and PKG can phosphorylate many cellular effector proteins, such as ion channels, G-protein coupled receptors, structural proteins, and transductive factors. Thus, cAMP and cGMP may control most of the physiological processes in many organs in such way. At the same time, cAMP and cGMP can also act directly on effector proteins, thereby playing the same role as described above. It is well known that cGMP can act directly on ion acceptors, thereby affecting the concentration of ions in cells. Phosphodiesterases (PDEs) hydrolyze cyclic monophosphates cAMP and cGMP, and convert them to inactivated monophosphates AMP and GMP.

Human PDE9 was first cloned and sequenced in 1998 and is a PDE having the highest selectivity for cGMP reported to date. The binding constant (Km) of PDE9 to cGMP is 170 nM, and the binding constant value of PDE9 to cAMP is up to 230,000 nM, and the selectivity is over 1000 times. Compared with PDE2A and PDE5A, the catalytic activity of PDE9 cannot be enhanced by cGMP, since PDE9 do not have a binding region to cGMP. Therefore, PDE9 inhibitors may increase the baseline cGMP concentration.

Conventional PDE inhibitors cannot inhibit human PDE9, therefore, the drugs IBMX, dipyridamole, SKF94120, rolipram, and vinpocetine have no or very low inhibition activity on PDE9.

There is no PDE9 inhibitor medicine on the market nowadays, and only some inhibitors are in clinical development phase, such as, two PDE9 inhibitors, PF-04447943 of Pfizer and BI-409306 of BI. Currently, the two compounds are in Clinical Phase I and II.

SUMMARY OF THE INVENTION

One purpose of the invention is to provide a class of compounds useful as PDE9 protease inhibitors, or pharmaceutically acceptable salts, stereoisomers thereof, which have good PDE9 protease inhibitory activity, selectivity and druggability (e.g., good pharmacokinetic properties, higher stability in liver microsome), can treat or prevent related diseases mediated by PDE9, and play an important role in the treatment of diseases related to cognitive impairment caused by central nervous system disorders.

The technical solutions of the present invention are as follows.

The present invention provides a compound shown in formula (I), or pharmaceutically acceptable salts or stereoisomers thereof:

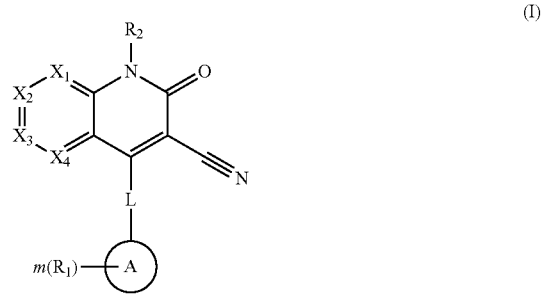

(I)

wherein, $X_1$, $X_2$, $X_3$, and $X_4$ are each independently $CR_3$ or N, and $X_1$, $X_2$, $X_3$, and $X_4$ are not simultaneously $CR_3$;

$R_3$, at each occurrence, is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, aminocarbonyl, $C_{1-6}$ alkylaminocarbonyl, $(C_{1-6}$ alkyl$)_2$ aminocarbonyl, 4-6 membered heterocyclylcarbonyl and 5-6 membered heteroaryloxy, wherein $C_{1-6}$ alkyl, $C_{1-6}$ alkoxy, $C_{1-6}$ alkylamino, $(C_{1-6}$ alkyl$)_2$ amino, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, aminocarbonyl, $C_{1-6}$ alkylaminocarbonyl, $(C_{1-6}$ alkyl$)_2$ aminocarbonyl, 4-6 membered heterocyclylcarbonyl and 5-6 membered heteroaryl-oxy are unsubstituted or optionally substituted with one or more groups independently selected from the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{1-6}$ alkylcarbonylamino, $C_{1-6}$ alkylsulfonylamino, $C_{1-6}$ alkylcarbonyloxy, $C_{3-6}$ cycloalkyl, $C_{2-8}$ alkynyl, halogenated $C_{1-6}$ alkyl, $C_{2-8}$ alkenyl, halogenated $C_{1-6}$ alkoxy, 4-6 membered heterocyclyl which is unsubstituted or optionally substituted with a substituent, and heteroaryl which is unsubstituted or optionally substituted with a substituent;

the substituent in the above 4-6 membered heterocyclyl optionally substituted with a substituent and heteroaryl optionally substituted with a substituent is selected from the group consisting of hydroxy, amino, carboxyl, cyano, nitro, halogen, $C_{1-6}$ alkyl and $C_{1-6}$ alkoxy;

L is a bond, —NH—$(CH_2)$t-, and t is 0, 1, 2 or 3;

ring A is selected from the group consisting of 3-12 membered heterocyclyl, aryl, 5-10 membered heteroaryl, 3-12 membered cycloalkyl, and 3-12 membered cycloalkenyl, wherein 3-12 membered heterocyclyl has an hetero atom selected from one of O, S, N or any combination thereof, and the S atom may be optionally oxidized to S(O) or $S(O)_2$, and the 5-10 membered heteroaryl has an hetero atom selected from one of O, S, N or any combination thereof;

each $R_1$ is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, 3-12 membered cycloalkyl, 3-12 membered cycloalkenyl, 3-12 membered heterocyclyl, aryl and 5-10 membered heteroaryl, wherein $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, 3-12 membered cycloalkyl, 3-12 membered cycloalkenyl, 3-12 membered heterocyclyl, aryl and 5-10 membered heteroaryl are unsubstituted or optionally substituted with a group selected form the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{1-6}$ alkylcarbonylamino, and $C_{1-6}$ alkylsulfonylamino;

m is 0, 1, 2 or 3; and $R_2$ is selected from the group consisting of hydrogen, $C_{1-6}$ alkyl, $C_{2-8}$ alkenyl, $C_{2-8}$ alkynyl, and halogenated $C_{1-6}$ alkyl.

In a preferred embodiment, $X_2$ is N, and $X_1$, $X_3$, and $X_4$ are each independently $CR_3$.

In another preferred embodiment, $X_4$ is N, and $X_1$, $X_2$, and $X_3$ are each independently $CR_3$.

Some embodiments of the present invention relate to the compound shown in formula (I), or pharmaceutically acceptable salts or stereoisomers thereof, wherein, $X_1$, $X_2$, $X_3$, and $X_4$ are each independently $CR_3$ or N, and $X_1$, $X_2$, $X_3$, and $X_4$ are not simultaneously $CR_3$;

$R_3$, at each occurrence, is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, aminocarbonyl, $C_{1-6}$ alkylaminocarbonyl, $(C_{1-6}$ alkyl$)_2$ aminocarbonyl, 4-6 membered heterocyclylcarbonyl and 5-6 membered heteroaryl-oxy, wherein the $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, aminocarbonyl, $C_{1-6}$ alkylaminocarbonyl, $(C_{1-6}$ alkyl$)_2$ aminocarbonyl, 4-6 membered heterocyclylcarbonyl and 5-6 membered heteroaryl-oxy are unsubstituted or optionally substituted with one or more groups independently selected from the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{1-6}$ alkylcarbonylamino, $C_{1-6}$ alkylsulfonylamino, $C_{1-6}$ alkylcarbonyloxy, $C_{3-6}$ cycloalkyl, $C_{2-8}$ alkynyl, halogenated $C_{1-6}$ alkyl, $C_{2-8}$ alkenyl, and halogenated $C_{1-6}$ alkoxy;

the substituent in the above 4-6 membered heterocyclyl optionally substituted with a substituent and heteroaryl optionally substituted with a substituent is selected from the group consisting of hydroxy, amino, carboxyl, cyano, nitro, halogen, $C_{1-6}$ alkyl and $C_{1-6}$ alkoxy;

L is a bond, —NH—$(CH_2)$t-, and t is 0, 1, 2 or 3;

ring A is selected from the group consisting of 3-12 membered heterocyclyl, aryl, and 5-10 membered heteroaryl, wherein the 3-12 membered heterocyclyl has an hetero atom selected from one of O, S, N or any combination thereof, and the S atom may be optionally oxidized to S(O) or $S(O)_2$, and the 5-10 membered heteroaryl has an hetero atom selected from one of O, S, N or any combination thereof;

each $R_1$ is independently selected from the group consisting of hydrogen, hydroxy, amino, cyano, halogen, $C_{1-6}$ alkyl, $C_{1-6}$ alkoxy, 3-12 membered cycloalkyl, 3-12 membered heterocyclyl, aryl, 5-10 membered heteroaryl, wherein the $C_{1-6}$ alkyl, $C_{1-6}$ alkoxy, 3-12 membered cycloalkyl, 3-12 membered heterocyclyl, aryl, and 5-10 membered heteroaryl are unsubstituted or optionally substituted with a group selected from the group consisting of $C_{1-6}$ alkyl, $C_{1-6}$ alkoxy, 3-12 membered cycloalkyl, 3-12 membered heterocyclyl, aryl, and 5-10 membered heteroaryl;

m is 0, 1, 2 or 3; and $R_2$ is hydrogen or $C_{1-6}$ alkyl.

In a preferred embodiment, $X_2$ is N, and $X_1$, $X_3$, and $X_4$ are each independently $CR_3$.

In another preferred embodiment, $X_4$ is N, and $X_1$, $X_2$, and $X_3$ are each independently $CR_3$.

Some embodiments of the present invention relate to the compound shown in formula (I), or pharmaceutically acceptable salts or stereoisomers thereof:

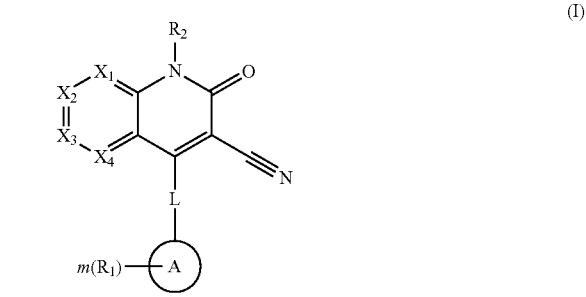

wherein, $X_1$, $X_2$, $X_3$, and $X_4$ are each independently $CR_3$ or N, and $X_1$, $X_2$, $X_3$ and $X_4$ are not simultaneously $CR_3$;

L is a bond, —NH—$(CH_2)$t-, and t is 0, 1, 2 or 3;

$R_3$, at each occurrence, is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, $C_{1-6}$ alkylaminocarbonyl, $(C_{1-6}$ alkyl$)_2$ aminocarbonyl, and aminocarbonyl, wherein the $C_{1-6}$ alkyl, $C_{1-6}$ alkoxy, $C_{1-6}$ alkylamino, $(C_{1-6}$ alkyl$)_2$ amino, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, $C_{1-6}$ alkylaminocarbonyl, $(C_{1-6}$ alkyl$)_2$ aminocarbonyl, and aminocarbonyl are unsubstituted or optionally substituted with one or more groups independently selected from the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{3-6}$ cycloalkyl, $C_{1-6}$ alkylcarbonylamino, $C_{1-6}$ alkylsulfonylamino, $C_{1-6}$ alkylcarbonyloxy, and unsubstituted or $C_{1-6}$ alkyl-substituted 4-6 membered heterocyclyl;

ring A is selected from the group consisting of 3-12 membered heterocyclyl, aryl, 5-10 membered heteroaryl, 3-12 membered cycloalkyl, and 3-12 membered cycloalkenyl, wherein the 3-12 membered heterocyclyl has an hetero atom selected from one of O, S, N or any combination thereof, and the S atom may be optionally oxidized to $S(O)$ or $S(O)_2$, and the 5-10 membered heteroaryl has an hetero atom selected from one of O, S, N, or any combination thereof;

each $R_1$ is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, 3-12 membered cycloalkyl, 3-12 membered cycloalkenyl, 3-12 membered heterocyclyl, aryl and 5-10 membered heteroaryl, wherein the $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, 3-12 membered cycloalkyl, 3-12 membered cycloalkenyl, 3-12 membered heterocyclyl, aryl and 5-10 membered heteroaryl are unsubstituted or optionally substituted with a group selected from the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{1-6}$ alkylcarbonylamino, and $C_{1-6}$ alkylsulfonylamino;

m is 0, 1, 2 or 3; and $R_2$ is selected from the group consisting of hydrogen, $C_{1-6}$ alkyl, $C_{2-8}$ alkenyl, $C_{2-8}$ alkynyl, and halogenated $C_{1-6}$ alkyl.

In a preferred embodiment, $X_2$ is N, and $X_1$, $X_3$, and $X_4$ are each independently $CR_3$.

In another preferred embodiment, $X_4$ is N, and $X_1$, $X_2$, and $X_3$ are each independently $CR_3$.

Some embodiments of the present invention relate to the compound shown in formula (II), or pharmaceutically acceptable salts or stereoisomers thereof:

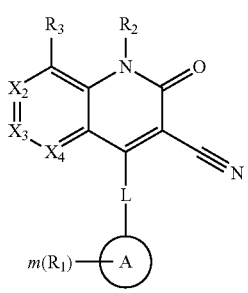

(II)

wherein, $X_2$, $X_3$, and $X_4$ are each independently $CR_3$ or N, and $X_2$, $X_3$, and $X_4$ are not simultaneously $CR_3$;

$R_3$, at each occurrence, is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, $C_{1-6}$ alkylaminocarbonyl, $(C_{1-6}$ alkyl$)_2$ aminocarbonyl, and aminocarbonyl, wherein the $C_{1-6}$ alkyl, $C_{1-6}$ alkoxy, $C_{1-6}$ alkylamino, $(C_{1-6}$ alkyl$)_2$ amino, halogenated $C_{1-6}$ alkoxy, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered heterocyclyl, $C_{1-6}$ alkylcarbonyl, $C_{1-6}$ alkylaminocarbonyl, $(C_{1-6}$ alkyl$)_2$ aminocarbonyl, and aminocarbonyl are unsubstituted or optionally substituted with one or more groups independently selected from the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{3-6}$ cycloalkyl, $C_{1-6}$ alkylcarbonylamino, $C_{1-6}$ alkylsulfonylamino, $C_{1-6}$ alkylcarbonyloxy, and unsubstituted or $C_{1-6}$ alkyl-substituted 4-6 membered heterocyclyl;

L is a bond, —NH—$(CH_2)t$-, and t is 0, 1, 2 or 3;

ring A is selected from the group consisting of 3-12 membered heterocyclyl, aryl, 5-10 membered heteroaryl, 3-12 membered cycloalkyl, and 3-12 membered cycloalkenyl, wherein the 3-12 membered heterocyclyl has an hetero atom selected from one of O, S, N or any combination thereof, and the S atom may be optionally oxidized to $S(O)$ or $S(O)_2$, and the 5-10 membered heteroaryl has an hetero atom selected from one of O, S, N or any combination thereof;

each $R_1$ is independently selected from the group consisting of hydrogen, hydroxy, amino, carboxyl, cyano, nitro, halogen, $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, 3-12 membered cycloalkyl, 3-12 membered cycloalkenyl, 3-12 membered heterocyclyl, aryl and 5-10 membered heteroaryl, wherein the $C_{1-6}$ alkyl, $C_{1-6}$ alkoxy, $C_{1-6}$ alkylamino, $(C_{1-6}$ alkyl$)_2$ amino, halogenated $C_{1-6}$ alkyl, halogenated $C_{1-6}$ alkoxy, $C_{2-8}$ alkenyl, $C_{2-8}$ alkynyl, $C_{1-6}$ alkylsulfonyl, $C_{1-6}$ alkylthio, 3-12 membered cycloalkyl, 3-12 membered cycloalkenyl, 3-12 membered heterocyclyl, aryl and 5-10 membered heteroaryl are unsubstituted or optionally substituted with a group selected from the group consisting of hydroxy, amino, carboxyl, cyano, nitro, halogen, $C_{1-6}$ alkyl, $C_{1-6}$ alkoxy, $C_{1-6}$ alkoxy $C_{1-6}$ alkoxy, $C_{1-6}$ alkylamino, $(C_{1-6}$ alkyl$)_2$ amino, $C_{1-6}$ alkylcarbonylamino, and $C_{1-6}$ alkylsulfonylamino;

m is 0, 1, 2 or 3; and $R_2$ is selected from the group consisting of hydrogen, $C_{1-6}$ alkyl, $C_{2-8}$ alkenyl, $C_{2-8}$ alkynyl, and halogenated $C_{1-6}$ alkyl.

In a preferred embodiment, $X_2$ is N, and $X_3$ and $X_4$ are each independently $CR_3$.

In another preferred embodiment, $X_4$ is N, and $X_2$ and $X_3$ are each independently $CR_3$.

Some embodiments of the present invention relate to the compound shown in formula (I) or (II), or pharmaceutically acceptable salts or stereoisomers thereof, wherein, $X_2$, $X_3$, and $X_4$ are each independently $CR_3$ or N, and $X_2$, $X_3$, and $X_4$ are not simultaneously $CR_3$;

$R_3$, at each occurrence, is independently selected from the group consisting of hydrogen, amino, carboxyl, cyano, halogen, $C_{1-6}$ alkyl, $C_{1-6}$ alkoxy, $C_{1-6}$ alkylamino, $(C_{1-6}$ alkyl$)_2$ amino, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered nitrogen-containing heterocyclyl, $C_{1-6}$ alkylcarbonyl, $C_{1-6}$ alkylaminocarbonyl, $(C_{1-6}$ alkyl$)_2$ aminocarbonyl, and aminocarbonyl, wherein the $C_{1-6}$ alkyl, $C_{1-6}$ alkoxy, $C_{1-6}$ alkylamino, $(C_{1-6}$ alkyl$)_2$ amino, $C_{2-8}$ alkenyl, $C_{2-8}$ alkynyl, $C_{1-6}$ alkylsulfonyl, $C_{1-6}$ alkylthio, $C_{3-6}$ cycloalkyl, 4-6 membered nitrogen-containing heterocyclyl, $C_{1-6}$ alkylcarbonyl, $C_{1-6}$ alkylaminocarbonyl, $(C_{1-6}$ alkyl$)_2$ aminocarbonyl and aminocarbonyl are unsubstituted or optionally substituted with one or more groups independently selected from the group consisting of hydroxy, amino, cyano, halogen, $C_{1-6}$ alkyl, $C_{1-6}$ alkoxy, $C_{1-6}$ alkylamino, $(C_{1-6}$ alkyl$)_2$ amino, $C_{1-6}$ alkylcarbonyloxy, $C_{3-6}$ cycloalkyl, and 4-6 membered heterocyclyl which is unsubstituted or optionally substituted with $C_{1-6}$ alkyl;

L is a bond;

ring A is 3-12 membered heterocyclyl, wherein the 3-12 membered heterocyclyl has an hetero atom selected from one of O, S, N or any combination thereof, and the S atom may be optionally oxidized to S(O) or S(O)$_2$;

each $R_1$ is independently selected from the group consisting of hydrogen, hydroxy, cyano, halogen, $C_{1-6}$ alkyl, $C_{1-6}$ alkoxy and 5-6 membered heteroaryl, wherein the $C_{1-6}$ alkyl, $C_{1-6}$ alkoxy and 5-6 membered heteroaryl are unsubstituted or substituted with hydroxy;

m is 0, 1, or 2; and $R_2$ is hydrogen or $C_{1-6}$ alkyl.

In a preferred embodiment, $X_2$ is N, and $X_3$ and $X_4$ are each independently CR$_3$.

In another preferred embodiment, $X_4$ is N, and $X_2$ and $X_3$ are each independently CR$_3$.

Some embodiments of the present invention relate to the compound shown in formula (I) or (II), or pharmaceutically acceptable salts or stereoisomers thereof, wherein, $X_2$ is N, and $X_3$ and $X_4$ are each independently CR$_3$ or N, preferably CR$_3$;

$R_3$, at each occurrence, is independently selected from the group consisting of hydrogen, amino, cyano, halogen, carboxyl, $C_{1-4}$ alkyl, $C_{1-4}$ alkoxy, $C_{1-4}$ alkylamino, $(C_{1-4}$ alkyl$)_2$ amino, $C_{2-6}$ alkenyl, $C_{2-6}$ alkynyl, $C_{1-4}$ alkylcarbonyl, $C_{1-4}$ alkylaminocarbonyl, $(C_{1-6}$ alkyl$)_2$ aminocarbonyl, $C_{1-4}$ alkylsulfonyl, $C_{1-4}$ alkylthio, aminocarbonyl, cyclopropyl, azetidinyl, morpholinyl and piperazinyl, wherein the $C_{1-4}$ alkyl, $C_{1-4}$ alkoxy, $C_{1-4}$ alkylamino, $(C_{1-4}$ alkyl$)_2$ amino, $C_{2-6}$ alkenyl, $C_{2-6}$ alkynyl, $C_{1-4}$ alkylcarbonyl, $C_{1-4}$ alkylaminocarbonyl, $(C_{1-6}$ alkyl$)_2$ aminocarbonyl, $C_{1-4}$ alkylsulfonyl, $C_{1-4}$ alkylthio, aminocarbonyl, cyclopropyl, azetidinyl, morpholinyl and piperazinyl are unsubstituted or optionally substituted with one or more groups independently selected from the group consisting of hydroxy, amino, cyano, halogen, $C_{1-4}$ alkyl, $C_{1-4}$ alkoxy, $C_{1-4}$ alkylamino, $(C_{1-4}$ alkyl$)_2$ amino, cyclopropyl, $C_{1-4}$ alkylcarbonyloxy, and 4-6 membered heterocyclyl which is unsubstituted or optionally substituted with $C_{1-6}$ alkyl;

L is a bond;

ring A is 4-12 membered heterocyclyl, wherein the 4-12 membered heterocyclyl has an hetero atom selected from one or a combination of two of O, S, and N, and contains at least one N, ring A is connected to L through N atom, and the S atom may be optionally oxidized to S(O)$_2$;

each $R_1$ is independently selected from the group consisting of hydrogen, hydroxy, cyano, halogen, $C_{1-4}$ alkyl, $C_{1-4}$ alkoxy, pyrazolyl, thiazolyl and triazolyl, wherein the $C_{1-4}$ alkyl, $C_{1-4}$ alkoxy, pyrazolyl, thiazolyl and triazolyl are unsubstituted or substituted with hydroxy; and m is 0, 1 or 2.

Some embodiments of the present invention relate to the compound shown in formula (I) or (II), or pharmaceutically acceptable salts or stereoisomers thereof, wherein, $X_2$ is N, $X_3$ is CR$_3$, and $X_4$ is CR$_3$ or N, preferably CR$_3$;

$R_3$, at each occurrence, is independently selected from the group consisting of hydrogen, amino, cyano, halogen, carboxyl, $C_{1-4}$ alkyl, $C_{1-4}$ alkoxy, $C_{1-4}$ alkylamino, $(C_{1-4}$ alkyl$)_2$ amino, $C_{2-6}$ alkenyl, $C_{2-6}$ alkynyl, $C_{1-4}$ alkylcarbonyl, $C_{1-4}$ alkylaminocarbonyl, $(C_{1-6}$ alkyl$)_2$ aminocarbonyl, $C_{1-4}$ alkylsulfonyl, $C_{1-4}$ alkylthio, aminocarbonyl, cyclopropyl, azetidinyl, morpholinyl and piperazinyl, wherein the $C_{1-4}$ alkyl, $C_{1-4}$ alkoxy, $C_{1-4}$ alkylamino, $(C_{1-4}$ alkyl$)_2$ amino, $C_{2-6}$ alkenyl, $C_{2-6}$ alkynyl, $C_{1-4}$ alkylcarbonyl, $C_{1-4}$ alkylaminocarbonyl, $(C_{1-6}$ alkyl$)_2$ aminocarbonyl, $C_{1-4}$ alkylsulfonyl, $C_{1-4}$ alkylthio, aminocarbonyl, cyclopropyl, azetidinyl, morpholinyl and piperazinyl are unsubstituted or optionally substituted with one or more groups independently selected from the group consisting of hydroxy, amino, cyano, halogen, $C_{1-4}$ alkyl, $C_{1-4}$ alkoxy, $C_{1-4}$ alkylamino, $(C_{1-4}$ alkyl$)_2$ amino, cyclopropyl, $C_{1-4}$ alkylcarbonyloxy, and 4-6 membered heterocyclyl which is unsubstituted or optionally substituted with $C_{1-6}$ alkyl;

L is a bond;

ring A is 4-12 membered heterocyclyl, wherein the 4-12 membered heterocyclyl has an hetero atom selected from one or a combination of two of O, S, and N, and contains at least one N, ring A is connected to L through N atom, and the S atom may be optionally oxidized to S(O)$_2$;

each $R_1$ is independently selected from the group consisting of hydrogen, hydroxy, cyano, halogen, $C_{1-4}$ alkyl, $C_{1-4}$ alkoxy, pyrazolyl, thiazolyl and triazolyl, wherein the $C_{1-4}$ alkyl, $C_{1-4}$ alkoxy, pyrazolyl, thiazolyl and triazolyl are unsubstituted or substituted with hydroxy; and m is 0, 1 or 2.

Some embodiments of the present invention relate to the compound shown in formula (I) or (II), or pharmaceutically acceptable salts or stereoisomers thereof, wherein, $X_2$ is N, $X_3$ is CR$_3$, and $X_4$ is CR$_3$ or N, preferably CR$_3$;

L is a bond;

ring A is 4-7 membered monoheterocyclyl, wherein the 4-7 membered monoheterocyclyl has an hetero atom selected from one or a combination of two of O, S, and N, and contains at least one N, ring A is connected to L through N atom, and the S atom can be optionally oxidized to S(O)$_2$;

preferably, ring A is saturated 4-7 membered nitrogen-containing monoheterocyclyl, further preferably:

still further preferably

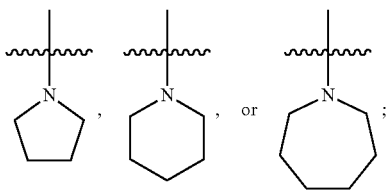

R$_3$, at each occurrence, is independently selected from the group consisting of hydrogen, halogen, C$_{1-4}$ alkyl, C$_{1-4}$ alkoxy, morpholinyl, C$_{2-6}$ alkenyl, C$_{1-4}$ alkylcarbonyl, C$_{1-4}$ alkylaminocarbonyl, (C$_{1-4}$ alkyl)$_2$ aminocarbonyl and aminocarbonyl, wherein the C$_{1-4}$ alkyl, C$_{1-4}$ alkoxy, morpholinyl, C$_{2-6}$ alkenyl, C$_{1-4}$ alkylcarbonyl, C$_{1-4}$ alkylaminocarbonyl, (C$_{1-4}$ alkyl)$_2$ aminocarbonyl and aminocarbonyl are unsubstituted or optionally substituted with one or more groups independently selected from the group consisting of hydroxy, C$_{1-4}$ alkoxy, cyclopropyl, amino, C$_{1-4}$ alkylamino, (C$_{1-4}$ alkyl)$_2$ amino, and 4-6 membered heterocyclyl which is unsubstituted or optionally substituted with C$_{1-4}$ alkyl;

each R$_1$ is independently selected from the group consisting of hydrogen, halogen, C$_{1-4}$ alkyl, C$_{1-4}$ alkoxy, pyrazolyl, thiazolyl, and triazolyl, wherein the C$_{1-4}$ alkyl, C$_{1-4}$ alkoxy, pyrazolyl, thiazolyl, and triazolyl are unsubstituted or substituted with hydroxy; and m is 0, 1 or 2.

Some embodiments of the present invention relate to the compound shown in formula (I) or (II), or pharmaceutically acceptable salts or stereoisomers thereof,
wherein, X$_2$ is N, and X$_3$ and X$_4$ are each independently CR$_3$;

R$_3$, at each occurrence, is independently selected from the group consisting of hydrogen, halogen, C$_{1-4}$ alkyl, C$_{1-4}$ alkoxy, C$_{2-6}$ alkenyl, C$_{1-4}$ alkylcarbonyl, C$_{1-4}$ alkylaminocarbonyl, and aminocarbonyl, wherein the C$_{1-4}$ alkyl, C$_{1-4}$ alkoxy, C$_{2-6}$ alkenyl, C$_{1-4}$ alkylcarbonyl, C$_{1-4}$ alkylaminocarbonyl, and aminocarbonyl are unsubstituted or optionally substituted with one or more groups independently selected from the group consisting of hydroxy, C$_{1-4}$ alkoxy, cyclopropyl, and 4-6 membered heterocyclyl which is unsubstituted or substituted with C$_{1-6}$ alkyl;

L is a bond;
ring A is

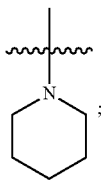

each R$_1$ is independently selected from the group consisting of hydrogen, C$_{1-4}$ alkyl, and C$_{1-4}$ alkoxy; and
m is 0, 1 or 2.

Some embodiments of the present invention relate to the compound shown in formula (I) or (II), or pharmaceutically acceptable salts or stereoisomers thereof,
wherein, X$_2$ is N, and X$_3$ and X$_4$ are each independently CR$_3$;

R$_3$, at each occurrence, is independently selected from the group consisting of hydrogen, halogen, C$_{1-4}$ alkyl, and morpholinyl, wherein the C$_{1-4}$ alkyl is unsubstituted or substituted with one or more hydroxy;

L is a bond;
ring A is

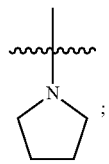 [SMILES: *N1CCCC1]

and each R$_1$ is independently selected from the group consisting of pyrazolyl, thiazolyl, and triazolyl.

Some embodiments of the present invention relate to the compound shown in formula (I) or (II), or pharmaceutically acceptable salts or stereoisomers thereof,
wherein, L is a bond;

X$_2$ is N, and X$_3$ and X$_4$ are independently CR$_3$ or N, preferably CR$_3$;

R$_3$, at each occurrence, is independently selected from the group consisting of hydrogen, amino, cyano, halogen, carboxyl, C$_{1-4}$ alkyl, C$_{1-4}$ alkoxy, C$_{1-4}$ alkylcarbonyl, C$_{2-6}$ alkynyl, C$_{1-4}$ alkylaminocarbonyl, (C$_{1-4}$ alkyl)$_2$ aminocarbonyl, C$_{1-4}$ alkylthio, C$_{1-4}$ alkylsulfonyl, C$_{1-4}$ alkylamino, (C$_{1-4}$ alkyl)$_2$ amino, azetidinyl, morpholinyl, piperazinyl, C$_{2-6}$ alkenyl and cyclopropyl, wherein the C$_{1-4}$ alkyl, C$_{1-4}$ alkoxy, C$_{1-4}$ alkylcarbonyl, C$_{2-6}$ alkynyl, C$_{1-4}$ alkylaminocarbonyl, (C$_{1-6}$ alkyl)$_2$ aminocarbonyl, C$_{1-4}$ alkylthio, C$_{1-4}$ alkylsulfonyl, C$_{1-4}$ alkylamino, (C$_{1-4}$ alkyl)$_2$ amino, azetidinyl, morpholinyl, piperazinyl, C$_{2-6}$ alkenyl and cyclopropyl are unsubstituted or optionally substituted with one or more groups independently selected from the group consisting of hydroxy, amino, halogen, C$_{1-4}$ alkyl, C$_{1-4}$ alkoxy, C$_{1-4}$ alkylamino, (C$_{1-4}$ alkyl)$_2$ amino, cyclopropyl, and C$_{1-4}$ alkylcarbonyloxy;

ring A is 7-12 membered spiroheterocyclyl, wherein the spiroheterocyclyl has one or more hetero atoms selected from the group consisting of O, S, and N, and contains at least one N, ring A is connected to L through N atom, and the S atom can be optionally oxidized to S(O)$_2$; preferably, the 7-12 membered spiroheterocyclyl is saturated 7-12 membered nitrogen-containing spiroheterocyclyl; more preferably, the saturated 7-12 membered nitrogen-containing spiroheterocyclyl is selected from the group consisting of:

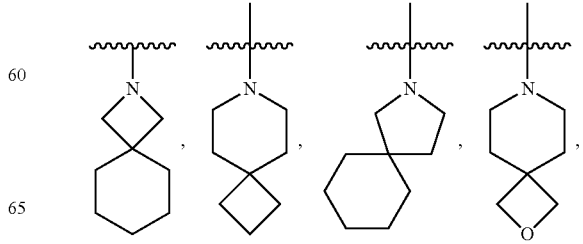

-continued

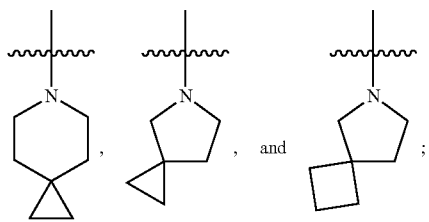

preferably, ring A is selected from the group consisting of

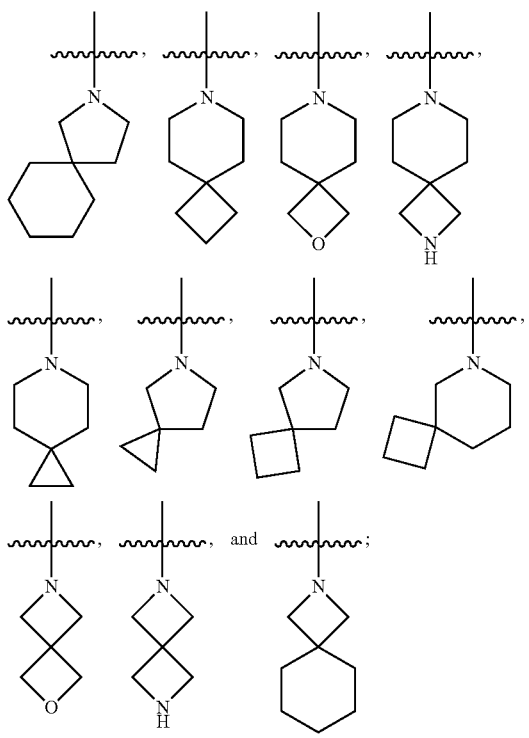

and more preferably, ringed is selected from the group consisting of

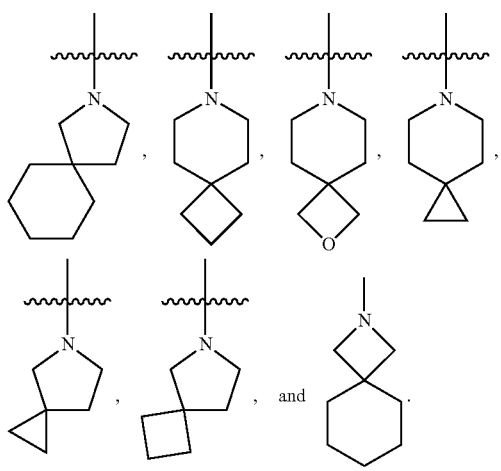

Some embodiments of the present invention relate to the compound shown in formula (I) or (II), or pharmaceutically acceptable salts or stereoisomers thereof,
wherein,
$X_2$, $X_3$, and $X_4$ are each independently $CR_3$ or N;
$R_3$, at each occurrence, is independently selected from the group consisting of hydrogen, cyano, amino, halogen, carboxyl, $C_{1-4}$ alkyl, $C_{1-4}$ alkoxy, $C_{2-6}$ alkenyl, $C_{1-4}$ alkylcarbonyl, $C_{2-6}$ alkynyl, $C_{1-4}$ alkylamino, $(C_{1-4}$ alkyl$)_2$ amino, $C_{1-4}$ alkylaminocarbonyl, $C_{1-4}$ alkylthio, $C_{1-4}$ alkylsulfonyl, cyclopropyl, azetidinyl, morpholinyl, and piperazinyl, wherein the $C_{1-4}$ alkyl, $C_{1-4}$ alkoxy, $C_{2-6}$ alkenyl, $C_{1-4}$ alkylcarbonyl, $C_{2-6}$ alkynyl, $C_{1-4}$ alkylamino, $(C_{1-4}$ alkyl$)_2$ amino, $C_{1-4}$ alkylaminocarbonyl, $C_{1-4}$ alkylthio, $C_{1-4}$ alkylsulfonyl, cyclopropyl, azetidinyl, morpholinyl, and piperazinyl are unsubstituted or optionally substituted with one or more groups independently selected from the group consisting of hydroxy, amino, halogen, $C_{1-4}$ alkyl, $C_{1-4}$ alkoxy, $C_{1-4}$ alkylamino, $(C_{1-4}$ alkyl$)_2$ amino, cyclopropyl, and $C_{1-4}$ alkylcarbonyloxy;
L is a bond;
ring A is selected from the group consisting of

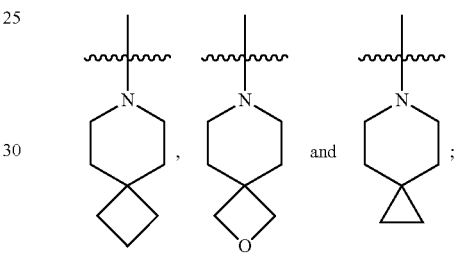

and
m is 0.
In a preferred embodiment, $X_2$ is N, and $X_3$ and $X_4$ are each independently $CR_3$.
In another preferred embodiment, $X_4$ is N, and $X_2$ and $X_3$ are each independently $CR_3$.
Some embodiments of the present invention relate to the compound shown in formula (I) or (II), or pharmaceutically acceptable salts or stereoisomers thereof,
wherein,
$X_2$, $X_3$, and $X_4$ are each independently $CR_3$ or N;
$R_3$, at each occurrence, is independently selected from the group consisting of hydrogen, amino, cyano, halogen, carboxyl, $C_{1-4}$ alkyl, $C_{1-4}$ alkoxy, $C_{1-4}$ alkylamino, $(C_{1-4}$ alkyl$)_2$ amino, $C_{2-6}$ alkenyl, $C_{2-6}$ alkynyl, $C_{1-4}$ alkylcarbonyl, $C_{1-4}$ alkylaminocarbonyl, $(C_{1-6}$ alkyl$)_2$ aminocarbonyl, $C_{1-4}$ alkylsulfonyl, $C_{1-4}$ alkylthio, aminocarbonyl, cyclopropyl, azetidinyl, morpholinyl and piperazinyl, wherein the $C_{1-4}$ alkyl, $C_{1-4}$ alkoxy, $C_{1-4}$ alkylamino, $(C_{1-4}$ alkyl$)_2$ amino, $C_{2-6}$ alkenyl, $C_{2-6}$ alkynyl, $C_{1-4}$ alkylcarbonyl, $C_{1-4}$ alkylaminocarbonyl, $(C_{1-6}$ alkyl$)_2$ aminocarbonyl, $C_{1-4}$ alkylsulfonyl, $C_{1-4}$ alkylthio, aminocarbonyl, cyclopropyl, azetidinyl, morpholinyl and piperazinyl are unsubstituted or optionally substituted with one or more groups independently selected from the group consisting of hydroxy, amino, cyano, halogen, $C_{1-4}$ alkyl, $C_{1-4}$ alkoxy, $C_{1-4}$ alkylamino, $(C_{1-4}$ alkyl$)_2$ amino, cyclopropyl, $C_{1-4}$ alkylcarbonyloxy, 4-6 membered heterocyclyl which is unsubstituted or optionally substituted with $C_{1-6}$ alkyl;
L is a bond;
each $R_1$ is independently selected from the group consisting of hydrogen, hydroxy, cyano, halogen, $C_{1-6}$ alkyl, $C_{1-6}$ alkoxy, pyrazolyl, thiazolyl, and triazolyl, wherein the $C_{1-6}$ alkyl, $C_{1-6}$ alkoxy, pyrazolyl, thiazolyl, and triazolyl are unsubstituted or substituted with hydroxy;

m is 0, 1 or 2;

ring A is a group selected from the group consisting of:

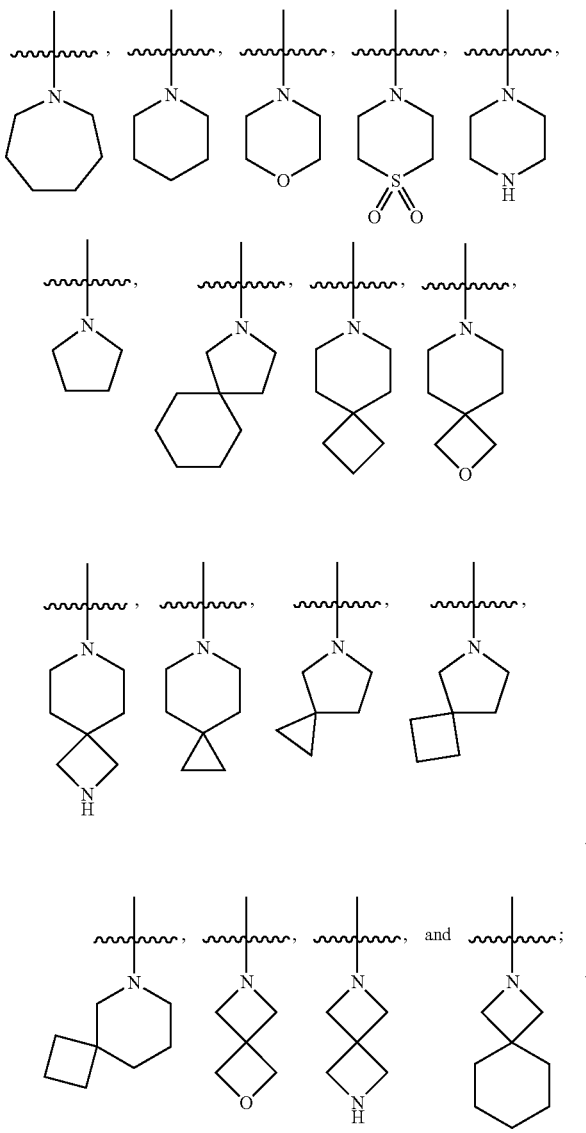

and preferably, ring A is selected from the group consisting of

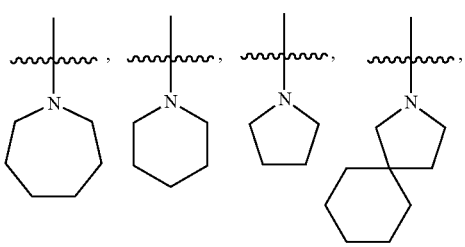

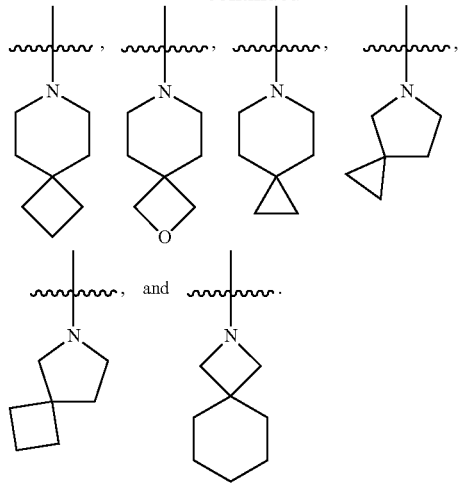

In a preferred embodiment, $X_2$ is N, and $X_3$ and $X_4$ are each independently $CR_3$.

In another preferred embodiment, $X_4$ is N, and $X_2$ and $X_3$ are each independently $CR_3$.

Some embodiments of the present invention relate to the compound shown in formula (I) or (II), or pharmaceutically acceptable salts or stereoisomers thereof, wherein, $X_2$ is N, and $X_3$ and $X_4$ are each independently $CR_3$ or N;

L is —NH—$(CH_2)_t$- or a bond, and t is 0, 1, or 2;

ring A is phenyl;

$R_3$, at each occurrence, is independently selected from the group consisting of hydrogen, amino, carboxyl, cyano, halogen, $C_{1-6}$ alkyl, $C_{1-6}$ alkoxy, $C_{1-6}$ alkylamino, $(C_{1-6}$ alkyl$)_2$ amino, $C_{2-8}$ alkenyl, $C_{2-6}$ alkynyl, $C_{1-6}$ alkylsulfonyl, $C_{1-6}$ alkylthio, $C_{3-6}$ cycloalkyl, 4-6 membered nitrogen-containing heterocyclyl, $C_{1-6}$ alkylcarbonyl, $C_{1-6}$ alkylaminocarbonyl, $(C_{1-6}$ alkyl$)_2$ aminocarbonyl, and aminocarbonyl, wherein the $C_{1-6}$ alkyl, $C_{1-6}$ alkoxy, $C_{1-6}$ alkylamino, $(C_{1-6}$ alkyl$)_2$ amino, $C_{2-8}$ alkenyl, $C_{2-6}$ alkynyl, $C_{1-6}$ alkylsulfonyl, $C_{1-6}$ alkylthio, $C_{3-6}$ cycloalkyl, 4-6 membered nitrogen-containing heterocyclyl, $C_{1-6}$ alkylcarbonyl, $C_{1-6}$ alkylaminocarbonyl, $(C_{1-6}$ alkyl$)_2$ aminocarbonyl, and aminocarbonyl are unsubstituted or optionally substituted with one or more groups independently selected from the group consisting of hydroxy, amino, cyano, halogen, $C_{1-6}$ alkyl, $C_{1-6}$ alkoxy, $C_{1-6}$ alkylamino, $(C_{1-6}$ alkyl$)_2$ amino, $C_{1-6}$ alkylcarbonyloxy, $C_{3-6}$ cycloalkyl, and 4-6 membered heterocyclyl which is unsubstituted or substituted with $C_{1-6}$ alkyl;

each $R_1$ is independently selected from the group consisting of hydrogen, hydroxy, amino, carboxyl, cyano, nitro, halogen, $C_{1-6}$ alkyl, and $C_{1-6}$ alkoxy, wherein the $C_{1-6}$ alkyl and $C_{1-6}$ alkoxy are unsubstituted or optionally substituted with a group selected from the group consisting of hydroxy, amino, carboxyl, cyano, nitro, halogen, $C_{1-6}$ alkyl, and $C_{1-6}$ alkoxy;

$R_2$ is hydrogen or $C_{1-6}$ alkyl; and m is 0, 1 or 2.

Some embodiments of the present invention relate to the compound shown in formula (I) or (II), or pharmaceutically acceptable salts or stereoisomers thereof, wherein, $X_2$ is N, and $X_3$ and $X_4$ are each independently $CR_3$ or N;

L is a bond;

$R_3$, at each occurrence, is independently selected from the group consisting of hydrogen, amino, carboxyl, cyano, halogen, $C_{1-6}$ alkyl, $C_{1-6}$ alkoxy, $C_{1-6}$ alkylamino, $(C_{1-6}$ alkyl$)_2$ amino, $C_{2-8}$ alkenyl, $C_{2-6}$ alkynyl, $C_{1-6}$ alkylsulfonyl, $C_{1-6}$ alkylthio, $C_{3-6}$ cycloalkyl, 4-6 membered nitrogen-containing heterocyclyl, $C_{1-6}$ alkylcarbonyl, $C_{1-6}$ alkylaminocarbonyl, $(C_{1-6}$ alkyl$)_2$ aminocarbonyl, and aminocarbonyl, wherein the $C_{1-6}$ alkyl, $C_{1-6}$ alkoxy, $C_{1-6}$ alkylamino, $(C_{1-6}$ alkyl$)_2$ amino, $C_{2-8}$ alkenyl, $C_{2-6}$ alkynyl, $C_{1-6}$ alkylsulfonyl, $C_{1-6}$ alkylthio, $C_{3-6}$ cycloalkyl, 4-6 membered nitrogen-containing heterocyclyl, $C_{1-6}$ alkylcarbonyl, $C_{1-6}$ alkylaminocarbonyl, $(C_{1-6}$ alkyl$)_2$ aminocarbonyl, and aminocarbonyl are unsubstituted or optionally substituted with one or more groups independently selected from the group consisting of hydroxy, amino, cyano, halogen, $C_{1-6}$ alkyl, $C_{1-6}$ alkoxy, $C_{1-6}$ alkylamino, $(C_{1-6}$ alkyl$)_2$ amino, $C_{1-6}$ alkylcarbonyloxy, $C_{3-6}$ cycloalkyl, and 4-6 membered heterocyclyl which is unsubstituted or substituted with $C_{1-6}$ alkyl;

L is a bond;

ring A is 5-10 membered heteroaryl, and the 5-10 membered heteroaryl has a hetero atom selected from one of O, S, N or any combination thereof;

each $R_1$ is independently selected from the group consisting of hydrogen, hydroxy, amino, carboxyl, cyano, nitro, halogen, $C_{1-6}$ alkyl, $C_{1-6}$ alkoxy, phenyl and 5-6 membered heteroaryl, wherein the $C_{1-6}$ alkyl, $C_{1-6}$ alkoxy, phenyl and 5-6 membered heteroaryl are unsubstituted or optionally substituted with a group selected from the group consisting of hydroxy, amino, carboxyl, cyano, nitro, halogen, $C_{1-6}$ alkyl, and $C_{1-6}$ alkoxy;

m is 0, 1 or 2; and $R_2$ is hydrogen or $C_{1-6}$ alkyl;

Preferably, ring A is 9-10 membered heteroaryl.

More preferably, ring A is 9-10 membered nitrogen-containing heteroaryl.

Most preferably, ring A is

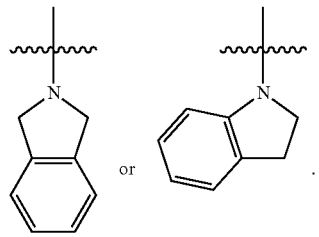 [SMILES: *N1Cc2ccccc2C1 ; *N1CCc2ccccc21]

In one embodiment of the present invention, the aforementioned compounds shown as formula (I) or (II), or pharmaceutically acceptable salts or stereoisomers thereof are shown in Table 1:

TABLE 1

| No. | Structure |
|---|---|
| 1 | |
| 2 | 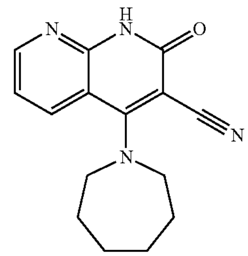 [SMILES: N#Cc1c(N2CCCCCC2)c2cccnc2[nH]c1=O] |
| 3 | 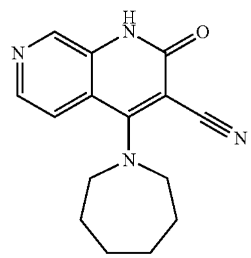 [SMILES: N#Cc1c(N2CCCCCC2)c2ccncc2[nH]c1=O] |
| 4 | 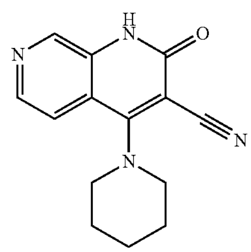 [SMILES: N#Cc1c(N2CCCCC2)c2ccncc2[nH]c1=O] |
| 5 | 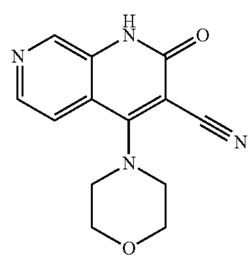 [SMILES: N#Cc1c(N2CCOCC2)c2ccncc2[nH]c1=O] |
| 6 | 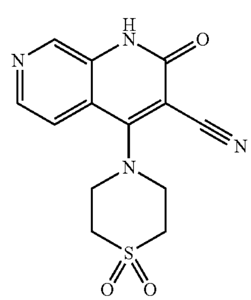 [SMILES: N#Cc1c(N2CCS(=O)(=O)CC2)c2ccncc2[nH]c1=O] |
| 7 | 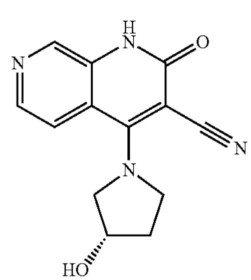 [SMILES: N#Cc1c(N2CC[C@H](O)C2)c2ccncc2[nH]c1=O] |

TABLE 1-continued

| No. | Structure |
|---|---|
| 8 | (1,7-naphthyridin-2(1H)-one with 3-CN and 4-[(2R)-2-methylmorpholin-4-yl]) |
| 9 | (1,7-naphthyridin-2(1H)-one with 3-CN and 4-[(2S)-2-methylmorpholin-4-yl]) |
| 10 | (1,7-naphthyridin-2(1H)-one with 3-CN and 4-(benzylamino)) |
| 11 | (1,7-naphthyridin-2(1H)-one with 3-CN and 4-[(4-chlorobenzyl)amino]) |
| 12 | (1,7-naphthyridin-2(1H)-one with 3-CN and 4-(4,4-difluoropiperidin-1-yl)) |
| 13 | (1,7-naphthyridin-2(1H)-one with 3-CN and 4-(2-azaspiro[3.5]non-2-yl)) |
| 14 | (1,7-naphthyridin-2(1H)-one with 3-CN and 4-[(cyclohexylmethyl)amino]) |
| 15 | (1,7-naphthyridin-2(1H)-one with 3-CN and 4-(2-azaspiro[4.5]dec-2-yl)) |
| 16 | (1,7-naphthyridin-2(1H)-one with 3-CN and 4-(2-azaspiro[3.5]... piperidine-spiro-cyclobutane)) |
| 17 | (1,7-naphthyridin-2(1H)-one with 3-CN and 4-(2,3-dihydro-1H-indol-1-yl)) |

TABLE 1-continued

| No. | Structure |
|-----|-----------|
| 18  | (4-chlorophenyl)amino-substituted 2-oxo-1,2-dihydro-1,7-naphthyridine-3-carbonitrile |
| 19  | 4-[(3R)-3-(1H-pyrazol-1-yl)pyrrolidin-1-yl]-2-oxo-1,2-dihydro-1,7-naphthyridine-3-carbonitrile |
| 20  | 4-(1,3-dihydro-2H-isoindol-2-yl)-2-oxo-1,2-dihydro-1,7-naphthyridine-3-carbonitrile |
| 21  | 4-(phenylamino)-2-oxo-1,2-dihydro-1,7-naphthyridine-3-carbonitrile |
| 22  | 4-[(4-ethylphenyl)amino]-2-oxo-1,2-dihydro-1,7-naphthyridine-3-carbonitrile |
| 23  | 6-chloro-4-[(3R)-3-(1H-pyrazol-1-yl)pyrrolidin-1-yl]-2-oxo-1,2-dihydro-1,7-naphthyridine-3-carbonitrile |
| 24  | 4-(2-oxa-7-azaspiro[3.5]non-7-yl)-2-oxo-1,2-dihydro-1,7-naphthyridine-3-carbonitrile |
| 25  | 4-(6-azaspiro[2.5]oct-6-yl)-2-oxo-1,2-dihydro-1,7-naphthyridine-3-carbonitrile |
| 26  | 4-(4-ethylphenyl)-2-oxo-1,2-dihydro-1,7-naphthyridine-3-carbonitrile |
| 27  | 6-methyl-4-[(3R)-3-(1H-pyrazol-1-yl)pyrrolidin-1-yl]-2-oxo-1,2-dihydro-1,7-naphthyridine-3-carbonitrile |

TABLE 1-continued

| No. | Structure |
|---|---|
| 28 | 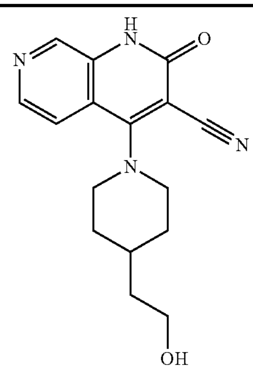 |
| 29 | 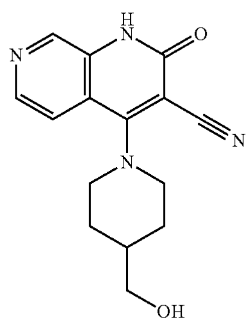 [SMILES: N#Cc1c(N2CCC(CO)CC2)c2ccncc2[nH]c1=O] |
| 30 | 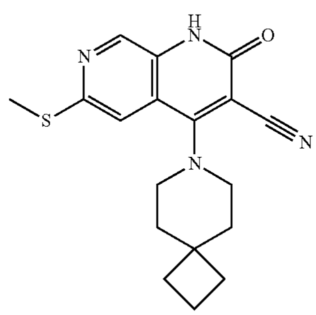 [SMILES: CSc1cc2c(N3CCC4(CCC4)CC3)c(C#N)c(=O)[nH]c2cn1] |
| 31 | 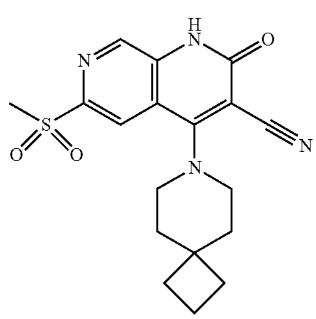 [SMILES: CS(=O)(=O)c1cc2c(N3CCC4(CCC4)CC3)c(C#N)c(=O)[nH]c2cn1] |
| 32 | 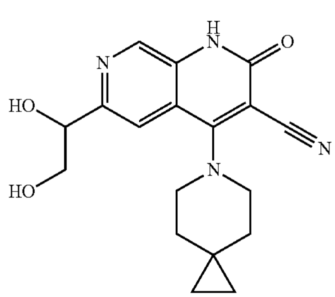 [SMILES: N#Cc1c(N2CCC3(CC2)CC3)c2cc(C(O)CO)ncc2[nH]c1=O] |
| 33 | |
| 34 | |
| 35 | |
| 36 | |
| 37 | |

TABLE 1-continued

| No. | Structure |
|---|---|
| 38 | (structure) |
| 39 | (structure) |
| 40 | (structure) |
| 41 | (structure) |
| 42 | (structure) |
| 43 | (structure) |
| 44 | (structure) |
| 45 | (structure) |
| 46 | (structure) |

TABLE 1-continued

| No. | Structure |
|-----|-----------|
| 47 | 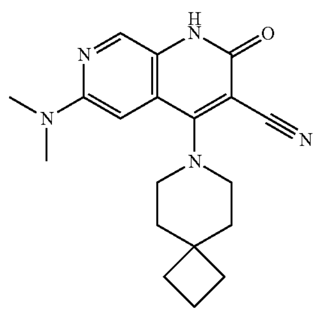 [SMILES: CN(C)c1cc2c(N3CCC4(CCC4)CC3)c(C#N)c(=O)[nH]c2cn1] |
| 48 | 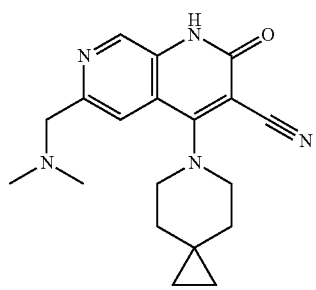 [SMILES: CN(C)Cc1cc2c(N3CCC4(CC3)CC4)c(C#N)c(=O)[nH]c2cn1] |
| 49 | 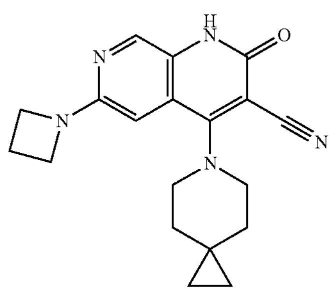 [SMILES: N#Cc1c(N2CCC3(CC2)CC3)c2cc(N3CCC3)ncc2[nH]c1=O] |
| 50 | 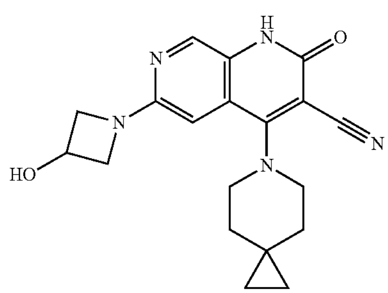 [SMILES: N#Cc1c(N2CCC3(CC2)CC3)c2cc(N3CC(O)C3)ncc2[nH]c1=O] |
| 51 | 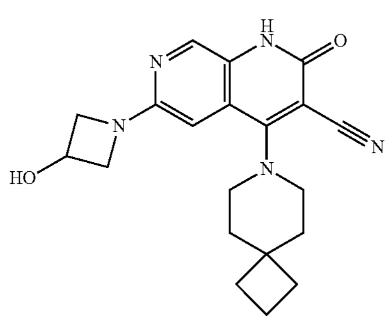 [SMILES: N#Cc1c(N2CCC3(CCC3)CC2)c2cc(N3CC(O)C3)ncc2[nH]c1=O] |
| 52 | |
| 53 | |
| 54 | |
| 55 | |
| 56 | |

TABLE 1-continued
| No. | Structure |
|---|---|
| 57 | 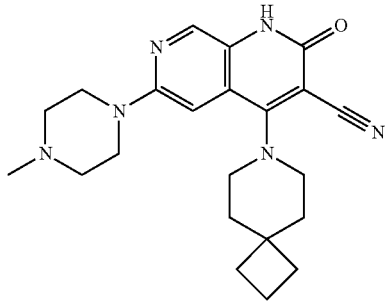 [SMILES: CN1CCN(c2cc3c(N4CCC5(CCC5)CC4)c(C#N)c(=O)[nH]c3cn2)CC1] |
| 58 | 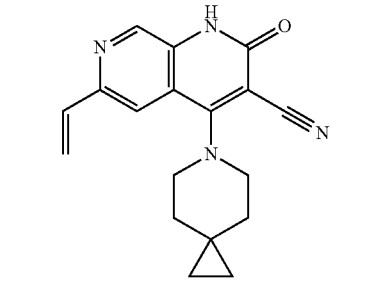 [SMILES: C=Cc1cc2c(N3CCC4(CC3)CC4)c(C#N)c(=O)[nH]c2cn1] |
| 59 | 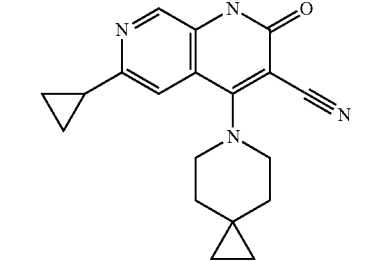 |
| 60 | 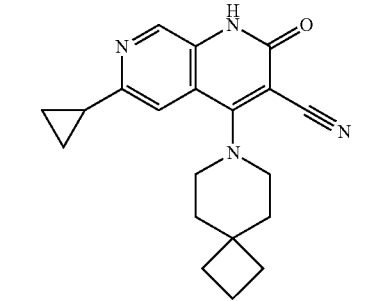 [SMILES: N#Cc1c(N2CCC3(CCC3)CC2)c2cc(C3CC3)ncc2[nH]c1=O] |
| 61 | 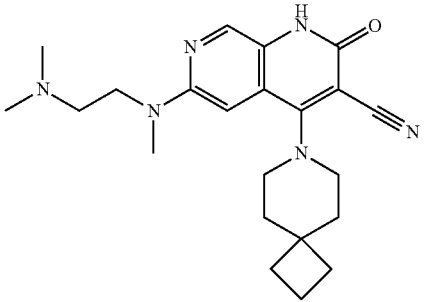 [SMILES: CN(C)CCN(C)c1cc2c(N3CCC4(CCC4)CC3)c(C#N)c(=O)[nH]c2cn1] |
| 62 | 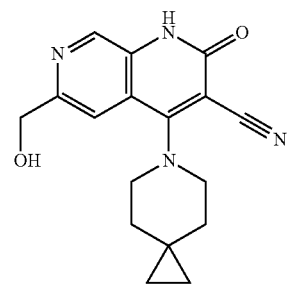 [SMILES: N#Cc1c(N2CCC3(CC2)CC3)c2cc(CO)ncc2[nH]c1=O] |
| 63 | 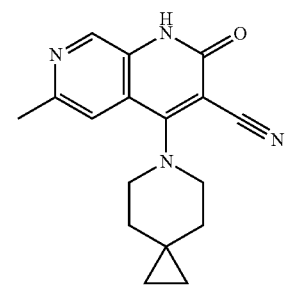 [SMILES: Cc1cc2c(N3CCC4(CC3)CC4)c(C#N)c(=O)[nH]c2cn1] |
| 64 | 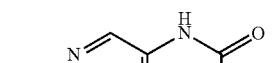 |
| 65 | 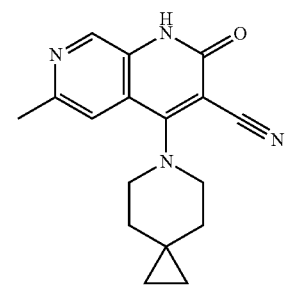 [SMILES: Cc1cc2c(N3CCC4(CC3)CC4)c(C#N)c(=O)[nH]c2cn1] |
| 66 | 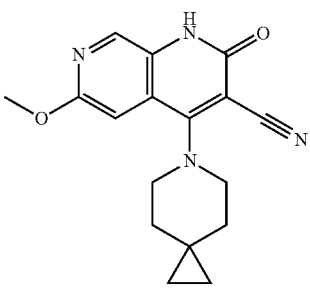 [SMILES: COc1cc2c(N3CCC4(CC3)CC4)c(C#N)c(=O)[nH]c2cn1] |

TABLE 1-continued
| No. | Structure |
|---|---|
| 67 | 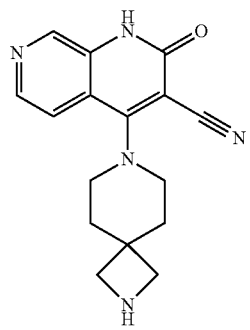 [SMILES: N#Cc1c(N2CCC3(CC2)CNC3)c2ccncc2[nH]c1=O] |
| 68 | 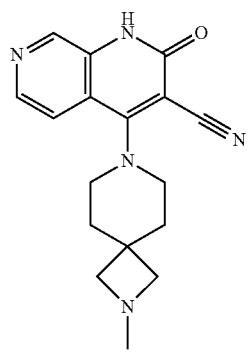 [SMILES: CN1CC2(CCN(c3c(C#N)c(=O)[nH]c4cnccc34)CC2)C1] |
| 69 | 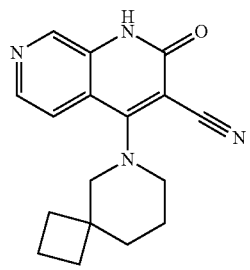 [SMILES: N#Cc1c(N2CCCC3(CCC3)C2)c2ccncc2[nH]c1=O] |
| 70 | 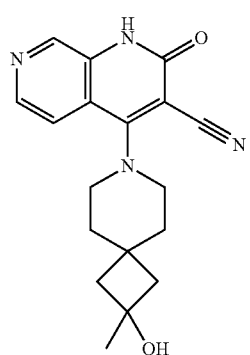 [SMILES: CC1(O)CC2(CCN(c3c(C#N)c(=O)[nH]c4cnccc34)CC2)C1] |
TABLE 1-continued
| No. | Structure |
|---|---|
| 71 | 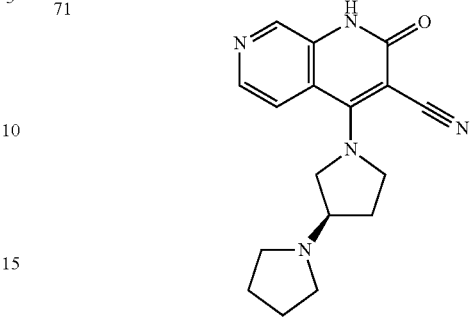 |
| 72 | 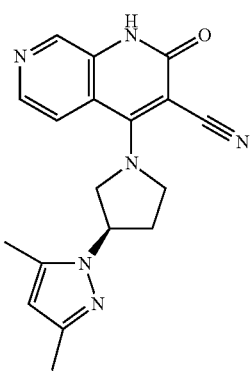 [SMILES: Cc1cc(C)n([C@@H]2CCN(c3c(C#N)c(=O)[nH]c4cnccc34)C2)n1] |
| 73 | 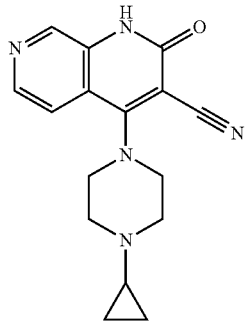 [SMILES: N#Cc1c(N2CCN(C3CC3)CC2)c2ccncc2[nH]c1=O] |
| 74 | 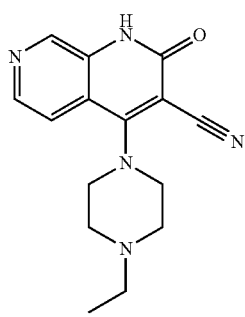 [SMILES: CCN1CCN(c2c(C#N)c(=O)[nH]c3cnccc23)CC1] |

TABLE 1-continued

| No. | Structure |
|---|---|
| 75 | 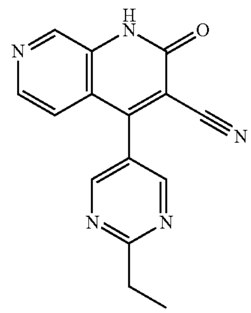 [SMILES: CCc1ncc(-c2c(C#N)c(=O)[nH]c3cnccc23)cn1] |
| 76 | 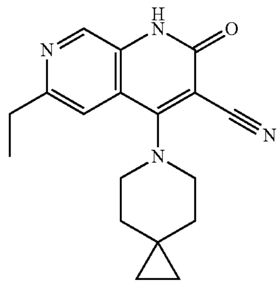 [SMILES: CCc1cc2c(N3CCC4(CC3)CC4)c(C#N)c(=O)[nH]c2cn1] |
| 77 | 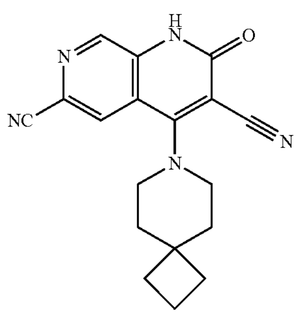 [SMILES: N#Cc1cc2c(N3CCC4(CCC4)CC3)c(C#N)c(=O)[nH]c2cn1] |
| 78 | 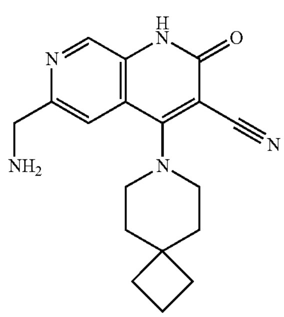 [SMILES: N#Cc1c(N2CCC3(CCC3)CC2)c2cc(CN)ncc2[nH]c1=O] |
| 79 | 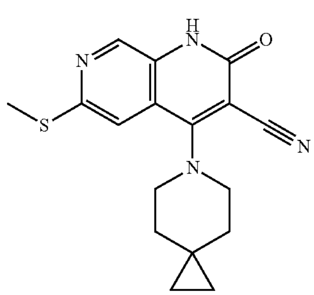 [SMILES: CSc1cc2c(N3CCC4(CC3)CC4)c(C#N)c(=O)[nH]c2cn1] |
| 80 | |
| 81 | |
| 82 | |
| 83 | |
| 84 | |

US 10,889,591 B2
TABLE 1-continued
| No. | Structure |
|---|---|
| 85 | 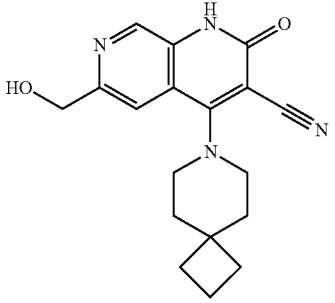 [SMILES: N#Cc1c(N2CCC3(CCC3)CC2)c2cc(CO)ncc2[nH]c1=O] |
| 86 | 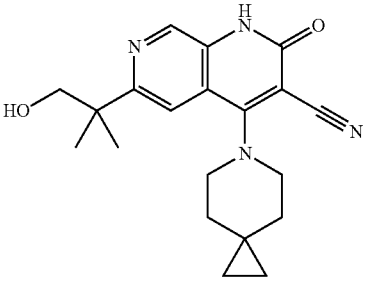 [SMILES: CC(C)(CO)c1cc2c(N3CCC4(CC3)CC4)c(C#N)c(=O)[nH]c2cn1] |
| 87 | 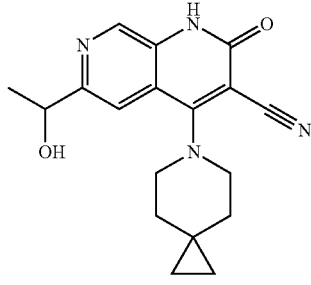 [SMILES: CC(O)c1cc2c(N3CCC4(CC3)CC4)c(C#N)c(=O)[nH]c2cn1] |
| 88 | 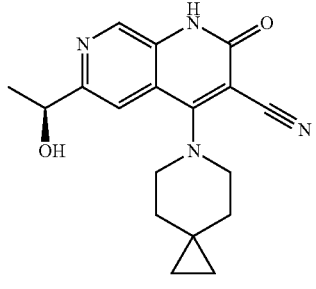 [SMILES: C[C@H](O)c1cc2c(N3CCC4(CC3)CC4)c(C#N)c(=O)[nH]c2cn1] |
| 89 | 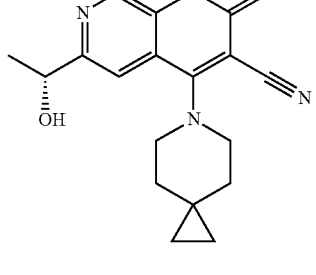 |
TABLE 1-continued
| No. | Structure |
|---|---|
| 90 | 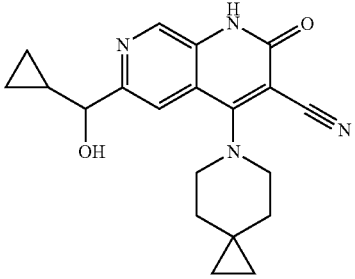 [SMILES: N#Cc1c(N2CCC3(CC2)CC3)c2cc(C(O)C3CC3)ncc2[nH]c1=O] |
| 91 | 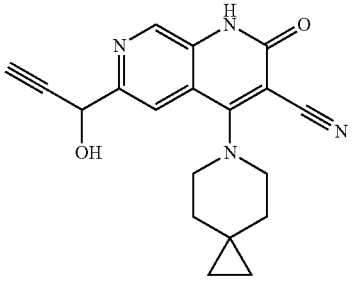 [SMILES: C#CC(O)c1cc2c(N3CCC4(CC3)CC4)c(C#N)c(=O)[nH]c2cn1] |
| 92 | 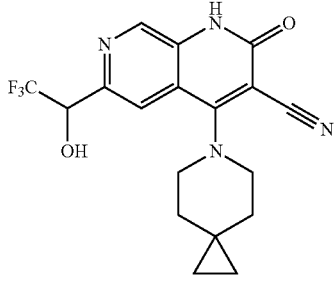 [SMILES: N#Cc1c(N2CCC3(CC2)CC3)c2cc(C(O)C(F)(F)F)ncc2[nH]c1=O] |
| 93 | 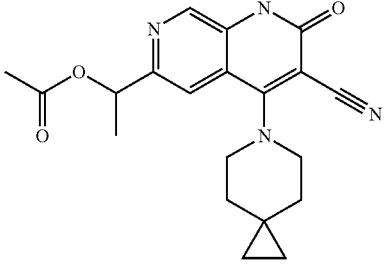 |
| 94 | 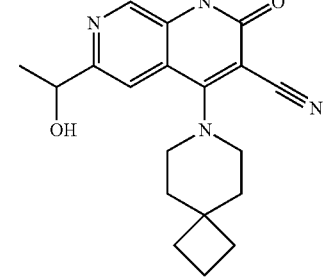 |

TABLE 1-continued

| No. | Structure |
|---|---|
| 95 | 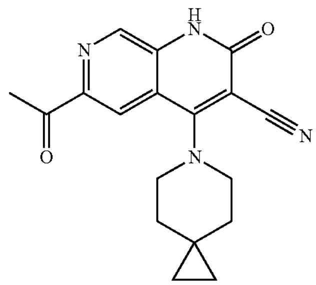 [SMILES: CC(=O)c1cc2c(N3CCC4(CC3)CC4)c(C#N)c(=O)[nH]c2cn1] |
| 96 | 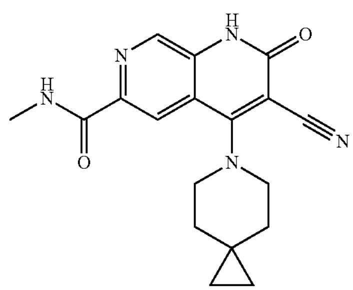 [SMILES: CNC(=O)c1cc2c(N3CCC4(CC3)CC4)c(C#N)c(=O)[nH]c2cn1] |
| 97 | 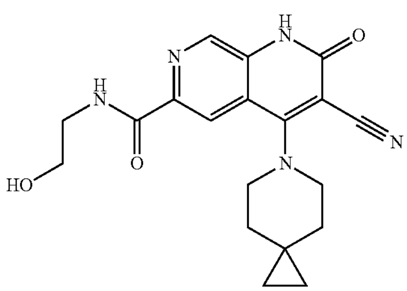 [SMILES: N#Cc1c(N2CCC3(CC2)CC3)c2cc(C(=O)NCCO)ncc2[nH]c1=O] |
| 98 | 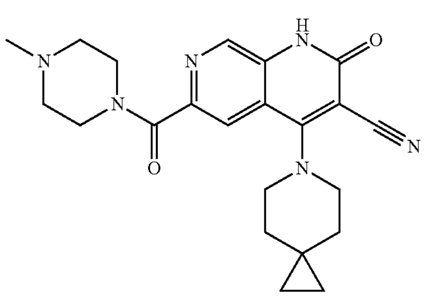 [SMILES: CN1CCN(C(=O)c2cc3c(N4CCC5(CC4)CC5)c(C#N)c(=O)[nH]c3cn2)CC1] |
| 99 | 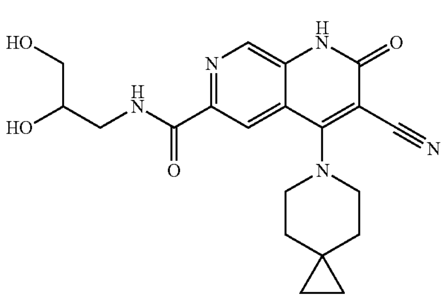 [SMILES: N#Cc1c(N2CCC3(CC2)CC3)c2cc(C(=O)NCC(O)CO)ncc2[nH]c1=O] |
| 100 | 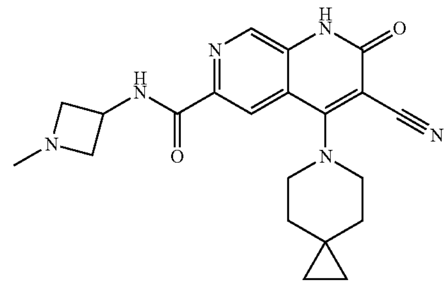 [SMILES: CN1CC(NC(=O)c2cc3c(N4CCC5(CC4)CC5)c(C#N)c(=O)[nH]c3cn2)C1] |
| 101 | 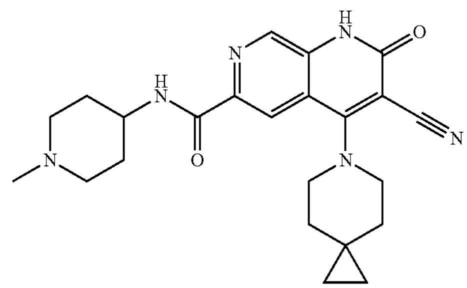 [SMILES: CN1CCC(NC(=O)c2cc3c(N4CCC5(CC4)CC5)c(C#N)c(=O)[nH]c3cn2)CC1] |
| 102 | 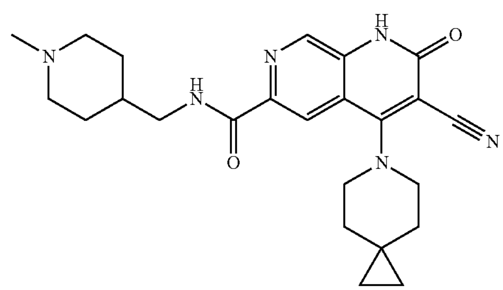 [SMILES: CN1CCC(CNC(=O)c2cc3c(N4CCC5(CC4)CC5)c(C#N)c(=O)[nH]c3cn2)CC1] |
| 103 | 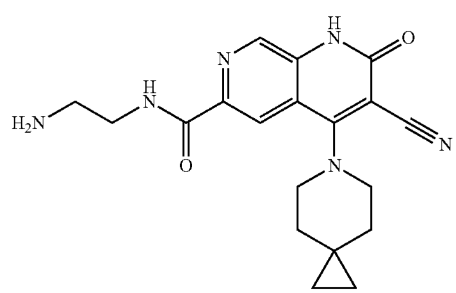 [SMILES: N#Cc1c(N2CCC3(CC2)CC3)c2cc(C(=O)NCCN)ncc2[nH]c1=O] |
| 104 | 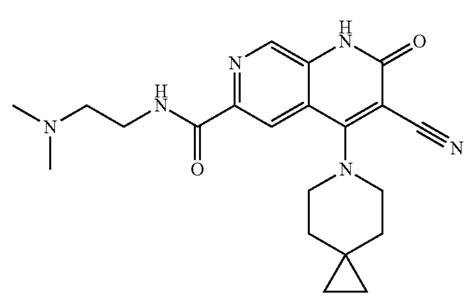 [SMILES: CN(C)CCNC(=O)c1cc2c(N3CCC4(CC3)CC4)c(C#N)c(=O)[nH]c2cn1] |

TABLE 1-continued

| No. | Structure |
|---|---|
| 105 | 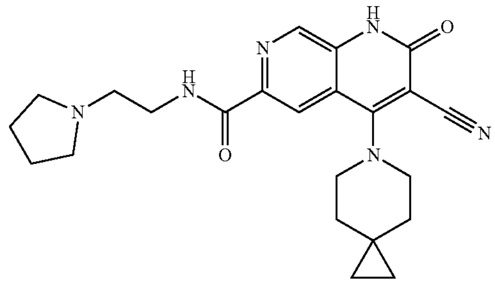 [SMILES: N#Cc1c(N2CCC3(CC2)CC3)c2cc(C(=O)NCCN3CCCC3)ncc2[nH]c1=O] |
| 106 | 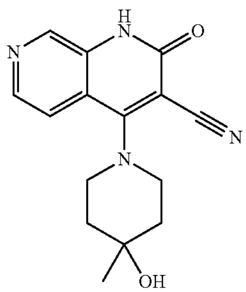 [SMILES: CC1(O)CCN(c2c(C#N)c(=O)[nH]c3cnccc23)CC1] |
| 107 | 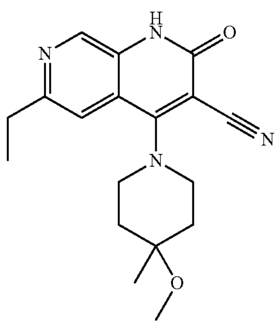 [SMILES: CCc1cc2c(N3CCC(C)(OC)CC3)c(C#N)c(=O)[nH]c2cn1] |
| 108 | 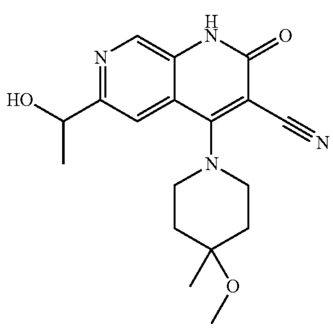 [SMILES: COC1(C)CCN(c2c(C#N)c(=O)[nH]c3cnc(C(C)O)cc23)CC1] |
| 109 | 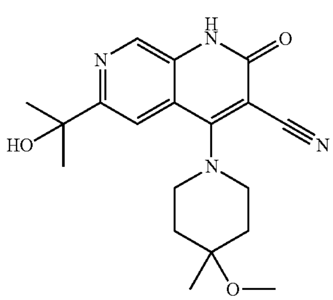 [SMILES: COC1(C)CCN(c2c(C#N)c(=O)[nH]c3cnc(C(C)(C)O)cc23)CC1] |
| 110 | |
| 111 | |
| 112 | |
| 113 | |

TABLE 1-continued

| No. | Structure |
|---|---|
| 114 | *(1,7-naphthyridin-2(1H)-one with 3-cyano and 4-[(3R)-3-(1H-1,2,4-triazol-1-yl)pyrrolidin-1-yl])* |
| 115 | *(6-(2-hydroxypropan-2-yl)-1,7-naphthyridin-2(1H)-one with 3-cyano and 4-[(3R)-3-(1H-pyrazol-1-yl)pyrrolidin-1-yl])* |
| 116 | *(1,7-naphthyridin-2(1H)-one with 3-cyano and 4-[(3S)-3-(4H-1,2,4-triazol-4-yl)pyrrolidin-1-yl])* |
| 117 | *(1,7-naphthyridin-2(1H)-one with 3-cyano and 4-[(3S)-3-(1H-1,2,4-triazol-1-yl)pyrrolidin-1-yl])* |
| 118 | *(1,7-naphthyridin-2(1H)-one with 3-cyano and 4-[(3R)-3-(2H-1,2,3-triazol-2-yl)pyrrolidin-1-yl])* |
| 119 | *(1,7-naphthyridin-2(1H)-one with 3-cyano and 4-[(3R)-3-(1H-1,2,3-triazol-1-yl)pyrrolidin-1-yl])* |
| 120 | *(1,7-naphthyridin-2(1H)-one with 3-cyano and 4-[(3R)-3-(1H-imidazol-1-yl)pyrrolidin-1-yl])* |
| 121 | *(1,7-naphthyridin-2(1H)-one with 3-cyano and 4-[3-(oxazol-2-yl)pyrrolidin-1-yl])* |

TABLE 1-continued
| No. | Structure |
|---|---|
| 122 | 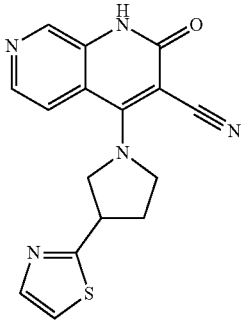 [SMILES: N#Cc1c(N2CCC(c3nccs3)C2)c2ccncc2[nH]c1=O] |
| 123 | 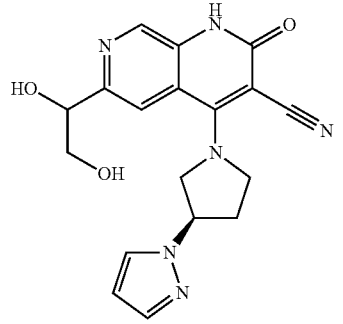 [SMILES: N#Cc1c(N2CC[C@@H](n3cccn3)C2)c2cc(C(O)CO)ncc2[nH]c1=O] |
| 124 | 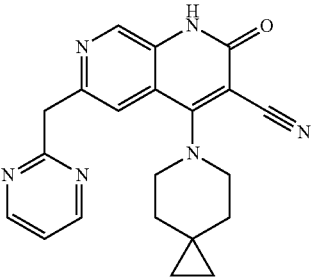 [SMILES: N#Cc1c(N2CCC3(CC2)CC3)c2cc(Cc3ncccn3)ncc2[nH]c1=O] |
| 125 | 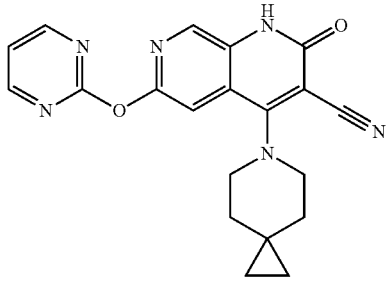 [SMILES: N#Cc1c(N2CCC3(CC2)CC3)c2cc(Oc3ncccn3)ncc2[nH]c1=O] |
| 126 | 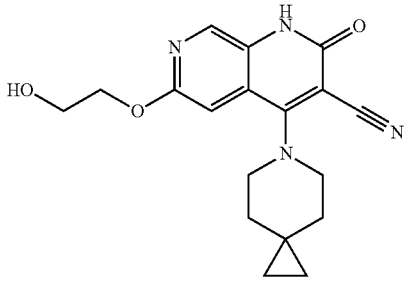 [SMILES: N#Cc1c(N2CCC3(CC2)CC3)c2cc(OCCO)ncc2[nH]c1=O] |
| 127 | 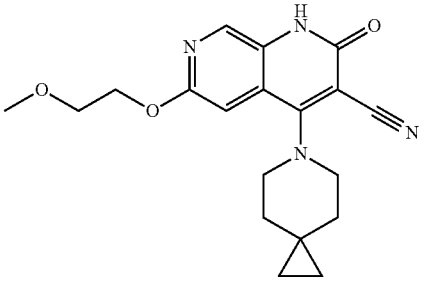 [SMILES: COCCOc1cc2c(N3CCC4(CC3)CC4)c(C#N)c(=O)[nH]c2cn1] |
| 128 | 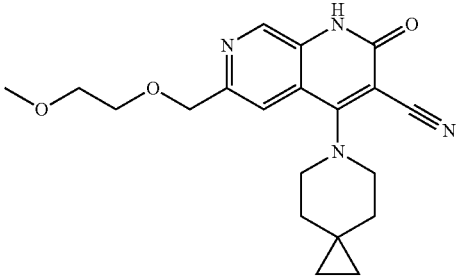 [SMILES: COCCOCc1cc2c(N3CCC4(CC3)CC4)c(C#N)c(=O)[nH]c2cn1] |
| 129 | 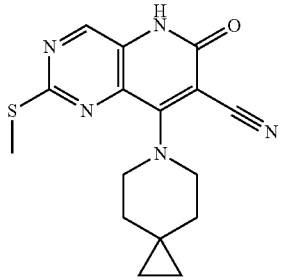 [SMILES: CSc1ncc2[nH]c(=O)c(C#N)c(N3CCC4(CC3)CC4)c2n1] |
| 130 | 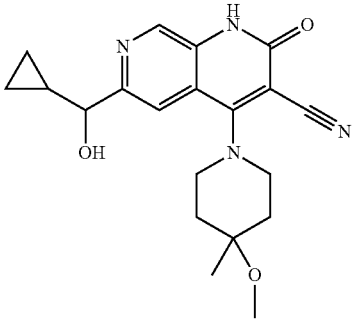 [SMILES: COC1(C)CCN(c2c(C#N)c(=O)[nH]c3cnc(C(O)C4CC4)cc23)CC1] |
| 131 | 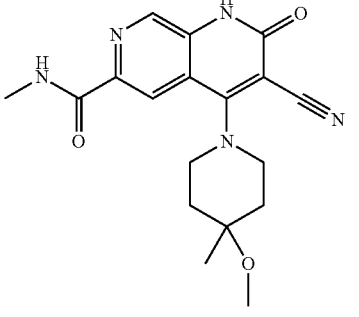 |

TABLE 1-continued
| No. | Structure |
|---|---|
| 132 | 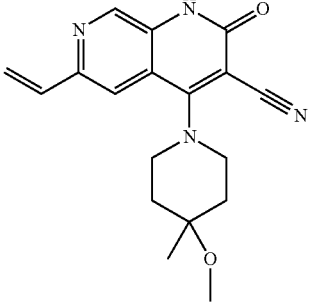 |
| 133 | 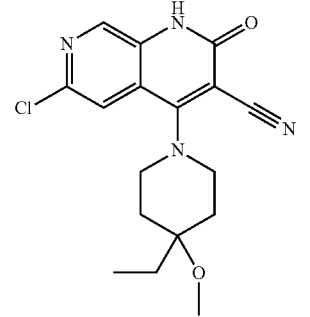 [SMILES: CCC1(OC)CCN(c2c(C#N)c(=O)[nH]c3cnc(Cl)cc23)CC1] |
| 134 | 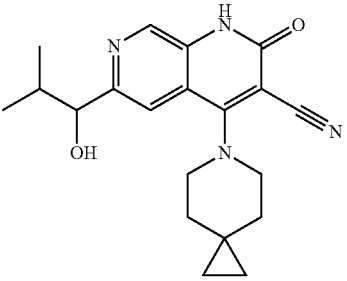 [SMILES: CC(C)C(O)c1cc2c(N3CCC4(CC3)CC4)c(C#N)c(=O)[nH]c2cn1] |
| 135 | 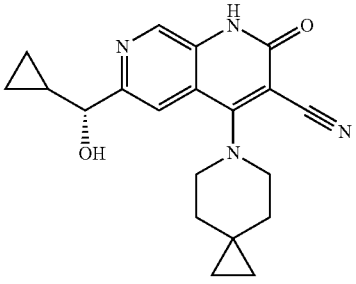 [SMILES: N#Cc1c(N2CCC3(CC2)CC3)c2cc([C@H](O)C3CC3)ncc2[nH]c1=O] |
| 136 | 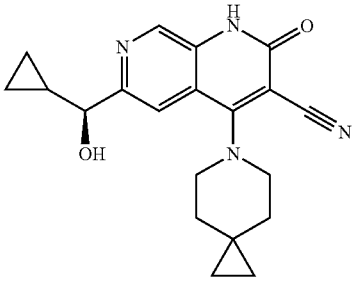 [SMILES: N#Cc1c(N2CCC3(CC2)CC3)c2cc([C@@H](O)C3CC3)ncc2[nH]c1=O] |
| 137 | 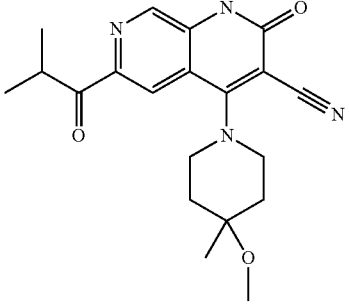 |
| 138 | 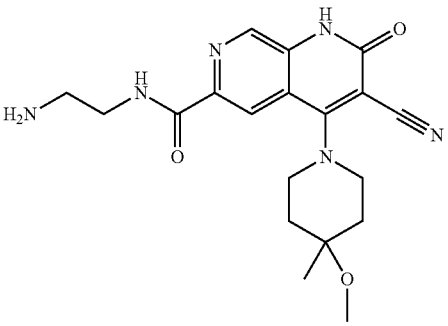 [SMILES: COC1(C)CCN(c2c(C#N)c(=O)[nH]c3cnc(C(=O)NCCN)cc23)CC1] |
| 139 | 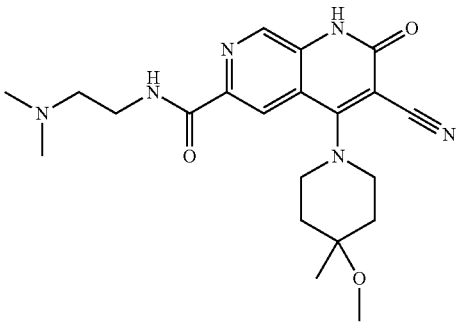 [SMILES: COC1(C)CCN(c2c(C#N)c(=O)[nH]c3cnc(C(=O)NCCN(C)C)cc23)CC1] |
| 140 | 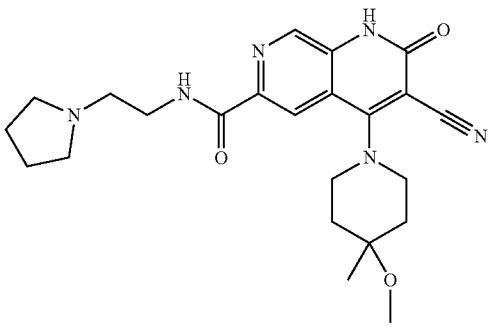 [SMILES: COC1(C)CCN(c2c(C#N)c(=O)[nH]c3cnc(C(=O)NCCN4CCCC4)cc23)CC1] |

TABLE 1-continued

| No. | Structure |
|-----|-----------|
| 141 | |
| 142 | |
| 143 | |
| 144 | |
| 145 | 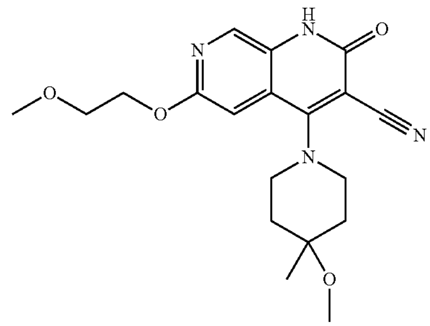 [SMILES: COCCOc1cc2c(N3CCC(C)(OC)CC3)c(C#N)c(=O)[nH]c2cn1] |
| 146 | 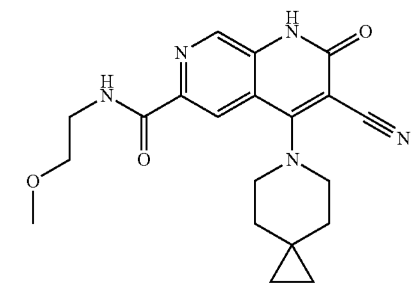 [SMILES: COCCNC(=O)c1cc2c(N3CCC4(CC3)CC4)c(C#N)c(=O)[nH]c2cn1] |
| 147 | 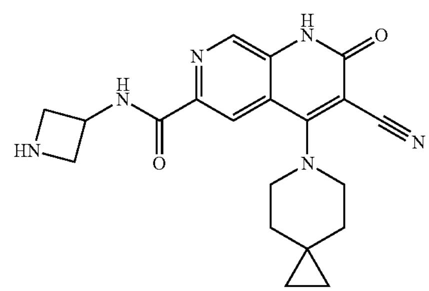 [SMILES: N#Cc1c(N2CCC3(CC2)CC3)c2cc(C(=O)NC3CNC3)ncc2[nH]c1=O] |
| 148 | 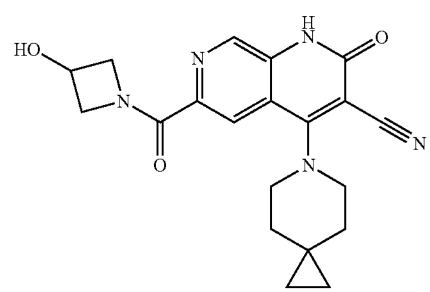 [SMILES: N#Cc1c(N2CCC3(CC2)CC3)c2cc(C(=O)N3CC(O)C3)ncc2[nH]c1=O] |
| 149 | 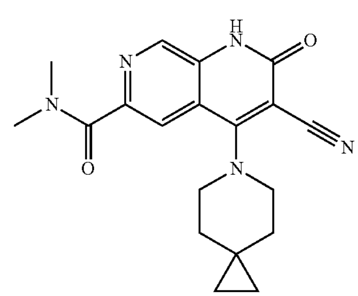 [SMILES: CN(C)C(=O)c1cc2c(N3CCC4(CC3)CC4)c(C#N)c(=O)[nH]c2cn1] |

TABLE 1-continued

| No. | Structure |
|---|---|
| 150 | (structure) |
| 151 | (structure) |
| 152 | (structure) |
| 153 | (structure) |
| 154 | (structure) |
| 155 | (structure) |
| 156 | (structure) |
| 157 | (structure) |
| 158 | (structure) |

TABLE 1-continued

| No. | Structure |
|---|---|
| 159 | 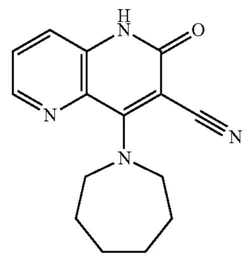 [SMILES: N#Cc1c(N2CCCCCC2)c2ncccc2[nH]c1=O] |
| 160 | 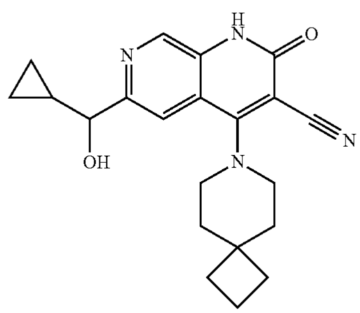 [SMILES: N#Cc1c(N2CCC3(CCC3)CC2)c2cc(C(O)C3CC3)ncc2[nH]c1=O] |
| 161 | 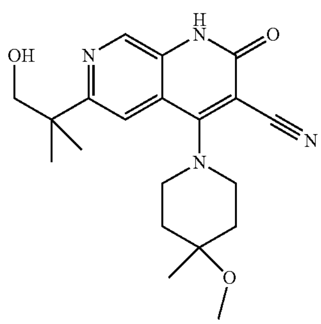 [SMILES: COC1(C)CCN(c2c(C#N)c(=O)[nH]c3cnc(C(C)(C)CO)cc23)CC1] |
| 162 | 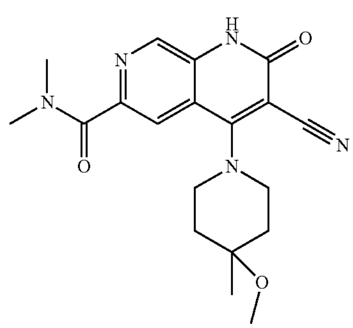 [SMILES: COC1(C)CCN(c2c(C#N)c(=O)[nH]c3cnc(C(=O)N(C)C)cc23)CC1] |

The present invention also provides a pharmaceutical composition comprising the compound shown in formula (I) or (II) or pharmaceutically acceptable salts or stereoisomers thereof, and one or more second therapeutically active agents.

In one specific embodiment of the present invention, the composition may be used by combined administration of a "therapeutically effective amount" of the compound shown in formula (I) or (II) or pharmaceutically acceptable salts or stereoisomers thereof, along with one or more second therapeutic active agents, such as sequential administration, simultaneous administration, or by administration of a compound formulation formulated by the compound provided herein or pharmaceutically acceptable salts or stereoisomers thereof and a second therapeutically active agent.

The present invention also provides a pharmaceutical formulation comprising the compound shown in formula (I) or (II), or pharmaceutically acceptable salts or stereoisomers thereof.

In some embodiments of the invention, the pharmaceutical formulation may comprise one or more pharmaceutically acceptable carriers.

The pharmaceutically acceptable carrier of the present invention may be one or more solid or liquid fillers or gel materials suitable for human use. The pharmaceutically acceptable carrier preferably has sufficient purity and sufficiently low toxicity, and is compatible with the compound or pharmaceutically acceptable salts or stereoisomers thereof provided by the present invention, and does not significantly reduce their pharmacological effects. For example, the pharmaceutically acceptable carrier can be a filler, a binder, a disintegrant, a lubricant, an aqueous solvent or a nonaqueous solvent, and the like.

The pharmaceutical formulation of the present invention can be formulated into any pharmaceutically acceptable dosage form, and administered to a patient or subject in need of such therapy in any suitable administration means, for example, oral, parenteral, rectal or pulmonary administration. For oral administration, it can be formulated into tablets, capsules, pills, granules and the like. For parenteral administration, it can be formulated into an injection solution, a sterile powder for injection, and the like.

The invention also provides use of the compound shown in formula (I) or (II) or pharmaceutically acceptable salts or stereoisomers thereof, the pharmaceutical formulation or the pharmaceutical composition in the manufacture of a medicament for treating or preventing a PDE9-mediated related disease. In particular, the PDE9-mediated related disease is cognitive impairment caused by a central nervous system disorder. More specifically, the cognitive impairment includes: perception, attention, memory and learning impairment, including but not limited to Alzheimer's disease, schizophrenia, age-related memory loss, vascular dementia, craniocerebral trauma, stroke, dementia after stroke, post-traumatic dementia, general attention impairment, children attention impairment with learning and memory problems, Alzheimer's disease, Lewy body dementia, frontallobe-dementia, corticobasal degeneration dementia, amyotrophic lateral sclerosis, Huntington's disease, multiple sclerosis, thalamic degeneration, Creutzfeldt-Jacob dementia, HIV dementia, schizophrenia, Korsakov psychosis or depression or bipolar disorder.

The invention also provides the compound shown in formula (I) or (II) or pharmaceutically acceptable salts or stereoisomers thereof, the pharmaceutical formulation or the pharmaceutical composition for use in treating or preventing a disease.

The invention also provides use of the compound shown in formula (I) or (II) or pharmaceutically acceptable salts or stereoisomers thereof, the pharmaceutical formulation or the pharmaceutical composition for use in treating or preventing a PDE9-mediated related disease. In particular, the PDE9-mediated related disease is cognitive impairment caused by a central nervous system disorder. More specifically, the cognitive impairment includes: perception, attention, memory, and learning impairment, including but not limited to Alzheimer's disease, schizophrenia, age-related memory loss, vascular dementia, craniocerebral trauma, stroke, dementia after stroke, post-traumatic dementia, general attention impairment, child attention impairment with learning and memory problems, Alzheimer's disease, Lewy body dementia, frontallobe-dementia, corticobasal degeneration dementia, amyotrophic lateral sclerosis, Huntington's disease, multiple sclerosis, thalamic degeneration, Creutzfeldt-Jacob dementia, HIV dementia, schizophrenia, Korsakov psychosis or depression or bipolar disorder.

The invention also provides a method for treating or preventing diseases. The method comprises administering to a patient in need thereof a therapeutically effective amount of the compound shown in formula (I) or (II), or pharmacologically acceptable salts or stereoisomers thereof, the pharmaceutical formulation or the pharmaceutical composition. The disease is a PDE9-mediated related disease. In particular, the PDE9-mediated related disease is cognitive impairment caused by a central nervous system disorder. More specifically, the cognitive impairment includes: perception, attention, memory, and learning impairment, including but not limited to Alzheimer's disease, schizophrenia, age-related memory loss, vascular dementia, craniocerebral trauma, stroke, dementia after stroke, post-traumatic dementia, general attention impairment, children attention impairment with learning and memory problems, Alzheimer's disease, Lewy body dementia, frontallobe-dementia, corticobasal degeneration dementia, amyotrophic lateral sclerosis, Huntington's disease, multiple sclerosis, thalamic degeneration, Creutzfeldt-Jacob dementia, HIV dementia, schizophrenia, Korsakov psychosis or depression or bipolar disorder.

DETAILED DESCRIPTION OF THE INVENTION

The "halogen" as used in the present invention means fluorine, chlorine, bromine, iodine and the like, preferably fluorine and chlorine.

The "halogenated" as used in the present invention means that any hydrogen atom in the substituent may be substituted with one or more halogen atoms which are identical or different. "Halogen" is defined as above.

The "$C_{1-6}$ alkyl" as used in the present invention means a linear or branched alkyl group derived by removing one hydrogen atom from a hydrocarbon moiety having 1 to 6 carbon atoms, such as methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, and 1-methyl-2-methylpropyl, etc. The "$C_{1-4}$ alkyl" means the above examples having 1 to 4 carbon atoms.

The "$C_{2-8}$ alkenyl" as used in the present invention means a linear or branched or cyclic alkenyl group derived by removing one hydrogen atom from an olefin moiety having 2 to 8 carbon atoms containing a carbon-carbon double bond, such as vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 1,4-hexadienyl, etc.

The "$C_{2-8}$ alkynyl" as used in the present invention means a linear or branched alkynyl group derived by removing one hydrogen atom from an alkyne moiety having 2 to 8 carbon atoms containing a carbon-carbon triple bond, such as ethynyl, propynyl, 2-butynyl, 2-pentynyl, 3-pentynyl, 4-methyl-2-pentynyl, 2-hexynyl, 3-hexynyl, etc.

The "$C_{1-6}$ alkoxy" as used in the present invention means a group in which a "$C_{1-6}$ alkyl" as defined above is linked to a parent moiety via an oxygen atom, that is, "$C_{1-6}$ alkyl-O—" group, such as methoxy, ethoxy, n-propoxy, iso-propoxy, n-butoxy, tert-butoxy, n-pentyloxy, neopentyloxy, n-hexyloxy, etc. The "$C_{1-4}$ alkoxy" refers to the above-mentioned examples having 1 to 4 carbon atoms, that is, "$C_{1-4}$ alkyl-O—" group.

The "$C_{1-6}$ alkylamino", "($C_{1-6}$ alkyl)$_2$ amino", "$C_{1-6}$ alkylcarbonylamino", "$C_{1-6}$ alkylsulfonylamino", "$C_{1-6}$ alkylaminocarbonyl", "($C_{1-6}$ alkyl)$_2$ aminocarbonyl", "$C_{1-6}$ alkoxycarbonyl", "$C_{1-6}$ alkylsulfonyl", "$C_{1-6}$ alkylthio", "$C_{1-6}$ alkylcarbonyl" as used in the present invention means $C_{1-6}$ alkyl-NH—, ($C_{1-6}$ alkyl)($C_{1-6}$ alkyl)N—, $C_{1-6}$ alkyl-C(O)—NH—, $C_{1-6}$ alkyl-S(O)$_2$—NH$_2$—, $C_{1-6}$ alkyl-NH—C(O)—, ($C_{1-6}$ alkyl)($C_{1-6}$ alkyl)N—C(O)—, $C_{1-6}$ alkyl-O—C(O)—, $C_{1-6}$ alkyl-S(O)$_2$—, $C_{1-6}$ alkyl-S—, $C_{1-6}$ alkyl-C(O)—, respectively. The "$C_{1-6}$ alkyl" is as defined above, preferably "$C_{1-4}$ alkyl".

The "fused ring" as used in the present invention means a polycyclic structure formed by two or more cyclic structures connected in the form of ortho-fused, spiro or bridged ring. The ortho-fused ring refers to a fused ring structure formed by two or more cyclic structures sharing two adjacent ring atoms with each other (i.e., sharing one bond). The bridged ring refers to a fused ring structure formed by two or more cyclic structures sharing two non-adjacent ring atoms with each other. The spiro ring refers to a fused ring structure formed by two or more cyclic structures sharing one ring atom with each other.

The "3-12 membered cycloalkenyl" as used in the present invention includes, unless otherwise specified, all monocyclic rings and fused rings (including fused in the form of ortho-fused ring, spiro ring, bridged ring) that may be formed, such as 3-8 membered monocycloalkenyl, 7-11 membered spiro cycloalkenyl, 7-11 membered ortho-fused cycloalkenyl, 6-11 membered bridged cycloalkenyl and the like.

The "cycloalkyl" as used in the present invention includes all monocyclic rings and fused rings (including fused in the form of ortho-fused ring, spiro ring, bridged ring) that may be formed. For example, "3-12 membered cycloalkyl" can be a monocyclic, bicyclic, or polycyclic cycloalkyl system (also known as a fused ring system). Unless otherwise specified, the monocyclic system is a cyclic hydrocarbon group having 3 to 8 carbon atoms. Examples of 3-8 membered cycloalkyl include, but are not limited to, cyclopropyl, cyclobutyl, cyclopentyl, cyclohexyl, cycloheptyl, cyclooctyl, and the like.

The fused cycloalkyl includes ortho-fused cycloalkyl, bridged cycloalkyl, and spiro cycloalkyl. The ortho-fused cycloalkyl may be a 6-11 membered ortho-fused cycloalkyl and 7-10 membered ortho-fused cycloalkyl, and representative examples thereof include, but are not limited to, bicyclo [3.1.1] heptane, bicyclo [2.2.1] heptane, bicyclo [2.2.2] octane, bicyclo [3.2.2] nonane, bicyclo [3.3.1] nonane and bicyclo [4.2.1] nonane. The spiro cycloalkyl may be a 7-12 membered spiro cycloalkyl and a 7-11 membered spiro cycloalkyl, and examples thereof include, but are not limited to:

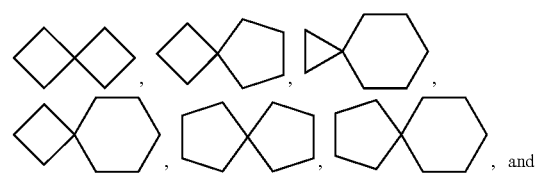

The bridged cycloalkyl may be a 6-11 membered bridged cycloalkyl and a 7-10 membered bridged cycloalkyl, and examples thereof include, but are not limited to:

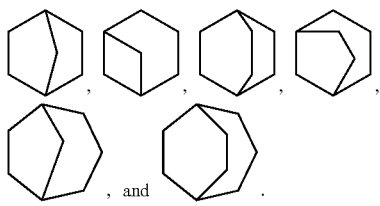

The "heterocyclyl" as used in the present invention means a 3-12 membered non-aromatic cyclic group in which at least one ring carbon atom is substituted with a hetero atom selected from O, S and N, preferably substituted with 1-3 hetero atoms, and wherein a carbon atom, a nitrogen atom and a sulfur atom can be oxidized.

"3-12 membered heterocyclyl" means monocyclic heterocyclyl, bicyclic heterocyclyl or polycyclic heterocyclyl system (also known as a fused ring system), including saturated and partially saturated heterocyclyl, but excluding aromatic rings. Unless otherwise specified, all monocyclic rings, fused rings (including fused in the form of ortho-fused ring, spiro ring, bridged ring), saturated rings, and partially saturated rings that may be formed are included.

The monoheterocyclyl may be 3-8 membered heterocyclyl, 3-8 membered saturated heterocyclyl, 3-6 membered heterocyclyl, 4-7 membered heterocyclyl, 5-7 membered heterocyclyl, 5-6 membered heterocyclyl, 5-6 membered oxygen-containing heterocyclyl, 3-8 membered nitrogen-containing heterocyclyl, 5-6 membered nitrogen-containing heterocyclyl, 5-6 membered saturated heterocyclyl and the like. The examples of "3-8 membered saturated heterocyclyl" include, but are not limited to, aziridinyl, oxiranyl, thiiranyl, azetidinyl, oxetanyl, thietanyl, tetrahydrofuranyl, pyrrolidinyl, tetrahydrothiophenyl, imidazolidinyl, pyrazolidinyl, 1,2-oxazolidinyl, 1,3-oxazolidinyl, 1,2-thiazolidinyl, 1,3-thiazolidinyl, tetrahydro-2H-pyranyl, tetrahydro-2H-thiopyranyl, piperidinyl, piperazinyl, morpholinyl, 1,4-dioxanyl, 1,4-oxathianyl. The examples of "3-8 membered partially saturated heterocyclyl" include, but are not limited to, 4,5-dihydroisooxazolyl, 4,5-dihydrooxazolyl, 2,5-dihydrooxazolyl, 2,3-dihydrooxazolyl, 3,4-dihydro-2H-pyrrolyl, 2,3-dihydro-1H-pyrrolyl, 2,5-dihydro-1H-imidazolyl, 4,5-dihydro-1H-imidazolyl, 4,5-dihydro-1H-pyrazolyl, 4,5-dihydrogen-3H-pyrazolyl, 4,5-dihydrothiazolyl, 2,5-dihydrothiazolyl, 2H-pyranyl, 4H-pyranyl, 2H-thiopyranyl, 4H-thiopyranyl, 2,3,4,5-tetrahydropyridyl, 1,2-isooxazinyl, 1,4-isooxazinyl, or 6H-1,3-oxazinyl and the like. The fused heterocyclic ring includes ortho-fused heterocyclyl, spiro heterocyclyl, bridged heterocyclyl, and may be saturated, partially saturated or unsaturated, but are not aromatic. The fused heterocyclyl is 5-6 membered monocyclic heterocyclic ring fused to benzene ring, 5-6 membered monocyclic cycloalkyl, 5-6 membered monocyclic cycloalkenyl, 5-6 membered monocyclic heterocyclyl, or 5-6 membered monocyclic heteroaryl. The ortho-fused heterocyclyl can be 6-12 membered ortho-fused heterocyclyl, 7-10 membered ortho-fused heterocyclyl, 6-10 membered ortho-fused heterocyclyl, and 6-12 membered saturated ortho-fused heterocyclyl, and the representative examples include, but are not limited to, 3-azabicyclo[3.1.0]hexyl, 3,6-diazabicyclo[3.2.0]heptyl, 3,8-diazabicyclo[4.2.0]octyl, 3,7-diazabicyclo[4.2.0]octyl, octahydropyrrolo[3,4-c]pyrrolyl, octahydropyrrolo[3,4-b]pyrrolyl, octahydropyrrolo[3,4-b][1,4]oxazinyl, octahydro-1H-pyrrolo[3,4-c]pyridinyl, 2,3-dihydrobenzofuran-2-yl, 2,3-dihydrobenzofuranyl-3-yl, indolin-1-yl, indolin-2-yl, indolin-3-yl, 2,3-dihydrobenzothiophen-2-yl, octahydro-1H-indolyl, octahydrobenzofuranyl. The spiroheterocyclyl may be 6-12 membered spiroheterocyclyl, 7-11 membered spiroheterocyclyl, 7-11 membered saturated spiroheterocyclyl, 6-12 membered saturated spirocyclyl, and the examples thereof include but not limited to:

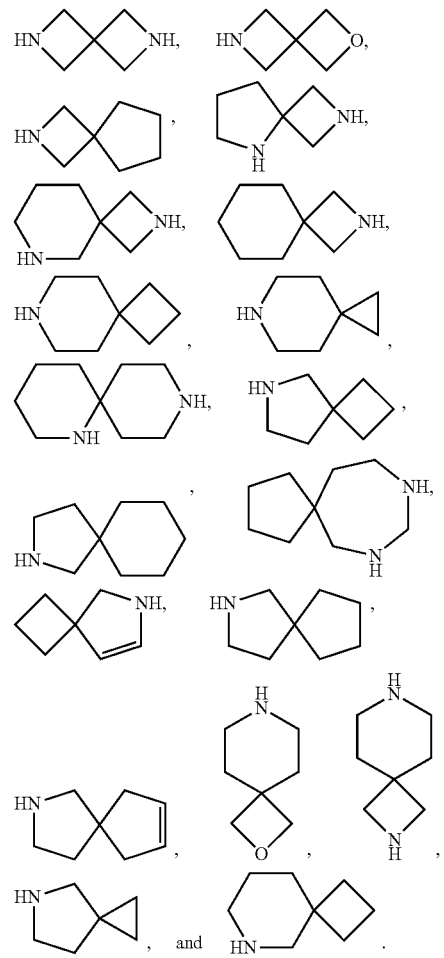

The bridged heterocyclyl may be 6-12 membered bridged heterocyclyl, 7-11 membered bridged heterocyclyl, and 6-12 membered saturated bridged heterocyclyl, and the examples thereof include but not limited to:

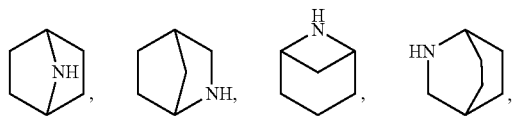

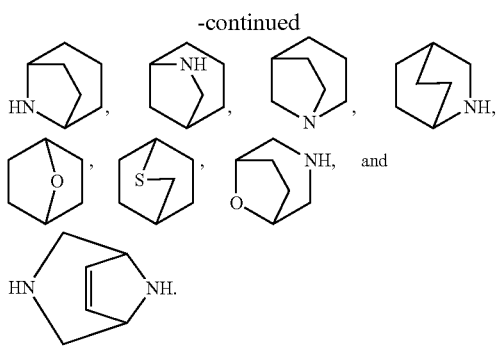

The "aryl" as used in the present invention means a cyclic aromatic group containing 6 to 14 carbon atoms, including, phenyl, naphthalene, phenanthrene, and the like.

The heteroaryl as used in the present invention include all monocyclic rings, fused rings, and all aromatic, partially aromatic system that may be formed. For example, "5-10 membered heteroaryl" refers to an aromatic cyclic group in which at least one ring carbon atom is substituted with a heteroatom selected from O, S and N, preferably 1 to 3 heteroatoms, including the condition that a carbon atom or a sulfur atom is oxidized, for example, the carbon atom is replaced with C(O), and the sulfur atom is replaced with S(O) or S(O)$_2$. Heteroaryl includes monocyclic heteroaryl and fused heteroaryl. Unless otherwise specified, the monocyclic heteroaryl can be a 5-7 membered heteroaryl or a 5-6 membered heteroaryl, and the examples of monocyclic heteroaryl include, but are not limited to furanyl, imidazolyl, isoxazolyl, thiazolyl, isothiazolyl, oxadiazolyl, oxazolyl, pyridyl, pyridazinyl, pyrimidinyl, pyrazinyl, pyrazolyl, pyrrolyl, tetrazolyl, thiadiazolyl, thienyl, triazolyl and triazinyl. In some embodiments, the fused heteroaryl refers to a group in which the monocyclic heteroaryl is fused to phenyl, cycloalkenyl, heteroaryl, cycloalkyl, or heterocyclyl.

The fused heteroaryl may be 8-12 membered ortho-fused heteroaryl, or 9-10 membered ortho-fused heteroaryl. The examples of fused heteroaryl include, but are not limited to, benzimidazolyl, benzofuranyl, benzothienyl, benzooxadiazolyl, benzothiadiazolyl, benzothiazolyl, cinnolinyl, 5,6-dihydroquinolin-2-yl, 5,6-dihydroisoquinolin-1-yl, furopyridinyl, indazolyl, indolyl, isoindolyl, isoquinolyl, naphthyridinyl, purinyl, quinolyl, 5,6,7,8-tetrahydroquinol-2-yl, 5,6,7,8-tetrahydroquinolyl, 5,6,7,8-tetrahydroquinol-4-yl, 5,6,7,8-tetrahydroisoquinol-1-yl, thienopyridinyl, 4,5,6,7-tetrahydro[c][1,2,5]oxadiazolyl and 6,7-dihydro[c][1,2,5]oxadiazole-4(5H) keto.

The "pharmaceutically acceptable salts" as used herein means pharmaceutically acceptable addition salts and solvates of acids and bases. Such pharmaceutically acceptable salts include salts of acids such as hydrochloric acid, phosphoric acid, hydrobromic acid, sulfuric acid, sulfurous acid, formic acid, toluenesulfonic acid, methanesulfonic acid, nitric acid, benzoic acid, citric acid, tartaric acid, maleic acid, hydroiodic acid, alkanoic acid (such as acetic acid, HOOC—(CH$_2$)$_n$—COOH (where n is 0 to 4)), and the like. The salts of bases include sodium, potassium, calcium, ammonium and the like. A variety of non-toxic pharmaceutically acceptable addition salts are known to those skilled in the art.

The "stereoisomer" of the compound of formula (I) of the present invention means an enantiomer in the case that the compound of formula (I) has an asymmetric carbon atom; a cis-trans isomer in the case that the compound has a carbon-carbon double bond or a cyclic structure; tautomers in the case that a ketone or oxime is present in the compound. The enantiomers, diastereomers, racemic isomers, cis-trans isomers, tautomers, geometric isomers, epimers of the compound of formula (I) and mixtures thereof are all included within the scope of the invention.

A "therapeutically effective amount" as used herein refers to an amount of the aforementioned compound, or a pharmaceutically acceptable salt, stereoisomer, composition or pharmaceutical preparation thereof, which is at least capable of alleviating the symptoms of a patient's condition when administered to a patient. The actual amount comprising a "therapeutically effective amount" will vary depending on a variety of circumstances including, but not limited to, the particular condition being treated, the severity of the condition, the physique and health of the patient, and the route of administration. Skilled medical practitioners can readily determine the appropriate amount using methods known in the field of medicine.

EMBODIMENTS

For abbreviations used herein, "DMF" means dimethylformamide; "CDI" means N,N'-carbonyldiimidazole; "DIPEA" means N,N-diisopropylethylamine; "EA" means ethyl acetate; "PE" means petroleum ether; "DIBAL-H" means diisobutylaluminum hydride; "THF" means tetrahydrofuran; "DCM" means dichloromethane; "TBAF" means tetrabutylammonium fluoride; "DMAP" means 4-dimethylaminopyridine; "HATU" means 2-(7-oxobenzotriazole)-N, N,N',N'-tetramethylurea hexafluorophosphate; "AD-mix-β" means a mixture containing 0.0016 mol of (DHQD) 2PHAL (hydrogenated quinidine 1,4-(2,3-naphthyridine)diether), 0.4988 mol of potassium carbonate powder, 0.4988 mol of potassium ferricyanide and 0.0007 mol of potassium osmate dihydrate; "DMAC" means dimethylacetamide; "MTBE" means methyl tert-butyl ether; "Boc" means tert-butyloxycarbonyl; "TFA" means trifluoroacetic acid; "Xphos" means 2-dicyclohexylphosphino-2,4,6-triisopropylbiphenyl; "DAST" means diethylaminosulfur trifluoride; "LiHMDS" means bistrimethylsilylamine lithium; "TMSCF3" means trifluoromethyl trimethylsilane.

Preparation Example 1: Synthesis of Intermediate 4-chloro-2-oxo-1,2-dihydro-1,7-naphthyridin-3-carbonitrile

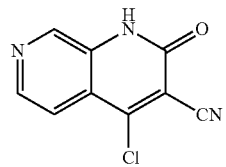 [SMILES: N#Cc1c(Cl)c2ccncc2[nH]c1=O]

Step 1: Synthesis of 2H-pyrido[3,4-d][1,3]oxazin-2, 4(1H)-dione

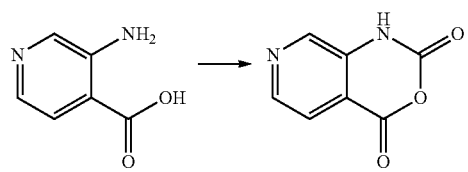 [SMILES: Nc1cnccc1C(=O)O ; O=c1[nH]c2cnccc2c(=O)o1]

The starting material, 3-aminoisonicotinic acid (1000 mg, 7.240 mmol, 1.0 eq) was dissolved in DMF (20 mL). The solution was cooled to 0° C. followed by batch addition of CDI (2000 mg, 12.334 mmol, 1.7 eq). The system was slowly warmed to room temperature and was reacted overnight with the reaction endpoint monitored by LC-MS. The reaction solution was cooled to room temperature, and the reaction solution obtained was directly subjected to the next step without treatment.

Step 2: Synthesis of 4-hydroxy-2-oxo-1,2-dihydro-1,7-naphthyridin-3-carbonitrile

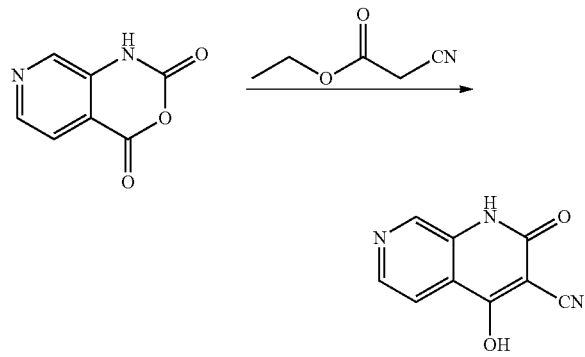

Ethyl cyanoacetate (819 mg, 7.240 mmol) and triethylamine (1581 mg, 14.480 mmol, 2 eq) were added to the reaction solution containing the intermediate 2H-pyrido[3,4-d][1,3]oxazin-2,4(1H)-dione (in terms of a theoretical value of 1188 mg, 7.240 mmol, 1 eq) obtained in the above step. The mixture was heated to 150° C., and reacted for about 4 h with the reaction endpoint monitored by LC-MS. The reaction solution was cooled to 50° C., and concentrated to dryness under reduced pressure to give a red semi-solid. The semi-solid was cooled to 10° C., and then water (5 mL) was added and stirred. The pH of the system was adjusted to 1 by adding hydrochloric acid (1 mol/L). The mixture was stirred for 15 minutes, and filtered by suction. The filter cake was washed with water, drained and dried at 40° C. under reduced pressure to give 4-hydroxy-2-oxo-1,2-dihydro-1,7-naphthyridin-3-carbonitrile (889 mg, yield 66%).

Step 3: Synthesis of 4-chloro-2-oxo-1,2-dihydro-1,7-naphthyridin-3-carbonitrile

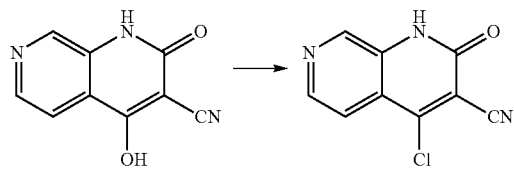 [SMILES: N#Cc1c(O)c2ccncc2[nH]c1=O ; N#Cc1c(Cl)c2ccncc2[nH]c1=O]

4-hydroxy-2-oxo-1,2-dihydro-1,7-naphthyridin-3-carbonitrile (789 mg, 4.216 mmol, 1 eq), phosphorus oxychloride (2908 mg, 18.970 mmol, 4.5 eq) and phosphorus pentachloride (1756 mg, 8.431 mmol, 2 eq) were charged into a reaction flask. The system was heated to 100° C. and reacted for 1 hour with the reaction endpoint monitored by LC-MS.

The reaction solution was cooled to room temperature, carefully added dropwise to ice until a large amount of solid was precipitated, and then filtered by suction. The filter cake was washed with water and dried under reduced pressure at 40° C. to give 4-chloro-2-oxo-1,2-dihydro-1,7-naphthyridin-3-carbonitrile (515 mg, yield: 60.0%).

Preparation Example 2: Synthesis of Intermediate 4,6-dichloro-2-oxo-1,2-dihydro-1,7-naphthyridin-3-carbonitrile Step 1: Synthesis of 6-chloro-2H-pyrido[3,4-d][1,3]oxazin-2,4(1H)-dione

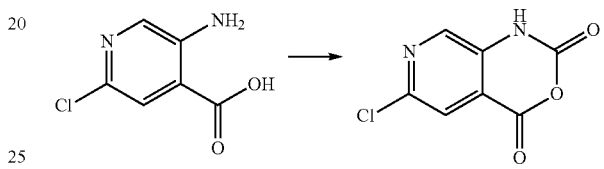

5-amino-2-chloroisonicotinic acid (30 g, 0.1738 mol, 1.0 eq) was dissolved in N,N-dimethylformamide (300 mL), and then N,N'-carbonyldiimidazole (48 g, 0.2955 mol, 1.7 eq) was added in batches at 0° C. The system was slowly warmed to room temperature and was reacted overnight with the reaction endpoint monitored by LC-MS. The reaction solution was cooled to room temperature and directly subjected to the next step without treatment.

Step 2: Synthesis of 6-chloro-4-hydroxy-2-oxo-1,2-dihydro-1,7-naphthyridin-3-carbonitrile

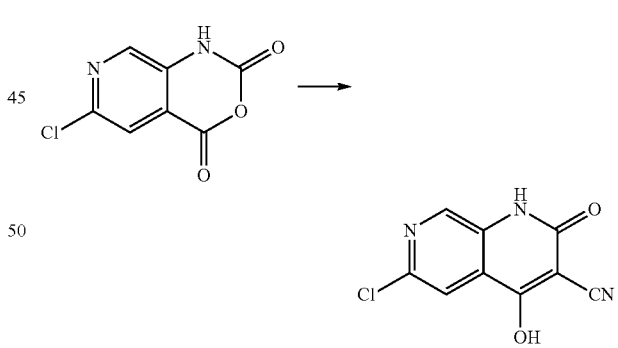

Triethylamine (35.182 g, 0.3478 mol, 2 eq) and ethyl cyanoacetate (19.665 g, 0.1738 mol) were added to the above reaction solution. The system was reacted at 150° C. for 3 h with the reaction endpoint monitored by LC-MS. The reaction solution was cooled to room temperature, concentrated under reduced pressure. Water (200 mL) was added and the pH of the system was adjusted to 1 by adding hydrochloric acid (1 mol/L). The mixture was stirred for 15 minutes, and filtered by suction. The filter cake was washed with EA twice and dried at 40° C. to give a light brick red solid (25.655 g, yield: 66%).

Step 3: Synthesis of 4,6-dichloro-2-oxo-1,2-dihydro-1,7-naphthyridin-3-carbonitrile

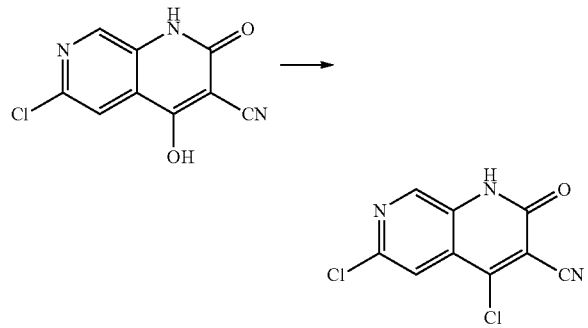

6-chloro-4-hydroxy-2-oxo-1,2-dihydro-1,7-naphthyridin-3-carbonitrile (5.0 g, 0.0226 mol, 1 eq) and phosphorus oxychloride (15 mL) were charged to a reaction flask. The reaction flask was placed in an oil bath which had been heated to 100° C., and reacted for 6 min. The solid began to dissolve slowly, and the color began to deepen gradually from pale yellow. The reaction endpoint was monitored by LC-MS. The system was cooled to room temperature, and an appropriate amount of DCM was added to the flask. The system was then poured to ice water (100 mL), and stirred for 10 min. The mixture was filtered by suction, and filter cake was washed with methyl tert-butyl ether, drained and dried in vacuum at 40° C. to give a pale yellow solid. A total of 25.655 g (0.1157 mol) 6-chloro-4-hydroxy-2-oxo-1,2-dihydro-1,7-naphthyridin-3-carbonitrile was charged in five batches to obtain 19.486 g of product (yield: 70.1%).

Example 1: Synthesis of 4-(azepan-1-yl)-2-oxo-1,2-dihydro-1,7-naphthyridin-3-carbonitrile (Compound 3)

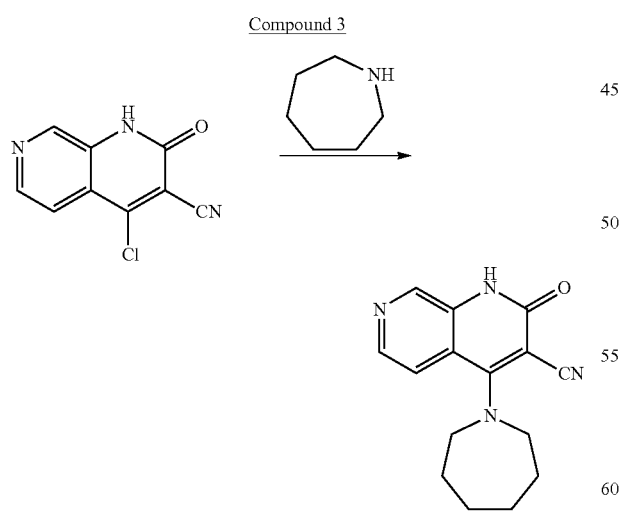

The starting material 4-chloro-2-oxo-1,2-dihydro-1,7-naphthyridin-3-carbonitrile (19 mg, 0.092 mmol, 1.0 eq) was dissolved in DMF (0.7 mL), followed by addition of azepane (17.4 mg, 0.204 mmol, 1.4 eq) and DIPEA (48 mg, 0.370 mmol, 4 eq). The mixture was warmed to 100° C., and was reacted for 4 h with the reaction endpoint monitored by LC-MS. The reaction solution was cooled to room temperature until solid was precipitated, and filtered by suction. The filter cake was washed with water (20 mL), drained and dried in vacuum to give 4-(azepan-1-yl)-2-oxo-1,2-dihydro-1,7-naphthyridin-3-carbonitrile (10.02 mg, 27.0%).

$^1$HNMR (400 MHz, DMSO-$d_6$) δ (ppm): 11.96 (s, 1H), 8.64 (s, 1H), 8.31-8.32 (d, 1H), 7.75-7.77 (d, 1H), 3.80-3.83 (t, 4H), 1.84 (s, 4H), 1.71 (s, 4H).

Molecular formula: $C_{15}H_{16}N_4O$, Molecular weight: 268.32, LC-MS (Pos, m/z)=269.2 [M+H$^+$].

Example 2: Synthesis of 2-oxo-4-(piperidin-1-yl)-1,2-dihydro-1,7-naphthyridin-3-carbonitrile (Compound 4)

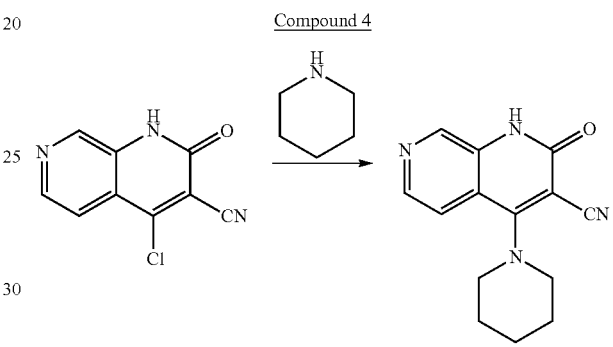

4-chloro-2-oxo-1,2-dihydro-1,7-naphthyridin-3-carbonitrile (30 mg, 0.146 mmol, 1.0 eq) was dissolved in DMF (1 mL), followed by addition of piperidine (17.4 mg, 0.204 mmol, 1.4 eq) and DIPEA (75.4 mg, 0.584 mmol, 4 eq). The system was warmed to 100° C. and reacted for 1.5 hours with the reaction endpoint monitored by LC-MS. The reaction solution was cooled, and filtered by suction. The filter cake was washed with water, and dried in vacuum to give a yellow solid product (10.02 mg, yield: 27.0%).

$^1$HNMR (400 MHz, DMSO-$d_6$) δ (ppm): 11.99 (s, 1H), 8.64 (s, 1H), 8.33-8.35 (d, 1H), 7.58-7.59 (d, 1H), 3.60 (s, 4H), 1.72-1.76 (m, 6H).

Molecular formula: $C_{14}H_{14}N_4O$, Molecular weight: 254.29, LC-MS (Pos, m/z)=255.0 [M+H]$^+$.

Example 3: Synthesis of 4-(benzylamino)-2-oxo-1,2-dihydro-1,7-naphthyridin-3-carbonitrile (Compound 10)

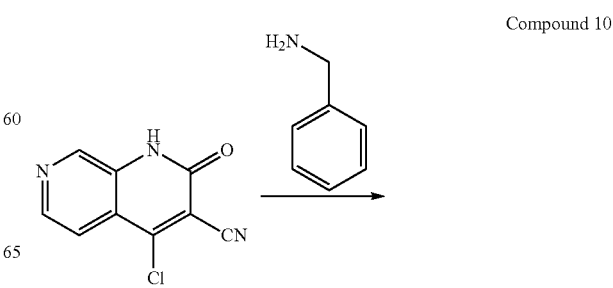

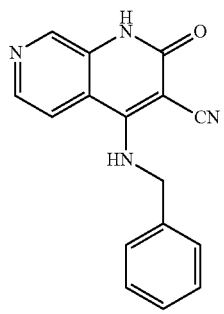

The starting material 4-chloro-2-oxo-1,2-dihydro-1,7-naphthyridin-3-carbonitrile (30 mg, 0.146 mmol, 1.0 eq) was dissolved in DMF (0.7 mL), followed by addition of benzylamine (22 mg, 0.204 mmol, 1.4 eq) and DIPEA (75.4 mg, 0.584 mmol, 4 eq). The system was warmed to 100° C. and reacted for 1.5 hours with the reaction endpoint monitored by LC-MS. Methyl tert-butyl ether (2 mL) was added to the reaction solution, followed by water (2 mL). The reaction solution was stirred until the solid was precipitated, and filtered by suction. The filter cake was dried in vacuum to give a yellow solid, 4-(benzylamino)-2-oxo-1,2-dihydro-1,7-naphthyridin-3-carbonitrile (9 mg, yield: 22.3%).

$^1$HNMR (400 MHz, DMSO-$d_6$) δ (ppm): 11.62 (s, 1H), 8.79-8.82 (t, 1H), 8.60 (s, 1H), 8.38-8.40 (d, 1H), 8.10-8.11 (d, 1H), 7.26-7.38 (m, 5H), 5.05-5.06 (d, 2H).

Molecular formula: $C_{16}H_{12}N_4O$, Molecular weight: 276.30, LC-MS (Pos, m/z)=277.02 [M+H$^+$].

Example 4: Synthesis of 4-((4-chlorobenzyl)amino)-2-oxo-1,2-dihydro-1,7-naphthyridin-3-carbonitrile (Compound 11)

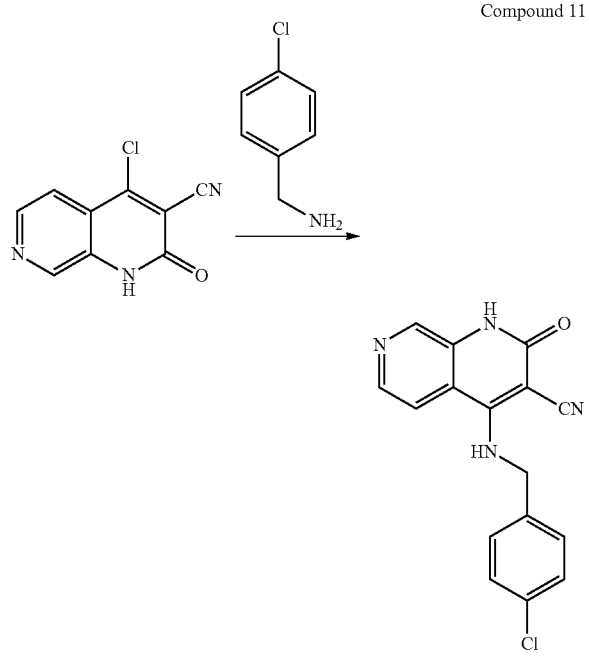

Compound 11

4-chloro-2-oxo-1,2-dihydro-1,7-naphthyridin-3-carbonitrile (30 mg, 0.146 mmol, 1.0 eq) was dissolved in DMF (0.7 mL), followed by addition of (4-chlorophenyl)methylamine (29 mg, 0.204 mmol, 1.4 eq) and DIPEA (75.4 mg, 0.584 mmol, 4 eq). The system was warmed to 100° C. and reacted for 1.5 hours with the reaction endpoint monitored by LC-MS. After addition of MTBE (2 mL), the mixture was stirred, followed by addition of water (2 mL), stirred for 15 min until the solid was precipitated, and filtered by suction. The filtered cake was washed with water and dried in vacuum to give a yellow solid product (19 mg, yield: 41.9%).

$^1$HNMR (400 MHz, DMSO-$d_6$) δ (ppm): 11.56 (s, 1H), 8.80 (s, 1H), 8.60 (s, 1H), 8.38-8.40 (d, 1H), 8.08-8.10 (d, 1H), 7.34-7.44 (t, 4H), 5.02 (s, 2H).

Molecular formula: $C_{16}H_{11}ClN_4O$, Molecular weight: 310.74, LC-MS (Neg, m/z)=3091 [M−H]$^-$.

Example 5: Synthesis of 2-oxo-4-(2-azaspiro[3.5]nonane-2-yl)-1,2-dihydro-1,7-naphthyridin-3-carbonitrile (Compound 13)

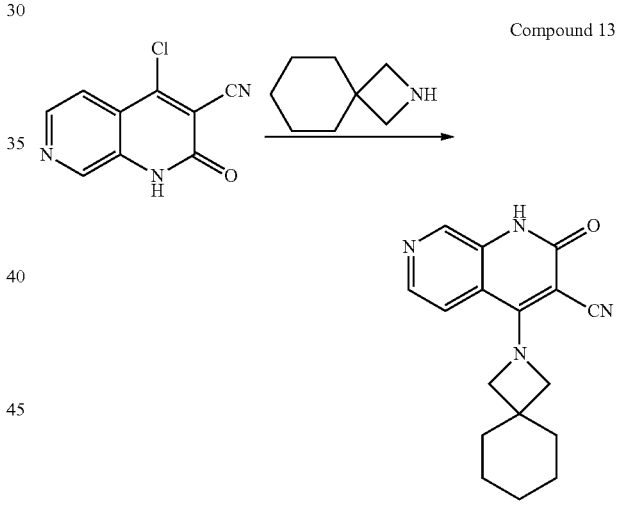

4-chloro-2-oxo-1,2-dihydro-1,7-naphthyridin-3-carbonitrile (50 mg, 0.234 mmol, 1.0 eq) was dissolved in DMF (1 mL), followed by addition of 2-azaspiro[3.5]nonane (43 mg, 0.340 mmol, 1.4 eq) and DIPEA (188 mg, 1.458 mmol, 4 eq). The system was warmed to 80° C. and reacted for 2 hours with the reaction endpoint monitored by LC-MS. The reaction solution was cooled and filtered by suction. The filter cake was washed with water and dried in vacuum to give an off-white solid product (27.42 mg, yield: 39.8%).

$^1$HNMR (400 MHz, DMSO-$d_6$) δ (ppm): 11.49 (s, 1H), 8.58 (s, 1H), 8.24-8.25 (d, 1H), 7.74-7.76 (d, 1H), 4.46 (s, 4H), 1.69 (s, 4H), 1.36-1.43 (d, 6H).

Molecular formula: $C_{17}H_{18}N_4O$, Molecular weight: 294.36, LC-MS (Pos, m/z)=295.1 [M+H]$^+$.

Example 6: Synthesis of 2-oxo-4-(7-azaspiro[3.5]nonane-7-yl)-1,2-dihydro-1,7-naphthyridin-3-carbonitrile (Compound 16)

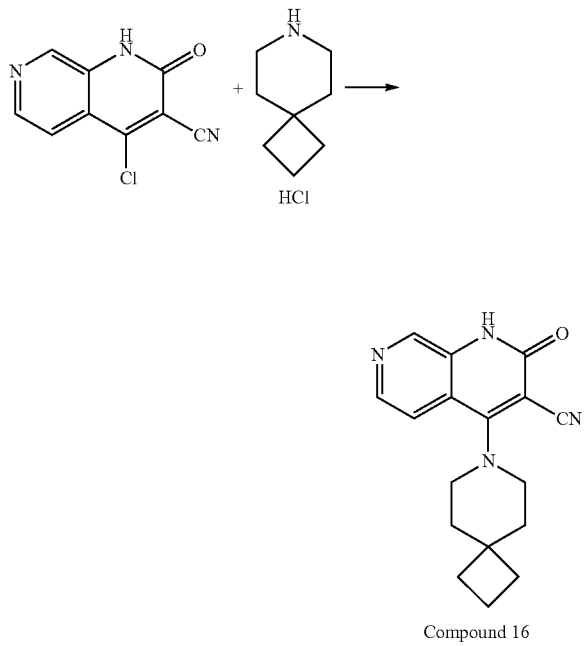

Compound 16

The starting material 4-chloro-2-oxo-1,2-dihydro-1,7-naphthyridin-3-carbonitrile (50 mg, 0.234 mmol, 1.0 eq) was dissolved in DMF (1 mL), followed by addition of 7-azaspiro[3.5]nonane hydrochloride (55 mg, 0.340 mmol, 1.4 eq) and DIPEA (188 mg, 1.458 mmol, 6 eq). The system was warmed to 80° C. and reacted for 2 hours with the reaction endpoint monitored by LC-MS. The reaction solution was cooled, and filtered by suction. The filter cake was washed with water, drained, and dried under reduced pressure to give pale-yellow solid, 2-oxo-4-(7-azaspiro[3.5]nonane-7-yl)-1,2-dihydro-1,7-naphthyridin-3-carbonitrile (23.24 mg, 33.7%).

¹HNMR (400 MHz, DMSO) δ (ppm): 11.98 (s, 1H), 8.64 (s, 1H), 8.32-8.34 (d, 1H), 7.59-7.60 (d, 1H), 3.53 (s, 4H), 3.41-3.47 (m, 4H), 1.79-1.92 (m, 6H).

Molecular formula; $C_{17}H_{18}N_4O$, Molecular weight: 294.36, LC-MS (Pos, m/z)=295.1 [M+H]⁺.

Example 7: Synthesis of 4-((4-chlorophenyl)amino)-2-oxo-1,2-dihydro-1,7-naphthyridin-3-carbonitrile (Compound 18)

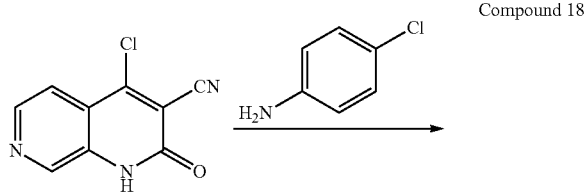

Compound 18

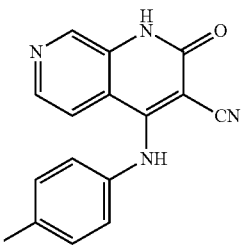

4-chloro-2-oxo-1,2-dihydro-1,7-naphthyridin-3-carbonitrile (200 mg, 0.973 mmol, 1.0 eq) was dissolved in DMF (3 mL), followed by addition of p-chloroaniline (174 mg, 1.362 mmol, 1.4 eq) and DIPEA (752 mg, 3.893 mmol, 4 eq). The system was warmed to 80° C. and reacted for 1.5 hours. The reaction solution was cooled, followed by addition of water (10 mL), and then extracted with EA. The organic phase was dried over anhydrous sodium sulfate and concentrated under reduced pressure. The crude product was dissolved by adding a small amount of DCM and methanol solution followed by a small amount of EA until solid was precipitated, and then filtered by suction. The filter cake was washed with a small amount of DCM, and dried to give a yellow solid product (44 mg, yield: 50.9%).

¹HNMR (400 MHz, DMSO-d₆) δ (ppm): 11.84 (s, 1H), 9.94 (s, 1H), 8.66 (s, 1H), 8.41-8.42 (d, 1H), 8.10-8.12 (d, 1H), 7.47-7.49 (d, 2H), 7.35-7.37 (d, 2H).

Molecular formula; $C_{15}H_9ClN_4O$, Molecular weight: 296.71, LC-MS (Pos, m/z)=296.96 [M+H]⁺.

Example 8: Synthesis of (R)-4-(3-(1H-pyrazol-1-yl)pyrrolidin-1-yl)-2-oxo-1,2-dihydro-1,7-naphthyridin-3-carbonitrile (Compound 19)

Step 1: Synthesis of Tert-Butyl (S)-3-hydroxypyrrolidin-1-carboxylate

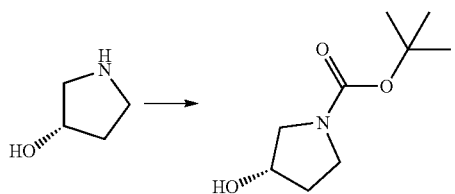

(S)-pyrrolidin-3-ol (3.0 g, 24.28 mmol, 1.0 eq) was dissolved in THF (54 mL), and cooled to 0° C., followed by dropwise addition of triethylamine (12.28 g, 121.38 mmol, 5 eq). (Boc)₂O (5.83 g, 26.70 mmol, 1.1 eq) was slowly added dropwise with stirring. The system was warmed to room temperature slowly and reacted for 2 days. The reaction solution was concentrated under reduced pressure, followed by addition of water, stirred, and extracted with DCM for three times. The organic phases were combined, dried over anhydrous sodium sulfate, and concentrated under reduced pressure to give a yellow oil, tert-butyl (S)-3-hydroxypyrrolidin-1-carboxylate (4.42 g, yield: 97.2%).

Step 2: Synthesis of Tert-Butyl (S)-3-((methylsulfonyl)oxy)pyrrolidin-1-carboxylate

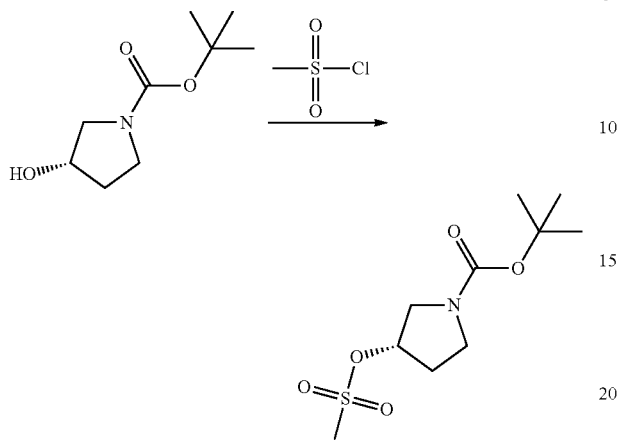

Tert-butyl (S)-3-hydroxypyrrolidin-1-carboxylate (3.0 g, 16.02 mmol, 1 eq) was charged into a reaction flask, and dissolved by adding THF (30 mL). The system was cooled to 0° C., and then triethylamine (3.24 g, 32.04 mmol, 2 eq) was added. Methanesulfonyl chloride (2.2 g, 19.23 mmol, 1.2 eq) was slowly added dropwise. The mixture was slowly warmed to room temperature and reacted for 3 hours with the reaction endpoint monitored by TLC. The reaction solution was filtered by suction, and the filtrate was concentrated under reduced pressure to give a pale yellow oil, tert-butyl (S)-3-((methylsulfonyl)oxy)pyrrolidin-1-carboxylate, which was directly subjected to the next step reaction without purification.

Step 3: Synthesis of Tert-Butyl (R)-3-(1H-pyrazol-1-yl)pyrrolidin-1-carboxylate

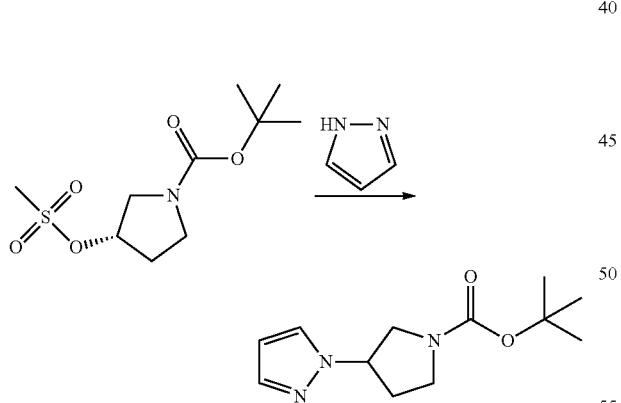

Pyrazole (1.2 g, 17.62 mmol, 1.1 eq) was dissolved in DMAC (72 mL), cooled to 0° C., followed by addition of sodium hydride (2051 mg, 51.27 mmol, 3.2 eq, content 60%), and then was reacted for 1 h under nitrogen protection. Tert-butyl (S)-3-((methylsulfonyl)oxy)pyrrolidin-1-carboxylate obtained in the above step was dissolved in a small amount of DMAC which was slowly added to the reaction solution dropwise, heated to 100° C. and reacted overnight under nitrogen protection. The reaction solution was cooled to room temperature, diluted by adding water, stirred, and extracted with EA. After liquid separation, the organic phases were combined, washed with water, dried over anhydrous sodium sulfate, and concentrated under reduced pressure. The crude product was purified by silica gel column chromatography (PE:EA=20:1) to give a colorless oil, tert-butyl (R)-3-(1H-pyrazol-1-yl)pyrrolidin-1-carboxylate (1.83 g, yield after the two steps: 48.2%).

Step 4: Synthesis of (R)-1-(pyrrolidin-3-yl)-1H-pyrazole

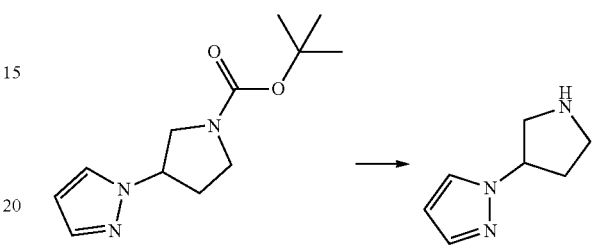

Tert-butyl (R)-3-(1H-pyrazol-1-yl)pyrrolidin-1-carboxylate (200 mg, 0.8428 mmol, 1.0 eq) was dissolved in DCM (4 mL), cooled to 0° C., followed by dropwise addition of trifluoroacetic acid (2 mL), and then was reacted for 2-3 hours with the reaction endpoint monitored by TLC. Then the reaction system was concentrated under reduced pressure, and was made alkaline by adding an appropriate amount of DIPEA to give (R)-1-(pyrrolidin-3-yl)-1H-pyrazole crude product, which was directly subjected to the next step.

Step 5: Synthesis of (R)-4-(3-(1H-pyrazol-1-yl)pyrrolidin-1-yl)-2-oxo-1,2-dihydro-1,7-naphthyridin-3-carbonitrile Compound 19

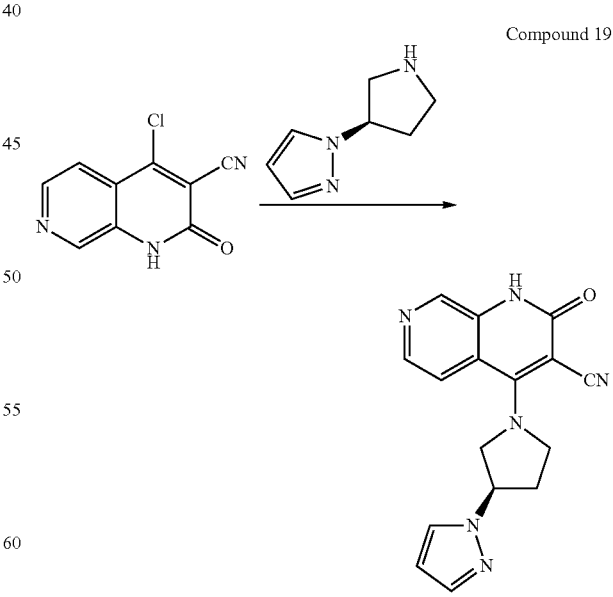

4-chloro-2-oxo-1,2-dihydro-1,7-naphthyridin-3-carbonitrile (124 mg, 0.602 mmol, 1.0 eq) was dissolved in DMAC (2 mL), followed by addition of the crude product (R)-1-(pyrrolidin-3-yl)-1H-pyrazole obtained in the above step and DIPEA (467 mg, 3.612 mmol, 6 eq). The system was warmed to 80° C. and reacted for 1.5 hours with the reaction endpoint monitored by LC-MS. The reaction solution was diluted by adding water (10 ml), and extracted with EA (50 mL×3). The organic phases were combined, washed with water (30 mL), dried over anhydrous $Na_2SO_4$, and concentrated under reduced pressure to give a brownish yellow solid. The solid was slurried by adding a small amount of DCM and EA, and filtered by suction. The filter cake was washed with a small amount of DCM and dried in vacuum to give a brownish yellow solid, (R)-4-(3-(1H-pyrazol-1-yl)pyrrolidin-1-yl)-2-oxo-1,2-dihydro-1,7-naphthyridin-3-carbonitrile (35.96 mg, yield after the two steps: 13.9%).

$^1$HNMR (400 MHz, DMSO-$d_6$) δ (ppm): 11.64 (s, 1H), 8.61 (s, 1H), 8.26-8.28 (d, 1H), 7.97-7.98 (d, 1H), 7.89-7.90 (d, 1H), 7.50-7.51 (d, 1H), 6.30 (s, 1H), 5.14-5.20 (m, 1H), 4.51-4.56 (q, 1H), 4.32-4.36 (q, 1H), 4.17-4.30 (m, 2H), 2.43-2.49 (m, 2H).

Molecular formula: $C_{16}H_{14}N_6O$, Molecular weight: 306.33, LC-MS (Pos, m/z)=307.0 [M+H$^+$].

Example 9: Synthesis of 2-oxo-4-(phenylamino)-1,2-dihydro-1,7-naphthyridin-3-carbonitrile (Compound 21)

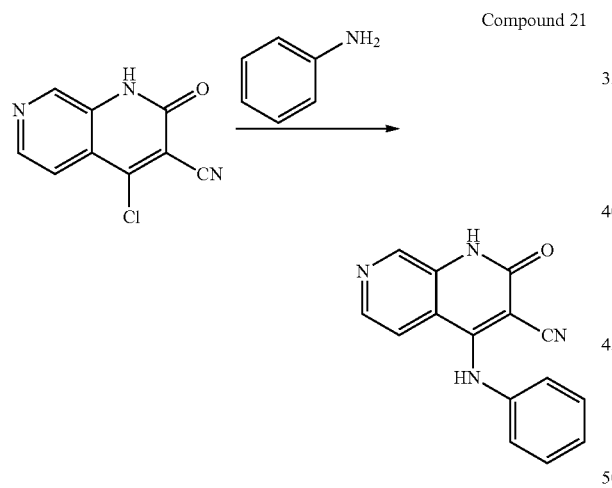

4-chloro-2-oxo-1,2-dihydro-1,7-naphthyridin-3-carbonitrile (50.0 mg, 0.243 mmol, 1.0 eq) and aniline (31.7 mg, 0.340 mmol, 1.4 eq) were dissolved in N,N-dimethylformamide (1.0 mL), added with NN-diisopropylethylamine (125.8 mg, 0.973 mmol, 4.0 eq), and heated to 80° C. to reflux for 2 h. The reaction endpoint was monitored by TLC. The system was cooled to room temperature, and filtered by suction. The filter cake was washed with water (4.0 mL) for 30 min, filtered by suction, and dried at 60° C. to give a yellow solid product (10.0 mg, yield: 20%).

$^1$HNMR (400 MHz, DMSO-$d_6$) δ (ppm): 11.80 (s, 1H), 9.93 (s, 1H), 8.67 (s, 1H), 8.42-8.41 (m, 1H), 8.15-8.14 (m, 1H), 7.46-7.42 (m, 2H), 7.35-7.29 (m, 3H).

Molecular formula: $C_{15}H_{10}N_4O$ Molecular weight: 262.27 LC-MS (Pos, m/z)=263.0 [M+H]$^+$.

Example 10: Synthesis of (R)-4-(3-(1H-pyrazol-1-yl)pyrrolidin-1-yl)-6-chloro-2-oxo-1,2-dihydro-1,7-naphthyridin-3-carbonitrile (Compound 23)

Step 1: Synthesis of (R)-1-(pyrrolidin-3-yl)-1H-pyrazole Hydrochloride

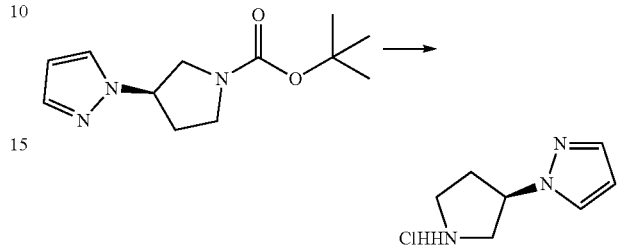

Tert-butyl (R)-3-(1H-pyrazol-1-yl)pyrrolidin-1-carboxylate (13.8 mg, 0.0583 mmol, 1.0 eq) was dissolved in ethanol (1.0 mL) and then hydrogen chloride ethanol solution (25%, 1.0 mL) was added at 0° C. The system was slowly warmed to room temperature and stirred for 1 h with the reaction endpoint monitored by TLC. The reaction solution was concentrated and the crude product was subjected to the next step.

Step 2: Synthesis of (R)-4-(3-(1H-pyrazol-1-yl)pyrrolidin-1-yl)-6-chloro-2-oxo-1,2-dihydro-1,7-naphthyridin-3-carbonitrile

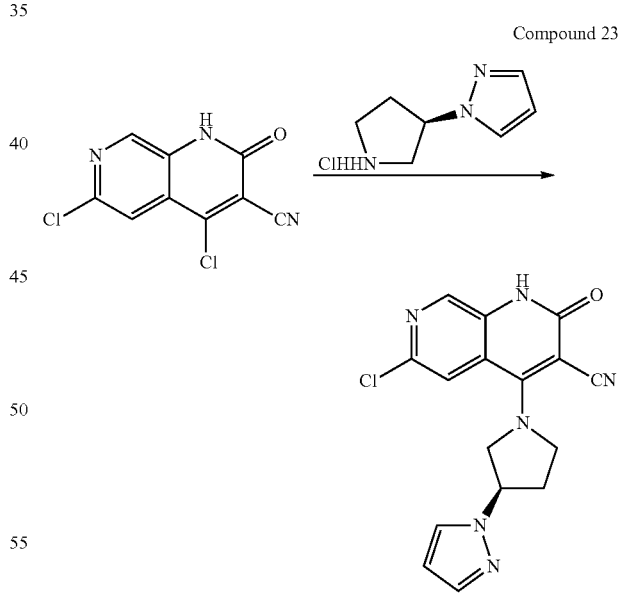

The above crude product was dissolved in N,N-dimethylformamide (1.0 mL), followed by addition of N,N-diisopropylethylamine (32.3 mg, 0.250 mmol, 6.0 eq) and 4,6-dichloro-2-oxo-1,2-dihydro-1,7-naphthyridin-3-carbonitrile (10.0 mg, 0.0416 mmol, 1.0 eq). The mixture was heated to 80° C. to reflux for 2 h with the reaction endpoint monitored by TLC. The reaction mixture was concentrated under reduced pressure. The crude product was purified by thin layer chromatography (DCM:MeOH=20:1) and silica gel column chromatography (DCM:MeOH=100:1-40:1) in sequence, to give a yellow solid product (6.49 mg, yield: 64.9%).

$^1$HNMR (400 MHz, DMSO-d$_6$) δ (ppm): 11.77 (s, 1H), 8.41 (s, 1H), 8.00 (m, 1H), 7.90-7.89 (m, 1H), 7.52-7.51 (m, 1H), 6.31-6.30 (m, 1H), 5.18-5.15 (m, 1H), 4.54-4.50 (m, 1H), 4.36-4.16 (m, 3H), 2.01-1.99 (m, 1H), 0.88 (m, 1H).

Molecular formulas C$_{16}$H$_{13}$ClN$_6$O Molecular weight: 340.77 LC-MS (Pos, m/z)=341.0 [M+H]$^+$.

Example 11: Synthesis of 2-oxo-4-(2-oxa-7-azaspiro[3.5]nonane-7-yl)-1,2-dihydro-1,7-naphthyridin-3-carbonitrile (Compound 24)

Step 1: Synthesis of 2-oxo-4-(2-oxa-7-azaspiro[3.5]nonane-7-yl)-1,2-dihydro-1,7-naphthyridin-3-carbonitrile

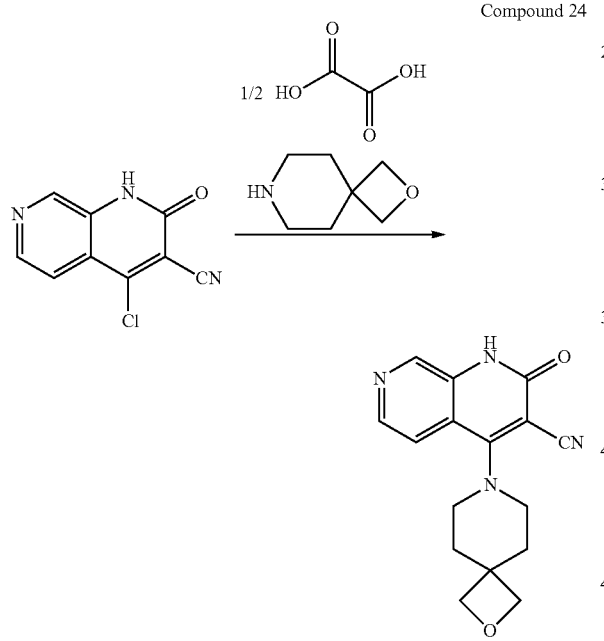

Compound 24

4-chloro-2-oxo-1,2-dihydro-1,7-naphthyridin-3-carbonitrile (50.0 mg, 0.243 mmol, 1.0 eq) and 2-oxa-7-azaspiro[3.5]nonane hemioxalate (58.6 mg, 0.170 mmol, 0.7 eq) were dissolved in N,N-dimethylformamide (1.0 mL), and then N,N-diisopropylethylamine (188.4 mg, 1.458 mmol, 6.0 eq) was added. The system was heated to 80° C. to reflux for 2 h with the reaction endpoint was monitored by TLC. The system was cooled to room temperature, and filtered by suction. The filter cake was washed with water (4.0 mL) for 30 min, filtered by suction, and dried at 60° C. to give a yellow solid product (10.0 mg, yield: 20%).

$^1$HNMR (400 MHz, DMSO-d$_6$) δ (ppm): 12.02 (s, 1H), 8.66 (s, 1H), 8.35-8.34 (m, 1H), 7.59-7.58 (m, 1H), 4.42 (s, 4H), 3.56-3.54 (m, 4H), 2.07-2.05 (m, 4H).

Molecular formula: C$_{16}$H$_{16}$N$_4$O$_2$ Molecular weight: 296.33 LC-MS (Pos, m/z)=297.2 [M+H]$^+$.

Example 12: Synthesis of 2-oxo-4-(6-azaspiro[2.5]octane-6-yl)-1,2-dihydro-1,7-naphthyridin-3-carbonitrile (Compound 25)

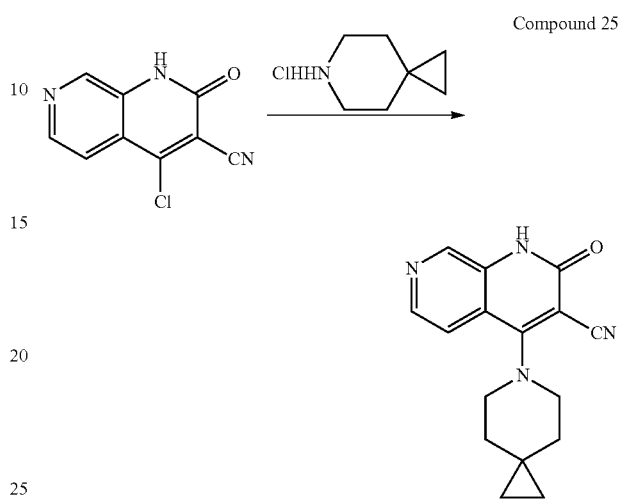

Compound 25

4-chloro-2-oxo-1,2-dihydro-1,7-naphthyridin-3-carbonitrile (50.0 mg, 0.243 mmol, 1.0 eq) and 6-azaspiro[2.5]octane hydrochloride (50.2 mg, 0.340 mmol, 1.4 eq) were dissolved in N,N-dimethylformamide (1.0 mL), and N,N-diisopropylethylamine (188.4 mg, 1.458 mmol, 6.0 eq) was added. The system was heated to 80° C. to reflux for 2 h with the reaction endpoint monitored by TLC. The reaction mixture was cooled to room temperature, and filtered by suction. The filter cake was washed with water (4.0 mL) for 30 min, filtered by suction, and dried at 60° C. to give a yellow solid product (18.0 mg, yield: 36%).

$^1$HNMR (400 MHz, DMSO-d$_6$) δ (ppm): 12.02 (s, 1H), 8.66 (s, 1H), 8.36-8.34 (m, 1H), 7.65-7.64 (m, 1H), 3.66-3.63 (m, 4H), 1.62 (m, 4H), 0.44 (s, 4H).

Molecular formula: C$_{16}$H$_{16}$N$_4$O Molecular weight: 280.33 LC-MS (Pos, m/z)=281.1 [M+H]$^+$.

Example 13: Synthesis of 4-(4-ethylphenyl)-2-oxo-1,2-dihydro-1,7-naphthyridin-3-carbonitrile (Compound 26)

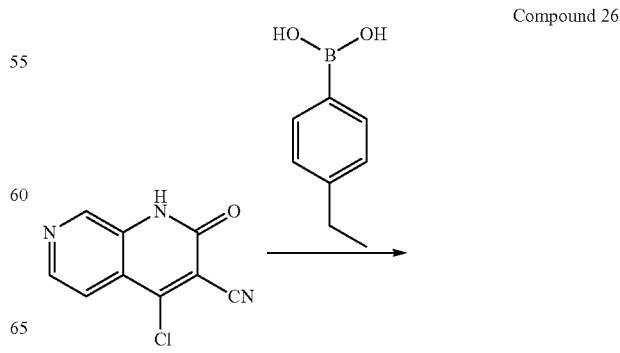

Compound 26

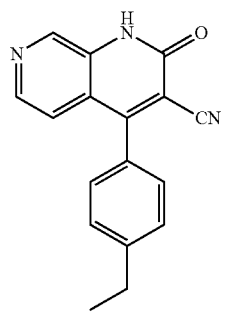

4-chloro-2-oxo-1,2-dihydro-1,7-naphthyridin-3-carbonitrile (300.0 mg, 1.459 mmol, 1.0 eq), (4-ethylphenyl)boronic acid (262.6 mg, 1.751 mmol, 1.2 eq), potassium phosphate (619.4 mg, 2.918 mmol, 2.0 eq) and 1,1'-bisdiphenylphosphinoferrocene palladium dichloride (47.5 mg, 0.0729 mmol, 0.05 eq) were dissolved in dioxane (9.0 mL) and water (4.5 mL). The system was heated to 115° C. to reflux overnight under nitrogen protection with the reaction endpoint was monitored by TLC. The reaction mixture was filtrated by suction, and the filtrate was extracted with ethyl acetate (10.0 mL×3), dried over anhydrous sodium sulfate, and concentrated. The crude product was purified by silica gel column chromatography (DCM:MeOH=200:1-40:1) to obtain a yellow solid product (100.0 mg, yield: 33.3%).

$^1$HNMR (400 MHz, DMSO-d$_6$) δ (ppm): 12.83 (s, 1H), 8.80 (s, 1H), 8.38-8.36 (m, 1H), 7.49 (m, 4H), 7.16-7.15 (m, 1H), 2.77-2.75 (m, 2H), 1.30-1.26 (m, 3H).

Molecular formula: $C_{17}H_{13}N_3O$ Molecular weight: 275.31 LC-MS (Pos, m/z)=276.1 [M+H]$^+$.

Example 14: Synthesis of 4-(3-(1H-pyrazol-1-yl) pyrrolidin-1-yl)-6-chloro-2-oxo-1,2-dihydro-1,7-naphthyridin-3-carbonitrile (Compound 27)

Step 1: Synthesis of 4-(3-(1H-pyrazol-1-yl)pyrrolidin-1-yl)-6-chloro-2-oxo-1,2-dihydro-1,7-naphthyridin-3-carbonitrile

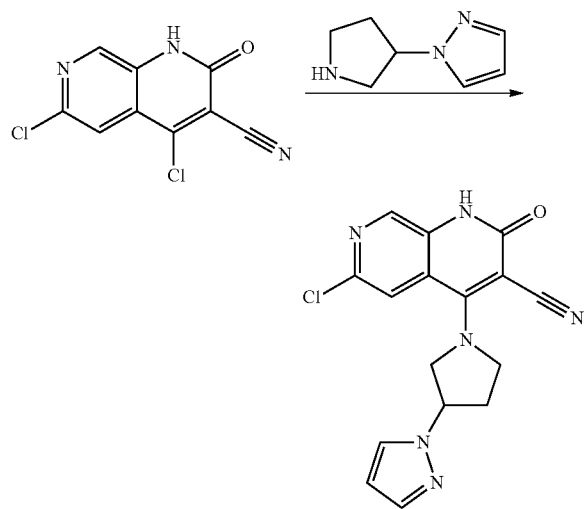

4,6-dichloro-2-oxo-1,2-dihydro-1,7-naphthyridin-3-carbonitrile (180 mg, 0.75 mmol, 1.0 eq) and 1-(pyrrolidin-3-yl)-1H-pyrazole (303 mg, 1.28 mmol, 1.7 eq, 57.6%) were dissolved in DMF (5 mL), and then DIEA (387 mg, 3.0 mmol, 4.0 eq) was added. The system was stirred at 80° C. for 2 h and cooled. The reaction solution was purified by reversed phase column chromatography (acetonitrile:water: ammonia solution=30:100:0.05%) to give a yellow solid product (200 mg, yield: 78.4%).

Step 2: Synthesis of 4-(3-(1H-pyrazol-1-yl)pyrrolidin-1-yl)-6-methyl-2-oxo-1,2-dihydro-1,7-naphthyridin-3-carbonitrile Compound 27

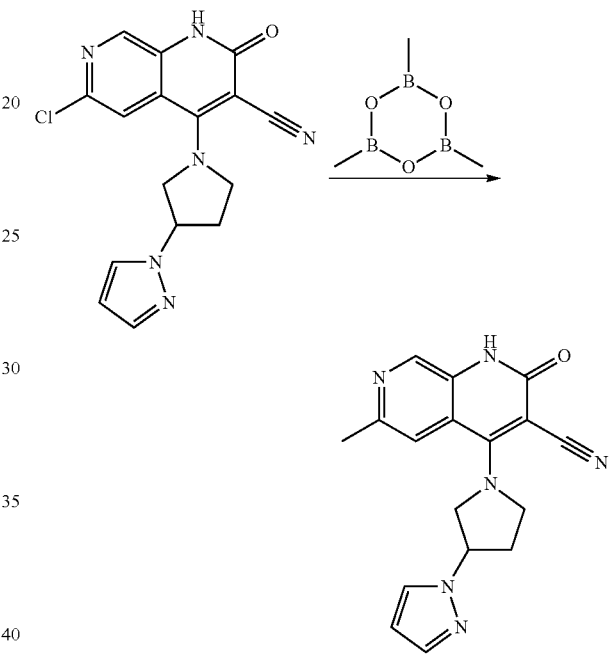

4-(3-(1H-pyrazol-1-yl)pyrrolidin-1-yl)-6-chloro-2-oxo-1,2-dihydro-1,7-naphthyridin-3-carbonitrile (112.0 mg, 0.33 mmol, 1.0 eq), trimethylcyclotriboroxane (330.0 mg, 1.30 mmol, 4.0 eq, 50%), cesium carbonate (322.0 mg, 0.99 mmol, 3.0 eq), potassium phosphate (70.0 mg, 0.33 mmol, 1.0 eq) and Pd(dppf)$_2$Cl$_2$ (120 mg, 0.16 mmol, 0.5 eq) were dissolved in 1,4-dioxane (4 mL). The system was warmed to 105° C. and stirred overnight under nitrogen protection. The reaction endpoint was monitored by TLC. The reaction solution was quenched by adding H$_2$O (10 mL), stirred for 30 min, cooled to room temperature, and filtered by suction. The filter cake was washed with a small amount of ethyl acetate. The filtrate was extracted with ethyl acetate (10.0 mL×3). After liquid separation, the organic phase was washed with saturated brine (10.0 mL×2), dried over anhydrous Na$_2$SO$_4$, and filtered by suction, and the filtrate was concentrated under reduced pressure. The crude product was purified by silica gel column chromatography (DCM:MeOH=80:1-60:1) to give a yellow solid product (55.0 mg, yield: 52.1%).

$^1$HNMR (400 MHz, DMSO-d$_6$) δ (ppm): 12.04 (s, 1H), 8.69 (s, 1H), 7.57 (m, 3H), 6.34 (s, 1H), 5.11 (s, 1H), 4.49-4.64 (m, 3H), 4.49 (s, 1H), 2.60-2.67 (m, 5H).

Molecular formula: $C_{17}H_{16}N_6O$ Molecular weight: 320.14 LC-MS (Neg, m/z)=319.17 [M−H]$^−$.

Example 15: Synthesis of 4-(4-(2-hydroxyethyl)piperidin-1-yl)-2-oxo-1,2-dihydro-1,7-naphthyridin-3-carbonitrile (Compound 28)

Compound 28

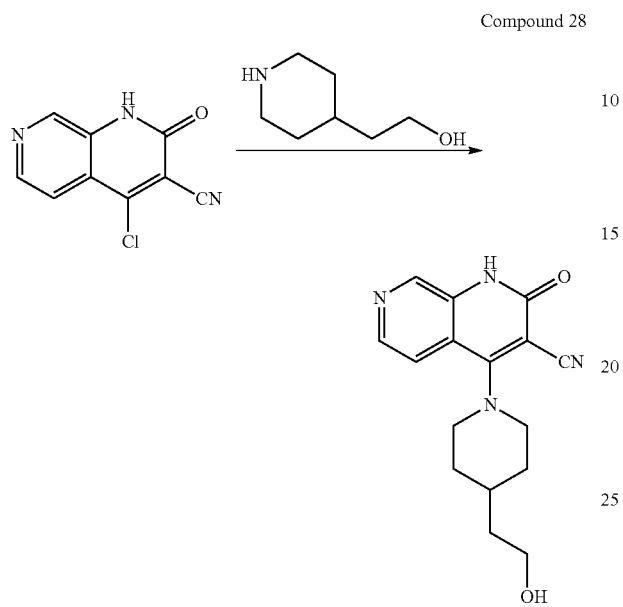

4-chloro-2-oxo-1,2-dihydro-1,7-naphthyridin-3-carbonitrile (60 mg, 0.29 mmol, 1.0 eq) was dissolved in N,N-dimethylformamide (1 mL). Then N,N-diisopropylethylamine (112 mg, 0.87 mmol, 3.0 eq) and 2-(piperidin-4-yl)ethane-1-ol (38 mg, 0.29 mmol, 1.0 eq) were added. The system was warmed to 80° C. and reacted for 2 hours, and cooled to room temperature until solid was precipitated, and then filtered. The filter cake was washed with tetrahydrofuran (1 mL) and petroleum ether (1 mL) in sequence and dried at 45° C. to give a yellow solid product (16 mg, yield: 18%).

$^1$HNMR (400 MHz, DMSO-$d_6$) δ (ppm): 11.98 (s, 1H), 8.65 (s, 1H), 8.33-8.35 (d, 1H), 7.58-7.80 (d, 1H), 4.40-4.42 (m, 1H), 3.83-3.86 (m, 2H), 3.48-3.53 (m, 2H), 3.37-3.43 (m, 2H), 1.84-1.87 (m, 2H), 1.74-1.80 (m, 1H), 1.45-1.50 (m, 4H).

Molecular formula: $C_{16}H_{18}N_4O_2$ Molecular weight: 298.35 LC-MS (Neg, m/z)=297.15 [M–H]$^-$

Example 16: Synthesis of 6-(methylthio)-2-oxo-4-(7-azaspiro[3.5]nonane-7-yl)-1,2-dihydro-1,7-naphthyridin-3-carbonitrile (Compound 30)

Step 1: Synthesis of 2-bromo-5-nitroisonicotinic Acid

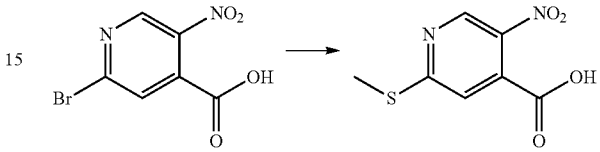

2-bromo-4-methyl-5-nitropyridine (2.5 g, 11.58 mmol) was dissolved in concentrated sulfuric acid (25 mL). The system was cooled to 0° C. in ice bath, followed by addition of chrome trioxide (3.88 g, 38.8 mmol), and then was warmed slowly to room temperature, and stirred overnight. The reaction solution was poured to ice water (75 mL), stirred for 10 minutes, and filtered by suction to give a white solid product (2.5 g, yield: 87.8%).

Step 2: Synthesis of 2-(methylthio)-5-nitroisonicotinic Acid

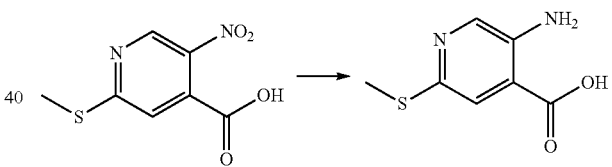

2-bromo-5-nitroisonicotinic acid (1.5 g, 6.1 mmol) was dissolved in DMF (30 mL), and the system was cooled to 0° C. in ice bath, followed by addition of sodium thiomethoxide (1.07 g, 15.25 mmol), and then was warmed slowly to room temperature, and stirred overnight with the reaction endpoint monitored by LC-MS. The reaction solution was concentrated under reduced pressure, poured to water (8 mL), adjusted to a pH of 2 with 1 mol/L hydrochloric acid until solid was precipitated, and then filtered by suction to give a red solid product (1.0 g crude product).

Step 3: Synthesis of 5-amino-2-(methylthio)isonicotinic Acid 2-(methylthio)-5-nitroisonicotinic acid (1.0 g crude product) was dissolved in ethanol (10 mL), and saturated aqueous ammonium chloride solution (5 mL) and iron powder (5.23 g, 93.5 mmol) were added. The system was heated to 70° C. and reacted overnight with the reaction endpoint monitored by LC-MS. The mixture was filtered by suction, and the filtrate was concentrated under reduced pressure. The crude product was purified by reversed phase column chromatography to obtain a product (400 mg, yield after the two steps: 35.6%)

Step 4: Synthesis of 6-(methylthio)-2H-pyrido[3,4-d][1,3]oxazin-2,4(1H)-dione

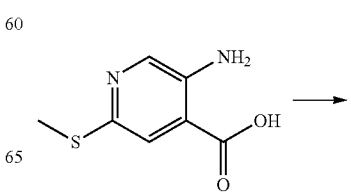

-continued

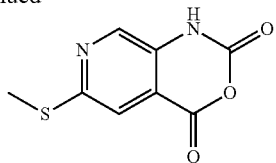

5-amino-2-(methylthio)isonicotinic acid (300.0 mg, 1.63 mmol) was dissolved in DMF (3 mL), and cooled to 0° C. in ice bath. CDI (449.4 mg, 2.77 mmol) was added. The system was slowly warmed to room temperature and stirred overnight with the reaction endpoint monitored by TLC. The product was obtained by concentrating under reduced pressure and directly subjected to the next step without purification.

Step 5: Synthesis of 4-hydroxy-6-methylthio-2-oxo-1,2-dihydro-1,7-naphthyridin-3-carbonitrile

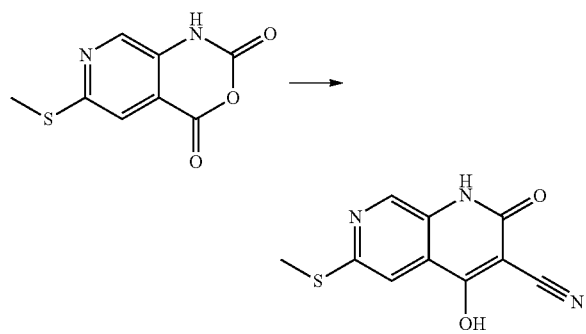

6-(methylthio)-2H-pyrido[3,4-d][1,3]oxazin-2,4(1H)-dione (300.0 mg crude product) was dissolved in DMF (3 mL). Ethyl cyanoacetate (193.6 mg, 1.71 mmol) and triethylamine (329.9 mg, 3.26 mmol) were added, and the system was stirred at 150° C. overnight with the reaction endpoint monitored by TLC. The mixture was concentrated under reduced pressure, followed by addition of water (10 mL), and then was adjusted to a pH of 1 with hydrochloric acid until solid was precipitated, and filtered by suction to give a product (140.0 mg crude product).

Step 6: Synthesis of 2,4-dichloro-6-methylthio-1,7-naphthyridin-3-carbonitrile

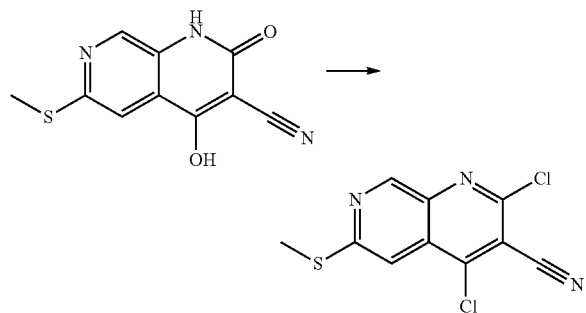

4-hydroxy-6-methylthio-2-oxo-1,2-dihydro-1,7-naphthyridin-3-carbonitrile (130.0 mg crude product) was dissolved in phosphorus oxychloride (2 mL), followed by addition of phosphorus pentachloride (168.7 mg, 1.1 mmol), and then was heated to 100° C. to reflux overnight. The reaction endpoint was monitored by TLC. The reaction solution was poured to ice water (15 mL), adjusted to a pH of 1 by adding saturated aqueous sodium bicarbonate solution, and filtered by suction. The filtrate was extracted with ethyl acetate and concentrated. The crude product is combined with the filter cake and purified by silica gel column chromatography (PE:EA=20:1) to give a yellow solid product (60.0 mg, yield after the three steps: 13.7%).

Step 7: Synthesis of 4-chloro-6-methylthio-2-oxo-1,2-dihydro-1,7-naphthyridin-3-carbonitrile

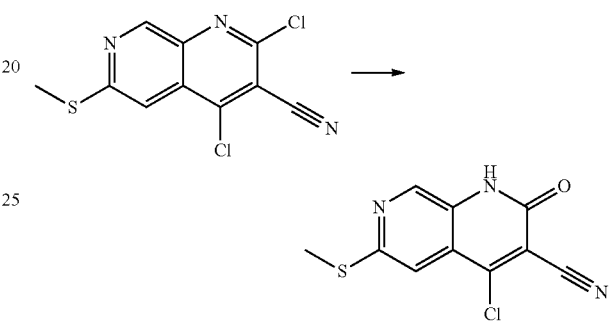

2,4-dichloro-6-methylthio-1,7-naphthyridin-3-carbonitrile (50.0 mg, 0.186 mmol) was dissolved in TFA (4 mL) and water (1 mL). The system was heated at 100° C. for 2 h with the reaction endpoint monitored by TCL. The reaction solution was concentrated under reduced pressure to give a product (68.0 mg crude product), which was directly subjected to the next step without purification.

Step 8: Synthesis of 6-methylthio-2-oxo-4-(7-azaspiro[3.5]nonane-7-yl)-1,2-dihydro-1,7-naphthyridin-3-carbonitrile

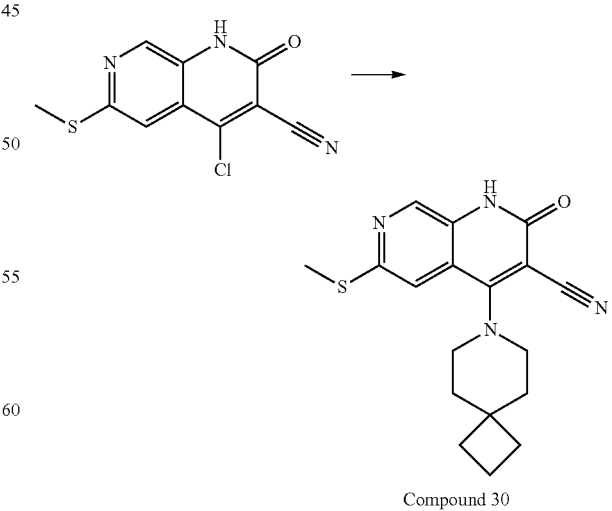

Compound 30

4-chloro-6-methylthio-2-oxo-1,2-dihydro-1,7-naphthyridin-3-carbonitrile (60.0 mg crude product) was dissolved in DMF (2 mL). 7-azaspiro[3.5]nonane hydrochloride (54.12 mg, 0.336 mmol) and DIPEA (93.53 mg, 0.72 mmol) were added. The mixture was heated at 70° C. for 2 h with the reaction endpoint monitored by TLC. The reaction solution was concentrated under reduced pressure, followed by addition of water and ethyl acetate, and liquid separation. The aqueous phase was extracted with ethyl acetate. The organic phase was combined, washed with water and saline solution, dried over anhydrous sodium sulfate and concentrated. The crude product was purified by silica gel column chromatography (DCM:MeOH=80:1, 60:1, 40:1) to give a product (50.0 mg, yield after the two steps: 79%).

$^1$HNMR (400 MHz, DMSO-d$_6$) δ (ppm): 11.94 (s, 1H), 8.54 (s, 1H), 7.33 (s, 1H), 3.50 (s, 4H), 2.55 (s, 3H), 1.92-1.80 (m, 10H).

Molecular formula: C$_{18}$H$_{20}$N$_4$OS Molecular weight: 340.45 LC-MS (Pos, m/z)=341.0 [M+H]$^+$.

Example 17: Synthesis of 6-(methylsulfonyl)-2-oxo-4-(7-azaspiro[3.5]nonane-7-yl)-1,2-dihydro-1,7-naphthyridin-3-carbonitrile (Compound 31)

Step 1: Synthesis of 6-(methylsulfonyl)-2-oxo-4-(7-azaspiro[3.5]nonane-7-yl)-1,2-dihydro-1,7-naphthyridin-3-carbonitrile

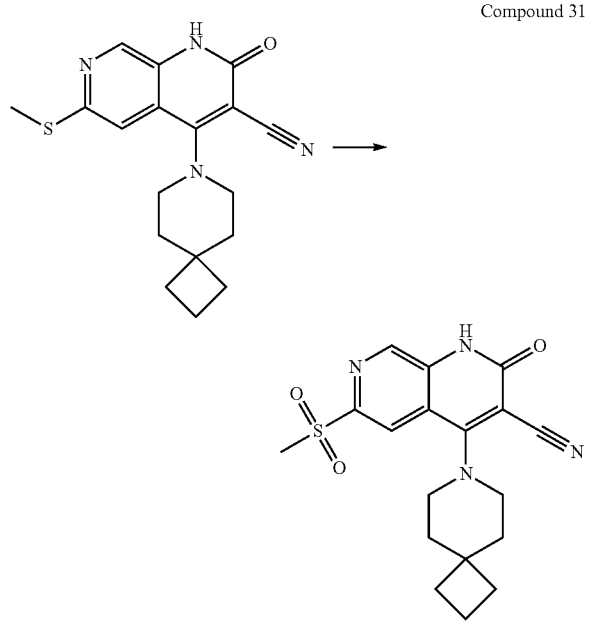

Compound 31

6-methylthio-2-oxo-4-(7-azaspiro[3.5]nonane-7-yl)-1,2-dihydro-1,7-naphthyridin-3-carbonitrile (40.0 mg, 0.12 mmol) was dissolved in dichloromethane (8 mL). The mixture was cooled to 0° C., followed by addition of m-chloroperoxybenzoic acid (59.2 mg, 0.24 mmol), and then was slowly warmed to room temperature to react. The reaction endpoint was monitored by TLC and LC-MS. Saturated aqueous sodium bicarbonate solution (10 mL) and dichloromethane (10 mL) were added. After liquid separation, the aqueous phase was extracted with dichloromethane, and the organic phases were combined, washed with water followed by saturated saline, dried over anhydrous sodium sulfate, filtered and concentrated. The crude product was purified by silica gel column chromatography (DCM:MeOH=100:1, 80:1) to obtain a yellow solid product (10.0 mg, yield: 20.4%).

$^1$HNMR (400 MHz, DMSO-d$_6$) δ (ppm): 12.44 (s, 1H), 8.75 (s, 1H), 8.19 (s, 1H), 3.57 (s, 4H), 3.26 (s, 3H), 1.94-1.82 (m, 10H).

Molecular formula: C$_{18}$H$_{20}$N$_4$O$_3$S Molecular weight: 372.44 LC-MS (Pos, m/z)+373.1 [M+H]$^-$.

Example 18: Synthesis of 6-(1,2-dihydroxyethyl)-2-oxo-4-(6-azaspiro[2.5]octane-6-yl)-1,2-dihydro-1,7-naphthyridin-3-carbonitrile (Compound 32)

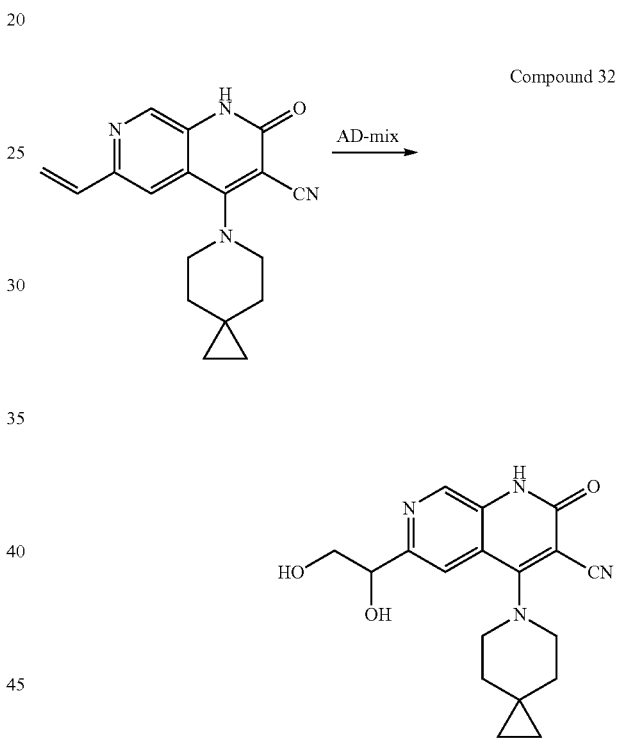

Compound 32

2-oxo-4-(6-azaspiro[2.5]octane-6-yl)-6-vinyl-1,2-dihydro-1,7-naphthyridin-3-carbonitrile (700.2 mg, 2.285 mmol, 1.0 eq) was dissolved in a mixture of tert-butanol (30 mL) and water (30 mL). The system was cooled to 0° C. in ice bath, followed by addition of methanesulfonamide (217.4 mg, 2.285 mmol, 1.0 eq) and AD-mix-β (7.76 g), and then was stirred vigorously at room temperature overnight. The reaction endpoint was monitored by TLC. The reaction solution was filtered by suction, and the filter cake was washed with water (30 mL×3), dried under vacuum to give a yellow solid (504.7 mg, yield: 64.9%).

$^1$HNMR (400 MHz, DMSO-d$_6$) δ (ppm): 11.97 (s, 1H), 8.60 (s, 1H), 7.77 (s, 1H), 5.56 (s, 1H), 4.69-4.65 (d, 2H), 3.65 (s, 5H), 3.50 (s, 1H), 1.63 (s, 4H), 0.45 (s, 4H).

Molecular formula: C$_{18}$H$_{20}$N$_4$O$_3$ Molecular weight: 340.38 LC-MS (Pos, m/z)=341.08 [M+H]$^+$.

Example 19: Synthesis of 6-(1,2-dihydroxyethyl)-2-oxo-4-(7-azaspiro[3.5]nonane-7-yl)-1,2-dihydro-1,7-naphthyridin-3-carbonitrile (Compound 33)

Step 1: Synthesis of 2-oxo-4-(7-azaspiro[3.5]nonane-7-yl)-6-vinyl-1,2-dihydro-1,7-naphthyridin-3-carbonitrile

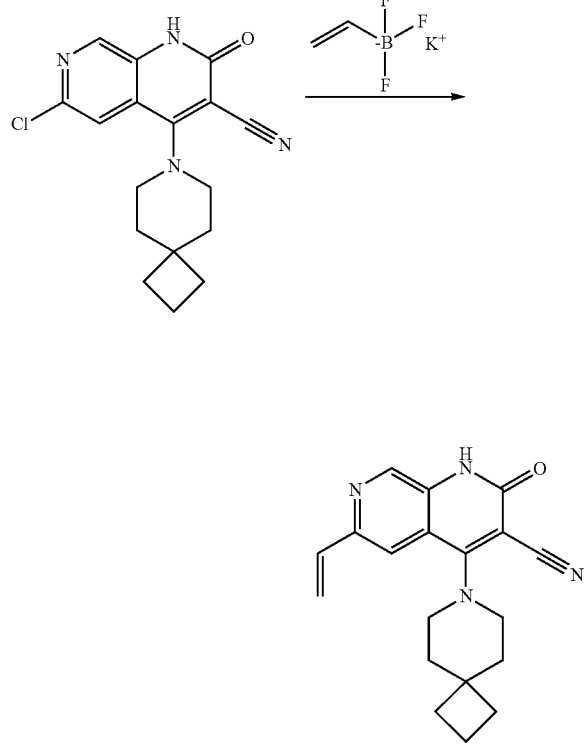

6-chloro-2-oxo-4-(7-azaspiro[3.5]nonane-7-yl)-1,2-dihydro-1,7-naphthyridin-3-carbo nitrile (4.61 g, 14.02 mmol, 1.0 eq), potassium trifluorovinylborate (3.05 g, 22.77 mmol, 3.0 eq), cesium carbonate (13.70 g, 42.06 mmol, 3.0 eq), Pd(PPh$_3$)$_4$ (810.1 mg, 0.70 mmol, 0.05 eq) and Pd(dppf)Cl$_2$ (512.9 mg, 0.70 mmol, 0.05 eq) were dissolved in a mixture of 1,4-dioxane (40 mL) and water (10 mL). The system was warmed to 105° C. and was stirred overnight under nitrogen protection. The reaction endpoint was monitored by TLC. H$_2$O (20 mL) was added to the reaction solution, and the system wad stirred for 30 min, cooled to room temperature, and filtered by suction. The filter cake was washed with a small amount of dichloromethane, and the filtrate was exacted with dichloromethane (20 mL×3). The organic phases were combined, washed with saturated saline (20 mL×2), dried over anhydrous Na$_2$SO$_4$, filtered by suction, and concentrated under reduced pressure. The crude product was first purified by silica gel column chromatography (DCM:MeOH=80:1-30:1), and then washed with ethyl acetate (10 mL) to give a yellow solid product (2.3 g, yield: 51.27%).

Step 2: Synthesis of 6-(1,2-dihydroxyethyl)-2-oxo-4-(7-azaspiro[3.5]nonane-7-yl)-1,2-dihydro-1,7-naphthyridin-3-carbonitrile

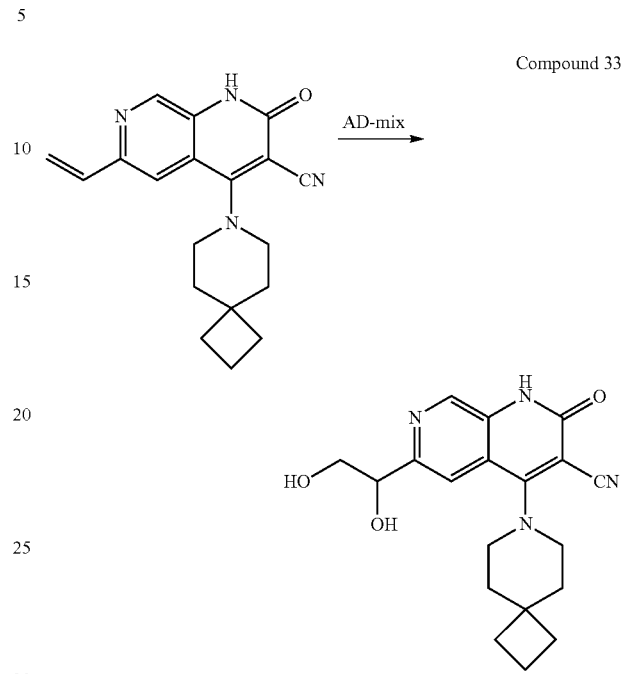

2-oxo-4-(7-azaspiro[3.5]nonane-7-yl)-6-vinyl-1,2-dihydro-1,7-naphthyridin-3-carbonitrile (2.3 g, 7.2 mmol, 1.0 eq) was dissolved in a mixture of tert-butanol (60 mL) and water (60 mL). The system was cooled to 0° C. in ice bath, followed by a slow addition of methanesulfonamide (682.0 mg, 7.2 mmol, 1.0 eq) and AD-mix-β (10 g), and then was stirred vigorously at room temperature overnight. The reaction endpoint was monitored by TLC. The reaction solution was filtered by suction, and the filter cake was washed with water (30 mL×3) and dried under vacuum to give a yellow solid product (857.0 mg, yield: 33.6%)

$^1$HNMR (400 MHz, DMSO-d$_6$) δ (ppm): 11.89 (s, 1H), 8.58 (s, 1H), 7.77 (s, 1H), 5.56 (s, 1H), 4.68 (m, 2H), 3.73 (s, 1H), 3.57 (m, 4H), 1.84-2.01 (m, 10H).

Molecular formula: C$_{19}$H$_{22}$N$_4$O$_3$ Molecular weight: 354.17 LC-MS (Pos, m/z)=355.11 [M+H]$^+$.

Example 20: Synthesis of 4-(4-ethylpiperidin-1-yl)-2-oxo-1,2-dihydro-1,7-naphthyridin-3-carbonitrile (Compound 34)

Step 1: Synthesis of Tert-Butyl 4-ethyl-4-hydroxypiperidin-1-carboxylate

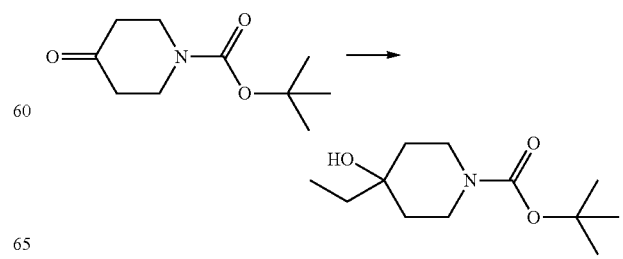

Tert-butyl 4-oxopiperidin-1-carboxylate (2.0 g, 0.038 mmol, 1.0 eq) was dissolved in tetrahydrofuran (10.0 mL), then ethyl magnesium chloride solution (10.04 mL, 20.075 mmol, 2.0 eq) diluted with THF (10.0 mL) was slowly added at 0° C. under nitrogen protection. The mixture was warmed slowly to room temperature and reacted overnight. When TLC showed completion of reaction, the crude product was purified by silica gel column chromatography (PE:EA=10:1 to 1:1) to give a product (800.0 mg, yield: 40%).

Step 2: Synthesis of Tert-Butyl 4-ethyl-3,6-dihydropyridin-1(2H)-carboxylate

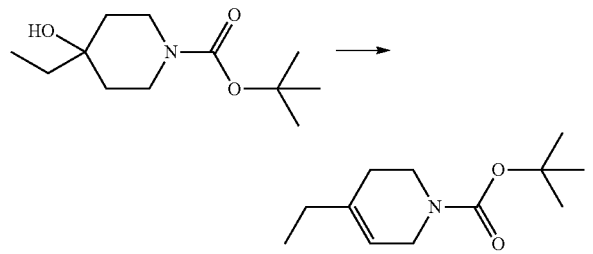

Tert-butyl 4-ethyl-4-hydroxypiperidin-1-carboxylate (800.0 mg, 3.488 mmol, 1.0 eq) was dissolved in dichloromethane (5.0 mL), and then pyridine (827.9 mg, 10.466 mmol, 3.0 eq) was added. Dichlorosulfoxide (830.1 mg, 6.977 mmol, 2.0 eq) was added slowly at 0° C. under nitrogen protection. The mixture was warmed slowly to room temperature and reacted overnight. When TLC showed completion of reaction, the reaction solution was poured to cold water, and extracted with ethyl acetate. The organic phase was washed with hydrochloric acid (1 mol/L) twice, dried over anhydrous Na$_2$SO$_4$ and concentrated. The crude product was purified by silica gel column chromatography (PE:EA=20:1-5:1) to give a yellow oil product (450.0 mg, yield: 56%).

Step 3: Synthesis of Tert-Butyl 4-ethylpiperidin-1-carboxylate

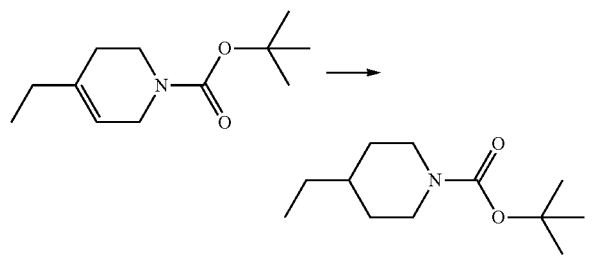

Tert-butyl 4-ethyl-3,6-dihydropyridin-1(2H)-carboxylate (450.0 mg, 2.129 mmol, 1.0 eq) was dissolved in methanol (10.0 mL), and then Pd/C (225.0 mg) was added. The air of the system was replaced by hydrogen and the reaction was carried out for 4 days. When TLC showed completion of reaction, the mixture was filtered, and the filtrate was concentrated under reduced pressure. The crude product was directly subjected to the next step.

Step 4: Synthesis of 4-ethylpiperidine Hydrochloride

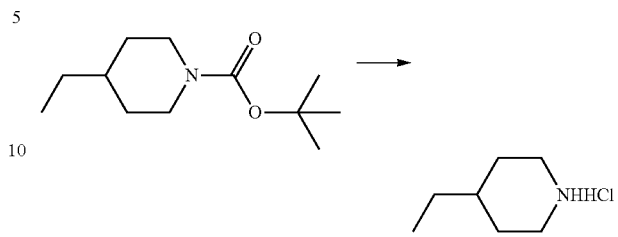

The above crude product was dissolved in ethanol (3.0 mL), and hydrogen chloride in ethanol (25%, 3.0 mL) was added dropwise to the reaction solution. The mixture was reacted at room temperature for 2 hours. When TLC showed completion of reaction, the reaction solution was concentrated under reduced pressure, and the crude product (102.0 mg) was directly subjected for the next step.

Step 5: Synthesis of 4-(4-ethylpiperidin-1-yl)-2-oxo-1,2-dihydro-1,7-naphthyridin-3-carbonitrile Compound 34

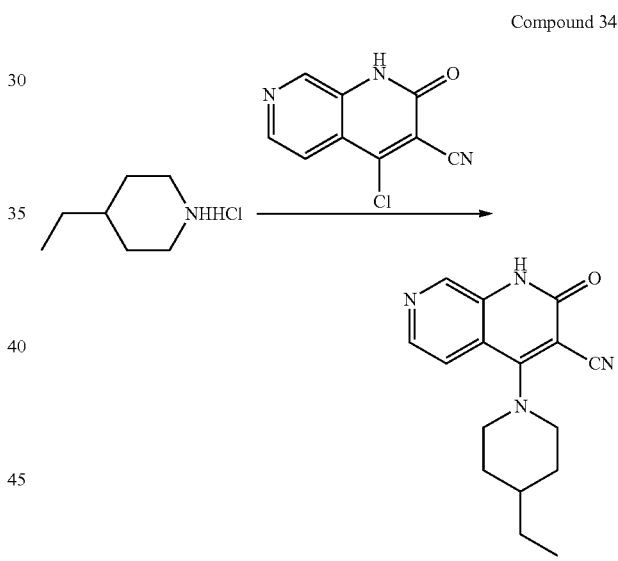

The crude product obtained in the previous step (102.0 mg, 0.681 mmol, 1.0 eq) was dissolved in N,N-dimethylformamide (3.0 mL), and N,N-diisopropylethylamine (528.1 mg, 4.086 mmol, 6.0 eq) and 4-chloro-2-oxo-1,2-dihydro-1,7-naphthyridine-3-carbonitrile (140.0 mg, 0.681 mmol, 1.0 eq) was added. The system was reacted at 80° C. for 2 h. When TLC showed completion of reaction, the mixture was concentrated under reduced pressure, slurried and washed with ethyl acetate (1.5 mL) and methyl tert-butyl ether (5.0 mL), and filtered by suction. The filter cake was washed with water to give a yellow solid product (100.0 mg, yield: 52.1%).

$^1$HNMR (400 MHz, DMSO-d$_6$) δ (ppm): 12.00 (s, 1H), 8.65 (s, 1H), 8.35-8.34 (m, 1H), 7.60-7.58 (m, 1H), 3.87-3.84 (m, 2H), 3.42-3.39 (m, 2H), 1.88-1.85 (m, 2H), 1.44-1.36 (m, 5H), 1.01-0.89 (m, 3H).

Molecular formula: C$_{16}$H$_{18}$N$_4$O Molecular weight: 282.35 LC-MS (Pos, m/z)=283.2 [M+H]$^+$.

Example 21: Synthesis of 4-(4,4-bis(hydroxymethyl)piperidin-1-yl)-2-oxo-1,2-dihydro-1,7-naphthyridin-3-carbonitrile (Compound 38)

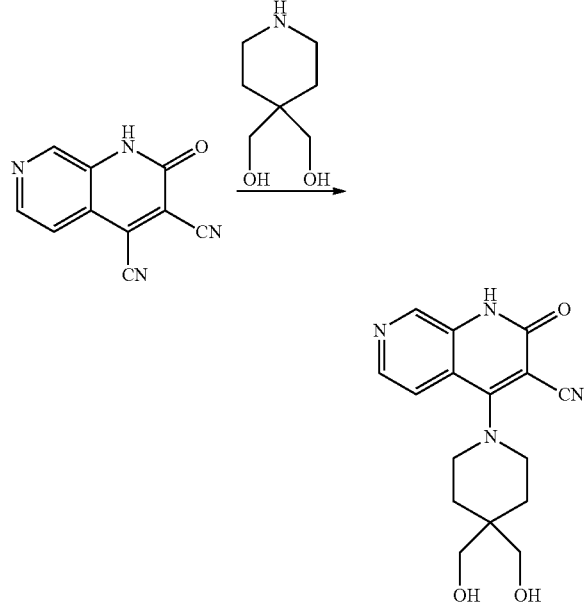

4-chloro-2-oxo-1,2-dihydro-1,7-naphthyridin-3-carbonitrile (200.0 mg, 0.97 mmol, 1.0 eq), piperidin-4,4-diyldimethanol (265.1 mg, 1.459 mmol, 1.5 eq) and DIPEA (1005.8 mg, 7.782 mmol, 8.0 eq) were dissolved in DMF (5 mL). The mixture was stirred at 80° C., and reacted for 3 h. The reaction endpoint was monitored by TLC. The mixture was concentrated under reduced pressure, washed for 3 h by adding water (10 mL) and ethyl acetate (10 mL), and filtered by suction. The filter cake was rinsed with a small amount of methanol to give a dark red solid product (55.0 mg, yield: 18.0%).

$^1$HNMR (400 MHz, DMSO-d$_6$) δ (ppm): 11.94 (s, 1H), 8.65 (s, 1H), 8.36-8.34 (d, 1H), 7.60-7.59 (d, 1H), 4.55 (t, 2H), 3.63 (t, 4H), 3.43-3.42 (d, 4H), 1.65 (t, 4H).

Molecular formula: C$_{16}$H$_{18}$O$_3$ Molecular weight: 314.35 LC-MS (Pos, m/z)=315.04 [M+H]$^+$.

Example 22: Synthesis of (R)-4-(3-(1H-pyrazol-1-yl)pyrrolidin-1-yl)-6-morpholino-2-oxo-1,2-dihydro-1,7-naphthyridin-3-carbonitrile (Compound 39)

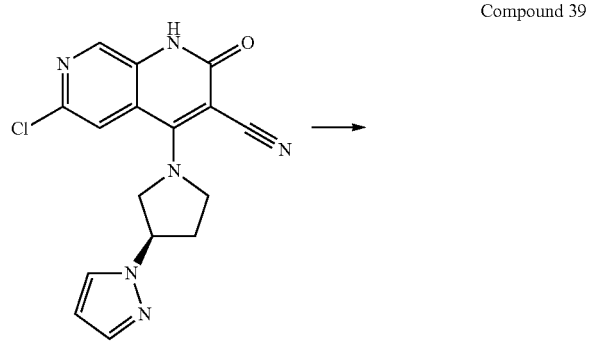

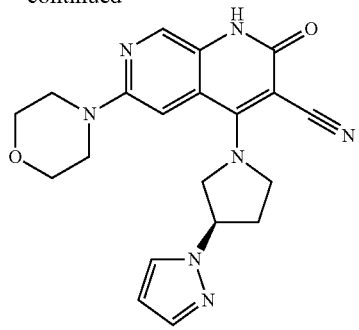

(R)-4-(3-(1H-pyrazol-1-yl)pyrrolidin-1-yl)-6-chloro-2-oxo-1,2-dihydro-1,7-naphthyridin-3-carbonitrile (60.0 mg, 0.176 mmol), morpholine (36.85 mg, 0.423 mmol), Pd$_2$(dba)$_3$ (6.7 mg, 0.007 mmol), sodium tert-butoxide (47.54 mg, 0.493 mmol) and XPhos (6.7 mg, 0.014 mmol) were dissolved in 1,4-dioxane (1 mL) and DMA (0.2 mL). The system was reacted under microwave at 110° C. for 4 hours. The reaction endpoint was monitored by TLC. The mixture was concentrated under reduced pressure, followed by addition of water, and then was extracted with ethyl acetate. The organic phases were combined, washed with water followed by saturated saline, dried over anhydrous sodium sulfate, filtered and concentrated. The crude product was purified by silica gel column chromatography (DCM:MeOH=80:1, 60:1, 40:1, 20:1) to give a red solid product (13.0 mg, 18.9%).

$^1$HNMR (400 MHz, DMSO-d$_6$) δ (ppm): 1130 (s, 1H), 8.30 (s, 1H), 7.89-7.88 (d, 1H), 7.50 (d, J=2 Hz, 1H), 7.15 (d, 1H), 6.30-6.29 (m, 1H), 5.17-5.15 (m, 1H), 4.52-4.48 (m, 1H), 4.36-4.32 (m, 1H), 4.29-4.16 (m, 2H), 3.74-3.72 (m, 4H), 3.37 (s, 3H), 2.46-2.33 (m, 2H).

Molecular formula: C$_{20}$H$_{21}$N$_7$O$_2$ Molecular weight: 391.44 LC-MS (Pos, m/z)=392.1 [M+H]$^+$.

Example 23: Synthesis of 4-(2-hydroxy-7-azaspiro[3.5]nonane-7-yl)-2-oxo-1,2-dihydro-1,7-naphthyridin-3-carbonitrile (Compound 40)

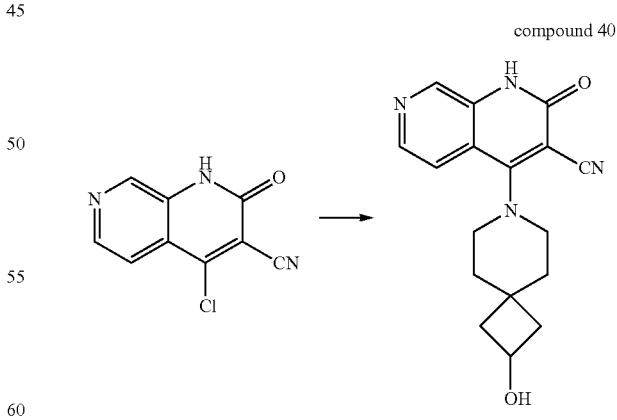

4-chloro-2-oxo-1,2-dihydro-1,7-naphthyridin-3-carbonitrile (50 mg, 0.24 mmol, 1.0 eq) was dissolved in DMF, and 7-azaspiro[3.5]nonane-2-ol hydrochloride (60.5 mg, 0.34 mmol, 1.4 eq) and DIPEA (188.5 mg, 1.46 mmol, 6.0 eq) was added. The system was reacted at 80° C. for 2 h. The reaction endpoint was monitored by LC-MS. MTBE (2 mL)

and H₂O (2 mL) were added. The mixture was vibrated and filtered by suction to give a product (37 mg, yield: 49.7%).

¹HNMR (400 MHz, DMSO-d₆) δ (ppm): 11.97 (s, 1H), 8.64 (s, 1H), 8.32-8.33 (m, 1H), 7.57-7.59 (m, 1H), 4.97-4.98 (m, 1H), 4.12-4.19 (m, 1H), 3.50-3.55 (m, 4H), 2.21-2.26 (m, 2H), 1.74-1.75 (m, 4H), 1.64-1.69 (m, 2H).

Molecular formula: C₁₇H₁₈N₄O₂ Molecular weight: 310.36 LC-MS (Pos, m/z)=311.02 [M+H]⁺.

Example 24: Synthesis of 4-(2-cyano-7-azaspiro [3.5]nonane-7-yl)-2-oxo-1,2-dihydro-1,7-naphthyridin-3-carbonitrile (Compound 42)

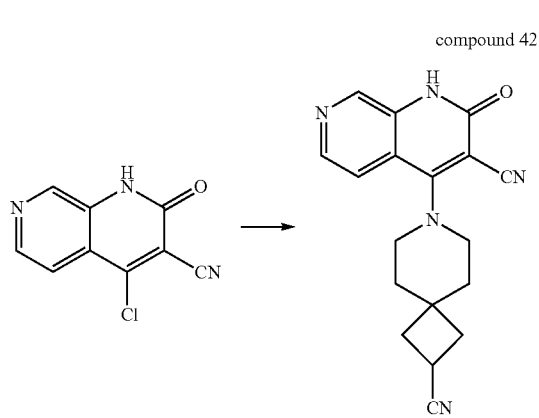 [SMILES: N#Cc1c(Cl)c2ccncc2[nH]c1=O ; N#Cc1c(N2CCC3(CC2)CC(C#N)C3)c2ccncc2[nH]c1=O]

compound 42

4-chloro-2-oxo-1,2-dihydro-1,7-naphthyridin-3-carbonitrile (50 mg, 0.24 mmol, 1.0 eq) was dissolved in DMF, and 7-azaspiro[3.5]nonane-2-carbonitrile hydrochloride (51.2 mg, 0.34 mmol, 1.4 eq) and DIPEA (188.5 mg, 1.46 mmol, 6.0 eq) were added. The system was reacted at 80° C. for 1.5 h with the reaction endpoint monitored by LC-MS. The mixture was filtered by suction to give a product (19 mg, yield: 24.4%).

¹HNMR (400 MHz, DMSO-d₆) δ (ppm): 12.00 (s, 1H), 864 (%, 1H), 8.32-8.34 (m, 1H), 7.57-7.58 (m, 1H), 3.52-3.55 (m, 4H), 3.38-3.46 (m, 1H), 2.29-2.34 (m, 2H), 2.15-2.20 (m, 2H), 1.84-1.88 (m, 4H).

Molecular formula: C₁₈H₁₇N₅O Molecular weight: 319.37 LC-MS (Pos, m/z)=320.05 [M+H]⁺.

Example 25: Synthesis of 4-(2,2-difluoro-7-azaspiro [3.5]nonane-7-yl)-2-oxo-1,2-dihydro-1,7-naphthyridin-3-carbonitrile (Compound 43)

Step 1: Synthesis of Tert-Butyl 2,2-difluoro-7-azaspiro[3.5]nonane-7-carboxylate

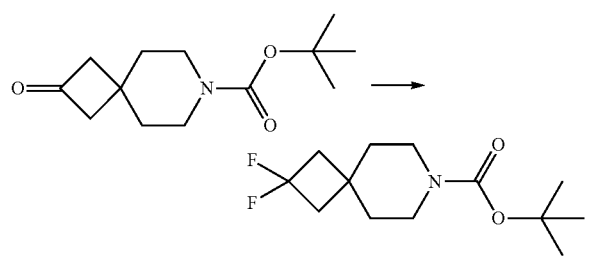

Tert-butyl 2-oxo-7-azaspiro[3.5]nonane-7-carboxylate (500.0 mg, 2.09 mmol) was dissolved in dichloromethane (4 mL). The system was cooled to 0° C. in ice bath, followed by addition of DAST (673.8 mg, 4.18 mmol), and was slowly warmed to room temperature and stirred overnight. The reaction endpoint was monitored by TLC. The reaction solution was added into a saturated aqueous sodium bicarbonate solution. The aqueous phase was extracted with dichloromethane. The organic phases were combined, washed with water and then with brine, and concentrated. The crude product was purified by silica gel column chromatography (PE:EA=30:1, 25:1, 20:1) to give a product (170.0 mg, yield: 31.2%).

Step 2: Synthesis of 2,2-difluoro-7-azaspiro[3.5]nonane

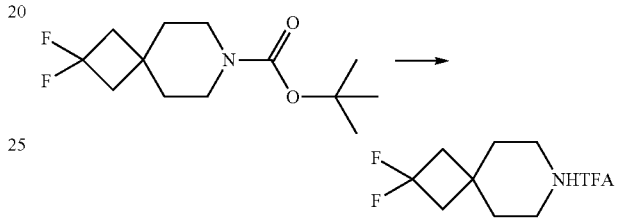

Tert-butyl 2,2-difluoro-7-azaspiro[3.5]nonane-7-carboxylate (170.0 mg, 0.65 mmol) was dissolved in dichloromethane (3 mL). The system was cooled to 0° C. in ice bath, followed by addition of trifluoroacetic acid (1.5 mL), and was slowly warmed to room temperature and stirred for 2 h. The reaction endpoint was monitored by TLC. The mixture was concentrated under reduced pressure to give a product (115.0 mg crude product).

Step 3: Synthesis of 4-(2,2-difluoro-7-azaspiro[3.5] nonane-7-yl)-2-oxo-1,2-dihydro-1,7-naphthyridin-3-carbonitrile

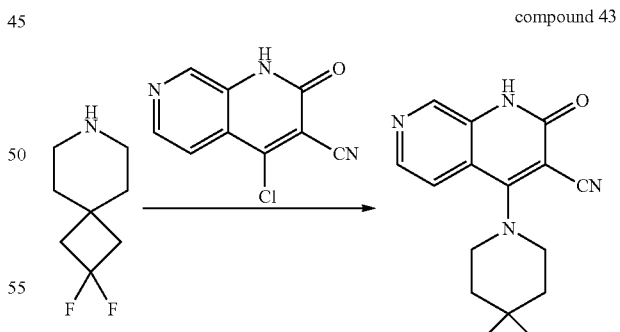

compound 43

4-chloro-2-oxo-1,2-dihydro-1,7-naphthyridin-3-carbonitrile (95.6 mg, 0.465 mmol) and 2,2-difluoro-7-azaspiro[3.5] nonane (104.72 mg of crude product) were dissolved in DMF (3 mL), and DIPEA (181.2 mg, 1.395 mmol) was added. The mixture was heated to 80° C. and reacted for 2 hours with the reaction endpoint monitored by TLC. The reaction solution was poured into water (10 mL), filtered by suction, and the filter cake was washed with ethyl acetate and petroleum ether to give a product (50.0 mg).

$^1$HNMR (400 MHz, DMSO-d$_6$) δ (ppm): 12.03 (s, 1H), 8.65 (s, 1H), 8.35-8.33 (d, 1H), 3.58 (s, 4H), 2.51 (s, 2H), 1.99-1.88 (d, 4H), 1.26-1.24 (d, 2H).

$^{19}$FNMR (400 MHz, DMSO-d$_6$) δ (ppm): −73.42, −84.55, −89.14.

Molecular formula: C$_{17}$H$_{16}$F$_2$N$_4$O Molecular weight: 330.34 LC-MS (Pos, m/z)=331.1 [M+H]$^+$.

Example 26: Synthesis of 6-amino-2-oxo-4-(6-azaspiro[2.5]octane-6-yl)-1,2-dihydro-1,7-naphthyridin-3-carbonitrile (Compound 44)

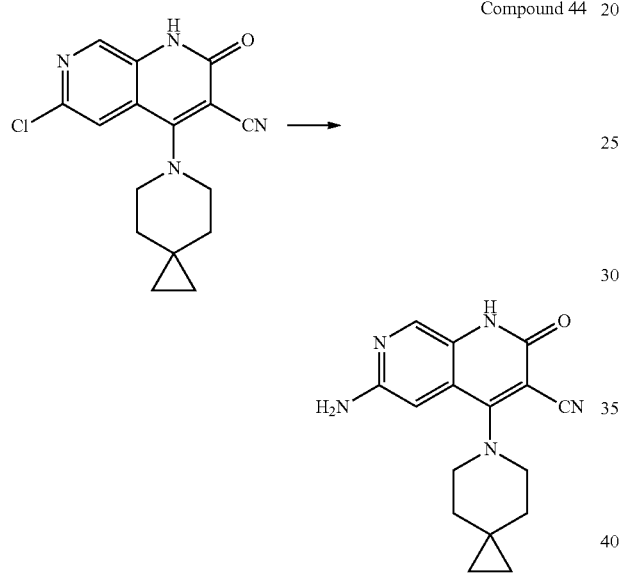

Compound 44

6-chloro-2-oxo-4-(6-azaspiro[2.5]octane-6-yl)-1,2-dihydro-1,7-naphthyridin-3-carbonitrile (30 mg, 0.095 mmol, 1.0 eq), LiHMDS in THF (1 mol/L, 1 mL), Pd$_2$(dba)$_3$ (9 mg, 0.0095 mmol, 0.1 eq) and 2-(dicyclohexylphosphino)biphenyl (7 mg, 0.0191 mmol, 0.2 eq) were added to a microwave tube, heated by microwave at 100° C. for 2 hours. The reaction solution was cooled, followed by addition of 1 mol/L hydrochloric acid (12 mL) and stirred for 20 min. The system was adjusted to alkalescent by aqueous sodium carbonate solution, and extracted with EA. The organic phase was dried over anhydrous sodium sulfate, and separated twice by using preparative thin layer chromatography plate (DCM:MeOH=30:1, 15:1) to give a product (1.03 mg, yield: 3.7%).

$^1$HNMR (400 MHz, DMSO-d$_6$) δ (ppm): 11.55 (s, 1H), 8.13 (s, 1H), 6.71 (s, 1H), 5.93 (s, 1H), 7.32-7.34 (t, 1H), 3.54-3.56 (t, 4H), 1.96-2.03 (m, 4H), 1.63 (m, 2H), 0.86 (m, 2H).

Molecular formula: C$_{16}$H$_{17}$N$_5$O Molecular weight: 295.35 LC-MS (Pos, m/z)=296.05 [M+H]$^+$.

Example 27: Synthesis of 6-methylamino-2-oxo-4-(6-azaspiro[2.5]octane-6-yl)-1,2-dihydro-1,7-naphthyridin-3-carbonitrile (Compound 45)

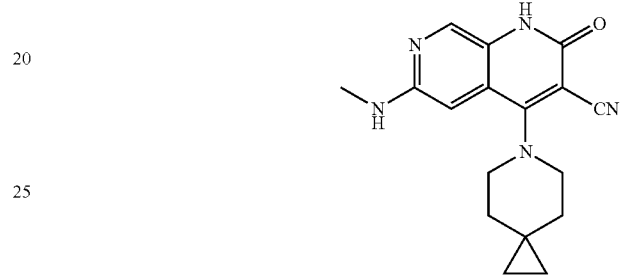

Compound 45

6-chloro-2-oxo-4-(6-azaspiro[2.5]octane-6-yl)-1,2-dihydro-1,7-naphthyridin-3-carbonitrile (50 mg, 0.159 mmol, 1.0 eq), methylamine in THF (1 mol/L, 0.8 mL, 0.794 mmol, 5 eq), Pd$_2$(dba)$_3$ (6 mg, 0.006 mmol, 0.04 eq), sodium tert-butoxide (46 mg, 0.476 mmol, 2.8 eq) and Xphos (6 mg, 0.013 mmol, 0.08 eq) were dissolved in 1,4-dioxane (1 mL) and DMAC (0.2 mL). The reaction solution was heated by microwave at 110° C. for 4 hours, cooled, followed by addition of water, and extracted with EA. The organic phase was dried over anhydrous sodium sulfate, and concentrated. The crude product was purified by silica gel column chromatography (DCM:MeOH=100:1-50:1) to give a product (5.69 mg, yield: 11.6%).

$^1$HNMR (400 MHz, DMSO-d$_6$) δ (ppm): 11.54 (s, 1H), 8.21 (s, 1H), 6.54-6.55 (d, 1H), 6.61 (s, 1H), 3.57 (m, 4H), 2.77-2.78 (d, 3H), 1.62 (m, 4H), 0.43 (m, 4H).

Molecular formula: C$_{17}$H$_{19}$N$_5$O Molecular weight: 309.37 LC-MS (Pos, m/z)=310.17 [M+H]$^+$.

Example 28: Synthesis of 6-dimethylamino-2-oxo-4-(6-azaspiro[2.5]octane-6-yl)-1,2-dihydro-1,7-naphthyridin-3-carbonitrile (Compound 46)

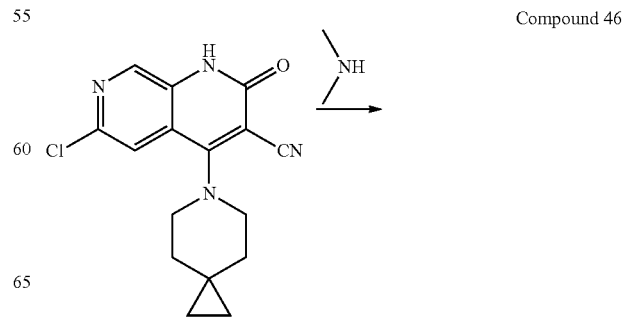

Compound 46

-continued

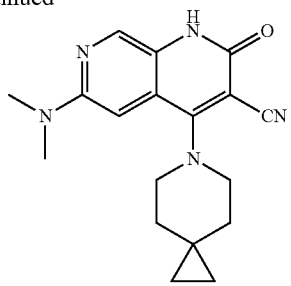

6-chloro-2-oxo-4-(6-azaspiro[2.5]octane-6-yl)-1,2-dihydro-1,7-naphthyridin-3-carbonitrile (50 mg, 0.159 mmol, 1.0 eq), dimethylamine in THF (2 mol/L, 0.4 mL, 0.794 mmol, 5 eq), Pd$_2$(dba)$_3$ (6 mg, 0.006 mmol, 0.04 eq), tert-butanol sodium (43 mg, 0.445 mmol, 2.8 eq) and Xphos (6 mg, 0.013 mmol, 0.08 eq) were dissolved in 1,4-dioxane (1 mL) and DMAC (0.2 mL). The reaction solution was heated by microwave at 110° C. for 4 hours, cooled, followed by addition of water, and extracted with EA. The organic phase was dried over anhydrous sodium sulfate. The crude product was separated by preparative thin layer chromatography (DCM:MeOH=20:1) to give a product (26.63 mg, yield: 51.8%).

$^1$HNMR (400 MHz, DMSO-d$_6$) δ (ppm): 11.58 (s, 1H), 8.34 (s, 1H), 6.63 (s, 1H), 3.62 (s, 4H), 3.05 (s, 6H), 1.62 (m, 4H), 0.44 (m, 4H).

Molecular formula: C$_{18}$H$_{21}$N$_5$O Molecular weight: 323.40 LC-MS (Pos, m/z)=324.1 [M+H]$^+$.

Example 29: Synthesis of 6-isopropyl-2-oxo-4-(7-azaspiro[3.5]nonane-7-yl)-1,2-dihydro-1,7-naphthyridin-3-carbonitrile (Compound 47)

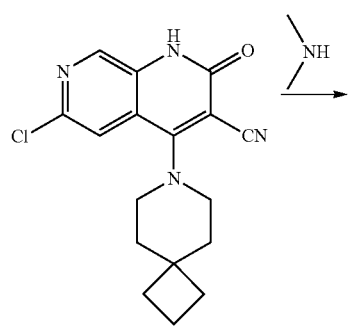

Compound 47

6-chloro-2-oxo-4-(7-azaspiro[3.5]nonane-7-yl)-1,2-dihydro-1,7-naphthyridin-3-carbo nitrile (50 mg, 0.152 mmol, 1.0 eq), dimethylamine in THF (2 mol/L, 0.38 mL, 0.76 mmol, 5 eq), Pd$_2$(dba)$_3$ (5.7 mg, 0.006 mmol, 0.04 eq), sodium tert-butoxide (41.5 mg, 0.43 mmol, 2.8 eq) and Xphos (5.72 mg, 0.012 mmol, 0.08 eq) were dissolved in 1,4-dioxane (1 mL) and DMAC (0.2 mL). The reaction solution was heated by microwave at 110° C. for 4 hours, cooled, followed by addition of water, and extracted with EA. The organic phase was dried over anhydrous sodium sulfate. The crude product was separated by preparative thin layer chromatography (developing agent: DCM:MeOH=20:1) to give 6-isopropyl-2-oxo-4-(7-azaspiro[3.5]nonane-7-yl)-1,2-dihydro-1,7-naphthyridin-3-carbonitrile (11.56 mg, yield: 22.5%).

$^1$HNMR (400 MHz, DMSO-d$_6$) δ (ppm): 11.57 (s, 1H), 8.30 (s, 1H), 6.59 (s, 1H), 3.51 (s, 4H), 3.03 (s, 6H), 1.79-2.07 (m, 10H).

Molecular formula: C$_{19}$H$_{23}$N$_3$O Molecular weight: 337.43 LC-MS (Pos, m/z)=338.15 [M+H]$^+$.

Example 30: Synthesis of 6-((dimethylamino)methyl)-2-oxo-4-(6-azaspiro[2.5]octane-6-yl)-1,2-dihydro-1,7-naphthyridin-3-carbonitrile (Compound 48)

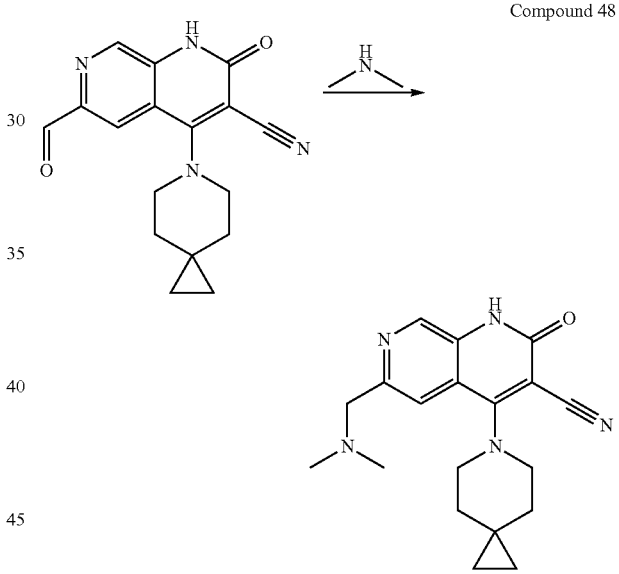

Compound 48

6-formyl-2-oxo-4-(6-azaspiro[2.5]octane-6-yl)-1,2-dihydro-1,7-naphthyridin-3-carbo nitrile (10 mg, 0.03 mmol, 1.0 eq) was dissolved in 1,2-dichloroethane (1 mL), and then a solution of dimethylamine in tetrahydrofuran (2 mol/L, 0.06 mL, 0.13 mmol, 4.0 eq) was added. The mixture was stirred at room temperature for 1 h. Sodium triacetoxyborohydride (21 mg, 0.10 mmol, 3.0 eq) was added under ice bath. The system was stirred at room temperature for 2 h, and quenched by adding water (1 mL). The mixture was extracted with dichloromethane (5 mL×2). The organic phases were combined and concentrated. The crude product was purified by silica gel column chromatography (dichloromethane:methanol=15:1) to give an off-white solid product (1.6 mg, yield: 14.8%).

$^1$HNMR (400 MHz, DMSO-d$_6$) δ (ppm): 12.03 (s, 1H), 8.62 (s, 1H), 7.66 (s, 1H), 3.64 (m, 6H), 2.26 (m, 6H), 1.62 (m, 4H), 0.45 (m, 4H).

Molecular formula: C$_{19}$H$_{23}$N$_3$O Molecular weight: 337.19 LC-MS (Neg, m/z)=336.17 [M−H]$^−$.

Example 31: Synthesis of 6-(azetidin-1-yl)-2-oxo-4-(6-azaspiro[2.5]octane-6-yl)-1,2-dihydro-1,7-naphthyridin-3-carbonitrile (Compound 49)

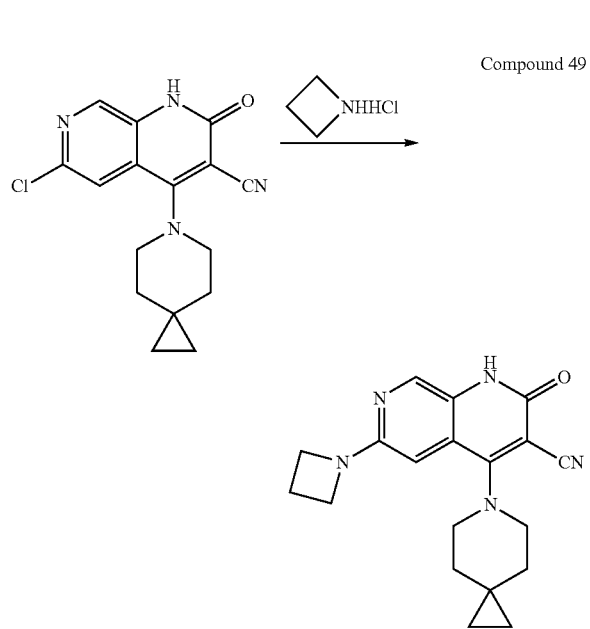

Compound 49

6-chloro-2-oxo-4-(6-azaspiro[2.5]octane-6-yl)-1,2-dihydro-1,7-naphthyridin-3-carbonitrile (50 mg, 0.159 mmol, 1.0 eq), azetidine hydrochloride (74 mg, 0.794 mmol, 5 eq), $Pd_2(dba)_3$ (6 mg, 0.006 mmol, 0.04 eq), sodium tert-butoxide (119 mg), 1.239 mmol, 7.8 eq) and Xphos (6 mg, 0.013 mmol, 0.08 eq) were dissolved in 1,4-dioxane (1 mL) and DMAC (0.2 mL). The reaction solution was heated by microwave at 110° C. for 4 hours, cooled, followed by addition of water, and extracted with EA. The organic phase was dried over anhydrous sodium sulfate. The crude product was purified by preparative thin layer chromatography (DCM:MeOH=20:1) to give a product (1.25 mg, yield: 2.4%).

$^1$HNMR (400 MHz, DMSO-$d_6$) δ (ppm): 11.65 (s, 1H), 8.28 (s, 1H), 6.42 (s, 1H), 3.92-3.95 (t, 4H), 3.59-3.62 (t, 4H), 2.29-2.36 (m, 2H), 1.60 (m, 4H), 0.432 (m, 4H).

Molecular formula: $C_{19}H_{21}N_5O$ Molecular weight: 335.41 LC-MS (Pos, m/z)=336.15 $[M+H]^+$.

Example 32: Synthesis of 6-(3-hydroxyazetidin-1-yl)-2-oxo-4-(6-azaspiro[2.5]octane-6-yl)-1,2-dihydro-1,7-naphthyridin-3-carbonitrile (Compound 50)

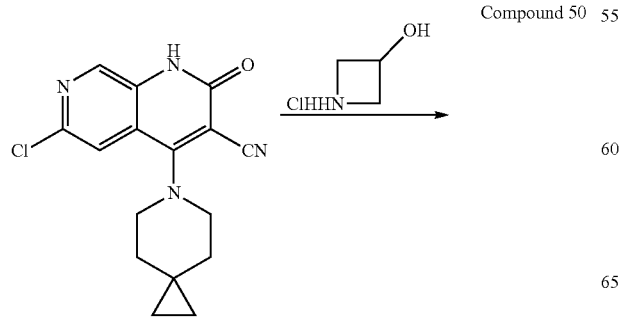

Compound 50

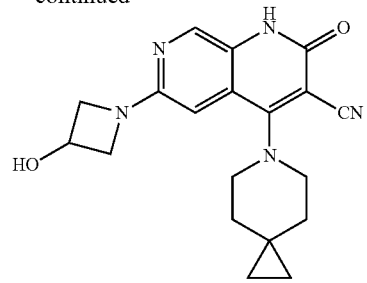

6-chloro-2-oxo-4-(6-azaspiro[2.5]octane-6-yl)-1,2-dihydro-1,7-naphthyridin-3-carbonitrile (200 mg, 0.64 mmol, 1.0 eq) and azetidine-3-ol hydrochloride (278 mg, 2.54 mmol, 4.0 eq) were dissolved in 1,4-dioxane (5 mL). Sodium butoxide (478 mg, 4.96 mmol, 7.8 eq), 2-dicyclohexylphosphine-2',4',6'-triisopropylbiphenyl (24 mg, 0.051 mmol, 0.08 eq) and $Pd_2(dba)_3$ (24 mg, 0.025 mmol, 0.04 eq) were added. The mixture was heated to 120° C. under nitrogen protection and reacted for 3 hours. The reaction endpoint was monitored by LC-MS. The reaction solution was concentrated under reduced pressure. The crude product was purified by silica gel column chromatography (DCM:MeOH=20:1), then slurried and washed with EA, and filtered by suction to give a product (74 mg, yield: 33%).

$^1$HNMR (400 MHz, DMSO-$d_6$) δ (ppm): 11.64 (s, 1H), 8.27 (s, 1H), 6.44 (s, 1H), 5.64-5.66 (t, 1H), 4.56-4.59 (m, 1H), 4.14-4.18 (t, 2H), 3.60-3.66 (m, 6H), 1.59 (m, 4H), 0.43 (m, 4H).

Molecular formula: $C_{19}H_{21}N_5O_2$ Molecular weight: 351.41 LC-MS (Pos, m/z)=352.17 $[M+H]^+$.

Example 33: Synthesis of 6-(3-hydroxyazetidin-1-yl)-2-oxo-4-(7-azaspiro[3.5]nonane-7-yl)-1,2-dihydro-1,7-naphthyridin-3-carbonitrile (Compound 51)

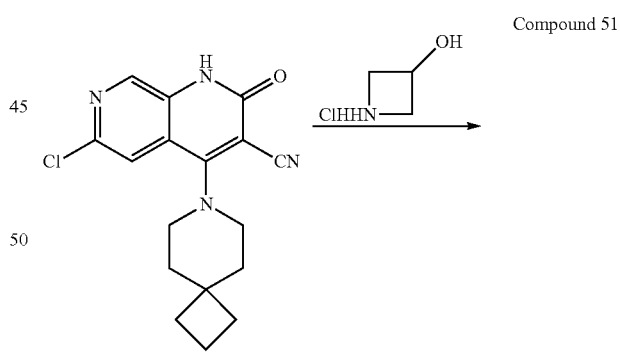

Compound 51

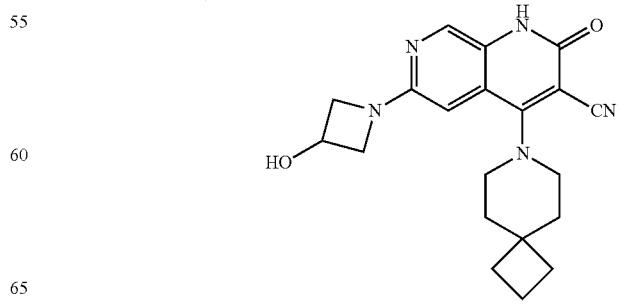

6-chloro-2-oxo-4-(7-azaspiro[3.5]nonane-7-yl)-1,2-dihydro-1,7-naphthyridin-3-carbo nitrile (80 mg, 0.243 mmol, 1.0 eq) and azetidine-3-ol hydrochloride (89 mg, 0.81 mmol, 3.3 eq) were dissolved in 1,4-dioxane (5 mL). Sodium butoxide (70 mg, 0.73 mmol, 3.0 eq), 2-dicyclohexylphosphine-2',4',6'-triisopropylbiphenyl (11 mg, 0.024 mmol, 0.1 eq) and Pd$_2$(dba)$_3$ (12 mg, 0.012 mmol, 0.05 eq) were added. The mixture was heated to 120° C. under nitrogen protection and reacted for 3 hours. The reaction endpoint was monitored by LC-MS. The reaction solution was filtered and concentrated. The crude product was purified by silica gel column chromatography (DCM:MeOH=10:1) to give a yellow solid product (9 mg, yield: 10%).

$^1$HNMR (400 MHz, DMSO-d$_6$) δ (ppm): 11.59 (s, 1H), 8.27 (s, 1H), 6.41 (s, 1H), 5.63-5.65 (d, 1H), 4.56-4.63 (m, 1H), 4.14-4.18 (m, 2H), 3.63-3.67 (m, 2H), 3.49 (s, 4H), 1.74-1.94 (m, 10H).

Molecular formula: C$_{20}$H$_{23}$N$_5$O$_2$ Molecular weight: 365.44 LC-MS (Pos, m/z)=366.14 [M+H]$^+$.

Example 34: Synthesis of 6-(3-aminoazetidin-1-yl)-2-oxo-4-(6-azaspiro[2.5]octane-6-yl)-1,2-dihydro-1,7-naphthyridin-3-carbonitrile (Compound 52)

Step 1: Synthesis of Tert-Butyl (1-(3-cyano-2-oxo-4-(6-azaspiro[2.5]octane-6-yl)-1,2-dihydro-1,7-naphthyridin-6-yl) azetidin-3-yl)carbamate

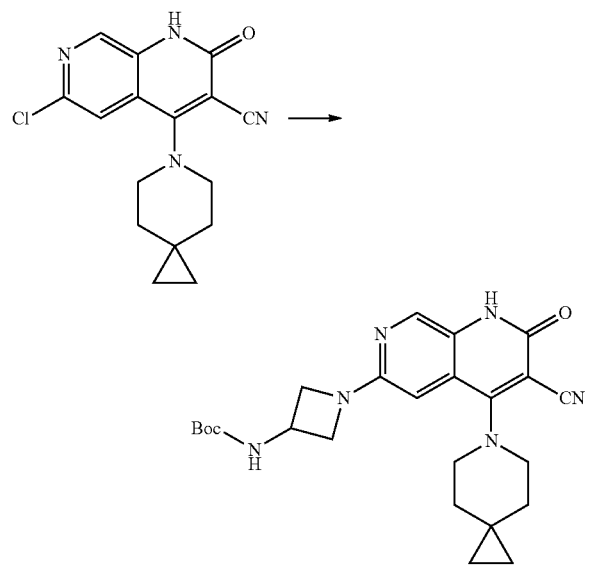

6-chloro-2-oxo-4-(6-azaspiro[2.5]octane-6-yl)-1,2-dihydro-1,7-naphthyridin-3-carbonitrile (300 mg, 0.95 mmol, 1.0 eq) and tert-butyl azetidine-3-yl carbamate (795.5 mg, 3.81 mmol, 4.0 eq) were dissolved in 1,4-dioxane, followed by addition of Pd$_2$(dba)$_3$ (36.1 mg, 0.04 mmol, 0.04 eq), t-BuONa (643.3 mg, 6.67 mmol, 7.0 eq) and Xphos (36.3 mg, 0.08 mmol, 0.08 eq). The mixture was reacted at 120° C. for 2 h. The reaction endpoint was monitored by LC-MS. The mixture was concentrated and the crude product was purified by silica gel column chromatography (DCM:MeOH=50:1-20:1) to give a product (177 mg, yield: 41.2%).

Step 2: Synthesis of 6-(3-aminoazetidin-1-yl)-2-oxo-4-(6-azaspiro[2.5]octane-6-yl)-1,2-dihydro-1,7-naphthyridin-3-carbonitrile

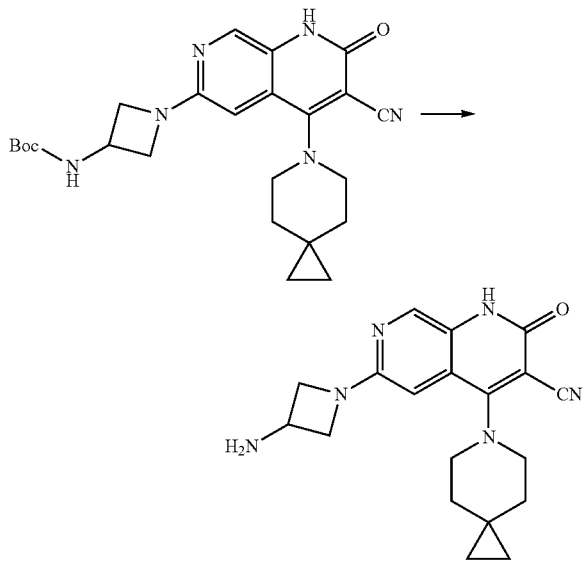

Compound 52

Tert-butyl (1-(3-cyano-2-oxo-4-(6-azaspiro[2.5]octane-6-yl)-1,2-dihydro-1,7-naphthyridine-6-yl)azetidin-3-yl)carbamate (177 mg, 0.39 mmol, 1.0 eq) was dissolved in DCM, and trifluoroacetic acid (1 mL) was added. The mixture was reacted at 25° C. for 0.5 h. The reaction endpoint was monitored by LC-MS. The mixture was concentrated and the crude product was purified by silica gel column chromatography (DCM:MeOH=10:1) to give a product (25.5 mg, yield: 18.7%).

$^1$HNMR (400 MHz, DMSO-d$_6$) δ (ppm): 8.29 (s, 1H), 6.46 (s, 1H), 3.94-4.18 (m, 3H), 3.67-3.70 (m, 2H), 3.60 (m, 4H), 1.60 (s, 4H), 1.09-1.13 (m, 2H), 0.81-0.85 (m, 4H).

Molecular formula: C$_{19}$H$_{22}$N$_6$O Molecular weight: 350.43 LC-MS (Pos, m/z)×351.15 [M+H]$^+$.

Example 35: Synthesis of 6-(3-aminoazetidin-1-yl)-2-oxo-4-(7-azaspiro[3.5]nonane-7-yl)-1,2-dihydro-1,7-naphthyridin-3-carbonitrile (Compound 53)

Step 1: Synthesis of (1-(3-cyano-2-oxo-4-(7-azaspiro[3.5]nonane-7-yl)-1,2-dihydro-1,7-naphthyridin-6-yl) azetidin-3-yl)carbamate

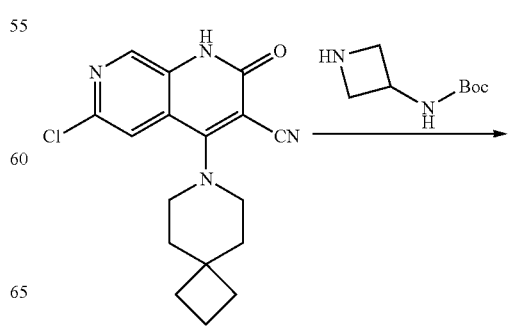

-continued

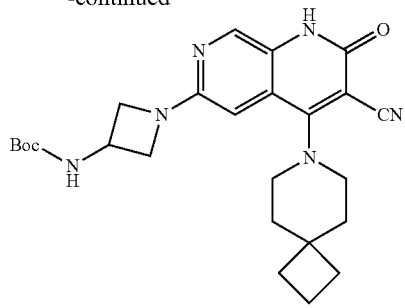

6-chloro-2-oxo-4-(7-azaspiro[3.5]nonane-7-yl)-1,2-dihydro-1,7-naphthyridin-3-carbo nitrile (200 mg, 0.61 mmol, 1.0 eq) and tert-butyl azetidin-3-yl carbamate (105 mg, 0.61 mmol, 1.0 eq) were dissolved in 1,4-dioxane (5 mL), followed by addition of sodium tert-butoxide (175 mg, 1.82 mmol, 3.0 eq), 2-dicyclohexylphosphine-2',4',6'-triisopropylbiphenyl (25 mg, 0.061 mmol, 0.1 eq) and $Pd_2(dba)_3$ (30 mg, 0.031 mmol, 0.05 eq). The temperature was raised to 120° C., and the system was reacted for 3 h under nitrogen protection. The completion of the reaction was detected by LC-MS. The reaction solution was filtered and concentrated. The crude product was purified by silica gel column chromatography (DCM:MeOH=20:1) to give a yellow solid product (140 mg, yield: 49%).

Step 2: Synthesis of 6-(3-aminoazetidin-1-yl)-2-oxo-4-(7-azaspiro[3.5]nonane-7-yl)-1,2-dihydro-1,7-naphthyridin-3-carbonitrile Compound 53

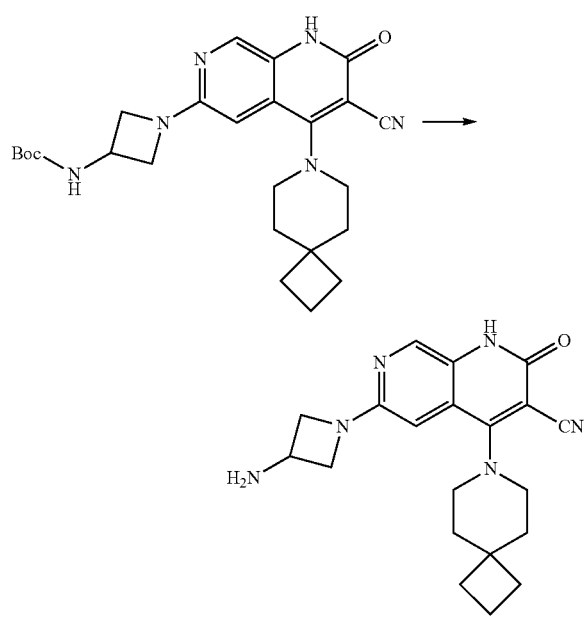

(1-(3-cyano-2-oxo-4-(7-azaspiro[3.5]nonane-7-yl)-1,2-dihydro-1,7-naphthyridin-6-yl) azetidin-3-yl)carbamate (140 mg, 0.30 mmol, 1.0 eq) was dissolved in dichloromethane (4 mL), followed by addition of trifluoroacetate (1 mL), and reacted for 2 h at room temperature. The completion of the reaction was detected by LC-MS. The solid was precipitated. The mixture was filtered, and the filter cake was rinsed with dichloromethane (5 mL×2) and dried at 45° C. to give a product (19 mg, yield: 17%).

$^1$HNMR (400 MHz, DMSO-$d_6$) δ (ppm): 8.26 (s, 1H), 6.39 (s, 1H), 4.10-4.14 (m, 2H), 3.79-3.85 (m, 1H), 3.50-3.53 (m, 6H), 1.79-1.93 (m, 10H).

Molecular formula: $C_{20}H_{24}N_6O$ Molecular weight: 364.45 LC-MS (Pos, m/z)=365.16 $[M+H]^+$ Example 36: Synthesis of 6-(azetidin-1-yl)-2-oxo-4-(7-azaspiro[3.5]nonane-7-yl)-1,2-dihydro-1,7-naphthyridin-3-carbonitrile (Compound 54)

Compound 54

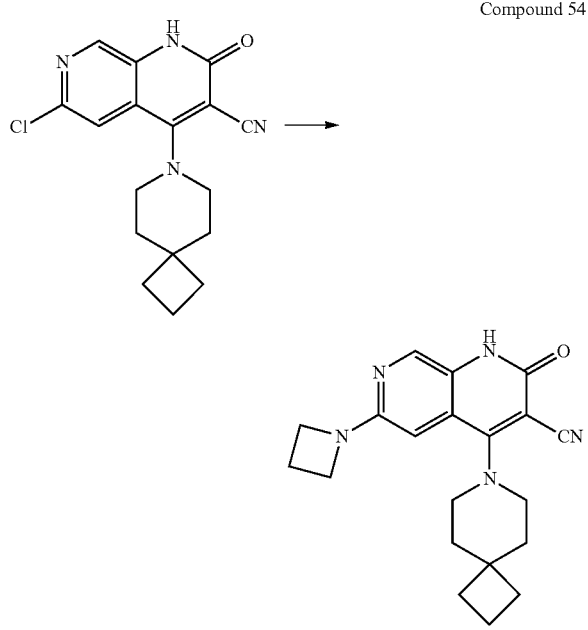

6-chloro-2-oxo-4-(7-azaspiro[3.5]nonane-7-yl)-1,2-dihydro-1,7-naphthyridin-3-carbo nitrile (150 mg, 0.46 mmol, 1.0 eq) and azetidine (130 mg, 2.28 mmol, 5.0 eq) were dissolved in tetrahydrofuran (5 mL) and DMAC (1 mL), followed by addition of sodium tert-butoxide (343 mg, 3.56 mmol, 7.8 eq), 2-dicyclohexylphosphine-2',4',6'-triisopropylbiphenyl (17 mg, 0.036 mmol, 0.08 eq) and $Pd_2(dba)_3$ (17 mg, 0.018 mmol, 0.04 eq). The temperature was raised to 110° C., and the system was reacted for 8 h under nitrogen protection. The completion of the reaction was detected by LC-MS. The reaction solution was poured into water, and exacted with EA. The organic phase was dried, and concentrated. The crude product was purified by preparative thin layer chromatography (DCM:MeOH=20:1) to give a product (61 mg, yield: 38%).

$^1$HNMR (400 MHz, DMSO-$d_6$) δ (ppm): 11.60 (s, 1H), 8.27 (s, 1H), 6.37 (s, 1H), 3.90-3.94 (1,4H), 3.48 (s, 4H), 2.30-2.36 (m, 2H), 1.78-1.92 (m, 10H).

Molecular formula: $C_{20}H_{23}N_5O$ Molecular weight: 349.44 LC-MS (Pos, m/z)=350.12 $[M+H]^+$.

Example 37: Synthesis of 6-chloro-2-oxo-4-(7-azaspiro[3.5]nonane-7-yl)-1,2-dihydro-1,7-naphthyridin-3-carbonitrile (Compound 55)

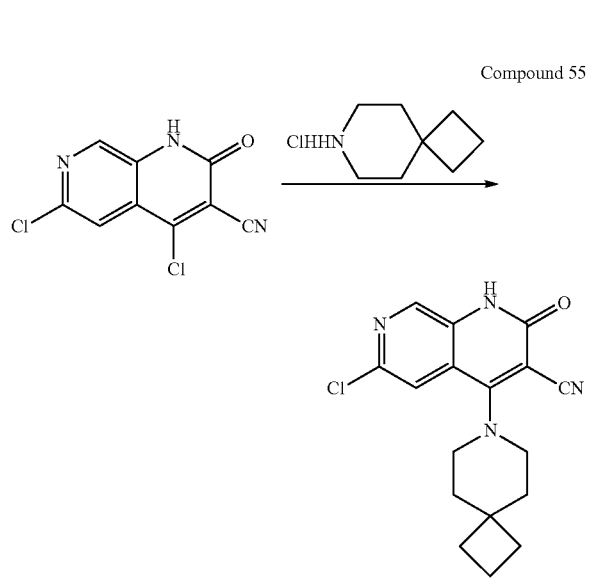

Compound 55

4,6-dichloro-2-oxo-1,2-dihydro-1,7-naphthyridin-3-carbonitrile (500.0 mg, 2.08 mmol, 1.0 eq), 7-azaspiro[3.5]nonane hydrochloride (505.1 mg, 3.12 mmol, 1.5 eq) and DIPEA (2153.6 mg, 16.66 mmol, 8.0 eq) were dissolved in DMF (10 mL), stirred to react for 3 h at 80° C. The completion of the reaction was detected by TLC. The system was concentrated under reduced pressure, followed by addition of water (10 mL) and ethyl acetate (10 mL) to slurry and wash for 3 h, and filtered by suction. The filter cake was rinsed with a small amount of methanol to give a dark red solid product (67.0 mg, yield: 9.8%).

$^1$HNMR (400 MHz, DMSO-$d_6$) δ (ppm): 12.11 (s, 1H), 8.45 (s, 1H), 7.59 (s, 1H), 3.54 (s, 4H), 1.86-1.80 (d, 10H).

Molecular formula: $C_{17}H_{17}ClN_4O$ Molecular weight: 328.80 LC-MS (Pos, m/z)=329.15 [M+H]$^+$.

Example 38: Synthesis of 6-morpholino-2-oxo-4-(7-azaspiro[3.5]nonane-7-yl)-1,2-dihydro-1,7-naphthyridin-3-carbonitrile (Compound 56)

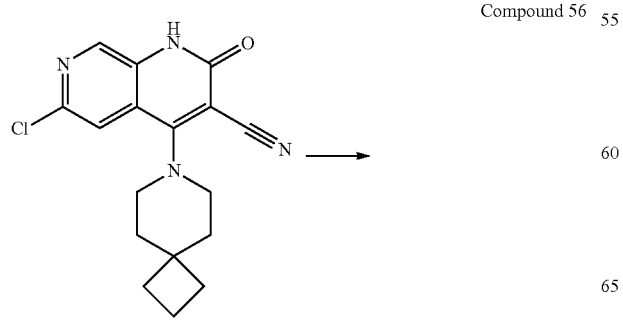

Compound 56

-continued

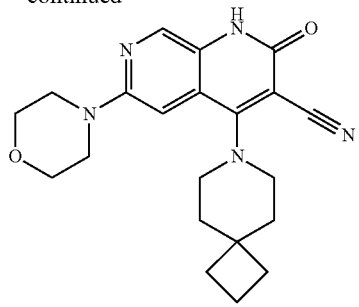

6-chloro-2-oxo-4-(7-azaspiro[3.5]nonane-7-yl)-1,2-dihydro-1,7-naphthyridin-3-carbo nitrile (50.0 mg, 0.152 mmol), morpholine (32.23 mg, 0.37 mmol), Pd$_2$(dba)$_3$ (5.7 mg, 0.006 mmol), sodium tert-butoxide (41.5 mg, 0.43 mmol) and XPhos (5.72 mg, 0.012 mmol) were dissolved in 1,4-dioxane (1 mL) and DMA (0.2 mL). Under protection of nitrogen, the system was reacted under microwave at 110° C. for 4 hours. The completion of the reaction was detected by TLC. The system was concentrated under reduced pressure, followed by addition of water, and extracted with ethyl acetate. The organic phases were combined, washed with water, washed with saturated saline, dried over anhydrous sodium sulfate, filtered and concentrated. The crude product was purified by silica gel column chromatography (DCM:MeOH=80:1-20:1) to give a product (15.0 mg).

$^1$HNMR (400 MHz, DMSO-$d_6$) δ (ppm): 11.67 (s, 1H), 8.35 (s, 1H), 6.78 (d, 1H), 3.76-3.74 (t, 4H), 3.52 (s, 4H), 3.38-3.35 (t, 4H), 1.99-1.80 (m, 10H).

Molecular formula: $C_{21}H_{25}N_5O_2$ Molecular weight: 379.46 LC-MS (Pos, m/z)=380.17 [M+H]$^+$.

Example 39: Synthesis of 6-(4-methylpiperazin-1-yl)-2-oxo-4-(7-azaspiro[3.5]nonane-7-yl)-1,2-dihydro-1,7-naphthyridin-3-carbonitrile (Compound 57)

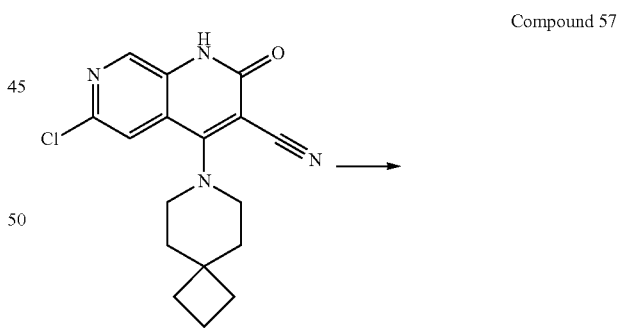

Compound 57

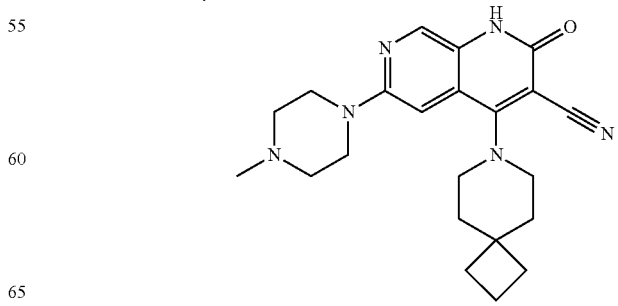

6-chloro-2-oxo-4-(7-azaspiro[3.5]nonane-7-yl)-1,2-dihydro-1,7-naphthyridin-3-carbo nitrile (80.0 mg, 0.243 mmol, 1.0 eq), N-methylpiperazine (58.4 mg, 0.584 mmol, 2.4 eq), sodium tert-butoxide (65.7 mg, 0.681 mmol, 2.8 eq), tris(dibenzylideneacetone)dipalladium (9.2 mg, 0.00972 mmol, 0.04 eq) and 2-dicyclohexylphosphine-2',4',6'-triisopropylbiphenyl (9.3 mg, 0.0194 mmol, 0.08 eq) were dissolved in 1,4-dioxane (2.0 mL) and N,N-dimethylacetamide (0.4 mL), and stirred at 120° C. overnight under nitrogen protection. The completion of the reaction was detected by TLC. The reaction solution was concentrated under reduced pressure, followed by addition of water (5.0 mL), exacted with ethyl acetate (5.0 mL), dried over anhydrous sodium sulfate, and concentrated. The crude product was purified by silica gel column chromatography (DCM:MeOH=80:1-20:1) to give a yellow solid product (20.0 mg, yield: 25%).

$^1$HNMR (400 MHz, DMSO-$d_6$) δ (ppm): 11.64 (s, 1H), 8.33 (s, 1H), 6.77 (s, 1H), 3.52-3.32 (m, 6H), 2.47 (s, 3H), 2.24 (m, 2H), 1.91-1.78 (m, 8H), 1.36 (m, 2H), 1.34-1.24 (m, 4H).

Molecular formula: $C_{22}H_{28}N_6O$ Molecular weight: 392.51 LC-MS (Pos, m/z)=393.21 [M+H]$^+$.

Example 40: Synthesis of 2-oxo-4-(6-azaspiro[2.5]octane-6-yl)-6-vinyl-1,2-dihydro-1,7-naphthyridin-3-carbonitrile (Compound 58)

Step 1: Synthesis of 6-chloro-2-oxo-4-(6-azaspiro[2.5]octane-6-yl)-1,2-dihydro-1,7-naphthyridin-3-carbonitrile

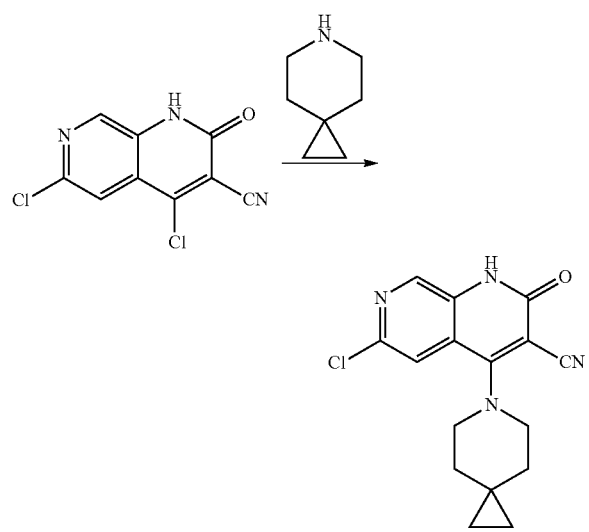

4,6-dichloro-2-oxo-1,2-dihydro-1,7-naphthyridin-3-carbonitrile (4.00 g, 16.66 mmol, 1.0 eq), 6-azaspiro[2.5]octane (2.22 g, 20.00 mmol, 1.2 eq) and DIPEA (8.61 g, 66.66 mmol, 4.0 eq) were dissolved in DMF (40 mL), stirred for 3 h at 80° C. The completion of the reaction was detected by TLC. The reaction solution was concentrated under reduced pressure, followed by addition of water (30 mL) and ethyl acetate (30 mL) to slurry and wash for 3 h, and filtered by suction. The filter cake was rinsed with a small amount of methanol to give a product as a yellow solid product (3.63 g, yield: 69.2%).

Step 2: Synthesis of 2-oxo-4-(6-azaspiro[2.5]octane-6-yl)-6-vinyl-1,2-dihydro-1,7-naphthyridin-3-carbonitrile

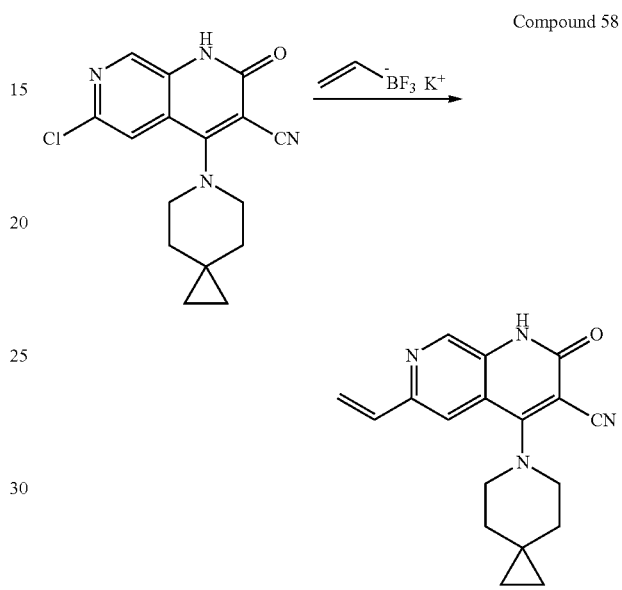

Compound 58

6-chloro-2-oxo-4-(6-azaspiro[2.5]octane-6-yl)-1,2-dihydro-1,7-naphthyridin-3-carbonitrile (4.63 g, 14.71 mmol, 1.0 eq), potassium trifluorovinylborate (5.91 g, 44.13 mmol, 3.0 eq), cesium carbonate (14.38 g, 44.13 mmol, 3.0 eq), Pd(PPh$_3$)$_4$ (849.9 mg, 0.74 mmol, 0.05 eq) and Pd(dppf)Cl$_2$ (538.1 mg, 0.74 mmol, 0.05 eq) were dissolved in a mixture of 1,4-dioxane (40 mL) and water (10 mL). The temperature was raised to 105° C., and the system was stirred to react overnight under nitrogen protection. The completion of the reaction was detected by TLC. H$_2$O (20 mL) was added. The reaction solution was stirred for 30 min, cooled to room temperature, and filtered by suction, and the filter cake was washed with a small amount of dichloromethane. The filtrate was extracted with dichloromethane (20 mL×3). The organic phases were combined, washed with saturated saline (20 mL×2), dried over anhydrous Na$_2$SO$_4$, filtered by suction, and concentrated under reduced pressure. The crude product was purified by silica gel column chromatography (DCM:MeOH=80:1-30:1), and washed with ethyl acetate (10 mL) to give a yellow solid product (1.28 g, yield: 28.4%).

$^1$HNMR (400 MHz, DMSO-$d_6$) δ (ppm): 12.09 (s, 1H), 8.65 (s, 1H), 7.590 (s, 1H), 6.96-6.89 (m, 1H), 6.17 (d, 16 Hz, 1H), 5.40 (d, 12 Hz, 1H), 3.68 (m, 4H), 1.64 (m, 4H), 0.44 (m, 4H).

Molecular formula: $C_{18}H_{18}N_4O$ Molecular weight: 306.15 LC-MS (Neg, m/z)=305.06 [M−H]$^-$.

Example 41: Synthesis of 6-cyclopropyl-2-oxo-4-(6-azaspiro[2.5]octane-6-yl)-1,2-dihydro-1,7-naphthyridin-3-carbonitrile (Compound 59)

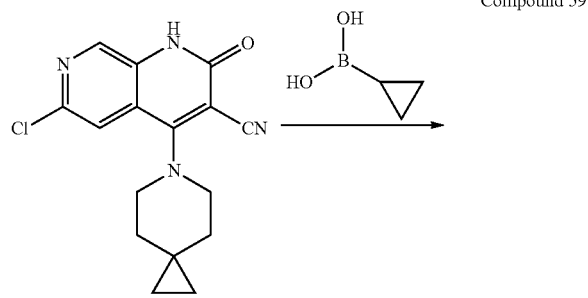

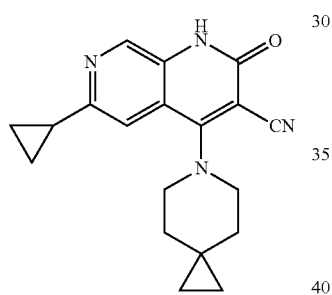

6-chloro-2-oxo-4-(6-azaspiro[2.5]octane-6-yl)-1,2-dihydro-1,7-naphthyridin-3-carbonitrile (50 mg, 0.16 mmol, 1.0 eq) and cyclopropylboronic acid (55 mg, 0.64 mmol, 4.0 eq) were dissolved in 1,4-dioxane (3 mL), and followed by addition of cesium carbonate (155 mg, 0.48 mmol, 3.0 eq), potassium phosphate (34 mg, 0.16 mmol, 1.0 eq) and [1,1'-bis(diphenylphosphino)ferrocene]palladium dichloride (12 mg, 0.016 mmol, 0.1 eq). The temperature was raised to 120° C., and the system was reacted for 3 h under nitrogen protection. The completion of the reaction was detected by LC-MS. The resulting mixture was filtered, and concentrated. The crude product was purified by silica gel column chromatography (DCM:MeOH=20:1) to give a product (2.5 mg, yield: 4.9%).

¹HNMR (400 MHz, DMSO-$d_6$) δ (ppm): 11.89 (s, 1H), 8.52 (s, 1H), 7.47 (s, 1H), 3.65 (m, 4H), 2.16-2.25 (m, 1H), 1.63 (s, 4H), 0.93-0.95 (m, 2H), 0.86-0.87 (m, 2H), 0.44 (m, 4H).

Molecular formula: $C_{19}H_{20}N_4O$ Molecular weight: 320.40 LC-MS (Pos, m/z)=321.13 [M+H]⁺.

Example 42: Synthesis of 6-cyclopropyl-2-oxo-4-(7-azaspiro[3.5]nonane-7-yl)-1,2-dihydro-1,7-naphthyridin-3-carbonitrile (Compound 60)

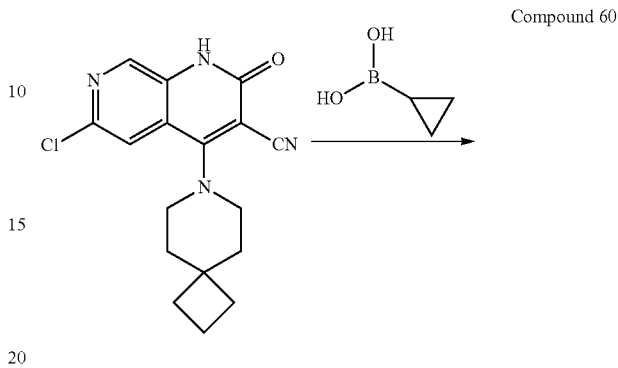

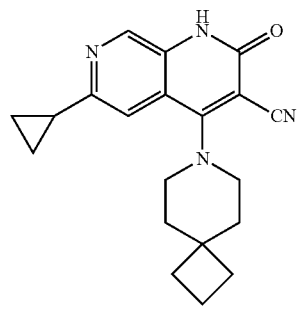

6-chloro-2-oxo-4-(7-azaspiro[3.5]nonane-7-yl)-1,2-dihydro-1,7-naphthyridin-3-carbo nitrile (50 mg, 0.15 mmol, 1.0 eq) and cyclopropylboronic acid (53 mg, 0.61 mmol, 4.0 eq) were dissolved in 1,4-dioxane (3 mL), followed by addition of cesium carbonate (149 mg, 0.46 mmol, 3.0 eq), potassium phosphate (33 mg, 0.15 mmol, 1.0 eq) and [1,1'-bis(diphenylphosphino)ferrocene]palladium dichloride (11 mg, 0.015 mmol, 0.1 eq). Under protection of nitrogen, the system was reacted under microwave at 120° C. for 3 hours. The completion of the reaction was detected by LC-MS. The reaction solution was filtered and concentrated. The crude product was purified by silica gel column chromatography (DCM:MeOH=20:1) to give a product (4 mg, yield: 8%).

¹HNMR (400 MHz, DMSO-$d_6$) δ (ppm): 11.83 (s, 1H), 8.51 (s, 1H), 7.43 (s, 1H), 3.54 (s, 4H), 2.23-2.25 (m, 1H), 2.17-2.22 (m, 10H), 0.93-0.95 (m, 2H), 0.87-0.88 (m, 2H).

Molecular formula: $C_{20}H_{22}N_4O$ Molecular weight: 334.42 LC-MS (Pos, m/z)=335.07 [M+H]⁺.

Example 43: Synthesis of 6-((2-(dimethylamino)ethyl)(methyl)amino)-2-oxo-4-(7-azaspiro[3.5]nonane-7-yl)-1,2-dihydro-1,7-naphthyridin-3-carbonitrile (Compound 61)

Example 44: Synthesis of 6-(hydroxymethyl)-2-oxo-4-(6-azaspiro[2.5]octane-6-yl)-1,2-dihydro-1,7-naphthyridin-3-carbonitrile (Compound 62)

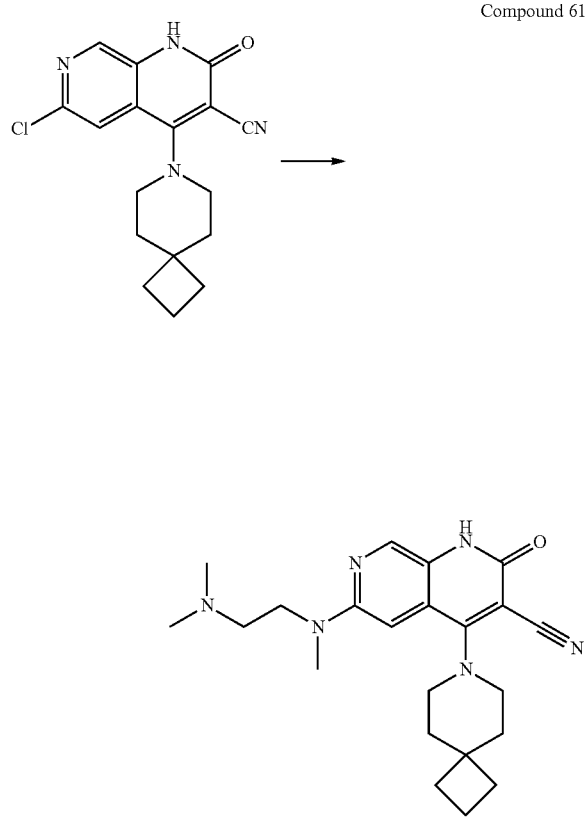

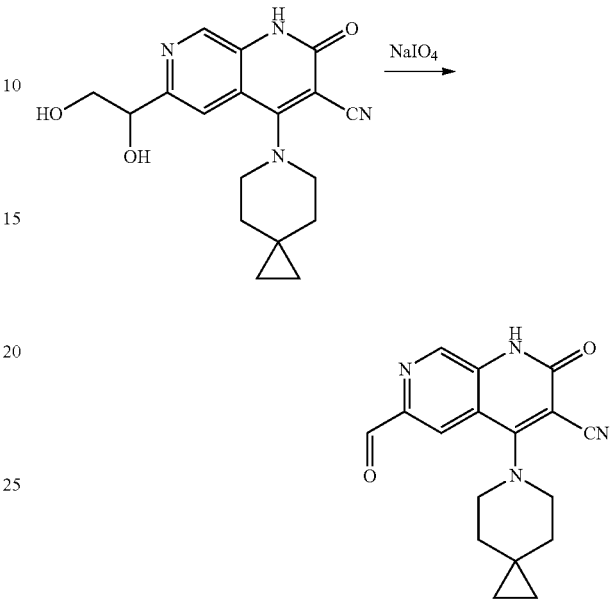

6-chloro-2-oxo-4-(7-azaspiro[3.5]nonane-7-yl)-1,2-dihydro-1,7-naphthyridin-3-carbo nitrile (50 mg, 0.15 mmol, 1.0 eq) and $N^1, N^1, N^2$-trimethylethane-1,2-diamine (78 mg, 0.76 mmol, 5.0 eq) were dissolved in tetrahydrofuran (2 mL) and DMAC (0.2 mL), and followed by addition of sodium tert-butoxide (114 mg, 1.19 mmol, 7.8 eq), 2-dicyclohexylphosphine-2',4',6'-triisopropylbiphenyl (6 mg, 0.012 mmol, 0.08 eq) and $Pd_2(dba)_3$ (6 mg, 0.006 mmol, 0.04 eq). The temperature was raised to 120° C., and the system was reacted for 8 h under nitrogen protection. The completion of the reaction was detected by LC-MS. The reaction solution was poured into water (10 mL), and exacted with EA. The organic phase was dried and concentrated. The crude product was purified by silica gel column chromatography (DCM:MeOH=10:1) to give a product (14 mg, yield: 23%).

$^1$HNMR (400 MHz,

DMSO-$d_6$) δ (ppm): 11.65 (s, 1H), 8.28-8.32 (d, 1H), 6.57-6.59 (d, 1H), 3.80 (s, 3H), 3.51 (s, 3H), 2.96-3.02 (t, 3H), 2.85 (s, 4H), 1.80-2.03 (d, 10H), 1.24-1.47 (t, 4H).

Molecular formula: $C_{22}H_{30}N_6O$ Molecular weight: 394.52 LC-MS (Pos, m/z)=395.24 $[M+H]^+$.

Sodium periodate (634.3 mg, 2.966 mmol, 1.0 eq) was dissolved in water (10 mL), followed by addition of tetrahydrofuran (10 mL), cooled to 0° C. in ice bath, followed by a slow addition 6-(1,2-dihydroxyethyl)-2-oxo-4-(6-azaspiro[2.5]octane-6-yl)-1,2-dihydro-1,7-naphthyridin-3-carbonitrile (504.7 mg, 1.483 mmol, 0.5 eq), and stirred to react for 3 h under room temperature. The completion of the reaction was detected by TLC. The mixture was exacted with dichloromethane (10 mL×3). The organic phases were combined, and washed with saturated saline (10 mL×2), dried over anhydrous sodium sulfate, and filtered by suction. The filtrate was concentrated under reduced pressure to give a yellow solid product (350.0 mg, yield: 38.4%).

Step 2: Synthesis of 6-(hydroxymethyl)-2-oxo-4-(6-azaspiro[2.5]octane-6-yl)-1,2-dihydro-1,7-naphthyridin-3-carbonitrile

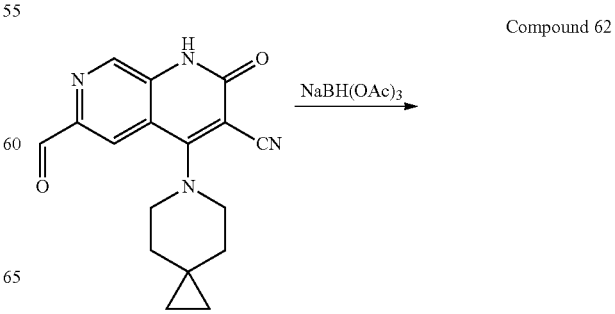

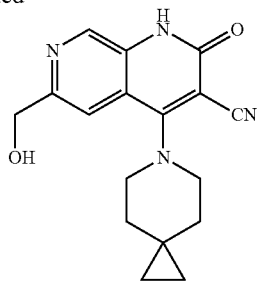

6-formyl-2-oxo-4-(6-azaspiro[2.5]octane-6-yl)-1,2-dihydro-1,7-naphthyridin-3-carbo nitrile (100.0 mg, 0.324 mmol, 1.0 eq) was dissolved in methanol (15 mL), cooled to 0° C. in ice bath, followed by addition of sodium triacetylborohydride (206.2 mg, 0.973 mmol, 3.0 eq), and stirred overnight at the room temperature. The completion of the reaction was detected by TLC. The reaction solution was quenched by adding H$_2$O (10 mL), stirred for 30 min, and concentrated under reduced pressure. The crude product was purified by silica gel column chromatography (DCM:MeOH=50:1-20:1) to give a yellow solid product (96.9 mg, yield: 96.4%).

$^1$HNMR (400 MHz, DMSO-d$_6$) δ (ppm): 11.97 (s, 1H), 8.59 (s, 1H), 7.72 (s, 1H), 5.58-5.55 (t, 1H), 4.62-4.60 (d, 2H), 3.66-3.63 (t, 4H), 1.63 (m, 4H), 0.45 (m, 4H).

Molecular formula: C$_{17}$H$_{18}$N$_4$O$_2$ Molecular weight: 310.36 LC-MS (Pos, m/z)=311.08 [M+H]$^+$.

Example 45: Synthesis of 6-methyl-2-oxo-4-(6-azaspiro[2.5]octane-6-yl)-1,2-dihydro-1,7-naphthyridin-3-carbonitrile (Compound 63)

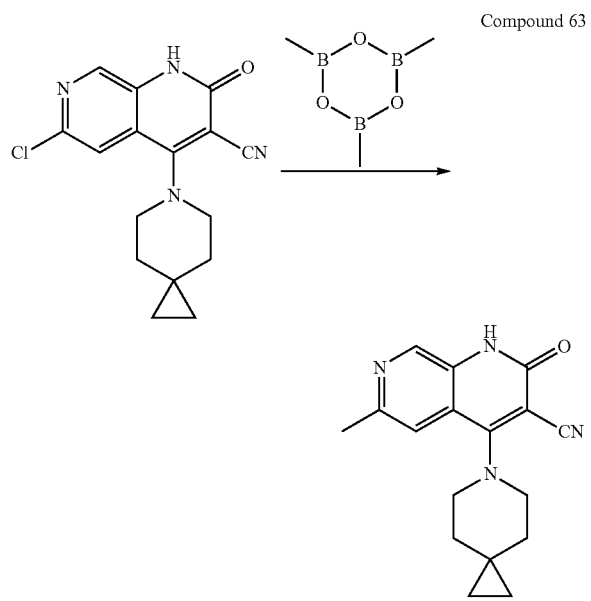

6-chloro-2-oxo-4-(6-azaspiro[2.5]octane-6-yl)-1,2-dihydro-1,7-naphthyridin-3-carbonitrile (50 mg, 0.16 mmol, 1.0 eq) and trimethylcyclotriborane (160 mg, 0.64 mmol, 4.0 eq, 50%) were dissolved in 1,4-dioxane (3 mL), followed by addition of cesium carbonate (155 mg, 0.48 mmol, 3.0 eq), potassium phosphate (34 mg, 0.16 mmol, 1.0 eq) and [1,1'-bis(diphenylphosphino)ferrocene]palladium dichloride (12 mg, 0.016 mmol, 0.1 eq). The temperature was raised to 120° C., and the system was reacted for 3 h under nitrogen protection. The completion of the reaction was detected by LC-MS. The reaction solution was filtered, and concentrated. The crude product was purified by silica gel column chromatography (DCM:MeOH=20:1) to give a light yellow solid product (10 mg, yield: 21%).

$^1$HNMR (400 MHz, DMSO-d$_6$) δ (ppm): 11.92 (s, 1H), 8.55 (s, 1H), 7.45 (s, 1H), 3.63 (m, 4H), 2.53 (s, 3H), 1.63 (m, 4H), 0.44 (m, 4H).

Molecular formula: C$_{17}$H$_{18}$N$_4$O Molecular weight: 294.36 LC-MS (Pos, m/z)=295.09 [M+H]$^+$.

Example 46: Synthesis of 6-methoxy-2-oxo-4-(6-azaspiro[2.5]octane-6-yl)-1,2-dihydro-1,7-naphthyridin-3-carbonitrile (Compound 64)

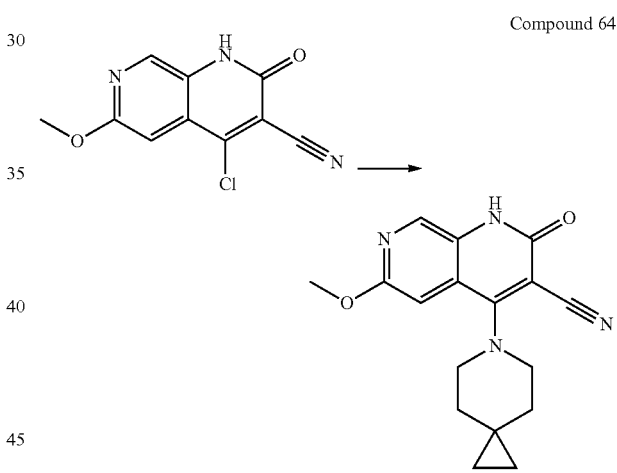

4-chloro-6-methoxy-2-oxo-1,2-dihydro-1,7-naphthyridin-3-carbonitrile (139.4 mg crude product) was dissolved in DMF (2 mL), followed by addition of 6-azaspiro[2.5]octane hydrochloride (122.5 mg, 0.83 mmol) and DIPEA (231.1 mg, 1.78 mmol). The temperature was raised to 80° C., and the system was reacted for 2 h. The completion of the reaction was detected by TLC. The reaction solution was concentrated under reduced pressure, followed by addition of ethyl acetate, washed with water, washed with saturated saline, and dried over anhydrous sodium sulfate. The crude product was purified by preparative thin layer chromatography (DCM:MeOH=20:1) to give a product (2.28 mg, yield: 1.23%).

$^1$HNMR (400 MHz, DMSO-d$_6$) δ (ppm): 11.82 (s, 1H), 8.32 (s, 1H), 6.98 (s, 1H), 3.88 (s, 3H), 3.63-3.61 (t, 4H), 160 (m, 4H), 0.43 (m, 4H).

Molecular formula: C$_{17}$H$_{18}$N$_4$O$_2$ Molecular weight: 310.36 LC-MS (Pos, m/z)=311.1 [M+H]$^+$.

Example 47: Synthesis of 6-methyl-2-oxo-4-(7-azaspiro[3.5]nonane-7-yl)-1,2-dihydro-1,7-naphthyridin-3-carbonitrile (Compound 65)

Compound 65

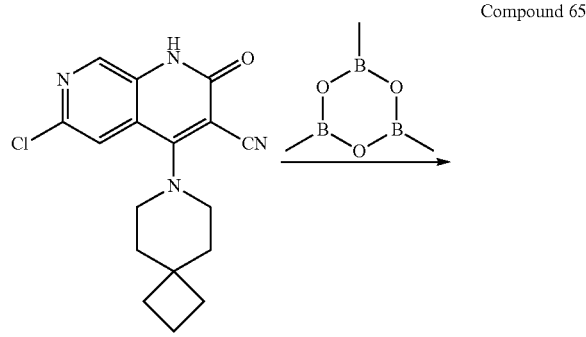

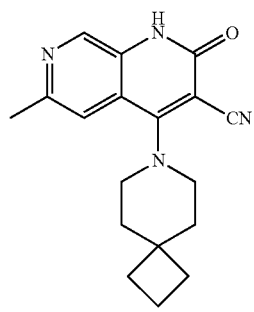

The material 6-chloro-2-oxo-4-(7-azaspiro[3.5]nonane-7-yl)-1,2-dihydro-1,7-naphthyridin-3-carbo nitrile (50 mg, 0.15 mmol, 1.0 eq) and trimethylcyclotriborane (153 mg, 0.61 mmol, 4.0 eq, 50%) were dissolved in 1,4-dioxane (3 mL), followed by addition of cesium carbonate (148 mg, 0.47 mmol, 3.0 eq), potassium phosphate (32 mg, 0.15 mmol, 1.0 eq) and [1,1'-bis(diphenylphosphino)ferrocene] palladium dichloride (11 mg, 0.015 mmol, 0.1 eq). The temperature was raised to 120° C., and the system was reacted for 3 h under nitrogen protection. The completion of the reaction was detected by LC-MS. The reaction solution was filtered and concentrated. The crude product was purified by silica gel column chromatography (DCM: MeOH=20:1) to give a light yellow solid product (15 mg, yield: 32%).

$^1$HNMR (400 MHz, DMSO-d$_6$) δ (ppm): 11.88 (s, 1H), 8.55 (s, 1H), 7.41 (s, 1H), 3.52 (s, 4H), 2.52 (s, 3H), 1.81-1.86 (m, 10H).

Molecular formula: C$_{18}$H$_{20}$N$_4$O Molecular weight: 308.39 LC-MS (Pos, m/z)=309.07 [M+H]$^+$.

Example 48: Synthesis of 6-methoxy-2-oxo-4-(7-azaspiro[3.5]nonane-7-yl)-1,2-dihydro-1,7-naphthyridin-3-carbonitrile (Compound 66)

Step 1: Synthesis of 6-methoxy-2H-pyrido[3,4-][1,3]oxazin-2,4(1H)-dione

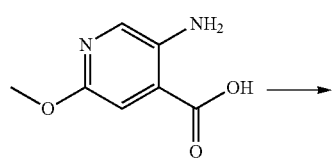

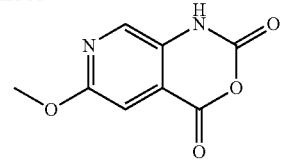

5-amino-2-methoxyisonicotinic acid (500.0 mg, 2.97 mmol) was dissolved in DMF (3.5 mL). The temperature was cooled to 0° C. in ice bath, and CDI (819.7 mg, 5.05 mmol) was added. The temperature was raised to room temperature slowly, and the system was stirred overnight. The completion of the reaction was detected by TLC. The reaction solution was concentrated under reduced pressure to give a product (700.0 mg crude product), which was directly subjected to the next step without purification.

Step 2: Synthesis of 4-hydroxy-6-methoxy-2-oxo-1,2-dihydro-1,7-naphthyridin-3-carbonitrile

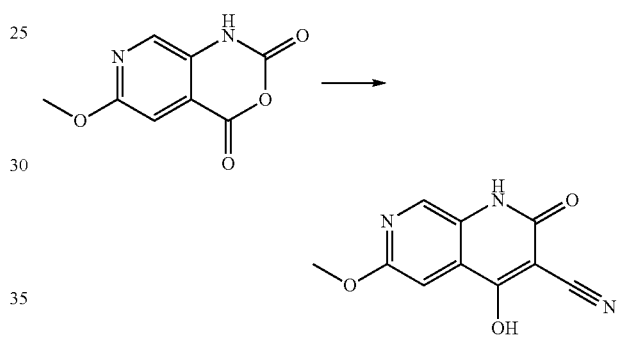

6-methoxy-2H-pyrido[3,4-d][1,3]oxazin-2,4(1H)-dione (576.3 mg crude product) was added to a flask (50 mL), followed by addition of ethyl cyanoacetate (353.0 mg, 3.12 mmol) and triethylamine (601.1 mg, 5.94 mmol), heated to 150° C. and reacted overnight. The completion of the reaction was detected by TLC. The reaction solution was concentrated under reduced pressure, followed by addition of water (10 mL), adjusted to a pH of 1 with hydrochloric acid to precipitate solid, and filtered by suction to give a product (500.0 mg crude product).

Step 3: Synthesis of 2,4-dichloro-6-methoxy-1,7-naphthyridin-3-carbonitrile

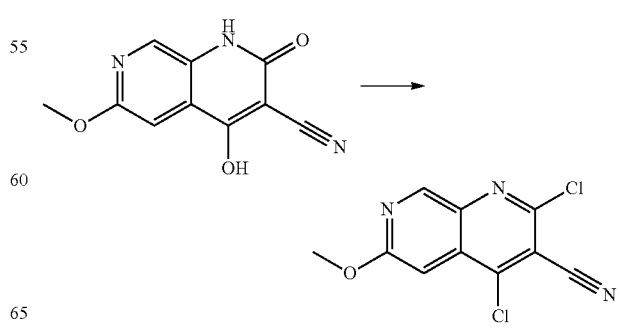

4-hydroxy-6-methoxy-2-oxo-1,2-dihydro-1,7-naphthyridin-3-carbonitrile (420.0 mg crude product) was dissolved in phosphorus oxychloride (1.34 g, 8.73 mmol), followed by addition of phosphopentate (807.9 mg, 3.88 mmol), heated to 100° C. and reacted overnight. The completion of the reaction was detected by LC-MS. The reaction solution was poured into the ice water (15 mL), adjusted to a pH of 1 with saturated aqueous sodium bicarbonate solution, and filtered by suction to give a product (260.0 mg crude product).

Step 4: Synthesis of 4-chloro-6-methoxy-2-oxo-1,2-dihydro-1,7-naphthyridin-3-carbonitrile

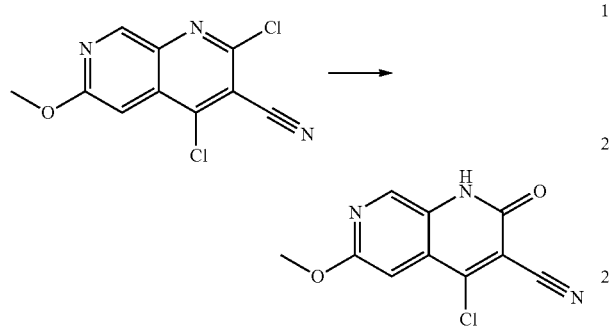

2,4-dichloro-6-methoxy-1,7-naphthyridin-3-carbonitrile (100.0 mg crude product) was dissolved in TFA (2 mL) and water (1 mL), heated to 100° C. and reacted for 2 h. When the reaction was not complete as detected by TLC, TFA (2 mL) was further added, and the system was reacted for 2 h at 100° C. After completion of the reaction detected by TLC, the reaction solution was concentrated under reduced pressure to give a product (50.0 mg crude product), which was directly subjected to the next step without purification.

Step 5: Synthesis of 6-methoxy-2-oxo-4-(7-azaspiro[3.5]nonane-7-yl)-1,2-dihydro-1,7-naphthyridin-3-carbonitrile Compound 66

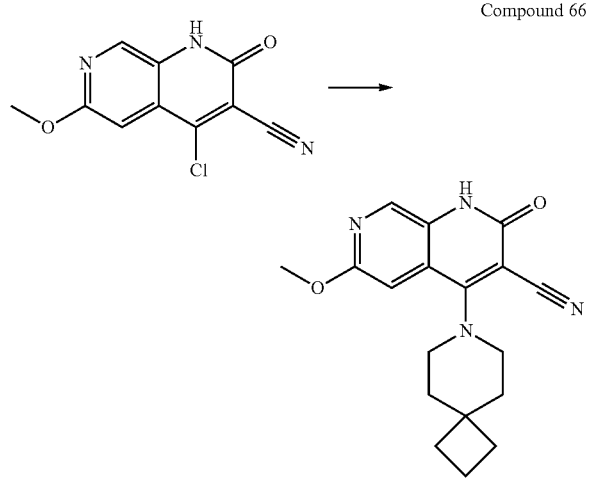

4-chloro-6-methoxy-2-oxo-1,2-dihydro-1,7-naphthyridin-3-carbonitrile (50.0 mg crude product) was dissolved in DMF (2 mL), followed by addition of 7-azaspiro[3.5]nonane hydrochloride (48.2 mg, 0.298 mmol) and DIPEA (83.0 mg, 0.639 mmol), heated to 80° C. and reacted overnight. The completion of the reaction was detected by TLC. The reaction solution was concentrated under reduced pressure. The crude product was purified by silica gel column chromatography (DCM:MeOH=80:1-40:1) to give a product (4.1 mg, yield after the five steps: 0.4%).

¹HNMR (400 MHz, DMSO-d₆) δ (ppm): 11.76 (s, 1H), 8.31 (s, 1H), 6.95 (d, 1H), 3.88 (s, 3H), 3.51-3.50 (t, 4H), 1.93-1.80 (m, 10H).

Molecular formula: $C_{18}H_{20}N_4O_2$ Molecular weight: 324.38 LC-MS (Pos, m/z)=325.1 [M+H]⁺.

Example 49: Synthesis of 6-ethyl-2-oxo-4-(6-azaspiro[2.5]octane-6-yl)-1,2-dihydro-1,7-naphthyridin-3-carbonitrile (Compound 76)

Compound 76

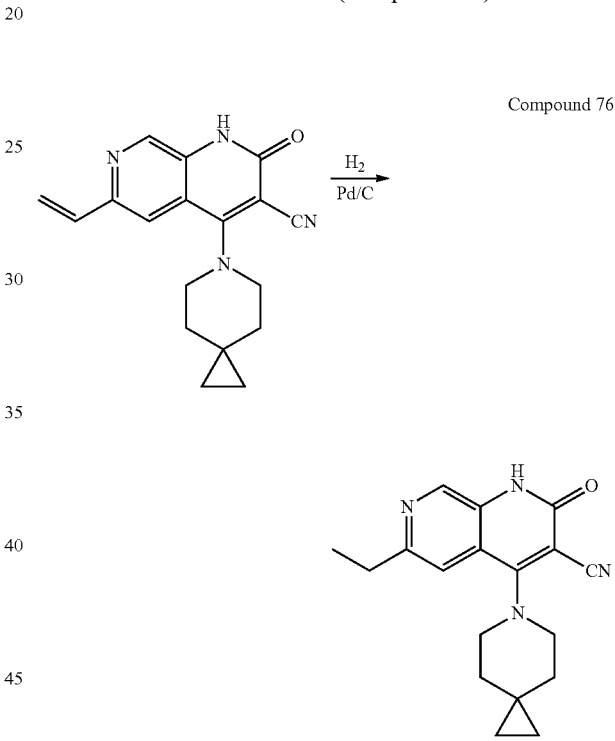

2-oxo-4-(6-azaspiro[2.5]octane-6-yl)-6-vinyl-1,2-dihydro-1,7-naphthyridin-3-carbonitrile (50.0 mg, 0.163 mmol) was dissolved in methanol (10 mL), followed by addition of palladium on carbon (10.0 mg), and stirred for 30 min at the room temperature under hydrogen atmosphere. The completion of the reaction was detected by TLC. The reaction solution was filtered by suction. The filter residue was washed with a small amount of methanol. The filtrate was concentrated under reduced pressure to obtain a product (48.9 mg, yield: 97.2%).

¹HNMR (400 MHz, DMSO-d₆) δ (ppm): 11.94 (s, 1H), 8.60 (s, 1H), 7.44 (s, 1H), 3.65 (t, 4H), 2.85-2.79 (m, 2H), 1.63 (s, 4H), 1.27-1.23 (t, 3H), 0.44 (m, 4H).

Molecular formula: $C_{18}H_{20}N_4O$ Molecular weight: 308.39 LC-MS (Pos, m/z)=309.08 [M+H]⁺.

Example 50: Synthesis of 2-oxo-4-(7-azaspiro[3.5]nonane-7-yl)-1,2-dihydro-1,7-naphthyridin-3,6-dicarbonitrile (Compound 77)

Step 1: Synthesis of 6-((hydroxyimino)methyl)-2-oxo-4-(7-azaspiro[3.5]nonane-7-yl)-1,2-dihydro-1,7-naphthyridin-3-carbonitrile

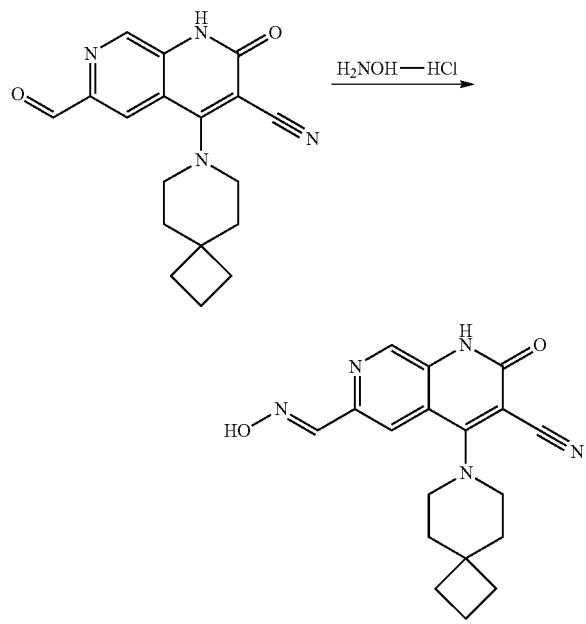

6-formyl-2-oxo-4-(7-azaspiro[3.5]nonane-7-yl)-1,2-dihydro-1,7-naphthyridin-3-carbo nitrile (200 mg, 0.62 mmol, 1.0 eq), hydroxylamine hydrochloride (66 mg, 0.93 mmol, 1.5 eq) and potassium carbonate (112 mg, 0.8 mmol, 1.3 eq) were dissolved in methanol (4.5 mL) and water (1.5 mL), stirred for 2 h at 65° C., cooled, and filtered. The filter cake was washed with water (2 mL×2) to give a white solid product (170 mg, yield: 81.36%).

Step 2: Synthesis of 2-oxo-4-(7-azaspiro[3.5]nonane-7-yl)-1,2-dihydro-1,7-naphthyridin-3,6-dinitrile

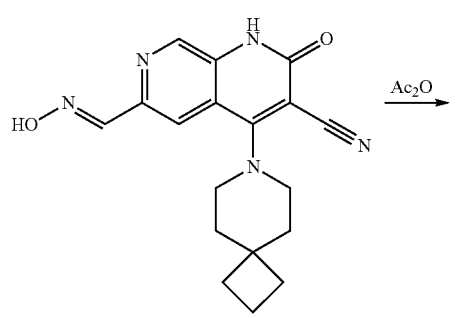

Compound 77

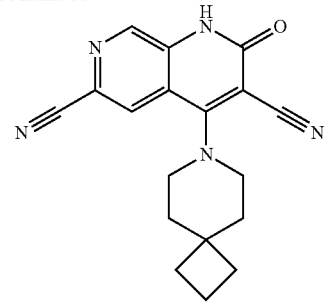

6-((hydroxyimino)methyl)-2-oxo-4-(7-azaspiro[3.5]nonane-7-yl)-1,2-dihydro-1,7-naphthyridin-3-carbonitrile (60 mg, 0.18 mmol, 1.0 eq) was dissolved in acetic anhydride (3 mL), and stirred for 2 h at 120° C. The reaction solution was cooled and filtered to give a yellow solid product (18 mg, yield: 31.3%).

$^1$HNMR (400 MHz, DMSO-$d_6$) δ (ppm): 12.25 (s, 1H), 8.70 (s, 1H), 8.08 (s, 1H), 3.55 (m, 4H), 1.82-1.91 (m, 10H).

Molecular formula: $C_{18}H_{17}N_5O$ Molecular weight: 319.14 LC-MS (Neg, m/z)=318.10 [M−H]⁻.

Example 51: Synthesis of 6-(aminomethyl)-2-oxo-4-(7-azaspiro[3.5]nonane-7-yl)-1,2-dihydro-1,7-naphthyridin-3-carbonitrile trifluoroacetate (Compound 78)

Compound 78

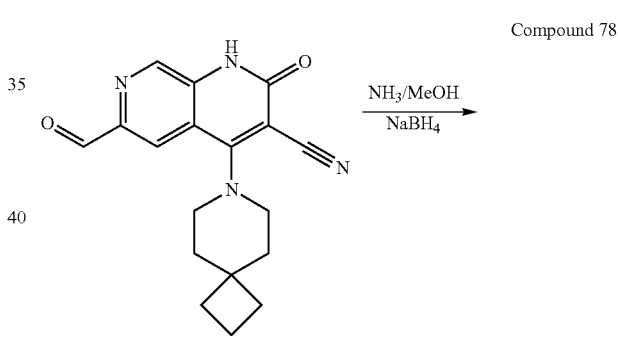

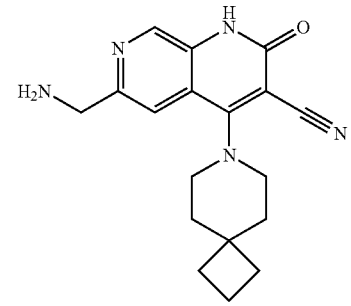

6-formyl-2-oxo-4-(7-azaspiro[3.5]nonane-7-yl)-1,2-dihydro-1,7-naphthyridin-3-carbo nitrile (100 mg, 0.31 mmol, 1.0 eq) and tetraisopropyl titanate (440.2 mg, 1.55 mmol, 5.0 eq) were dissolved in ammonia methanol (10 mL), stirred for 18 h at the room temperature, cooled to 0° C. in ice bath, followed by a slow addition of sodium borohydride (350 mg, 1.24 mmol, 4.0 eq), and stirred for 1 h at room temperature. The completion of the reaction was detected by TLC. Water (1 mL) was added to quench the reaction. The crude product was purified by reversed phase column chromatography (acetonitrile:water:trifluoroacetic acid=30:100:0.05%) to give a yellow solid product (16.27 mg, yield: 16.2%).

$^1$HNMR (400 MHz, DMSO-d$_6$) δ (ppm): 12.09 (s, 1H), 8.67 (s, 1H), 8.29 (brs, 2H), 7.66 (s, 1H), 4.25 (m, 2H), 3.63 (m, 4H), 1.88-1.83 (s, 10H).

Molecular formula: C$_{18}$H$_{21}$N$_5$O Molecular weight: 323.17 LC-MS (Neg, m/z)=324.14 [M−H]$^−$.

Example 52: Synthesis of 6-(methylthio)-2-oxo-4-(6-azaspiro[2.5]octane-6-yl)-1,2-dihydro-1,7-naphthyridin-3-carbonitrile (Compound 79)

Step 1: Synthesis of 4-chloro-6-(methylthio)-2-oxo-1,2-dihydro-1,7-naphthyridin-3-carbonitrile

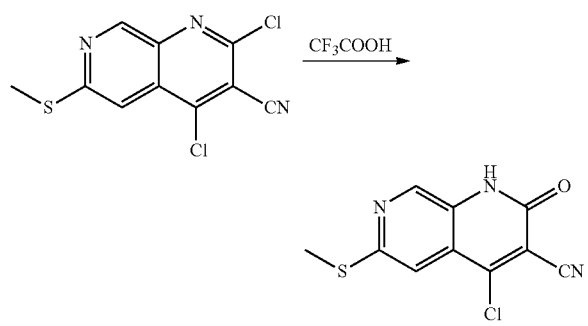

2,4-dichloro-6-(methylthio)-1,7-naphthyridin-3-carbonitrile (180.0 mg, 0.666 mmol) was dissolved in a mixture of trifluoroacetate (4.0 mL) and water (1.0 mL), and stirred for 1 h at 100° C. The completion of the reaction was detected by TLC. The mixture was concentrated under reduced pressure to give a dark red solid (180 mg crude product), which was directly subjected to the next step.

Step 2: Synthesis of 6-(methylthio)-2-oxo-4-(6-azaspiro[2.5]octane-6-yl)-1,2-dihydro-1,7-naphthyridin-3-carbonitrile

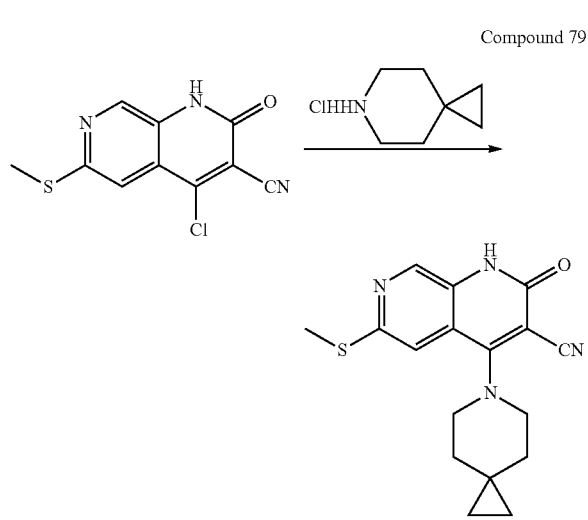

4-chloro-6-(methylthio)-2-oxo-1,2-dihydro-1,7-naphthyridin-3-carbonitrile (167.7 mg, 0.666 mmol, 1.0 eq), 6-azaspiro[2.5]octane hydrochloride (118.1 mg, 0.800 mmol, 1.2 eq) and DIPEA (688.9 mg, 5.331 mmol, 8.0 eq) were dissolved in DMF (5 mL), and stirred for 3 h at 80° C. The completion of the reaction was detected by TLC. The mixture was concentrated under reduced pressure to remove most of DMF, dissolved with dichloromethane (5 mL), and concentrated under reduced pressure. The above process was repeated for 3 times. The crude product was purified by silica gel column chromatography (DCM:MeOH=100:1-60:1) to give a yellow solid product (21.0 mg, yield: 9.66%).

$^1$HNMR (400 MHz, DMSO-d$_6$) δ (ppm): 11.95 (s, 1H), 8.56 (s, 1H), 7.37 (s, 1H), 3.65-3.63 (t, 4H), 2.56 (s, 4H), 1.62 (m, 4H), 0.44 (m, 3H).

Molecular formula: C$_{17}$H$_{18}$N$_4$OS Molecular weight: 326.42 LC-MS (Pos, m/z)=327.20 [M+H]$^+$.

Example 53: Synthesis of 2-oxo-4-(6-azaspiro[2.5]octane-6-yl)-1,2-dihydro-1,5-naphthyridin-3-carbonitrile (Compound 80)

Step 1: Synthesis of 2H-pyrido[3,2-d][1,3]oxazin-2,4(1H)-dione

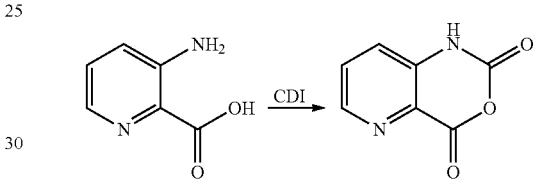

3-aminopicolinic acid (460 mg, 3.3 mmol, 1.0 eq) was dissolved in tetrahydrofuran (8 mL), followed by addition of N,N-carbonyldiimidazole (920 mg, 5.7 mmol, 1.7 eq) in batches in ice bath, stirred at room temperature for 24 h, and filtered. The filtrate was concentrated to give a yellow solid product (235 mg, crude product).

Step 2: Synthesis of 4-hydroxy-2-oxo-1,2-dihydro-1,5-naphthyridin-3-carbonitrile

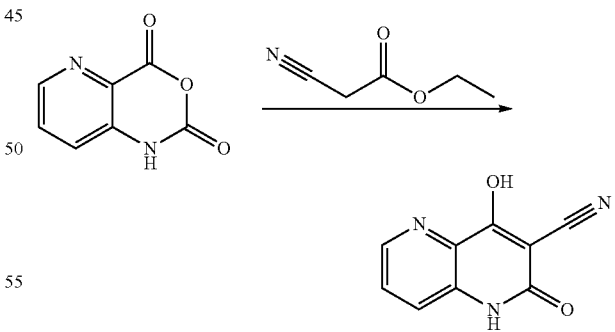

Ethyl cyanoacetate (172 mg, 1.5 mmol, 1.05 eq) was dissolved in tetrahydrofuran (4 mL), followed by addition of sodium hydride (128 mg, 3.2 mmol, 2.2 eq) in batches under ice bath, and refluxed for 30 minutes. 2H-pyrido[3,2-d][1,3]oxazin-2,4-(1H)-dione (235 mg, 1.43 mmol, 1.0 eq) was added under reflux and the reaction was continued for 18 h. The reaction solution was cooled, poured into ice bath, and adjusted to a pH of 3 to 4 until solid was precipitated, and filtered to give a black solid product (130 mg, yield: 48.5%).

Step 3: Synthesis of 4-chloro-2-oxo-1,2-dihydro-1,5-naphthyridin-3-carbonitrile

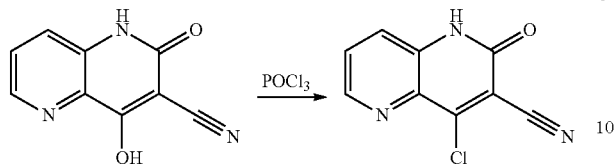

4-hydroxy-2-oxo-1,2-dihydro-1,5-naphthyridin-3-carbonitrile (130 mg, 0.69 mmol, 1.0 eq) was dissolved in phosphorus oxychloride (3 mL) and stirred at 80° C. for 2 h. The reaction solution was cooled, poured into ice bath until black solid was precipitated, and filtered to give a product as a black solid product (60 mg, crude product).

Step 4: Synthesis of 2-oxo-4-(6-azaspiro[2.5]octane-6-yl)-1,2-dihydro-1,5-naphthyridin-3-carbonitrile

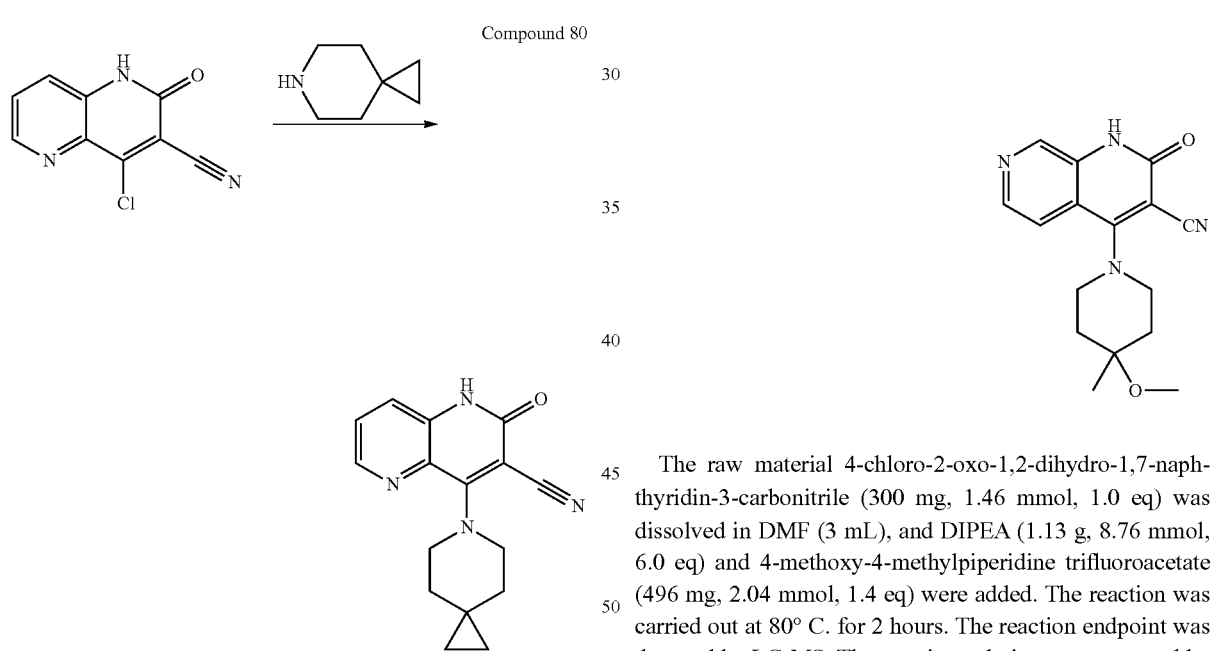

4-chloro-2-oxo-1,2-dihydro-1,5-naphthyridin-3-carbonitrile (38 mg, 0.18 mmol, 1.0 eq) and 6-azaspiro[2.5]octane hydrochloride (30 mg, 0.20 mmol, 1.1 eq) were dissolved in DMF (2 mL), followed by addition of triethylamine (73 mg, 0.72 mmol, 4.0 eq). The reaction solution was heated to 80° C. and stirred for 2 h. The reaction solution is cooled, and purified by reverse phase column chromatography (acetonitrile:water:ammonia solution=30:100:0.05%) to give a product as a white solid product (15.1 mg, yield: 30.0%).

$^1$HNMR (400 MHz, DMSO-d$_6$) δ (ppm): 11.66 (s, 1H), 8.49 (d, J=4 Hz, 1H), 7.67-7.64 (m, 1H), 7.60-7.58 (m, 1H), 3.88 (m, 4H), 1.60 (m, 4H), 0.41 (m, 4H).

Molecular formula: C$_{16}$H$_{16}$N$_4$O Molecular weight: 280.33 LC-MS (Pos, m/z)=281.35 [M−H]$^+$.

Example 54: Synthesis of 4-(4-methoxy-4-methylpiperidin-1-yl)-2-oxo-1,2-dihydro-1,7-naphthyridin-3-carbonitrile (Compound 81)

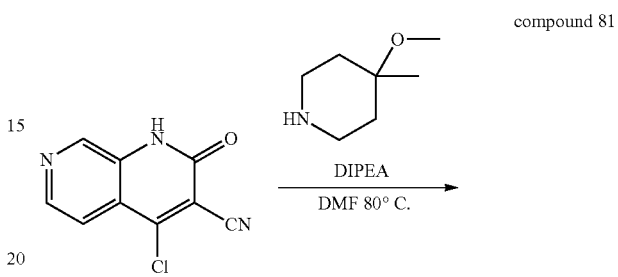

The raw material 4-chloro-2-oxo-1,2-dihydro-1,7-naphthyridin-3-carbonitrile (300 mg, 1.46 mmol, 1.0 eq) was dissolved in DMF (3 mL), and DIPEA (1.13 g, 8.76 mmol, 6.0 eq) and 4-methoxy-4-methylpiperidine trifluoroacetate (496 mg, 2.04 mmol, 1.4 eq) were added. The reaction was carried out at 80° C. for 2 hours. The reaction endpoint was detected by LC-MS. The reaction solution was extracted by adding water (10 mL) and dichloromethane (10 mL×3). The organic phase was washed with water (10 mL×3), dried over anhydrous sodium sulfate, filtered and concentrated under reduced pressure. The crude product was purified by silica gel column chromatography (DCM:MeOH=20:1) to give a product as a yellow solid product (210 mg, yield: 48%).

$^1$HNMR (400 MHz, DMSO-d$_6$) δ (ppm): 11.99 (s, 1H), 8.65 (s, 1H), 8.33-8.34 (d, 1H), 7.61-7.62 (d, 1H), 3.50-3.62 (m, 4H), 3.19 (s, 3H), 1.90-1.92 (d, 2H), 1.77-1.82 (m, 2H), 1.21 (s, 3H).

Molecular formula: C$_{16}$H$_{18}$N$_4$O$_2$ Molecular weight: 298.35 LC-MS (Pos, m/z)=299.14 [M+H]$^+$.

117

Example 55: Synthesis of 6-(2-hydroxypropan-2-yl)-2-oxo-4-(7-azaspiro[3.5]nonane-7-yl)-1,2-dihydro-1,7-naphthyridin-3-carbonitrile (Compound 82)

Step 1: Synthesis of 6-acetyl-2-oxo-4-(7-azaspiro[3.5]nonane-7-yl)-1,2-dihydro-1,7-naphthyridin-3-carbonitrile

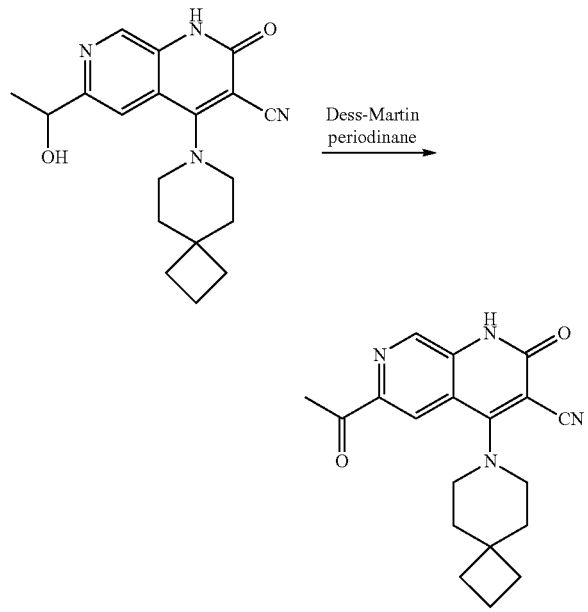

6-(1-hydroxyethyl)-2-oxo-4-(7-azaspiro[3.5]nonane-7-yl)-1,2-dihydro-1,7-naphthyridin-3-carbonitrile (220 mg, 0.65 mmol, 1.0 eq) was dissolved in dichloromethane (4 mL), followed by addition of Dess-Martin oxidizer (552 mg, 1.3 mmol, 2.0 eq) and stirred at room temperature for 18 hours. Water (10 mL) and dichloromethane (30 mL) were added. The organic phase was separated, washed with saturated brine, dried and concentrated. The crude product was purified by silica gel column chromatography (dichloromethane:methanol=30:1) to give a product (170 mg, yield: 77.8%).

Step 2: Synthesis of 6-acetyl-2-oxo-4-(7-azaspiro[3.5]nonane-7-yl)-1,2-dihydro-1,7-naphthyridin-3-carbonitrile compound 82

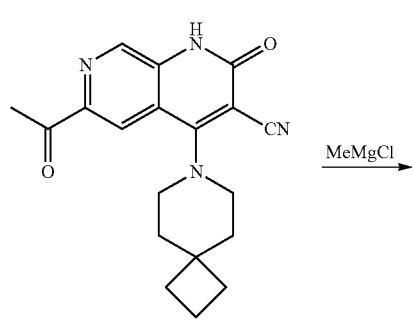

118

-continued

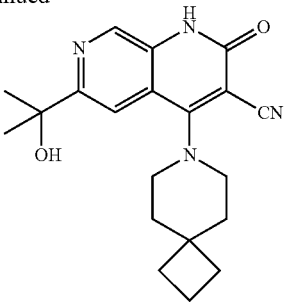

6-acetyl-2-oxo-4-(7-azaspiro[3.5]nonane-7-yl)-1,2-dihydro-1,7-naphthyridin-3-carbonitrile (60 mg, 0.18 mmol, 1.0 eq) was dissolved in tetrahydrofuran (2 mL). Under protection of nitrogen, methylmagnesium chloride (3.0 mol/L tetrahydrofuran solution, 0.12 mL, 0.37 mmol, 2.0 eq) was added at −10° C., and the mixture was warmed to 0° C. and stirred for 2 hours, quenched with saturated aqueous ammonium chloride (5 mL) under ice bath, followed by addition of ethyl acetate (20 mL). After Liquid separation, the organic phase was dried, concentrated. The crude product was purified by silica gel column chromatography (dichloromethane:methanol=60:1) to give a product (17.4 mg, yield: 27.4%).

$^1$H NMR (400 MHz, CDCl$_3$) δ (ppm): 8.74 (s, 1H), 7.73 (s, 1H), 3.65-3.84 (m, 4H), 1.84-2.07 (m, 10H), 1.47-1.77 (m, 6H).

Molecular formula: $C_{20}H_{24}N_4O_2$ Molecular weight: 352.19 LC-MS (Neg, m/z)=351.15 [M−H]$^-$.

Example 56: Synthesis of 3-cyano-2-oxo-4-(6-azaspiro[2.5]octane-6-yl)-1,2-dihydro-1,7-naphthyridin-6-carboxylic acid (Compound 83)

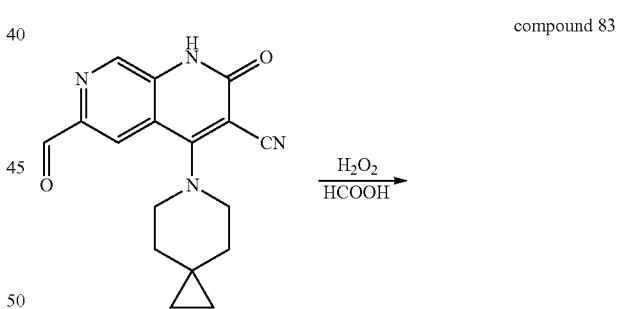

compound 83

6-formyl-2-oxo-4-(6-azaspiro[2.5]octane-6-yl)-1,2-dihydro-1,7-naphthyridin-3-carbo nitrile (92.8 mg, 0.301 mmol, 1.0 eq) was dissolved in formic acid (10 mL) and cooled to 0° C. under ice bath. Hydrogen peroxide (30%, 2.4 mL, 24.08 mmol, 80.0 eq) was added dropwise. After completion of the dropwise addition, the reaction was stirred overnight under ice bath. The reaction endpoint was monitored by TLC. The reaction solution was filtered, and the filter cake was washed with water (3 mL×3), and dried at 40° C. for 2 h to give a yellow solid product (46.6 mg, yield: 47.7%).

$^1$H NMR (400 MHz, DMSO-$d_6$) δ (ppm): 13.24 (s, 1H), 12.32 (s, 1H), 8.70 (s, 1H), 8.34 (s, 1H), 3.68 (t, 4H), 1.63 (s, 4H), 0.46 (s, 4H).

Molecular formula: $C_{17}H_{16}N_4O_3$ Molecular weight: 324.34 LC-MS (Pos, m/z)=325.10 [M+H]$^+$.

Example 57: Synthesis of 6-(2-hydroxypropan-2-yl)-2-oxo-4-(6-azaspiro[2.5]octane-6-yl)-1,2-dihydro-1,7-naphthyridin-3-carbonitrile (Compound 84)

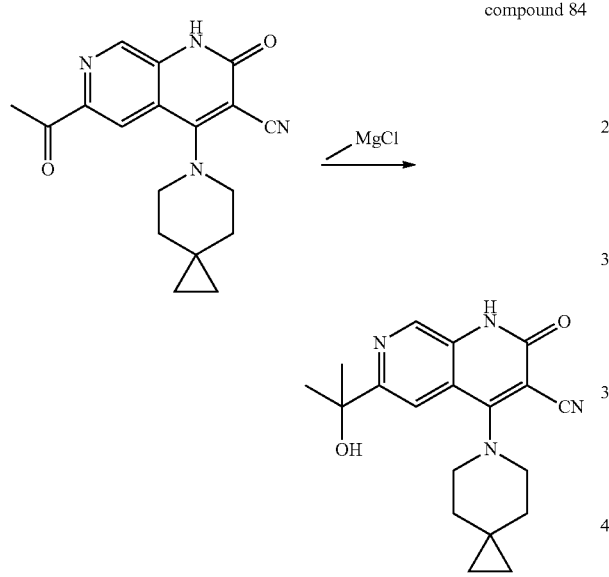

compound 84

6-acetyl-2-oxo-4-(6-azaspiro[2.5]octane-6-yl)-1,2-dihydro-1,7-naphthyridin-3-carbonitrile (277.6 mg, 0.86 mmol, 1.0 eq) was dissolved in anhydrous tetrahydrofuran (20 mL), and was cooled to −10° C. under nitrogen protection. A solution of methylmagnesium chloride in tetrahydrofuran (3 mol/L, 1.2 mL, 3.44 mmol, 4.0 eq) was added dropwise. After completion of the dropwise addition, the mixture was stirred to react for 4 to 5 hours under ice bath (0° C.). The reaction endpoint was monitored by TLC. The reaction was quenched by the addition of saturated aqueous NH$_4$Cl solution (10 mL). The mixture was extracted with dichloromethane (10 mL×3). The organic phase was separated from the reaction, washed with saturated brine (10 mL×2), dried over anhydrous sodium sulfate, filtered by suction, and concentrated under reduced pressure. The crude product was purified by silica gel column chromatography (DCM:MeOH=40:1-15:1) to give a yellow solid product (257.4 mg, yield: 88.3%).

$^1$H NMR (400 MHz, DMSO-$d_6$) δ (ppm): 11.93 (s, 1H), 8.60 (s, 1H), 7.95 (s, 1H), 5.35 (s, 1H), 3.66-3.64 (t, 4H), 1.63 (s, 4H), 1.45 (s, 6H), 0.45 (s, 4H).

Molecular formula: $C_{19}H_{22}N_4O_2$ Molecular weight: 338.41 LC-MS (Pos, m/z)=339.20 [M+H]$^+$ Example 58: Synthesis of 6-(hydroxymethyl)-2-oxo-4-(7-azaspiro[3.5]nonane-7-yl)-1,2-dihydro-1,7-naphthyridin-3-carbonitrile (Compound 85)

Step 1: Synthesis of 6-formyl-2-oxo-4-(7-azaspiro[3.5]nonane-7-yl)-1,2-dihydro-1,7-naphthyridin-3-carbonitrile

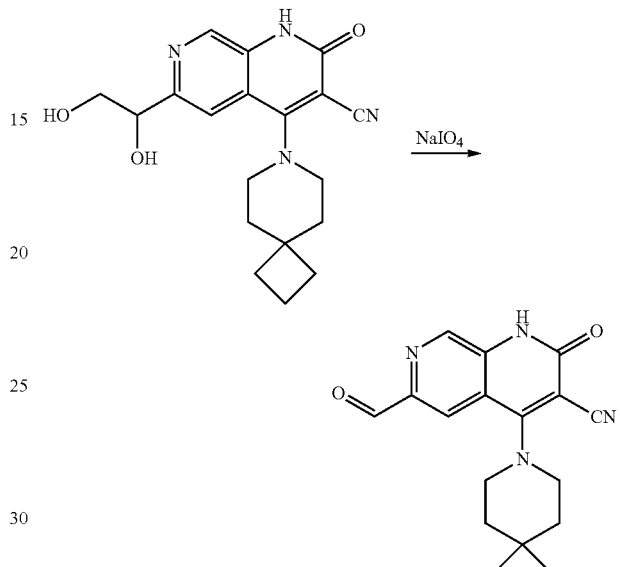

Sodium periodate (1.63 g, 7.6 mmol, 1.0 eq) was dissolved in water (50 mL), followed by addition of tetrahydrofuran (50 mL), cooled to 0° C. under ice bath, followed by a slow addition of 6-(1,2-dihydroxyethyl)-2-oxo-4-(7-azaspiro[3.5]nonane-7-yl)-1,2-dihydro-1,7-naphthyridin-3-carbonitrile (2.7 g, 7.6 mmol, 0.5 eq), and stirred at room temperature for 3 h. The reaction endpoint was monitored by TLC. The mixture was extracted with dichloromethane (100 mL×3). The organic phase was washed with saturated brine (40 mL×2), dried over anhydrous sodium sulfate, filtered by suction, concentrated under reduced pressure to give a product (857.0 mg, yield: 34.89%).

Step 2: Synthesis of 6-(hydroxymethyl)-2-oxo-4-(7-azaspiro[3.5]nonane-7-yl)-1,2-dihydro-1,7-naphthyridin-3-carbonitrile compound 85

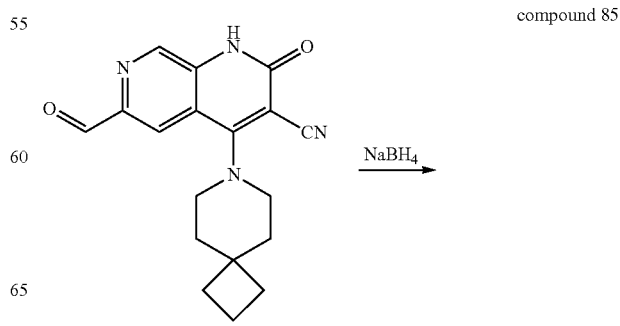

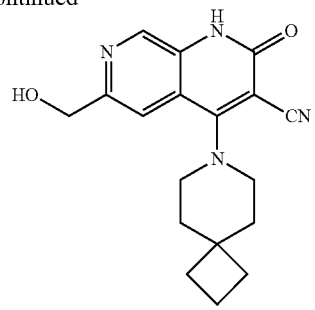

6-formyl-2-oxo-4-(7-azaspiro[3.5]nonane-7-yl)-1,2-dihydro-1,7-naphthyridin-3-carbo nitrile (100.0 mg, 0.324 mmol, 1.0 eq) was dissolved in methanol (15 mL), cooled to 0° C. under ice bath, followed by addition of sodium borohydride (36.8 mg, 0.973 mmol, 3.0 eq) and stirred at room temperature overnight. The reaction endpoint was monitored by TLC, and the reaction was quenched by the addition of H$_2$O (10 mL). The reaction solution was concentrated under reduced pressure, and the crude product was purified by silica gel column chromatography (DCM:MeOH=50:1-20:1) to give a product (96.9 mg, yield: 96.3%).

$^1$H NMR (400 MHz, DMSO-d$_6$) δ (ppm): 11.97 (s, 1H), 8.58 (s, 1H), 7.68 (s, 1H), 5.58-5.55 (m, 1H), 4.60 (d, 2H), 3.66-3.63 (t, 4H), 1.94-1.81 (s, 10H).

Molecular formula: C$_{18}$H$_{20}$N$_4$O$_2$ Molecular weight: 324.16 LC-MS (Neg, m/z)=323.15 [M−H]$^−$.

Example 59: Synthesis of 6-(1-hydroxy-2-methyl-propan-2-yl)-2-oxo-4-(6-azaspiro[2.5]octane-6-yl)-1,2-dihydro-1,7-naphthyridin-3-carbonitrile (Compound 86)

Step 1: Synthesis of 1-(tert-butyl) 3-ethyl-2-(4-(methoxycarbonyl)-5-nitropyridin-2-yl)malonate

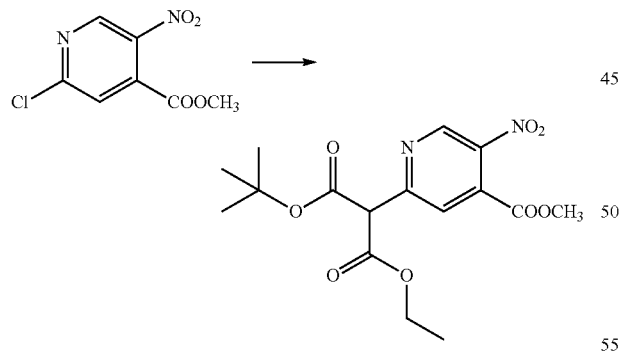

The starting material tert-butyl ethyl malonate (41.7 g, 222 mmol, 1.2 eq) was dissolved in anhydrous DMF (100 mL), cooled to 0° C. under ice bath, stirred for 0.5 h, followed by addition of NaH (14.8 g, 370 mmol, 2 eq), stirred for 0.5 h, then followed by a slow addition of methyl 2-chloro-5-nitroisonicotinate (40.0 g, 185 mmol, 1.0 eq) and stirred at room temperature for 5 h. The reaction endpoint was monitored by TLC, and the reaction was quenched by the addition of H$_2$O at 0° C. The reaction solution was concentrated and extracted with EA (3×500 mL). The organic phase was dried over anhydrous sodium sulfate, filtered by suction, and the filtrate was concentrated under reduced pressure. The crude product was purified by silica gel column chromatography (PE:EA=10:1) to give a product (35 g, yield: 51.4%).

Step 2: Synthesis of methyl 2-(2-ethoxy-2-oxoethyl)-5-nitroisonicotinate

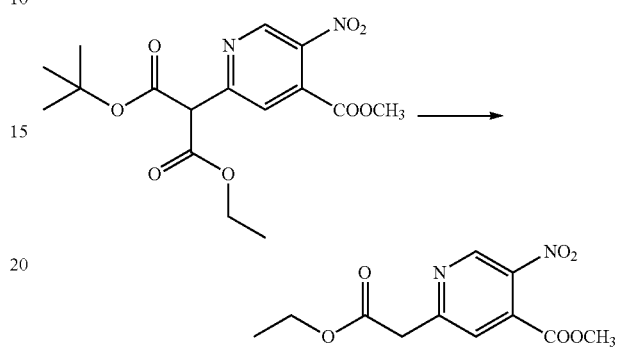

Intermediate 1-(tert-butyl) 3-ethyl-2-(4-(methoxycarbonyl)-5-nitropyridin-2-yl)malonate (36.0 g, 97.8 mmol, 1.0 eq) was dissolved in trifluoroacetic acid (55.7 g, 0.5 mol, 5 eq) at 0° C., stirred at room temperature for 0.5 h, and the reaction endpoint was monitored by TLC. Saturated aqueous sodium bicarbonate solution was added dropwise at 0° C., and stirred for 0.5 h, extracted with EA (3×500 mL). The organic phase was dried over anhydrous sodium sulfate, filtered by suction, and the filtrate was concentrated under reduced pressure. The crude product was purified by silica gel column chromatography (PE:EA=10:1) to give a product (23 g, yield: 87.7%).

Step 3: Synthesis of methyl 2-(1-ethoxy-2-methyl-1-oxopropan-2-yl)-5-nitroisonicotinate

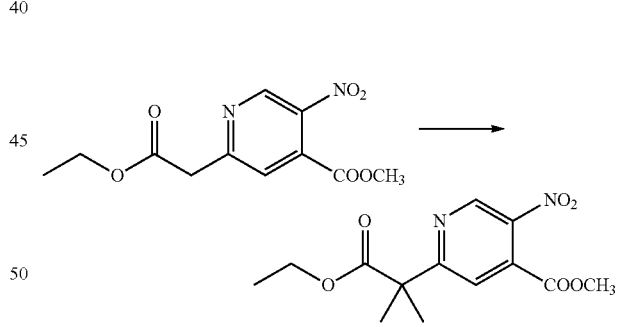

The intermediate methyl 2-(2-ethoxy-2-oxoethyl)-5-nitroisonicotinate (10.7 g, 40.2 mmol, 1.0 eq) was dissolved in DMF (100 mL), stirred at 0° C. for 0.5 h, followed by addition of NaH (1.1 g, 44.2 mmol, 1.1 eq), slowly warmed to room temperature, stirred for 0.5 h, then cooled to 0° C., followed by a slow dropwise addition of CH$_3$I (6.2 g, 44.2 mmol, 1.1 eq), warmed to room temperature and stirred for 1 h. The completion of reaction of starting materials was monitored by TLC, and the temperature was cooled to 0° C. The above operation was repeated. The reaction endpoint was monitored by LC-MS. The reaction was quenched by the addition of H$_2$O at 0° C. The reaction solution was stirred for 0.5 h, concentrated and extracted with EA (3×100 mL). The organic phase was dried over anhydrous sodium sulfate, filtered by suction, and the filtrate was concentrated under reduced pressure. The crude product was purified by silica gel column chromatography (PE:EA=10:1) to give a product (5.3 g, yield: 44.5%).

Step 4: Synthesis of methyl 5-amino-2-(1-ethoxy-2-methyl-1-oxopropan-2-yl)isonicotinate

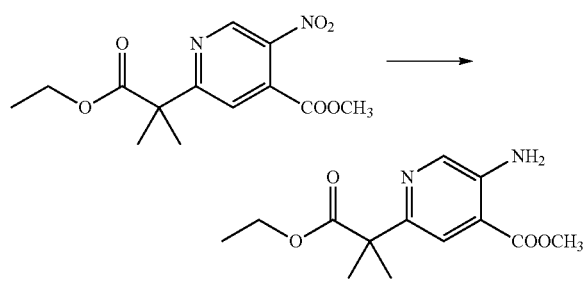

The intermediate methyl 2-(1-ethoxy-2-methyl-1-oxopropan-2-yl)-5-nitroisonicotinate (5.0 g, 16.9 mmol, 1.0 eq) was dissolved in methanol (30 mL), and palladium on carbon (500.0 mg) was added thereto. The atmosphere of the system was replaced by hydrogen and the reaction was carried out at room temperature. The reaction endpoint was monitored by LC-MS. The reaction solution was filtered with celite. The filtrate was concentrated, followed by addition of ethyl acetate (30 mL), dried over anhydrous sodium sulfate, filtered by suction, and the filtrate was concentrated under reduced pressure to give a product (4.3 g, yield: 95.6%).

Step 5: Synthesis of methyl 5-(2-cyanoacetamido)-2-(1-ethoxy-2-methyl-1-oxopropan-2-yl)isonicotinate

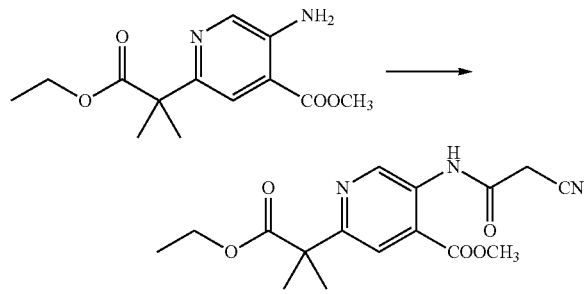

The intermediate methyl 5-amino-2-(1-ethoxy-2-methyl-1-oxopropan-2-yl)isonicotinate (4.0 g, 15.0 mmol, 1.0 eq) and cyanoacetic acid (2.6 g, 30.0 mmol, 2.0 eq) were dissolved in DMF (20 mL), followed by addition of EDCI (8.6 g, 45.0 mmol, 3.0 eq) at 0° C. and reacted at room temperature. The reaction endpoint was monitored by LC-MS. The reaction solution was concentrated, followed by addition of water, and extracted with EA (3×100 mL). The organic phase was dried over anhydrous sodium sulfate, filtered by suction, and the filtrate was concentrated under reduced pressure. The crude product was purified by silica gel column chromatography (PE:EA=2:1) to give a product (3.4 g, yield: 68.1%).

Step 6: Synthesis of Ethyl 2-(3-cyano-4-hydroxy-2-oxo-1,2-dihydro-1,7-naphthyridin-6-yl)-2-methyl-propionate

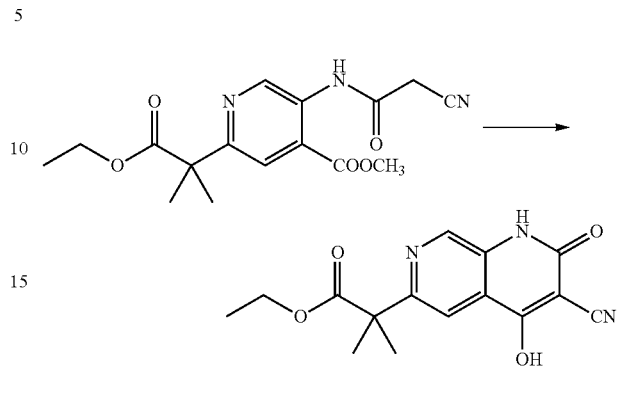

The intermediate methyl 5-(2-cyanoacetamido)-2-(1-ethoxy-2-methyl-1-oxopropan-2-yl)isonicotinate (4.0 g. 12.0 mmol, 1.0 eq) and sodium ethoxide (1.8 g, 26.4 mmol, 2.2 eq) were added sequentially to ethanol (30 mL) at 0° C. and stirred at room temperature. The reaction endpoint was monitored by LC-MS. The above reaction solution was added dropwise to ice water (150 mL), adjusted to a pH of 2 until a large amount of solid was precipitated, then filtered, and the filter cake was dried to give a product (3.4 g, yield: 94.1%).

Step 7: Synthesis of ethyl 2-(4-chloro-3-cyano-2-oxo-1,2-dihydro-1,7-naphthyridin-6-yl)-2-methyl propionate

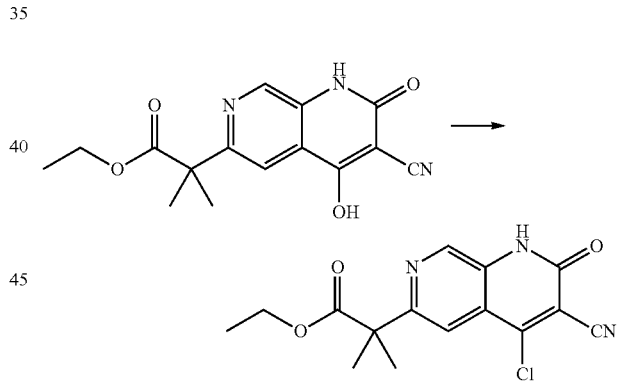

The intermediate methyl 2-(3-cyano-4-hydroxy-2-oxo-1,2-dihydro-1,7-naphthyridin-6-yl)-2-methylpropionate (2.0 g, 6.6 mmol, 1.0 eq) was dissolved in phosphorus oxychloride (5 mL) at 0° C., reacted at 100° C. for 0.5 h. The reaction endpoint was monitored by LC-MS, and the temperature was cooled to 0° C. The reaction solution was quenched by slowly adding water, and extracted with EA (3×80 mL). The organic phases were combined, dried over anhydrous sodium sulfate, filtered, and concentrated. Trifluoroacetic acid (3 mL) was added to the crude product, and heated to reflux. The complete reaction of the dichloro substituted product was monitored by LC-MS. The temperature was cooled to 0° C. Water was added dropwise slowly to the reaction solution. The mixture was extracted with EA (3×20 mL). The organic phases were combined, dried with anhydrous sodium sulfate, filtered, and concentrated to give a product (1.3 g, yield: 61.7%).

Step 8: Synthesis of ethyl 2-(3-cyano-2-oxo-4-(6-azaspiro[2.5]octane-6-yl)-1,2-dihydro-1,7-naphthyridin-6-yl)-2-methylpropionate

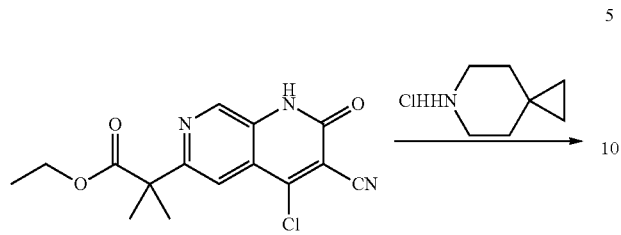

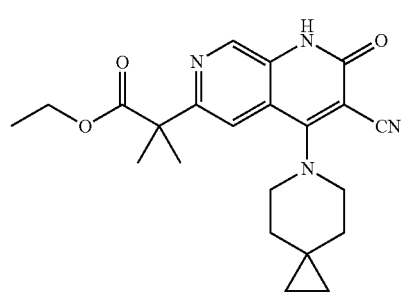

The intermediate ethyl 2-(4-chloro-3-cyano-2-oxo-1,2-dihydro-1,7-naphthyridin-6-yl)-2-methylpropionate (800.0 mg, 2.5 mmol, 1.0 eq) was dissolved in DMF (5 mL), and followed by addition of 6-azaspiro[2.5]octane hydrochloride (404.2 mg, 2.75 mmol, 1.1 eq) and DIPEA (1.9 g, 15.0 mmol, 6.0 eq) sequentially, and reacted at 80° C. for 0.5 h. The reaction endpoint was monitored by TLC. The reaction solution was concentrated, followed by addition of water, and extracted with EA (3×60 mL). The organic phases were combined, dried with anhydrous sodium sulfate, filtered and concentrated. The crude product was purified by silica gel column chromatography (PE:EA=3:2) to give a product (500.0 mg, yield: 50.7%).

Step 9: Synthesis of 6-(1-hydroxy-2-methylpropan-2-yl)-2-oxo-4-(6-azaspiro[2.5]octane-6-yl)-1,2-dihydro-1,7-naphthyridin-3-carbonitrile Compound 86

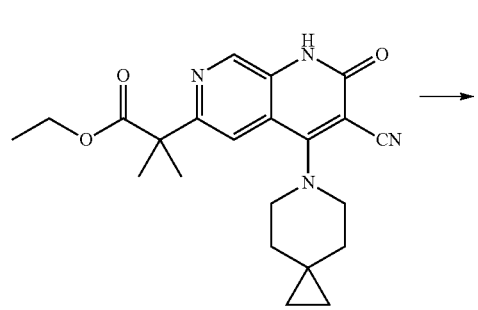

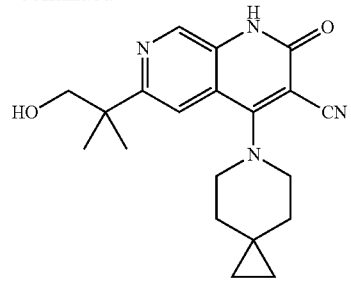

The intermediate ethyl 2-(3-cyano-2-oxo-4-(6-azaspiro [2.5]octane-6-yl)-1,2-dihydro-1,7-naphthyridin-6-yl)-2-methylpropionate (400.0 mg, 1.01 mmol, 1.0 eq) was dissolved in anhydrous 2-methyltetrahydrofuran (5 mL), added dropwise with DIBAL-H (1.5 mol/L toluene solution, 3.4 mL, 5.05 mmol, 5.0 eq) at −60° C. under nitrogen protection, then gradually warmed to room temperature and stirred for 6 h, quenched by dropwise adding water at 0° C., concentrated, and extracted with EA (3×60 mL). The organic phases were combined, dried with anhydrous sodium sulfate, filtered and concentrated. The crude product was purified by silica gel column chromatography (PE:EA=3:2) to give a yellow solid product (150.0 mg, yield: 42.2%).

$^1$H NMR (400 MHz, DMSO-$d_6$) δ (ppm): 11.93 (s, 1H), 8.64 (s, 1H), 7.58 (s, 1H), 4.65 (t, 1H), 3.63-3.66 (m, 4H), 3.53 (d, 2H), 1.63 (s, 4H), 1.28 (s, 6H), 0.45 (s, 4H).

Molecular formula: $C_{20}H_{24}N_4O_2$ Molecular weight: 352.44 LC-MS (Pos, m/z)=353 [M+H]$^+$.

Example 60: Synthesis of 6-(1-hydroxyethyl)-2-oxo-4-(6-azaspiro[2.5]octane-6-yl)-1,2-dihydro-1,7-naphthyridin-3-carbonitrile (Compound 87)

Step 1: Synthesis of 6-formyl-2-oxo-4-(6-azaspiro[2.5]octane-6-yl)-1,2-dihydro-1,7-naphthyridin-3-carbonitrile

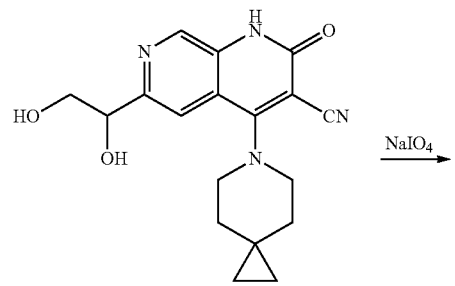

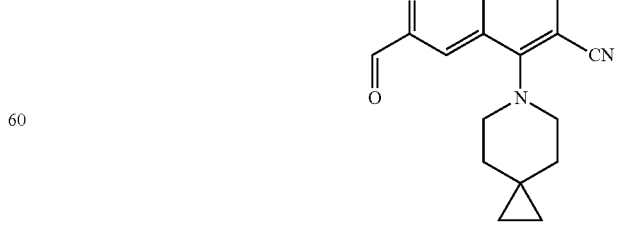

Sodium periodate (4.00 g, 18.70 mmol, 2.0 eq) was dissolved in water (10 mL), followed by addition of tetrahydrofuran (100 mL), cooled to 0° C. in ice bath, followed by a slow addition of 6-(1,2-dihydroxyethyl)-2-oxo-4-(6-azaspiro[2.5]octane-6-yl)-1,2-dihydro-1,7-naphthyridin-3-carbonitrile (3.18 g, 9.35 mmol, 1.0 eq), and stirred at room temperature for 3 h. The reaction endpoint was monitored by TLC, and the reaction solution was extracted with dichloromethane (20 mL×3). The organic phase was washed with saturated brine (20 mL×2) and dried over anhydrous sodium sulfate, and filtered by suction, then the filtrate was concentrated under reduced pressure to give a yellow solid product (1.50 g, yield: 52.0%).

Step 2: synthesis of 6-(1-hydroxyethyl)-2-oxo-4-(6-azaspiro[2.5]octane-6-yl)-1,2-dihydro-1,7-naphthyridin-3-carbonitrile

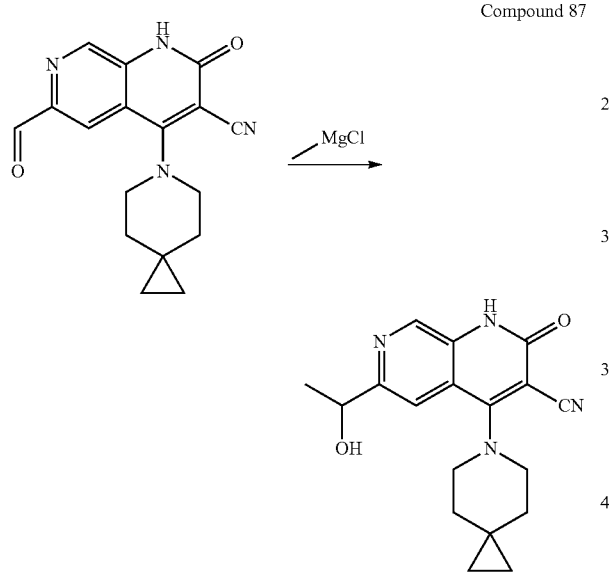

6-formyl-2-oxo-4-(6-azaspiro[2.5]octane-6-yl)-1,2-dihydro-1,7-naphthyridin-3-carbonitrile (1.00 g, 3.24 mmol, 1.0 eq) was dissolved in anhydrous tetrahydrofuran (50 mL), cooled to −10° C. under nitrogen protection, followed by a dropwise addition of a solution of methyl magnesium chloride in tetrahydrofuran (3 mol/L, 4.3 mL, 12.97 mmol, 4.0 eq), and then stirred to react for 4 to 5 hours in ice bath. The reaction endpoint was monitored by TLC. The reaction solution was quenched by the addition of a saturated aqueous NH₄Cl solution (20 mL), and extracted with dichloromethane (20 mL×3). The organic phase was washed with saturated brine (20 mL×2), dried with anhydrous sodium sulfate, filtered by suction, and the filtrate was concentrated under reduced pressure. The crude product was purified by silica gel column chromatography (DCM:MeOH=40:1-15:1) to give a yellow solid product (0.95 g, yield: 90.4%).

¹H NMR (400 MHz, DMSO-d₆) δ (ppm): 11.96 (s, 1H), 8.59 (s, 1H), 7.78 (s, 1H), 5.50-5.49 (d, 1H), 4.81-4.77 (m, 1H), 3.65 (s, 4H), 1.63 (s, 4H), 1.40-1.38 (d, 3H), 0.45 (s, 4H).

Molecular formula: $C_{18}H_{20}N_4O_2$ Molecular weight: 324.38 LC-MS (Pos, m/z)=325.10 [M+H]⁺.

Example 61: Synthesis of 6-(cyclopropyl (hydroxy) methyl)-2-oxo-4-(6-azaspiro[2.5]octane-6-yl)-1,2-dihydro-1,7-naphthyridin-3-carbonitrile (Compound 90)

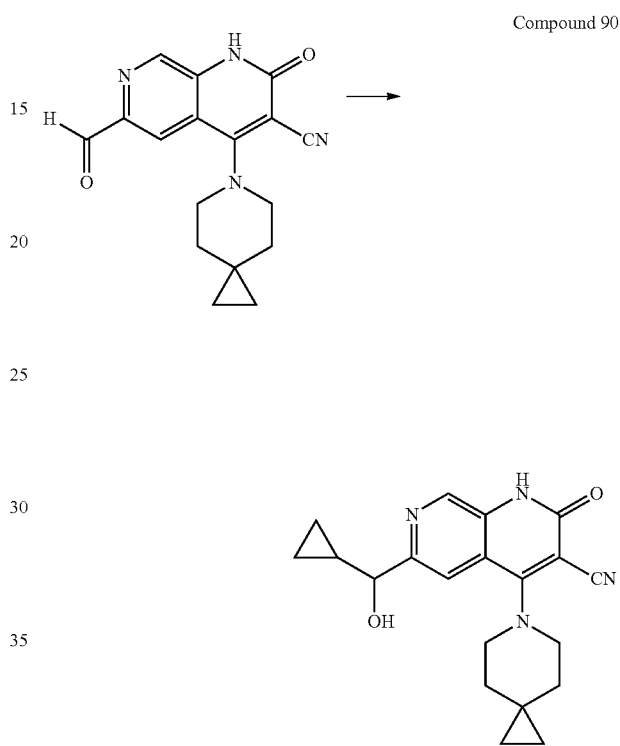

The intermediate 6-formyl-2-oxo-4-(6-azaspiro[2.5]octane-6-yl)-1,2-dihydro-1,7-naphthyridin-3-carbonitrile (200.0 mg, 0.65 mmol, 1.0 eq) was dissolved in dry THF (5 mL), and cyclopropylmagnesium bromide (1.95 mL, 1.95 mmol, 3.0 eq) was added to the above reaction solution at −10° C. under nitrogen protection. The reaction was slowly warmed to 0° C. and stirred for 1 h. After completion of the reaction, the reaction solution was quenched by the addition of a saturated aqueous ammonium chloride solution, concentrated, and extracted with ethyl acetate (3×30 mL). The organic phases were combined and dried with anhydrous sodium sulfate, filtered and concentrated. The crude product was purified by silica gel column chromatography (DCE:MeOH=100:1-75:1) to give an off-white solid product (92 mg, yield: 40.4%).

¹H NMR (400 MHz, DMSO-d₆) δ (ppm): 11.96 (br, 1H), 8.60 (s, 1H), 7.74 (s, 1H), 5.44 (s, 1H), 4.24-4.27 (m, 1H), 3.65 (t, 4H), 1.63 (s, 4H), 1.12-1.18 (m, 1H), 0.45 (s, 4H), 0.40-0.43 (m, 4H).

Molecular formula: $C_{20}H_{22}N_4O_2$ Molecular weight: 350.42 LC-MS (m/z)=351 [M+H]⁺.

Example 62: Synthesis of Intermediate 4-methoxy-4-methylpiperidine Trifluoroacetate

Step 1: Synthesis of Tert-Butyl 4-hydroxy-4-methylpiperidin-1-carboxylate

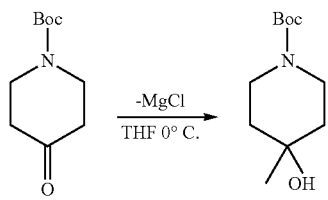

The raw material tert-butyl 4-oxopiperidin-1-carboxylate (5.0 g, 25 mmol, 1.0 eq) was dissolved in tetrahydrofuran (25 mL) and followed by addition of methylmagnesium chloride reagent (9 mL, 27 mmol, 1.1 eq) at 0° C. under nitrogen atmosphere. After 2 hours of reaction, the reaction endpoint was monitored by TLC. The reaction solution was adjusted to a pH of 4 by adding diluted hydrochloric acid, then followed by addition of water (30 mL) and extracted with ethyl acetate (30 mL×3). The organic phase was dried, filtered and concentrated under reduced pressure, and the crude product was purified by silica gel column chromatography (PE:EA=5:1) to give a product (5.2 g, yield: 96%).

Step 2: Synthesis of Tert-Butyl 4-methoxy-4-methylpiperidin-1-carboxylate

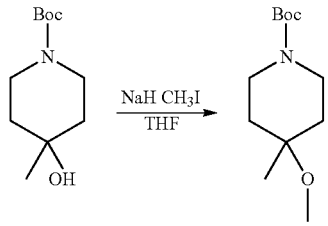

The intermediate tert-butyl 4-hydroxy-4-methylpiperidin-1-carboxylate (500 mg, 2.32 mmol, 1.0 eq) was dissolved in tetrahydrofuran (5 mL), followed by addition of sodium hydrogen (186 mg, 4.64 mmol, 2.0 eq) to react for 1 h, and followed by addition of iodomethane (659 mg, 4.64 mmol, 2.0 eq) to react for 8 h. The reaction endpoint was monitored by TLC. Water (10 mL) was added to the reaction flask and the reaction solution was extracted with ethyl acetate (20 mL×3). The organic phase was dried, filtered and concentrated under reduced pressure, and the crude product was purified by silica gel column chromatography (PE:EA=20:1) to give a product (306 mg, yield: 57%).

Step 3: Synthesis of 4-methoxy-4-methylpiperidine Trifluoroacetate

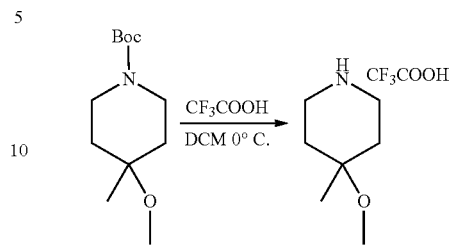

The intermediate tert-butyl 4-methoxy-4-methylpiperidin-1-carboxylate (500 mg, 2.18 mmol, 1.0 eq) was dissolved in dichloromethane (4 mL), followed by addition of trifluoroacetic acid (3 mL) at 0° C., and reacted for 1 h. The reaction endpoint was monitored by TLC, and the reaction solution was concentrated under reduced pressure to give a product (530 mg, yield: 100%).

Example 63: Synthesis of 6-(1-hydroxyprop-2-yn-1-yl)-2-oxo-4-(6-azaspiro[2.5]octane-6-yl)-1,2-dihydro-1,7-naphthyridin-3-carbonitrile (Compound 91)

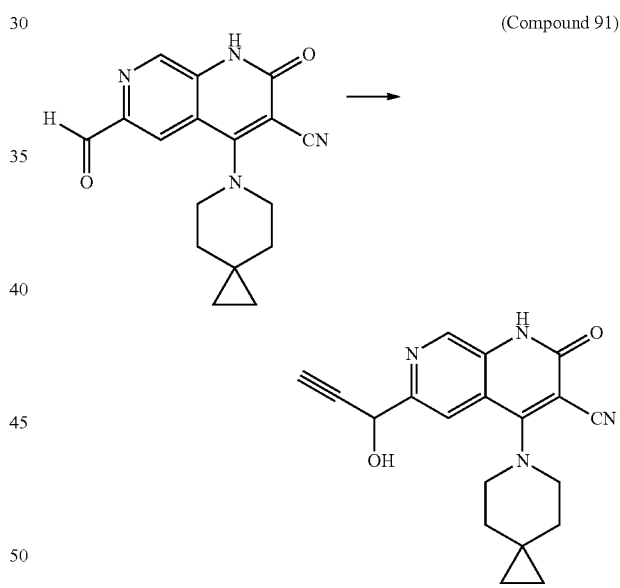

The intermediate 6-formyl-2-oxo-4-(6-azaspiro[2.5]octane-6-yl)-1,2-dihydro-1,7-naphthyridin-3-acetonitrile (200.0 mg, 0.65 mmol, 1.0 eq) was dissolved in anhydrous THF (5 mL), and ethynyl magnesium bromide (6.48 mL, 3.25 mmol, 5.0 eq) was added to the above reaction solution under nitrogen protection at −10° C. The reaction solution was slowly warmed to 0° C. and stirred for 1 h. After completion of the reaction, the solution was quenched by the addition of a saturated aqueous ammonium chloride solution, concentrated, and extracted with ethyl acetate (3×30 mL). The organic phases were combined, dried over anhydrous sodium sulfate, filtered and concentrated, and the crude product was purified by silica gel column chromatography (DCE:MeOH=100:1-75:1) to give a white solid product (40 mg, yield: 18.4%).

¹H NMR (400 MHz, DMSO-d₆) δ (ppm): 12.05 (brs, 1H), 8.61 (s, 1H), 7.86 (s, 1H), 6.36 (d, 1H), 5.39-5.42 (m, 1H), 3.64 (s, 4H), 3.51 (d, 1H), 1.64 (s, 4H), 0.45 (m, 4H).

Molecular formula: $C_{19}H_{18}N_4O_2$ Molecular weight: 334.38 LC-MS (m/z)=335 [M+H]⁺.

Example 64: Synthesis of 2-oxo-4-(6-azaspiro[2.5]octane-6-yl)-6-(2,2,2-trifluoro-1-hydroxyethyl)-1,2-dihydro-1,7-naphthyridin-3-carbonitrile (Compound 92)

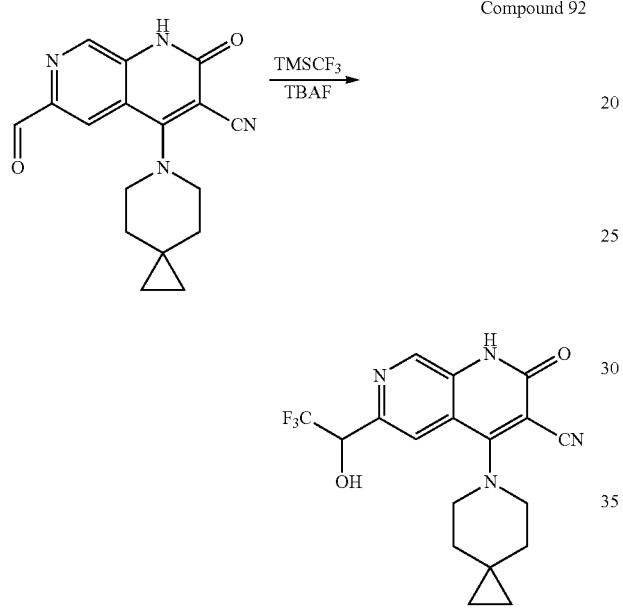

6-formyl-2-oxo-4-(6-azaspiro[2.5]octane-6-yl)-1,2-dihydro-1,7-naphthyridin-3-carbo nitrile (300 mg, 0.973 mmol, 1.0 eq) was dissolved in anhydrous N,N-dimethylacetamide (20 mL), cooled to −10° C. under nitrogen atmosphere, followed by addition of TMSCF₃ (1.44 mL, 9.730 mmol, 10.0 eq), added dropwise with anhydrous TBAF in tetrahydrofuran (0.96 mL, 0.96 mmol), and then stirred at −10° C. to react overnight. The reaction endpoint was monitored by TLC. The reaction solution was followed by addition of dichloromethane (20 mL), washed with saturated brine (20 mL×2) and water (20 mL×4), dried over anhydrous magnesium sulfate, filtered by suction and concentrated under reduced pressure. The crude product was purified by silica gel column chromatography (DCE:MeOH=30:1-15:1) to give a yellow solid product (116 mg, yield: 31.5%).

¹H NMR (400 MHz, DMSO-d₆) δ (ppm): 12.11 (s, 1H), 8.65 (s, 1H), 7.87 (s, 1H), 7.13-7.12 (d, 1H), 5.24-5.22 (t, 1H), 3.64 (s, 4H), 1.63 (s, 4H), 0.45 (s, 4H).

Molecular formula: $C_{18}H_{17}F_3N_4O_2$ Molecular weight: 378.36 LC-MS (Pos, m/z)=379.20 [M+H]⁺.

Example 65: Synthesis of ethyl 1-(3-cyano-2-oxo-4-(6-azaspiro[2.5]octane-6-yl)-1,2-dihydro-1,7-naphthyridin-6-yl) Acetate (Compound 93)

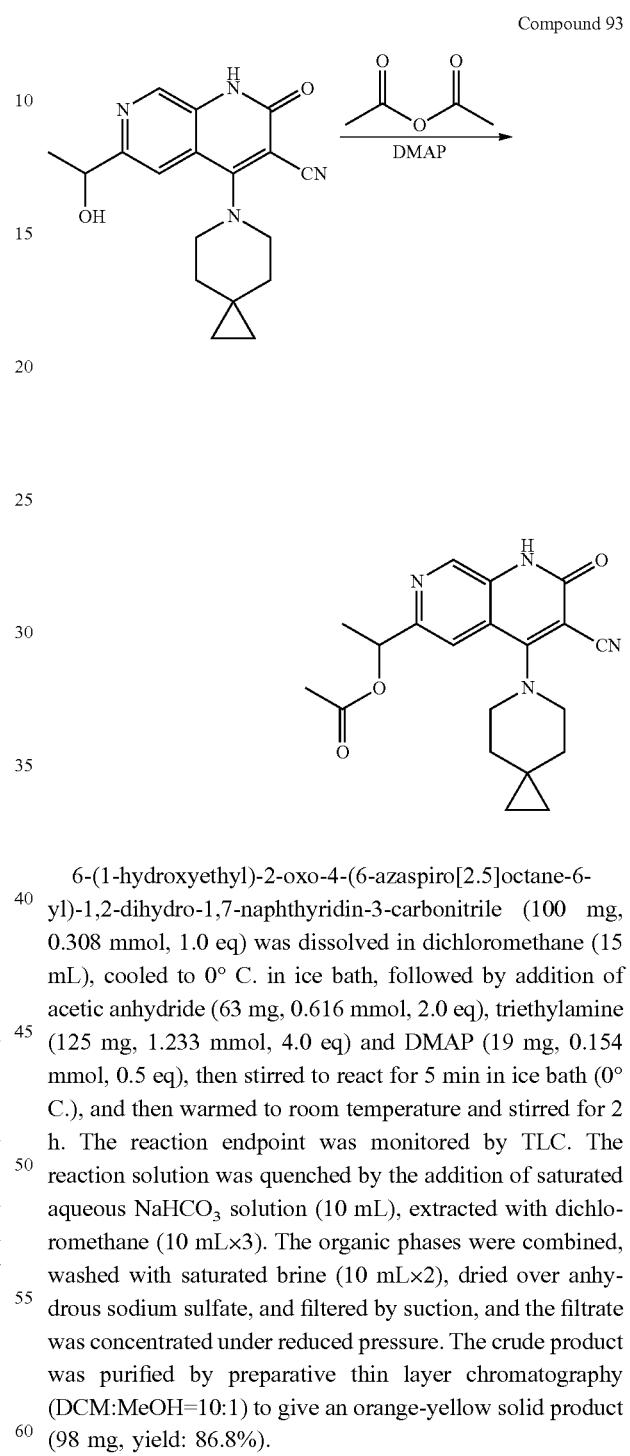

6-(1-hydroxyethyl)-2-oxo-4-(6-azaspiro[2.5]octane-6-yl)-1,2-dihydro-1,7-naphthyridin-3-carbonitrile (100 mg, 0.308 mmol, 1.0 eq) was dissolved in dichloromethane (15 mL), cooled to 0° C. in ice bath, followed by addition of acetic anhydride (63 mg, 0.616 mmol, 2.0 eq), triethylamine (125 mg, 1.233 mmol, 4.0 eq) and DMAP (19 mg, 0.154 mmol, 0.5 eq), then stirred to react for 5 min in ice bath (0° C.), and then warmed to room temperature and stirred for 2 h. The reaction endpoint was monitored by TLC. The reaction solution was quenched by the addition of saturated aqueous NaHCO₃ solution (10 mL), extracted with dichloromethane (10 mL×3). The organic phases were combined, washed with saturated brine (10 mL×2), dried over anhydrous sodium sulfate, and filtered by suction, and the filtrate was concentrated under reduced pressure. The crude product was purified by preparative thin layer chromatography (DCM:MeOH=10:1) to give an orange-yellow solid product (98 mg, yield: 86.8%).

¹H NMR (400 MHz, DMSO-d₆) δ (ppm): 12.05 (s, 1H), 8.64 (s, 1H), 7.62 (s, 1H), 5.90-5.85 (q, 1H), 3.64 (s, 4H), 2.06 (s, 3H), 1.64 (s, 4H), 1.55-1.53 (d, 3H), 0.45 (s, 4H).

Molecular formula: $C_{20}H_{22}N_4O_3$ Molecular weight: 366.42 LC-MS (Pos, m/z)=367.20 [M+H]⁺.

Example 66: Synthesis of 6-(1-hydroxyethyl)-2-oxo-4-(7-azaspiro[3.5]nonane-7-yl)-1,2-dihydro-1,7-naphthyridin-3-carbonitrile (Compound 94)

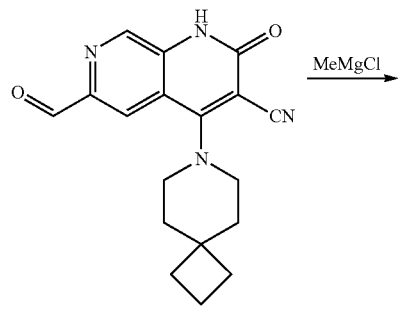

6-formyl-2-oxo-4-(7-azaspiro[3.5]nonane-7-yl)-1,2-dihydro-1,7-naphthyridin-3-carbo nitrile (530.0 mg, 1.65 mmol, 1.0 eq) was dissolved in tetrahydrofuran (10 mL), cooled to −10° C., followed by a slow addition of 3 mol/L methyl magnesium chloride (1.7 mL, 5.1 mmol, 3.0 eq), stirred for 2 h in ice bath. The reaction endpoint was monitored by TLC. The reaction solution was quenched by the addition of saturated aqueous ammonium chloride solution (10 mL), and extracted with ethyl acetate (20 mL×2). The organic phases were combined, and concentrated under reduced pressure, and the crude product was purified by silica gel column chromatography (DCM:MeOH=50:1-20:1) to give a product (56.1 mg, yield: 10.1%).

$^1$H NMR (400 MHz, DMSO-$d_6$) δ (ppm): 11.92 (s, 1H), 8.58 (s, 1H), 7.73 (s, 1H), 5.49 (d, 1H, J=4.64 Hz), 4.71-4.82 (m, 1H), 3.50-3.61 (m, 4H), 1.79-1.98 (m, 10H), 1.38 (d, 3H, J=6.48 Hz).

Molecular formula: $C_{19}H_{22}N_4O_2$ Molecular weight: 338.17 LC-MS (Neg, m/z)=337.15 [M−H]$^-$.

Example 67: Synthesis of 6-acetyl-2-oxo-4-(6-azaspiro[2.5]octane-6-yl)-1,2-dihydro-1,7-naphthyridin-3-carbonitrile (Compound 95)

6-(1-hydroxyethyl)-2-oxo-4-(6-azaspiro[2.5]octane-6-yl)-1,2-dihydro-1,7-naphthyridin-3-carbonitrile (0.85 g, 2.62 mmol, 1.0 eq) was dissolved in anhydrous dichloromethane (60 mL), cooled to 0° C. under nitrogen atmosphere, followed by addition of Dess-Martin oxidant (2.22 g, 5.24 mmol, 2.0 eq) and stirred at room temperature overnight. The reaction endpoint was monitored by TLC. The reaction solution was quenched with saturated aqueous NaHCO$_3$ solution (20 mL), and filtered by suction with celite. The filtrate was extracted with dichloromethane (20 mL×3). After liquid separation, the organic phase was washed with saturated brine (20 mL×2), dried over anhydrous sodium sulfate, and filtrated by suction, and the filtrate was concentrated under reduced pressure. The crude product was purified by silica gel column chromatography (DCM:MeOH=80:1-50:1) to give a product as a yellow solid (0.35 g, yield: 41.4%).

$^1$H NMR (400 MHz, DMSO-$d_6$) δ (ppm): 12.35 (s, 1H), 8.72 (s, 1H), 8.25 (s, 1H), 3.68 (t, 4H), 2.64 (s, 3H), 1.64 (s, 4H), 0.46 (s, 4H).

Molecular formula: $C_{18}H_{18}N_4O_2$ Molecular weight: 322.37 LC-MS (Pos, m/z)=323.10 [M+H]$^+$.

Example 68: Synthesis of 3-cyano-N-methyl-2-oxo-4-(6-azaspiro[2.5]octane-6-yl)-1,2-dihydro-1,7-naphthyridin-6-formamide (Compound 96)

Compound 96

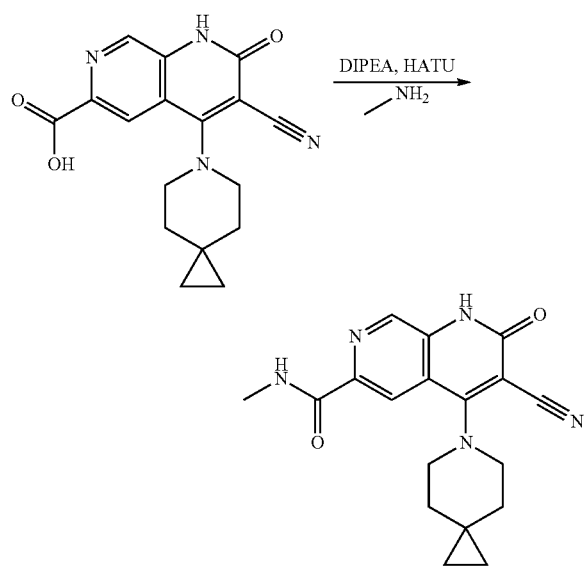

The intermediate 3-cyano-2-oxo-4-(6-azaspiro[2.5]octane-6-yl)-1,2-dihydro-1,7-naphthyridin-6-carboxylic acid (130 mg, 0.4 mmol, 1.0 eq) was dissolved in N,N-dimethylformamide (2 mL), followed by addition of N,N-diisopropylethylamine (155 mg, 1.2 mmol, 3.0 eq) and HATU (228 mg, 0.6 mmol, 1.5 eq) to react at room temperature for 1 h, and then followed by addition of methylamine in methanol (0.5 mL) to react at room temperature for 2 h. The reaction endpoint was monitored by LC-MS. The reaction solution was concentrated under reduced pressure, and the crude product was purified by silica gel column chromatography (DCM:MeOH=15:1) to give a product (50 mg, yield: 37%).

$^1$H NMR (400 MHz, DMSO-d$_6$) δ (ppm): 12.19 (s, 1H), 8.72-8.73 (m, 1H), 8.64 (s, 1H), 8.32 (s, 1H), 3.66-3.68 (s, 4H), 2.83-2.84 (d, 3H), 1.64 (m, 4H), 0.46 (s, 4H).

Molecular formula: $C_{18}H_{19}N_5O_2$ Molecular weight: 337.38 LC-MS (Pos, m/z)=338.16 [M+H]$^+$

Example 69: Synthesis of 3-cyano-N-(2-hydroxyethyl)-2-oxo-4-(6-aza-spiro[2.5]oct-6-yl)-1,2-dihydro-1,7-naphthyridin-6-carboxamide (Compound 97)

Compound 97

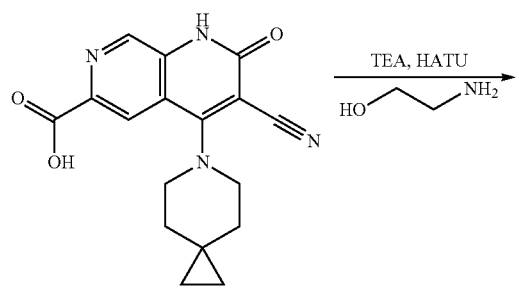

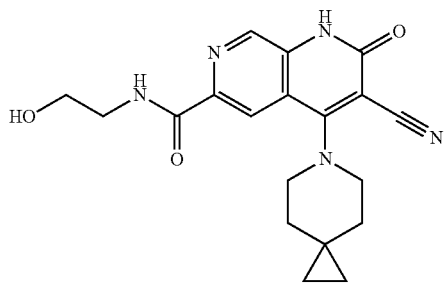

The intermediate 3-cyano-2-oxo-4-(6-azaspiro[2.5]octane-6-yl)-1,2-dihydro-1,7-naphthyridin-6-carboxylic acid (162 mg, 0.5 mmol, 1.0 eq) was dissolved in N,N-dimethylformamide (2 mL), followed by addition of triethylamine (152 mg, 1.5 mmol, 3.0 eq) and HATU (285 mg, 0.75 mmol, 1.5 eq) to react at room temperature for 1 h, and then followed by addition of ethanolamine (31 mg, 0.5 mmol, 1.0 eq) to react at room temperature for 2 h. The reaction endpoint was monitored by LC-MS. The reaction solution was concentrated under reduced pressure, and the crude product was purified by silica gel column chromatography (DCM:MeOH=15:1) to give a product (60 mg, yield: 33%).

$^1$H NMR (400 MHz, DMSO-d$_6$) δ (ppm): 12.24 (s, 1H), 8.61-8.65 (m, 2H), 8.33 (s, 1H), 4.77-4.80 (m, 1H), 3.66-3.69 (m, 4H), 3.51-3.56 (m, 2H), 3.38-3.42 (m, 2H), 1.65 (m, 4H), 0.46 (s, 4H).

Molecular formula: $C_{19}H_{21}N_5O_3$ Molecular weight: 367.41 LC-MS (POS, m/z)=368.28 [M+H]$^+$

Example 70: Synthesis of 4-(4-hydroxy-4-methylpiperidin-1-yl)-2-oxo-1,2-dihydro-1,7-naphthyridin-3-carbonitrile (Compound 106)

Step 1: Synthesis of 4-methylpiperidin-4-ol Trifluoroacetate

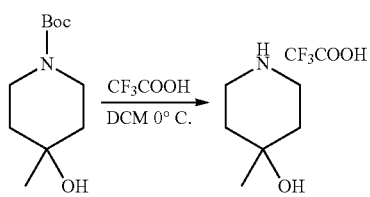

The raw material tert-butyl 4-hydroxy-4-methylpiperidin-1-carboxylate (380 mg, 1.77 mmol, 1.0 eq) was dissolved in dichloromethane (5 mL), followed by addition of trifluoroacetic acid (3 mL) at 0° C., and reacted for 1 h. The reaction endpoint was monitored by TLC. The reaction solution was concentrated under reduced pressure to give a product (404 mg, yield: 100%).

Step 2: Synthesis of 4-(4-hydroxy-4-methylpiperidin-1-yl)-2-oxo-1,2-dihydro-1,7-naphthyridin-3-carbonitrile Compound 106

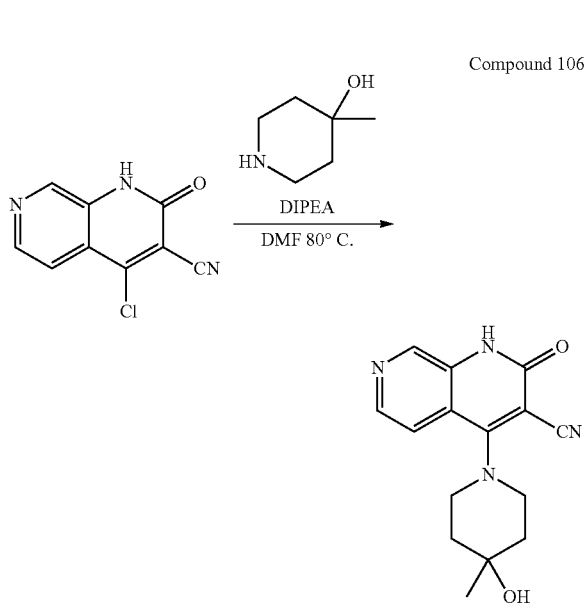

The intermediate 4-chloro-2-oxo-1,2-dihydro-1,7-naphthyridin-3-carbonitrile (200 mg, 0.97 mmol, 1.0 eq) was dissolved in DMF (3 mL), followed by addition of N,N-diisopropylethylamine (753 mg, 5.87 mmol, 6.0 eq) and 4-methylpiperidin-4-ol trifluoroacetate (312 mg, 1.36 mmol, 1.4 eq), and reacted at 80° C. for 2 hours. The reaction endpoint was monitored by LC-MS. The reaction solution was added dropwise into water (5 mL) and stirred for 10 min, and filtered by suction. The filter cake was then slurried with dichloromethane (5 mL), filtered by suction, and dried at 50° C. to give a product as a yellow solid (136 mg, yield: 49%).

¹HNMR (400 MHz, DMSO-d₆) δ (ppm): 11.95 (s, 1H), 8.62-8.65 (d, 1H), 8.33-8.34 (d, 1H), 7.59-7.61 (d, 1H), 4.56-4.61 (m, 1H), 3.68-3.79 (m, 2H), 3.58-3.62 (d, 2H), 1.77-1.83 (m, 2H), 1.66-1.76 (m, 2H), 1.24 (s, 3H).

Molecular formula: $C_{15}H_{16}N_4O_2$ Molecular weight: 284.32 LC-MS (Pos, m/z)=285.13 [M+H]⁺.

Example 71: Synthesis of 6-ethyl-4-(4-methoxy-4-methylpiperidin-1-yl)-2-oxo-1,2-dihydro-1,7-naphthyridin-3-carbonitrile (Compound 107)

Step 1: Synthesis of 6-chloro-4-(4-methoxy-4-methylpiperidin-1-yl)-2-oxo-1,2-dihydro-1,7-naphthyridin-3-carbonitrile Compound 151

The intermediate 4,6-dichloro-2-oxo-1,2-dihydro-1,7-naphthyridin-3-carbonitrile (2.0 g, 8.33 mmol, 1.0 eq) was dissolved in DMF (10 mL), followed by addition of DIPEA (6.45 g, 50 mmol, 6.0 eq) and 4-methoxy-4-methylpiperidine trifluoroacetate (2.2 g, 9.16 mmol, 1.1 eq) and reacted at 80° C. for 2 hours. The reaction endpoint was monitored by LC-MS. The reaction solution was followed by addition of water (10 mL), and extracted with dichloromethane (10 mL×3). The organic phase was washed with water (10 mL×3), dried over anhydrous sodium sulfate, filtered, and concentrated under reduced pressure to give product as a yellow solid (2.7 g, crude product).

¹H NMR (400 MHz, DMSO-d₆) δ (ppm): 12.11 (s, 1H), 8.45 (s, 1H), 7.61 (s, 1H), 3.61-3.59 (m, 4H), 3.18 (s, 3H), 1.91-1.88 (m, 2H), 1.81-1.76 (m, 2H), 1.21 (s, 3H)

Molecular formula: $C_{16}H_{17}N_4O_2Cl$ Molecular weight: 332.79 LC-MS (Pos, m/z)=333.7 [M+H]⁺

Step 2: Synthesis of 4-(4-methoxy-4-methylpiperidin-1-yl)-2-oxo-6-vinyl-1,2-dihydro-1,7-naphthyridin-3-carbonitrile The intermediate 6-chloro-4-(4-methoxy-4-methylpiperidin-1-yl)-2-oxo-1,2-dihydro-1,7-naphthyridine-3-carbonitrile (2.7 g crude product, 8.11 mmol, 1.0 eq) was dissolved in 1,4-dioxane (20 mL) and H₂O (5 mL), followed by addition of potassium vinyl trifluoroborate (1.63 g, 12.17 mmol, 1.5 eq), cesium carbonate (3.965 g, 12.17 mmol, 1.5 eq) and [1,1'-bis(diphenylphosphino)ferrocene] palladium dichloride (297 mg, 0.41 mmol, 0.05 eq), and reacted at 100° C. for 8 hours under nitrogen protection. The reaction endpoint was monitored by LC-MS. The reaction solution was followed by addition of water (20 mL), and extracted with dichloromethane (30 mL×3). The organic phase was dried over anhydrous sodium sulfate, filtered, and concentrated under reduced pressure, and the crude product was purified by silica gel column chromatography (DCM: MeOH=70:1) to give product as a yellow solid (1.15 g, yield: 43%).

Step 3: Synthesis of 6-ethyl-4-(4-methoxy-4-methylpiperidin-1-yl)-2-oxo-1,2-dihydro-1,7-naphthyridin-3-carbonitrile

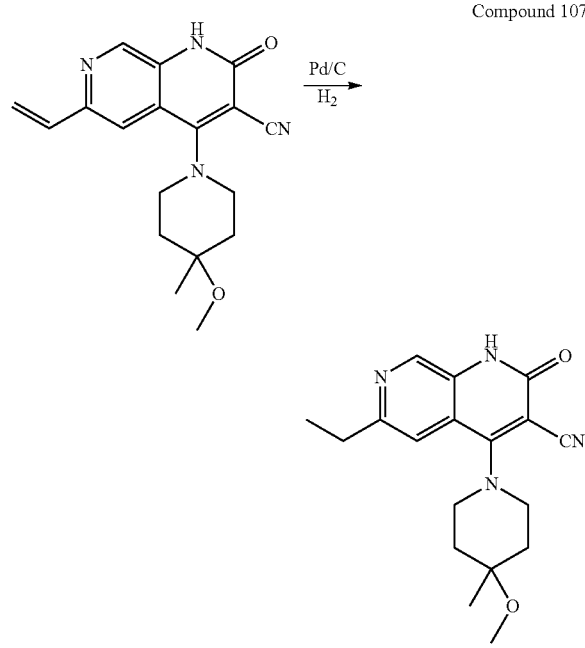

Compound 107

The intermediate 4-(4-methoxy-4-methylpiperidin-1-yl)-2-oxo-6-vinyl-1,2-dihydro-1,7-naphthyridine-3-carbonitrile (150 mg, 0.46 mmol, 1.0 eq) was dissolved in methanol (5 mL). Pd/C (100 mg) was added to the reaction. The air of the system was replaced by hydrogen for three times, and the reaction was carried out for 1 hour under hydrogen atmosphere. The reaction endpoint was monitored by LC-MS. The reaction solution was filtered by suction, and the filtrate was concentrated under reduced pressure to give a product (120 mg, yield: 80%).

¹HNMR (400 MHz, DMSO-d₆) δ (ppm): 11.89 (s, 1H), 8.59 (s, 1H), 7.41 (s, 1H), 3.60-3.62 (m, 4H), 3.19 (s, 3H), 2.79-2.84 (m, 2H), 1.89-1.93 (m, 2H), 1.75-1.82 (m, 2H), 1.22-1.27 (m, 6H).

Molecular formula: $C_{18}H_{22}N_4O_2$ Molecular weight: 326.40 LC-MS (Pos, m/z)=327.26 [M+H]⁺.

Example 72: Synthesis of 6-(1-hydroxyethyl)-4-(4-methoxy-4-methylpiperidin-1-yl)-2-oxo-1,2-dihydro-1,7-naphthyridine-3-carbonitrile (Compound 108)

Step 1: Synthesis of 6-(1,2-dihydroxyethyl)-4-(4-methoxy-4-methylpiperidin-1-yl)-2-oxo-1,2-dihydro-1,7-naphthyridine-3-carbonitrile

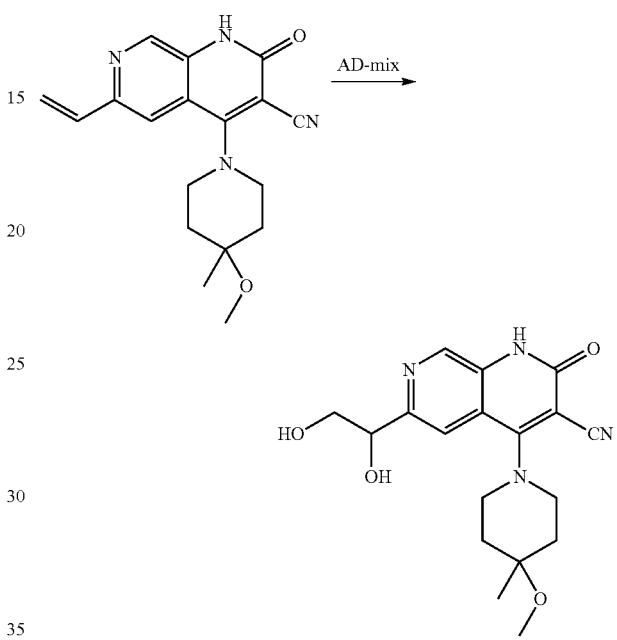

The intermediate 4-(4-methoxy-4-methylpiperidin-1-yl)-2-oxo-6-vinyl-1,2-dihydro-1,7-naphthyridine-3-carbonitrile (500 mg, 1.542 mmol, 1.0 eq) was dissolved in tert-butanol (10 mL) and water (10 mL), followed by addition of methanesulfonamide (147 mg, 1.542 mmol, 1.0 eq) and AD-mix-β (6.0 g), and reacted at room temperature for 12 hours. The reaction endpoint was monitored by LC-MS. The reaction solution was followed by addition of water (10 mL), and extracted with dichloromethane (30 mL×3). The organic phase was dried over anhydrous sodium sulfate, filtered, and concentrated under reduced pressure to give a product (552 mg, yield: 100%).

Step 2: Synthesis of 6-formyl-4-(4-methoxy-4-methylpiperidin-1-yl)-2-oxo-1,2-dihydro-1,7-naphthyridin-3-carbonitrile

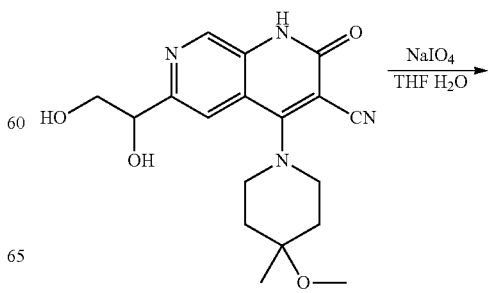

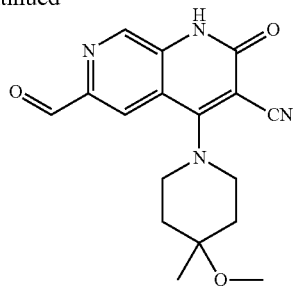

The intermediate 6-(1,2-dihydroxyethyl)-4-(4-methoxy-4-methylpiperidin-1-yl)-2-oxo-1,2-dihydro-1,7-naphthyridin-3-carbonitrile (552 mg, 1.542 mmol, 1.0 eq) was dissolved in tetrahydrofuran (10 mL) and water (2 mL), followed by addition of sodium periodate (650 mg, 3.084 mmol, 2.0 eq) and reacted for 4 hours. The reaction endpoint was monitored by LC-MS. The reaction solution was followed by addition of water (10 mL), and extracted with ethyl acetate (20 mL×3). The organic phase was dried over anhydrous sodium sulfate, filtered, and concentrated under reduced pressure, and the crude product was purified by silica gel column chromatography (DCM:MeOH=60:1) to give a product as a yellow solid (160 g, yield after the two steps: 32%).

Step 3: Synthesis of 6-(1-hydroxyethyl)-4-(4-methoxy-4-methylpiperidin-1-yl)-2-oxo-1,2-dihydro-1,7-naphthyridin-3-carbonitrile

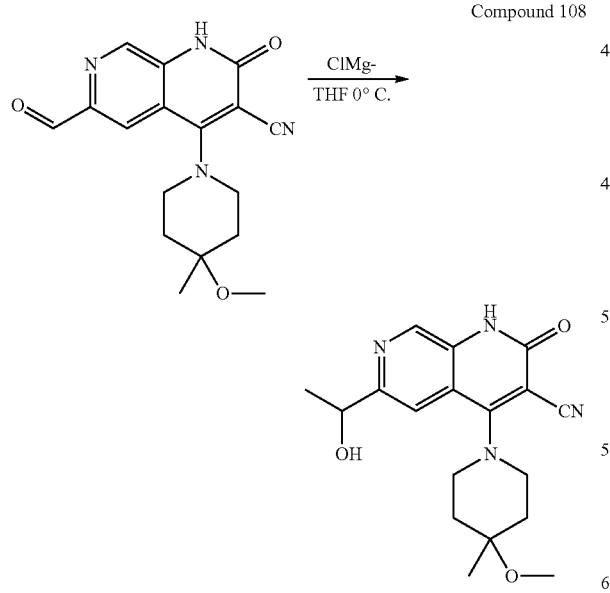

The intermediate 6-formyl-4-(4-methoxy-4-methylpiperidin-1-yl)-2-oxo-1,2-dihydro-1,7-naphthyridin-3-carbonitrile (160 mg, 0.49 mmol, 1.0 eq) was dissolved in tetrahydrofuran (5 mL), followed by dropwise addition of methylmagnesium chloride (1 mL) at 0° C., and reacted for 1 hour. The reaction endpoint was monitored by LC-MS. The reaction solution was followed by addition of water (10 mL) and extracted with ethyl acetate (20 mL×3). The organic phase was dried over anhydrous sodium sulfate, filtered, and concentrated under reduced pressure, and the crude product was purified by silica gel column chromatography (DCM:MeOH=40:1) to give a product (108 mg, yield: 64%).

$^1$H NMR (400 MHz, DMSO-$d_6$) δ (ppm): 11.93 (s, 1H), 8.58 (s, 1H), 7.72 (s, 1H), 5.48-5.49 (d, 1H), 4.75-4.81 (m, 1H), 3.56-3.65 (m, 4H), 3.20 (s, 3H), 1.91-1.95 (m, 2H), 1.73-1.79 (m, 2H), 1.38-1.40 (d, 3H), 1.23 (s, 3H).

Molecular formula: $C_{18}H_{22}N_4O_3$ Molecular weight: 342.40 LC-MS (Pos, m/z)=343.17 [M+H]$^+$.

Example 73: Synthesis of 6-(2-hydroxypropan-2-yl)-4-(4-methoxy-4-methylpiperidin-1-yl)-2-oxo-1,2-dihydro-1,7-naphthyridine-3-carbonitrile (Compound 109)

Step 1: Synthesis of 6-acetyl-4-(4-methoxy-4-methylpiperidin-1-yl)-2-oxo-1,2-dihydro-1,7-naphthyridin-3-carbonitrile

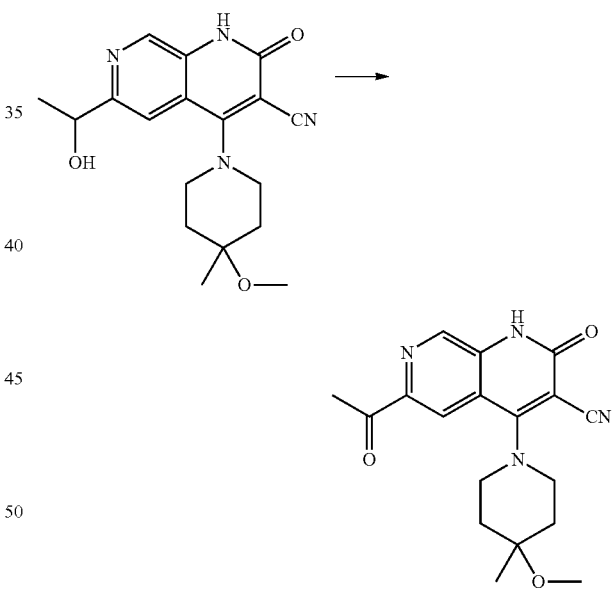

The intermediate 6-(1-hydroxyethyl)-4-(4-methoxy-4-methylpiperidin-1-yl)-2-oxo-1,2-dihydro-1,7-naphthyridin-3-carbonitrile (187 mg, 0.55 mmol, 1.0 eq) was dissolved in dry dichloromethane (5 mL). The temperature was cooled to 0-5° C. and Dess-Martin oxidant (463.5 mg, 1.10 mmol, 2.0 eq) was added. After the addition, the temperature was naturally raised to room temperature to react for 2 h. The reaction endpoint was monitored by TLC. The reaction solution was concentrated under reduced pressure. The crude product was purified by silica gel column chromatography (MeOH:DCM=1:100-1:50) to give a product (185.8 mg, yield: 100%).

Step 2: Synthesis of 6-(2-hydroxypropan-2-yl)-4-(4-methoxy-4-methylpiperidin-1-yl)-2-oxo-1,2-dihydro-1,7-naphthyridin-3-carbonitrile Compound 109

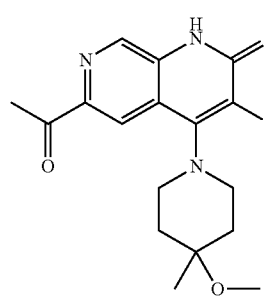

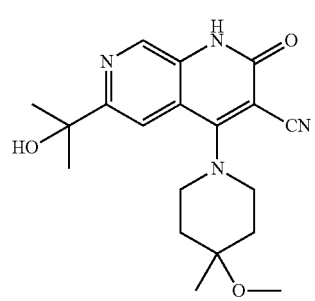

The intermediate 6-acetyl-4-(4-methoxy-4-methylpiperidin-1-yl)-2-oxo-1,2-dihydro-1,7-naphthyridine-3-carbonitrile (185.8 mg, 0.55 mmol, 1.0 eq) was dissolved in N,N-dimethylacetamide (3 mL), and the temperature was cooled to −10-0° C. 3 mol/L solution of methylmagnesium chloride in tetrahydrofuran (0.6 mL, 3.0 eq) was added dropwise under nitrogen protection. After the addition, the mixture was naturally warmed to room temperature and stirred overnight. A large amount of remaining raw materials were detected by TCL. The reaction solution was supplemented with 3 mol/L solution of methylmagnesium chloride in tetrahydrofuran (0.6 mL, 3.0 eq) to react for 3 h, then supplemented with 3 mol/L solution of methyl magnesium chloride in tetrahydrofuran (0.6 mL, 3.0 eq) to react for 2 h, cooled to 0-10° C., adjusted to a pH of 5-6 with acetic acid, and concentrated. The crude product was purified by silica gel column chromatography (MeOH:DCM=1:100-1:70) to give a product (63.9 mg, yield: 32.8%).

$^1$H NMR (400 MHz, DMSO-$d_6$) δ (ppm): 11.91 (s, 1H), 8.59 (s, 1H), 7.89 (s, 1H), 5.35 (s, 1H), 3.62-3.60 (m, 4H), 3.20 (s, 3H), 1.95-1.92 (m, 2H), 1.80-1.73 (m, 2H), 1.45 (s, 6H), 1.23 (s, 3H).

Molecular formula: $C_{19}H_{24}N_4O_3$ Molecular weight: 356.43 LC-MS (Pos, m/z)=357.25 [M+H]$^+$.

Example 74: Synthesis of (S)-4-(3-(1H-1,2,4-triazol-1-yl)pyrrolidin-1-yl)-2-oxo-1,2-dihydro-1,7-naphthyridine-3-carbonitrile (Compound 112)

Step 1: Synthesis of Tert-Butyl (S)-3-(1H-1,2,4-triazol-1-yl)pyrrolidin-1-carboxylate

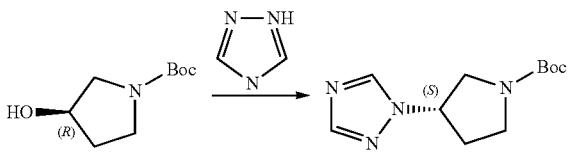

The starting material tert-butyl (R)-3-hydroxypyrrolidin-1-carboxylate (1.0 g, 5.34 mmol, 1.0 eq) was dissolved in anhydrous tetrahydrofuran (20 mL), and 1H-1,2,4-triazole (368 mg, 5.34 mmol, 1.0 eq) and triphenylphosphine (2.8 g, 10.68 mmol, 2.0 eq) were added. After the addition, the temperature was reduced to 0° C., and diethyl azodicarboxylate (1.86 g, 10.68 mmol, 2.0 eq) was added dropwise. After the addition, the reaction was carried out at room temperature for 12 h. The reaction endpoint was monitored by TLC. The reaction solution was concentrated under reduced pressure. The crude product was purified by silica gel column chromatography (EA:PE=1:15-1:2) to give a product (559 mg, yield: 44%).

Step 2: Synthesis of (S)-1-(pyrrolidin-3-yl)-1H-1,2,4-triazole hydrochloride

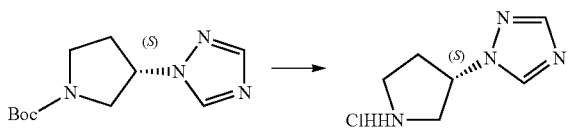

The intermediate tert-butyl (S)-3-(1H-1,2,4-triazol-1-yl)pyrrolidin-1-carboxylate (559 mg, 2.34 mmol, 1.0 eq) was dissolved in anhydrous methanol (5 mL), followed by addition of 30% hydrogen chloride in ethanol solution (5 mL), and reacted at room temperature for 2 h to precipitate a white solid. The reaction endpoint was monitored by TLC. The reaction solution was concentrated under reduced pressure, followed by addition of water (10 mL), and extracted with EA (3×5 mL). The aqueous phase was lyophilized to give an off-white solid product (410 mg, yield: 100%).

Step 3: Synthesis of (S)-4-(3-(1H-1,2,4-triazol-1-yl)pyrrolidin-1-yl)-2-oxo-1,2-dihydro-1,7-naphthyridine-3-carbonitrile Compound 112

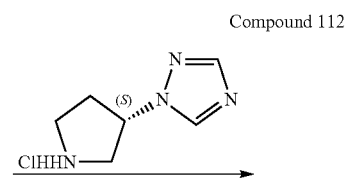

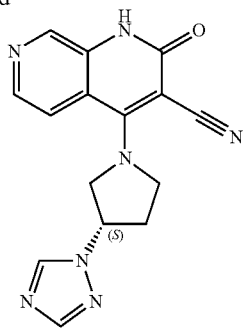

The intermediate 4-chloro-2-oxo-1,2-dihydro-1,7-naphthyridin-3-carbonitrile (346.2 mg, 1.68 mmol, 1.0 eq) was dissolved in DMF (3 mL), and (S)-1-(pyrrolidin-3-yl)-1H-1,2,4-triazole hydrochloride (410 mg, 2.34 mmol, 1.4 eq) and DIPEA (1.1 g, 8.4 mmol, 5.0 eq) were added. After the addition, the temperature was raised to 80° C. and the reaction was carried out for 2 h. The reaction endpoint was monitored by LC-MS, and the temperature was reduced to room temperature. The reaction solution was separated by reverse phase column chromatography (0.1% aqueous hydrochloric acid solution:acetonitrile=70:30) to give a product (226 mg, yield: 43.8%).

$^1$HNMR (400 MHz, DMSO-$d_6$) δ (ppm): 11.68 (s, 1H), 8.70 (s, 1H), 8.62 (s, 1H), 8.28-8.27 (d, 1H), 8.04 (s, 1H), 7.98-7.97 (s, 1H), 5.33-5.30 (m, 1H), 4.61-4.57 (m, 1H), 4.35-4.28 (m, 2H), 4.23-4.17 (m, 1H), 2.55-2.51 (m, 1H), 2.50-2.47 (m, 1H).

Molecular formula: $C_{15}H_{13}N_7O$ Molecular weight: 307.21 LC-MS (Pos, m/z)=307.98 [M+H]$^+$.

Example 75: Synthesis of 2-oxo-4-(3-(thiazol-2-yl)pyrrolidin-1-yl)-1,2-dihydro-1,7-naphthyridin-3-carbonitrile (Compound 113)

Step 1: Synthesis of Tert-Butyl 3-(thiazol-2-yl)-2,5-dihydro-1H-pyrrole-1-carboxylate

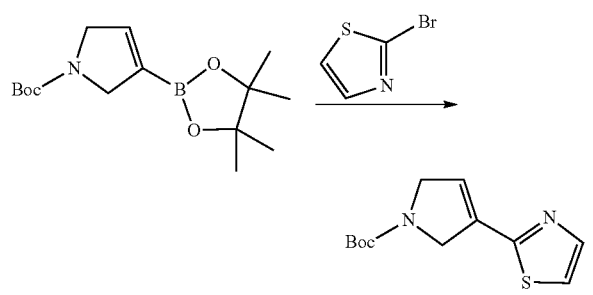

The starting material tert-butyl 3-(4,4,5,5-tetramethyl-1,3,2-dioxaborolan-2-yl)-2,5-dihydro-1H-pyrrole-1-carboxylate (1.0 g, 3.39 mmol, 1.0 eq) was dissolved in 1,4-dioxane (20 mL), and 2-bromothiazole (666.6 mg, 4.06 mmol, 1.2 eq), anhydrous sodium carbonate (897.5 mg, 8.47 mmol, 2.5 eq) and water (4 mL) were added. The air of the system was replaced by nitrogen for three times, and [1,1'-bis(diphenylphosphino)ferrocene]palladium dichloride (247.8 mg, 0.34 mmol, 0.1 eq) was added to the reaction. The air of the system was replaced by nitrogen for three times, and the temperature was raised to 80° C. to react for 2 h. The reaction endpoint was monitored by TLC. The temperature was lowered to room temperature. The mixture was followed by addition of water (10 mL) and extracted with ethyl acetate (50 mL×3). The mixture is separated and the organic phases were combined, dried over anhydrous sodium sulfate, and filtered. The mother liquor was concentrated under reduced pressure, and the crude product was purified by silica gel column chromatography (EA:PE=1:30-1:20) to give a pale yellow oily product (719 mg, yield: 84.2%).

Step 2: Synthesis of Tert-Butyl 3-(thiazol-2-yl)pyrrolidin-1-carboxylate

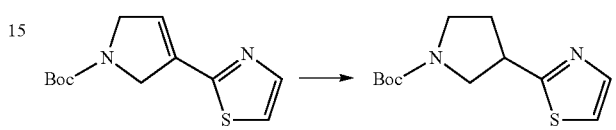

The intermediate tert-butyl 3-(thiazol-2-yl)-2,5-dihydro-1H-pyrrole-1-carboxylate (719 mg, 2.84 mmol, 1.0 eq) was dissolved in anhydrous ethanol (20 mL), followed by addition of 10% palladium on carbon (0.5 g). After the addition, the air of the system was replaced by hydrogen for three times, and the temperature was raised to 50° C. to react for 12 hours. The reaction endpoint was monitored by TLC, and the temperature was reduced to room temperature. The reaction solution was filtered, and the filter cake was rinsed with ethanol. The mother liquor was concentrated under reduced pressure to give a pale yellow oily product (653 mg, yield: 90.5%).

Step 3: Synthesis of 2-(pyrrolidin-3-yl)thiazole hydrochloride

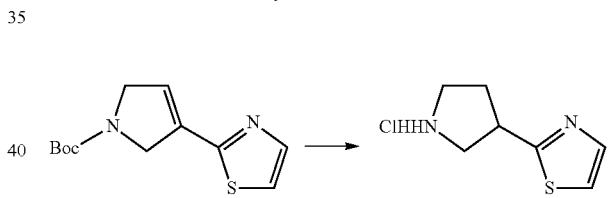

The intermediate tert-butyl 3-(thiazol-2-yl)pyrrolidin-1-carboxylate (653 mg, 2.57 mmol, 1.0 eq) was dissolved in anhydrous methanol (2 mL), followed by addition of 30% hydrogen chloride in ethanol solution (5 mL) and reacted at room temperature for 2 h. The reaction endpoint was monitored by LC-MS. The reaction solution was concentrated under reduced pressure to give a product (880 mg crude product), which was directly subjected to next step without purification.

Step 4: Synthesis of 2-oxo-4-(3-(thiazol-2-yl)pyrrolidin-1-yl)-1,2-dihydro-1,7-naphthyridin-3-carbonitrile Compound 113

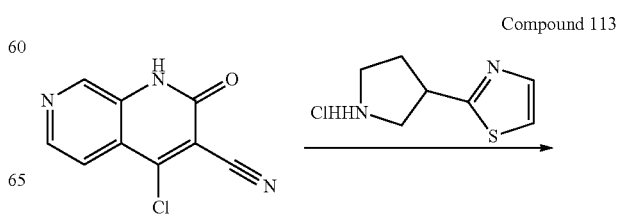

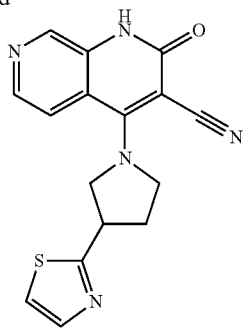

The intermediate 4-chloro-2-oxo-1,2-dihydro-1,7-naphthyridin-3-carbonitrile (210 mg, 1.02 mmol, 1.0 eq) was dissolved in DMF (2 mL), and 2-(pyrrolidin-3-yl)thiazole hydrochloride (195 mg, 1.02 mmol, 1.0 eq) and DIPEA (792.7 mg, 6.14 mmol, 6.0 eq) were added to the reaction. After the addition, the temperature was increased to 80° C. to react for 2 h. The reaction endpoint was monitored by LC-MS and the temperature was reduced to room temperature. The mixture was purified by preparative HPLC (0.1% aqueous trifluoroacetic acid solution:acetonitrile=70:30), lyophilized, dissolved by adding water (1 mL), adjusted to pH of about 8 with saturated aqueous sodium carbonate solution until solid was precipitated, and then filtered. The filter cake was dried to give a product (92 mg, yield: 27.8%).

$^1$H NMR (400 MHz, DMSO-d$_6$) δ (ppm): 11.63 (s, 1H), 8.61 (s, 1H), 8.28-8.27 (d, 1H), 7.99-7.98 (d, 1H), 7.79-7.78 (d, 1H), 7.70-7.69 (d, 1H), 4.48-4.44 (m, 1H), 4.34-4.30 (m, 1H), 4.27-4.15 (m, 2H), 4.06-4.00 (m, 1H), 2.50 (m, 1H), 2.30-2.27 (m, 1H).

Molecular formula: C$_{16}$H$_{13}$N$_5$OS Molecular weight: 323.37 LC-MS (Pos, m/z)=346.14 [M+Na]$^+$.

Example 76: Synthesis of 2-(methylthio)-6-oxo-8-(6-azaspiro[2.5]octane-6-yl)-5,6-dihydropyrido[3,2-d]pyrimidin-7-carbonitrile (Compound 129)

Step 1: Synthesis of 6-(methylthio)-2H-pyrimido[5,4-d][1,3]oxazin-2,4-(1H)-dione

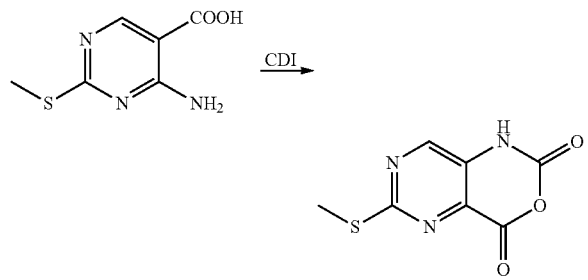

4-amino-2-(methylthio)pyrimidin-5-carboxylic acid (2.00 g, 10.80 mmol, 1.0 eq) was dissolved in anhydrous tetrahydrofuran (100.0 mL), followed by addition of N,N'-carbonyldiimidazole (3.50 g, 21.60 mmol, 2.0 eq) under ice bath, and stirred at room temperature to react for 16 h. The reaction endpoint was monitored by TLC. The solid was filtered, and the filtrate was directly subjected to the next reaction.

Step 2: Synthesis of 8-hydroxy-2-(methylthio)-6-oxo-5,6-dihydropyrido[3,2-d]pyrimidin-7-carbonitrile

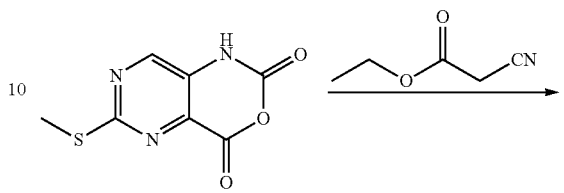

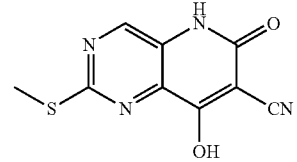

Sodium hydride (60%, 1.88 g, 46.96 mmol, 4.35 eq) was slowly added to anhydrous tetrahydrofuran (100.0 mL), stirred for 10 min, and slowly added dropwise with ethyl cyanoacetate (3.50 g, 30.95 mmol, 2.86 eq) under ice bath. The mixture was stirred at 75° C. for 20 min under nitrogen protection, followed by a slow dropwise addition of 6-(methylthio)-2H-pyrimido[5,4-d][1,3]oxazin-2,4-(1H)-dione in THF, and then stirred at 75° C. overnight under nitrogen protection. The reaction endpoint was monitored by TLC. The reaction solution was followed by addition of ice water (30 mL), adjusted to pH of 3-4 with concentrated hydrochloric acid, and filtered by suction to obtain a yellow solid product (880.0 mg, yield after the two steps: 34.8%).

Step 3: Synthesis of 8-chloro-2-(methylthio)-6-oxo-5,6-dihydropyrido[3,2-d]pyrimidin-7-carbonitrile

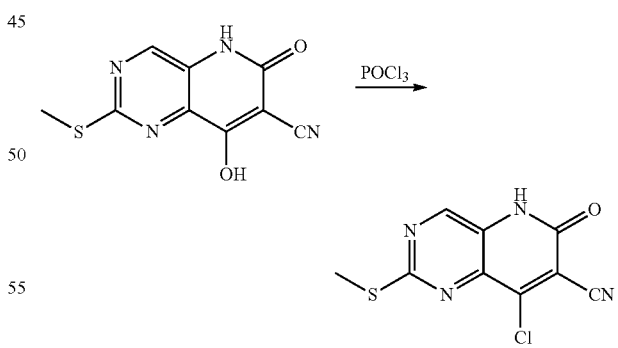

8-hydroxy-2-(methylthio)-6-oxo-5,6-dihydropyrido[3,2-d]pyrimidin-7-carbonitrile (705 mg, 3.01 mmol) was added to a mixed solvent of POCl$_3$ (10 mL) and 1,2-dichloroethane (20 mL), and stirred at 75° C. to react for 3-4 h under nitrogen protection. The reaction endpoint was monitored by TLC. The reaction solution was cooled in ice bath, followed by addition of ice water (10 mL), then stirred and filtered by suction to give a product (400.0 mg, yield: 52.6%).

Step 4: Synthesis of 2-(methylthio)-6-oxo-8-(6-azaspiro[2.5]octane-6-yl)-5,6-dihydropyrido[3,2-d]pyrimidin-7-carbonitrile

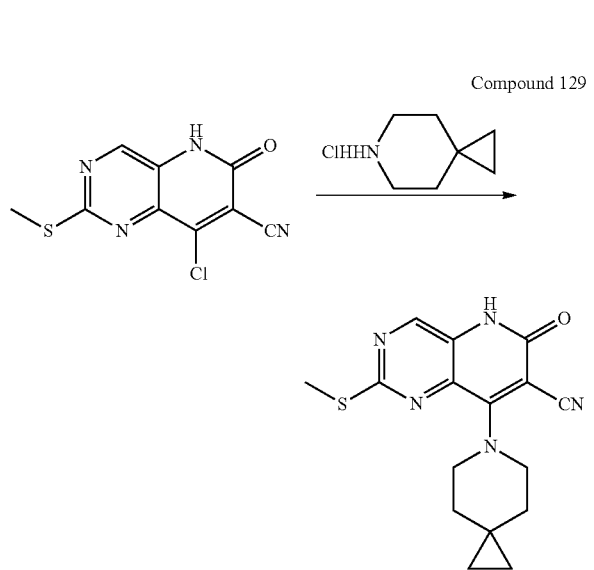

Compound 129

8-chloro-2-(methylthio)-6-oxo-5,6-dihydropyrido[3,2-d]pyrimidin-7-carbonitrile (400 mg, 1.58 mmol, 1.0 eq), 6-azaspiro[2.5]octane hydrochloride (280.5 mg, 1.90 mmol, 1.2 eq) and DIPEA (1636.7 mg, 12.66 mmol, 8.0 eq) were added to DMF (20 mL) and stirred at 80° C. to react for 3 h. After completion of the reaction as monitored by TLC, the mixture was concentrated under reduced pressure, followed by addition of EA (5 mL) and water (10 mL), stirred for 2 h, and filtered by suction. The filter cake was slurried by adding EA (5 mL) for 1 h once again, and a product was obtained by filtration (59.0 mg, yield: 11.4%).

$^1$H NMR (400 MHz, DMSO-$d_6$) δ (ppm): 11.58 (s, 1H), 8.69 (s, 1H), 3.90 (t 4H), 2.53 (s, 3H), 1.61 (t, 4H), 0.42 (s, 4H).

Molecular formula: $C_{16}H_{17}N_5OS$ Molecular weight: 327.41 LC-MS (Pos, m/z)=328.10 [M+H]$^+$.

Example 77: Synthesis of 6-(cyclopropyl(hydroxy)methyl)-4-(4-methoxy-4-methylpiperidin-1-yl)-2-oxo-1,2-dihydro-1,7-naphthyridin-3-carbonitrile (Compound 130)

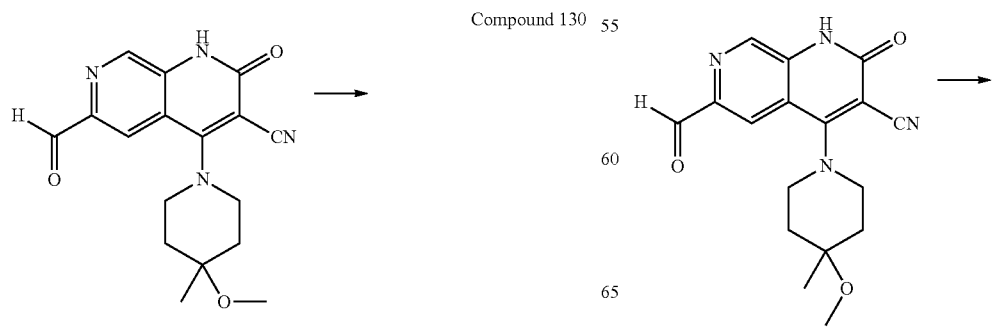

Compound 130

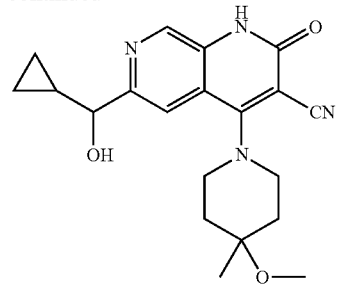

The intermediate 6-formyl-4-(4-methoxy-4-methylpiperidin-1-yl)-2-oxo-1,2-dihydro-1,7-naphthyridin-3-carbonitrile (500 mg, 1.53 mmol, 1.0 eq) was dissolved in anhydrous tetrahydrofuran (20 mL), and the temperature was reduced to −10° C., under nitrogen protection. 1 mol/L solution of cyclopropylmagnesium bromide in tetrahydrofuran (4.6 mL, 4.60 mmol, 3 eq) was added dropwise to the reaction. After the addition, the reaction was carried out at 0° C. for 3 h. 20% of the starting materials were remained as detected by LC-MS, so 1 mol/L solution of cyclopropylmagnesium bromide in tetrahydrofuran (3 mL, 3 mmol, 2 eq) was added to react for 2 to 3 h. 10% of the starting materials were remained as detected by LC-MS, so the mixture was adjusted to pH of about 5-6 by adding acetic acid, and concentrated under reduced pressure. The crude product was purified by silica gel column chromatography (MeOH:DCM=1:100-1:40) to obtain a product (225.7 mg, yield: 40.0%).

$^1$H NMR (400 MHz, DMSO-$d_6$) δ (ppm): 11.93 (s, 1H), 8.59 (s, 1H), 7.68 (s, 1H), 5.42-5.40 (d, 1H), 4.24-4.22 (m, 1H), 3.63-3.60 (m, 4H), 3.19 (s, 3H), 1.95-1.91 (m, 2H), 1.79-1.72 (m, 2H), 1.23 (s, 3H), 1.23 (s, 1H), 0.42 (m, 4H).

Molecular formula: $C_{20}H_{24}N_4O_3$ Molecular weight: 368.44 LC-MS (Pos, m/z)=369.40 [M+H]$^+$.

Example 78: Synthesis of 3-cyano-4-(4-methoxy-4-methylpiperidin-1-yl)-N-methyl-2-oxo-1,2-dihydro-1,7-naphthyridin-6-carboxamide (Compound 131)

Step 1: Synthesis of 3-cyano-4-(4-methoxy-4-methylpiperidin-1-yl)-2-oxo-1,2-dihydro-1,7-naphthyridin-6-carboxylic Acid

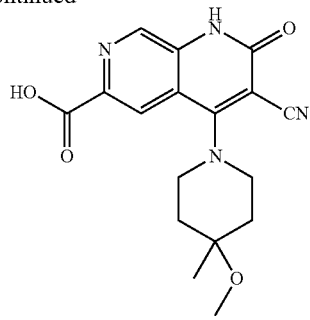

The intermediate 6-formyl-4-(4-methoxy-4-methylpiperidin-1-yl)-2-oxo-1,2-dihydro-1,7-naphthyridin-3-carbonitrile (681 mg, 2.09 mmol, 1.0 eq) was dissolved in formic acid (5 mL), and the temperature was reduced to −5 to 0° C. 30% hydrogen peroxide (1.32 mL, 10.44 mmol, 5 eq) was added to the reaction. After the addition, the reaction was carried out at 0° C. for 12 h, and then 30% hydrogen peroxide (1.32 mL, 10.44 mmol, 5 eq) was added to react at room temperature for 2-3 h. The reaction endpoint was monitored by TLC. The reaction solution was poured into methyl t-butyl ether (50 mL) to precipitate a pale yellow solid, and then filtered. The filter cake was dried to give a product (300 mg, yield: 42.0%).

Step 2: Synthesis of 3-cyano-4-(4-methoxy-4-methylpiperidin-1-yl)-N-methyl-2-oxo-1,2-dihydro-1,7-naphthyridin-6-carboxamide

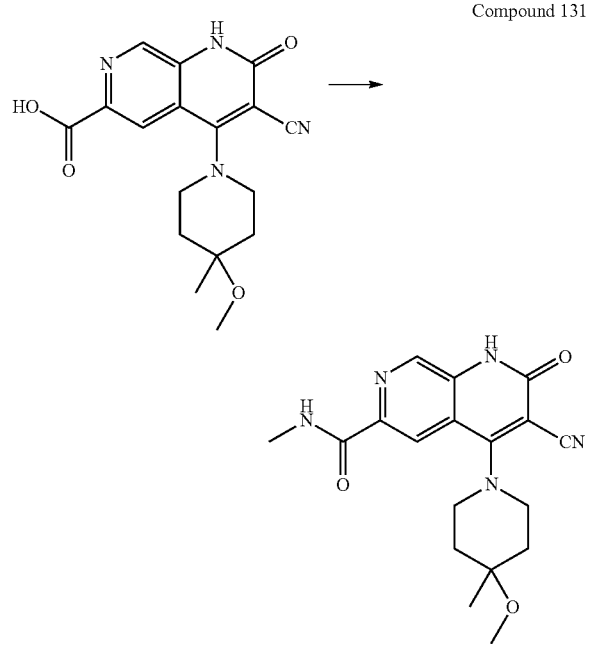

The intermediate 3-cyano-4-(4-methoxy-4-methylpiperidin-1-yl)-2-oxo-1,2-dihydro-1,7-naphthyridine-6-carboxylic acid (300 mg, 0.88 mmol, 1.0 eq) was dissolved in anhydrous N,N-dimethylacetamide (3 mL), followed by addition of DIPEA (565.8 mg, 4.38 mmol, 5.0 eq). After the addition, the reaction mixture was reduced to 0° C., followed by addition of HATU (499.7 mg, 1.31 mmol, 1.5 eq), stirred at room temperature for 0.5 to 1 h, then followed by addition of methylamine hydrochloride (118.2 mg, 1.75 mmol, 2.0 eq) and reacted at room temperature for 1 h, and solid was precipitated. The reaction endpoint was monitored by TLC. Water (50 mL) was added to the reaction solution, stirred for 5 min, and filtered. The filter cake was rinsed with water, added to ethyl acetate (10 mL) and heated to reflux for 1 h, filtered when it was hot and dried to give a product (199 mg, yield: 63.8%).

$^1$H NMR (400 MHz, DMSO-d$_6$) δ (ppm): 12.21 (s, 1H), 8.74-8.73 (s, 1H), 8.64 (s, 1H), 8.27 (s, 1H), 3.64-3.62 (m, 4H), 3.20 (s, 3H), 2.84-2.83 (d, 3H), 1.96 (m, 1H), 1.93 (m, 1H), 1.79-1.77 (m, 2H), 1.24 (s, 3H).

Molecular formula: C$_{18}$H$_{21}$N$_5$O$_3$ Molecular weight: 355.40 LC-MS (Pos, m/z)=356.26 [M+H]$^+$.

Example 79: Synthesis of 4-(4-methoxy-4-methylpiperidin-1-yl)-2-oxo-6-vinyl-1,2-dihydro-1,7-naphthyridin-3-carbonitrile (Compound 132)

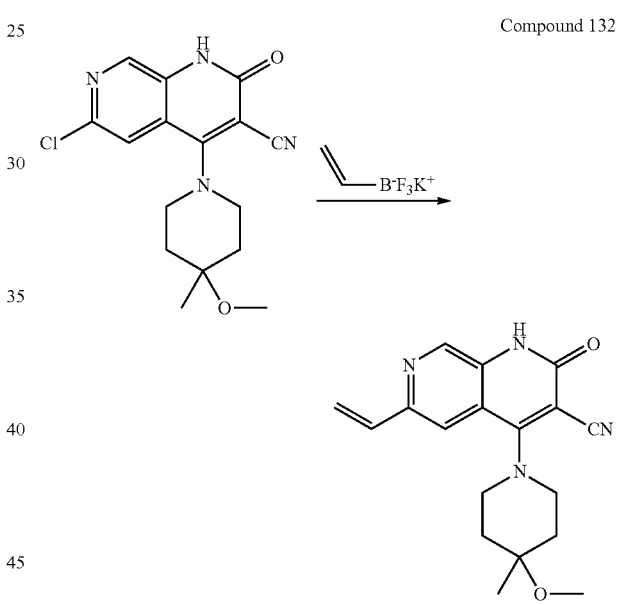

The intermediate 6-chloro-4-(4-methoxy-4-methylpiperidin-1-yl)-2-oxo-1,2-dihydro-1,7-naphthyridin-3-carbonitrile (20.1 g, 60.40 mmol, 1.0 eq) was dissolved in 1,4-dioxane (600 mL) and H2O (150 mL), followed by addition of potassium trifluoro(vinyl)borate (12.14 g, 90.6 mmol, 1.5 eq), cesium carbonate (58 g, 181.2 mmol, 3.0 eq) and [1,1'-bis(diphenylphosphino)ferrocene] palladium dichloride (4.4 g, 6.04 mmol, 1.0 eq), and reacted at 100° C. for 8 hours under nitrogen protection. The reaction endpoint was monitored by LC-MS. The reaction solution was followed by addition of water (20 mL), and extracted with dichloromethane (30 mL×3). The organic phase was washed with water (10 mL×3), dried over anhydrous sodium sulfate, filtered, and concentrated under reduced pressure, and the crude product was purified by silica gel column chromatography (DCM:MeOH=50:1) to give a product (14.63 g, yield: 74%).

$^1$H NMR (400 MHz, DMSO-d$_6$) δ (ppm): 12.03 (s, 1H), 8.64 (s, 1H), 7.56 (s, 1H), 6.89-6.96 (m, 1H), 6.15-6.19 (m, 1H), 5.39-5.42 (m, 1H), 3.61-3.64 (m, 4H), 3.19 (s, 3H), 1.77-1.93 (m, 4H), 1.21 (s, 3H).

Molecular formula: $C_{18}H_{20}N_4O_2$ Molecular weight: 324.38 LC-MS (Pos, m/z)=325.16 [M+H]$^+$.

Example 80: Synthesis of 6-(1-hydroxy-2-methylpropyl)-2-oxo-4-(6-azaspiro[2.5]octane-6-yl)-1,2-dihydro-1,7-naphthyridin-3-carbonitrile (Compound 134)

Step 1: Synthesis of 6-formyl-2-oxo-4-(6-azaspiro[2.5]octane-6-yl)-1,2-dihydro-1,7-naphthyridin-3-carbonitrile

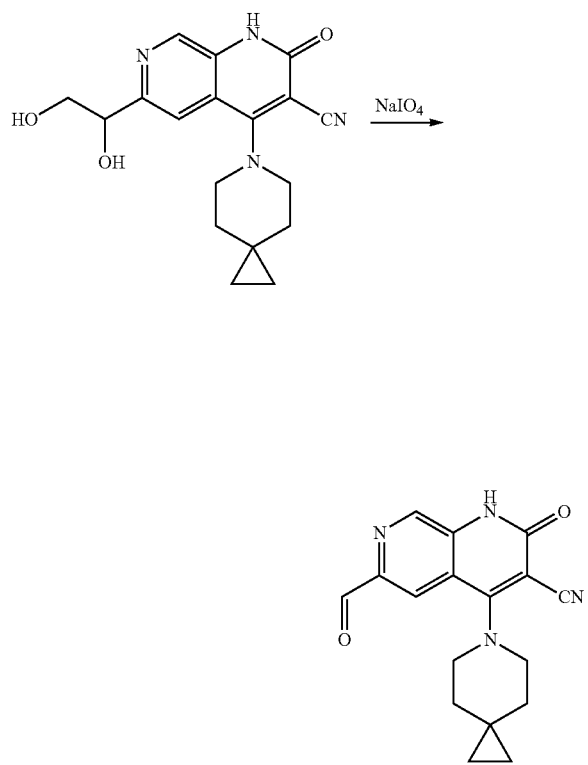

Sodium periodate (4.00 g, 18.70 mmol, 2.0 eq) was dissolved in water (10 mL) and then followed by addition of tetrahydrofuran (100 mL), cooled to 0° C. in ice bath, followed by a slow addition of 6-(1,2-dihydroxyethyl)-2-oxo-4-(6-azaspiro [2.5]octane-6-yl)-1,2-dihydro-1,7-naphthyridin-3-carbonitrile (3.18 g, 9.35 mmol, 1.0 eq), and stirred at room temperature for 3 h. After completion of the reaction as monitored by TLC, the mixture was extracted with dichloromethane (20 mL×3). The organic phase was separated, washed with saturated brine (20 mL×2), dried over anhydrous $Na_2SO_4$ (0.8 g), filtered by suction, and concentrated under reduced pressure to give a product as a yellow solid (1.50 g, yield: 52.0%).

Step 2: Synthesis of 6-(1-hydroxy-2-methylpropyl)-2-oxo-4-(6-azaspiro[2.5]octane-6-yl)-1,2-dihydro-1,7-naphthyridin-3-carbonitrile

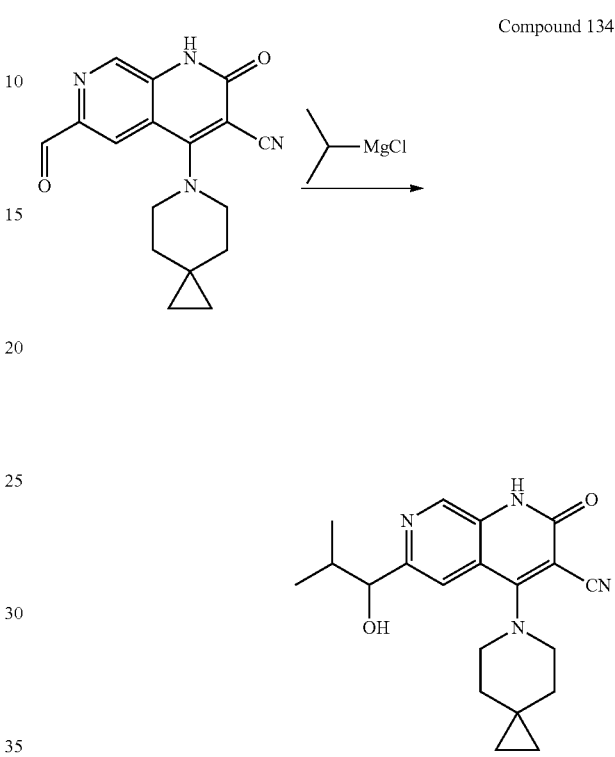

Compound 134

6-formyl-2-oxo-4-(6-azaspiro[2.5]octane-6-yl)-1,2-dihydro-1,7-naphthyridin-3-carbo nitrile (968.0 mg, 3.14 mmol, 1.0 eq) was dissolved in freshly distilled tetrahydrofuran (100 mL), cooled to −30° C. under nitrogen protection in dry ice ethanol bath, and then quickly added dropwise with a solution of isopropylmagnesium chloride in tetrahydrofuran (2 mol/L, 7.85 mL, 15.70 mmol, 5.0 eq). After the completion of the dropwise addition, the mixture was stirred at −30° C. to react for 30 min. The reaction endpoint was monitored by TLC. The reaction solution was quenched with saturated aqueous $NH_4Cl$ (30 mL), and extracted with dichloromethane (30 mL×3). The organic phase was separated, washed with saturated brine (30 mL×2), dried over anhydrous $Na_2SO_4$ (0.8 g), filtered by suction, and concentrated under reduced pressure, and the crude product was purified by silica gel column chromatography (DCM:MeOH=40:1-20:1) to give a yellow solid product (564.0 mg, yield: 50.9%).

$^1$H NMR (400 MHz, DMSO-d$_6$) δ (ppm): 11.96 (s, 1H), 8.59 (s, 1H), 7.71 (s, 1H), 5.36-5.35 (d, 1H), 4.47-4.45 (t, 1H), 3.66-3.63 (t, 4H), 2.09-2.01 (m, 1H), 1.63 (s, 4H), 0.90-0.88 (d, 3H), 0.75-0.73 (d, 3H), 0.45 (m, 4H).

Molecular formula: $C_{20}H_{24}N_4O_2$ Molecular weight: 352.44 LC-MS (Pos, m/z)=353.26 [M+H]$^+$.

Example 81: Synthesis of N-(2-aminoethyl)-3-cyano-4-(4-methoxy-4-methylpiperidin-1-yl)-2-oxo-1,2-dihydro-1,7-naphthyridin-6-carboxamide (Compound 138) hydrochloride

Step 1: Synthesis of Tert-Butyl (2-(3-cyano-4-(4-methoxy-4-methylpiperidin-1-yl)-2-oxo-1,2-dihydro-1,7-naphthyridin)-6-formylamino)ethyl)carbamate

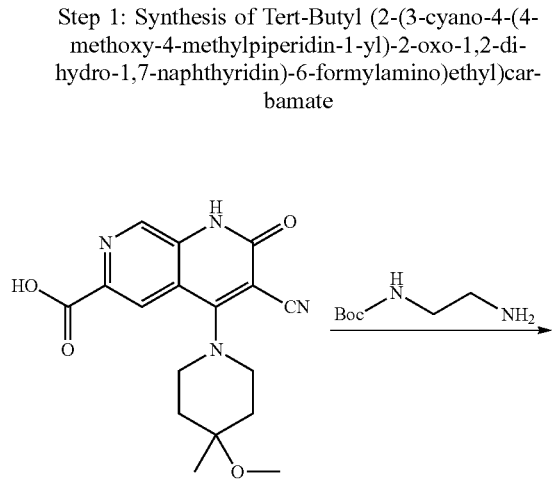

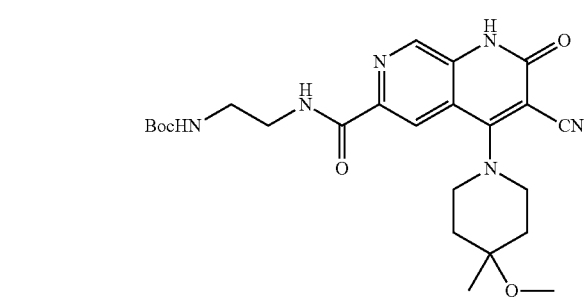

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq), HATU (333 mg, 0.88 mmol, 1.5 eq) and DIPEA (376 mg, 1.76 mmol, 3.0 eq) were dissolved in DMAC (2 mL), stirred at room temperature for 30 min, then followed by addition of tert-butyl (2-aminoethyl)carbamate (281 mg, 1.76 mmol, 2.0 eq) and reacted at room temperature for 1 h. The reaction endpoint was monitored by LC-MS. The reaction solution was followed by addition of water (10 mL), and extracted with dichloromethane (10 mL×3). The organic phase was washed with water (10 mL×3), dried over anhydrous sodium sulfate, filtered, and concentrated under reduced pressure. The crude product was purified by silica gel column chromatography (DCM:MeOH=30:1) to give a product (220 mg, yield: 78.3%).

Step 2: Synthesis of N-(2-aminoethyl)-3-cyano-4-(4-methoxy-4-methylpiperidin-1-yl)-2-oxo-1,2-dihydro-1,7-naphthyridin-6-carboxamide Hydrochloride

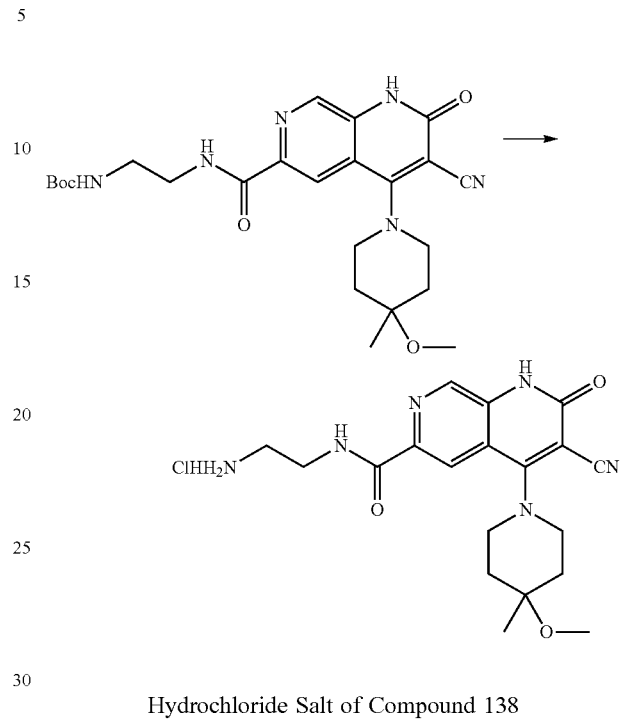

Hydrochloride Salt of Compound 138

The intermediate tert-butyl (2-(3-cyano-4-(4-methoxy-4-methylpiperidin-1-yl)-2-oxo-1,2-dihydro-1,7-naphthyridin-6-formylamino)ethyl)carbamate (220 mg, 0.45 mmol, 1.0 eq) was dissolved in methanol (3 mL), followed by addition of hydrogen chloride in ethanol solution (25%, 2 mL), and reacted at room temperature for 2 h. The reaction endpoint was monitored by TLC. Solid was precipitated from the solution, and the mixture was filtered. The filter cake was dried to give a product (150 mg, yield: 79%).

$^1$HNMR (400 MHz, DMSO-$d_6$) δ (ppm): 12.28 (s, 1H), 9.01-90.1 (m, 1H), 8.68 (s, 1H), 8.29 (s, 1H), 7.91 (s, 3H), 3.55-3.64 (m, 6H), 3.21 (s, 3H), 3.00-3.02 (m, 2H), 194-1.97 (d, 2H), 1.73-1.80 (d, 2H), 1.24 (s, 3H).

Molecular formula: $C_{19}H_{24}N_6O_3$ Molecular weight: 384.44 LC-MS (Pos, m/z)=385.19 [M+H]$^+$.

Example 82: Synthesis of 3-cyano-N-(2-(dimethylamino)ethyl)-4-(4-methoxy-4-methylpiperidin-1-yl)-2-oxo-1,2-dihydro-1,7-naphthyridin-6-carboxamide (Compound 139)

Compound 139

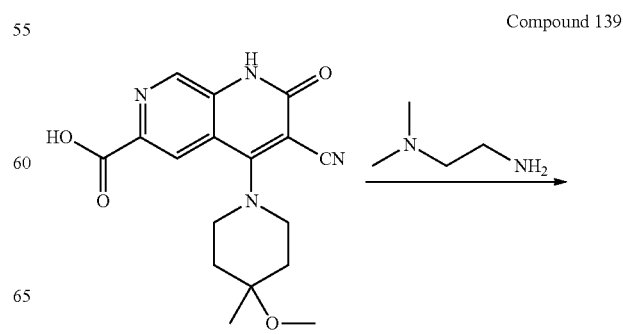

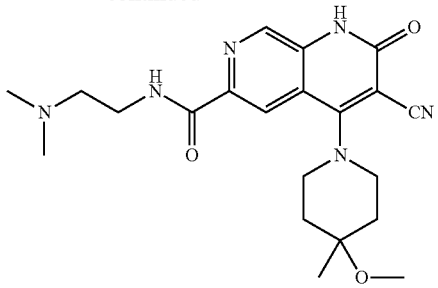

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq), HATU (333 mg, 0.88 mmol, 1.5 eq) and DIPEA (226 mg, 1.76 mmol, 3.0 eq) were dissolved in DMAC (2 mL), stirred at room temperature for 30 min, followed by addition of N,N-dimethylethylenediamine (103 mg, 1.16 mmol, 2.0 eq), and reacted at room temperature for 1 h. The reaction endpoint was monitored by LC-MS. Water (10 mL) was added to the reaction solution, and the reaction solution was extracted with dichloromethane (10 mL×3). The organic phase was washed with water (10 mL×3), dried over anhydrous sodium sulfate, filtered and concentrate under reduced pressure, and the crude product was purified by silica gel column chromatography (DCM:MeOH=20:1) to give a product (86 mg, yield: 36%).

$^1$HNMR (400 MHz, DMSO-d$_6$) δ (ppm): 12.20 (s, 1H), 8.79 (s, 1H), 8.66 (s, 1H), 8.28 (s, 1H), 3.62-3.64 (d, 4H), 3.50-3.51 (d, 2H), 3.21 (s, 3H), 2.76 (s, 2H), 2.44 (s, 6H), 1.94-1.97 (d, 2H), 1.74-1.81 (m, 2H), 1.25 (s, 3H).

Molecular formula: $C_{21}H_{28}N_6O_3$ Molecular weight: 412.49 LC-MS (Pos, m/z)=413.22 [M+H]$^+$.

Example 83: Synthesis of 3-cyano-4-(4-methoxy-4-methylpiperidin-1-yl)-2-oxo-N-(2-(pyrrolidin-1-yl)ethyl)-1,2-dihydro-1,7-naphthyridin-6-carboxamide (Compound 140)

Compound 140

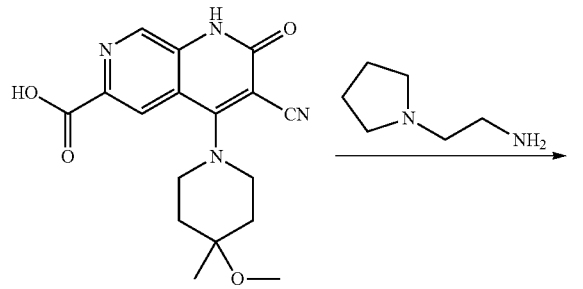

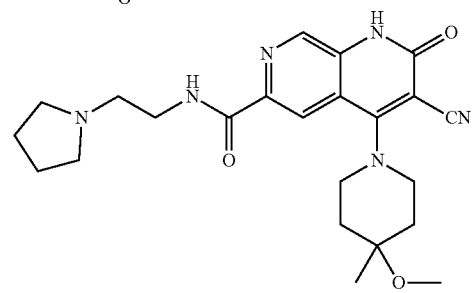

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq), HATU (333 mg, 0.88 mmol, 1.5 eq) and DIPEA (226 mg, 1.76 mmol, 3.0 eq) were dissolved in DMAC (2 mL), stirred at room temperature for 30 min, followed by addition of 2-(pyrrolidin-1-yl)ethan-1-amine (134 mg, 1.16 mmol, 2.0 eq), and reacted at room temperature for 1 h. The reaction endpoint was monitored by LC-MS. The reaction solution was followed by addition of water (10 mL), and extracted with dichloromethane (10 mL×3). The organic phase was washed with water (10 mL×3), dried over anhydrous sodium sulfate, filtered, and concentrated under reduced pressure, and the crude product was purified by silica gel column chromatography (DCM:MeOH=20:1) to give a product (106 mg, yield: 41%).

$^1$HNMR (400 MHz, DMSO-d$_6$) δ (ppm): 12.26 (s, 1H), 9.08-9.11 (m, 1H), 8.67 (s, 1H), 8.30 (s, 1H), 3.63-3.64 (d, 8H), 3.06-3.20 (m, 6H), 1.73-1.98 (m, 9H), 1.25 (s, 3H).

Molecular formula: $C_{23}H_{30}N_6O_3$ Molecular weight: 438.53 LC-MS (Pos, m/z)=439.24 [M+H]$^+$.

Example 84: Synthesis of 3-cyano-4-(4-methoxy-4-methylpiperidin-1-yl)-N-((1-methylpiperidin-4-yl)methyl)-2-oxo-1,2-dihydro-1,7-naphthyridin-6-carboxamide (Compound 141) Trifluoroacetate

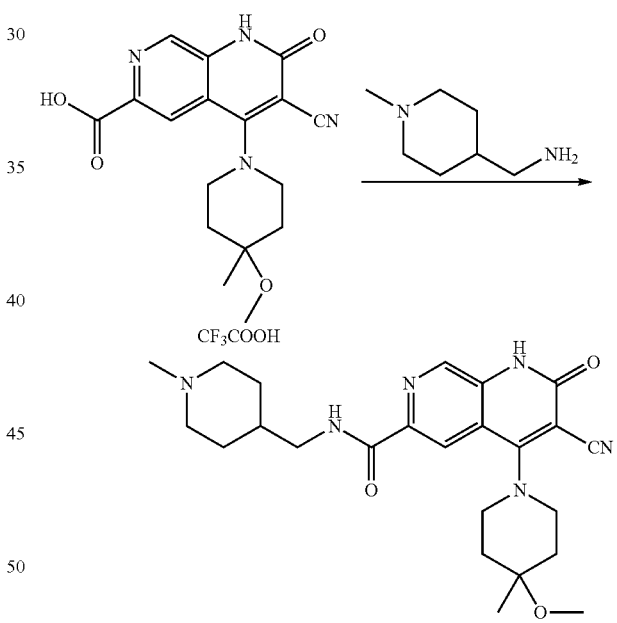

Trifluoroacetate Salt of Compound 141

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq) was dissolved in anhydrous N,N-dimethylacetamide (2 mL), followed by addition of DIPEA (226.3 mg, 1.75 mmol, 3.0 eq) and HATU (333.1 mg), 0.88 mmol, 1.5 eq), stirred at room temperature for 0.5-1 h, followed by addition of (1-methylpiperidin-4-yl)methanamine (150 mg, 1.17 mmol, 2.0 eq), and reacted for 1 h at room temperature. When the starting materials were still remained as monitored by LC-MS, (1-methylpiperidin-4-yl)methanamine (150 mg, 1.17 mmol, 2.0 eq) was added to further react for 2 h. The mixture was purified by preparative HPLC (0.1% aqueous trifluoroacetic acid:acetonitrile=70:30) to give a product (68.8 mg, yield: 20.7%).

$^1$H NMR (400 MHz, DMSO-d$_6$) δ (ppm): 12.22 (s, 1H), 9.00-8.99 (s, 1H), 8.95-8.94 (s, 1H), 8.65 (s, 1H), 8.28 (s, 1H), 3.63-3.62 (m, 4H), 3.43-3.40 (m, 2H), 3.23 (s, 3H), 295-2.83 (m, 2H), 2.75-2.74 (m, 2H), 1.97-1.94 (m, 2H), 1.85-1.80 (m, 2H), 1.78-1.75 (m, 3H), 1.24 (s, 3H).

Molecular formula: C$_{24}$H$_{32}$N$_6$O$_3$ Molecular weight: 452.56 LC-MS (Pos, m/z)=453.45 [M+H]$^+$.

Example 85: Synthesis of 3-cyano-4-(4-methoxy-4-methylpiperidin-1-yl)-N-(1-methylazetidin-3-yl)-2-oxo-1,2-dihydro-1,7-naphthyridin-6-carboxamide (Compound 142) Trifluoroacetate

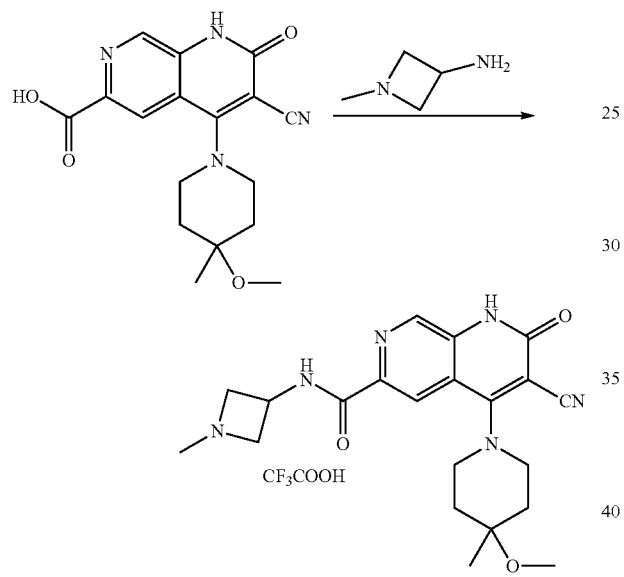

Trifluoroacetate Salt of Compound 142

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq) was dissolved in anhydrous N,N-dimethylacetamide (2 mL), followed by addition of DIPEA (226.3 mg, 1.75 mmol, 3.0 eq) and HATU (333.1 mg), 0.88 mmol, 1.5 eq), stirred at room temperature for 0.5 to 1 h, followed by addition of 1-methylazetidin-3-amine (100.6 mg, 1.17 mmol, 2.0 eq), and reacted at room temperature for 12 h. The crude product was purified by preparative HPLC (0.1% aqueous trifluoroacetic acid:acetonitrile=70:30) to give a product (113.13 mg, yield: 37.1%).

$^1$H NMR (400 MHz, DMSO-d$_6$) δ (ppm): 12.27 (s, 1H), 9.59-9.53 (s, 2H), 8.68 (s, 1H), 8.27 (s, 1H), 4.90-4.86 (m, 1H), 4.45 (m, 2H), 4.16 (m, 2H), 3.63-3.62 (m, 4H), 3.20 (s, 3H), 2.91 (s, 3H), 1.96-1.93 (m, 2H), 1.79-1.72 (m, 2H), 1.24 (s, 3H).

Molecular formula: C$_{21}$H$_{26}$N$_6$O$_3$ Molecular weight: 410.48 LC-MS (Pos, m/z)=411.40 [M+H]$^+$.

Example 86: Synthesis of 3-cyano-4-(4-methoxy-4-methylpiperidin-1-yl)-N-(1-methylpiperidin-4-yl)-2-oxo-1,2-dihydro-1,7-naphthyridin-6-carboxamide (Compound 143)

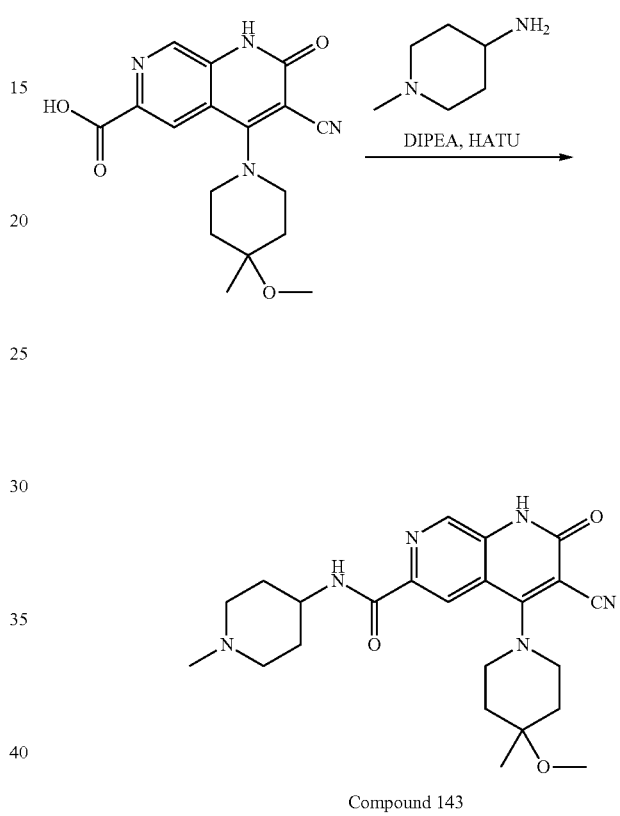

Compound 143

The starting material 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq) was dissolved in N,N-dimethylformamide (2 mL), followed by addition of N,N-diisopropylethylamine (226 mg, 1.75 mmol, 3.0 eq) and HATU (333 mg, 0.87 mmol, 1.5 eq), reacted at room temperature for 1 h, followed by addition of 1-methylpiperidin-4-amine (67 mg, 0.58 mmol, 1.0 eq), and reacted at room temperature for 2 h. The reaction endpoint was monitored by LC-MS. The reaction solution was purified by preparative HPLC (0.1% aqueous trifluoroacetic acid:acetonitrile=70:30) to give a product (49 mg, yield: 19%).

$^1$HNMR (400 MHz, DMSO-d$_6$) δ (ppm): 12.22 (s, 1H), 9.37 (s, 1H), 8.90 (m, 1H), 8.67 (s, 1H), 8.27 (s, 1H), 4.02-4.04 (m, 1H), 3.62-3.64 (m, 4H), 3.46-3.48 (m, 2H), 3.21 (s, 3H), 3.09 (m, 1H), 2.78 (s, 3H), 1.88-2.01 (m, 6H), 1.73-1.80 (m, 2H), 1.24 (s, 1H).

Molecular formula: C$_{23}$H$_{30}$N$_6$O$_3$ Molecular weight: 438.53 LC-MS (Pos, m/z)=439.37 [M+H]$^+$

Example 87: Synthesis of 3-cyano-N-(2,3-dihydroxypropyl)-4-(4-methoxy-4-methylpiperidin-1-yl)-2-oxo-1,2-dihydro-1,7-naphthyridin-6-carboxamide (Compound 144)

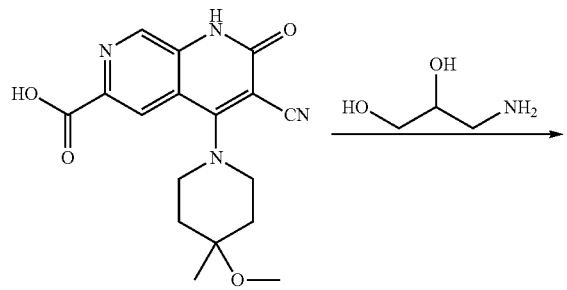

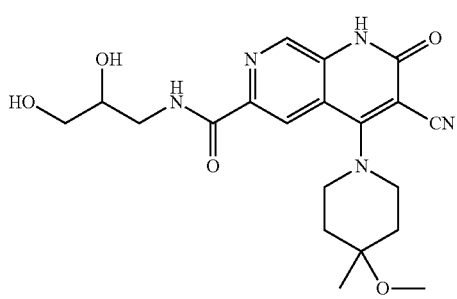

Compound 144

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq) was dissolved in anhydrous N,N-dimethylacetamide (2 mL), followed by addition of DIPEA (226.3 mg, 1.75 mmol, 3.0 eq) and HATU (333.1 mg, 0.88 mmol, 1.5 eq), stirred at room temperature for 0.5 to 1 h, then followed by addition of 3-aminopropane-1,2-diol (106.4 mg, 1.17 mmol, 2.0 eq), and reacted at room temperature for 12 h. The crude product was purified by preparative HPLC (0.1% aqueous trifluoroacetic acid:acetonitrile=70:30) and lyophilized to obtain a sample (93.79 mg). The sample was dissolved in water, adjusted to a pH of 8 with aqueous sodium bicarbonate solution, and extracted with n-butanol (20 mL×5), and the organic phase was concentrated to give a product (47.2 mg, yield: 19.4%).

$^1$H NMR (400 MHz, DMSO-$d_6$) δ (ppm): 8.42-8.39 (s, 1H), 8.36 (s, 1H), 8.08 (s, 1H), 4.96 (s, 1H), 4.66 (s, 1H), 3.49 (m, 1H), 3.47-3.45 (m, 6H), 3.25-3.23 (m, 2H), 3.19 (s, 3H), 1.91-1.88 (m, 2H), 1.75-1.70 (m, 2H), 1.23 (s, 3H).

Molecular formula: $C_{20}H_{25}N_5O_5$ Molecular weight: 415.45 LC-MS (Neg, m/z)=414.34 [M-H]$^-$.

Example 88: Synthesis of 4-(4-methoxy-4-methylpiperidin-1-yl)-6-(2-methoxyethoxy)-2-oxo-1,2-dihydro-1,7-naphthyridin-3-carbonitrile (Compound 145)

Step 1: Synthesis of methyl 2-(2-methoxyethoxy)-5-nitroisonicotinate

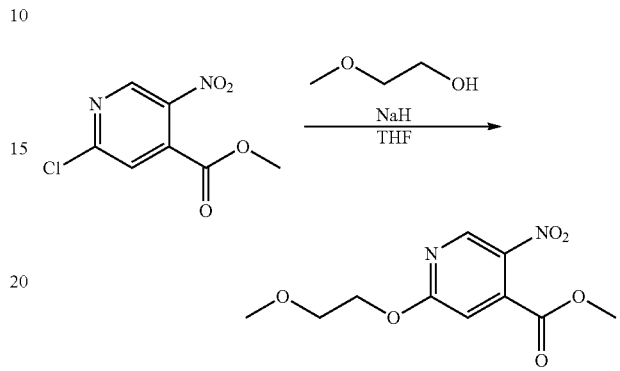

The raw material ethylene glycol monomethyl ether (3.5 g, 46.17 mmol, 1.0 eq) was dissolved in tetrahydrofuran (50 mL), cooled to 0° C., followed by addition of sodium hydride (3.7 g, 92.34 mmol, 2.0 eq). After 1 hour of reaction, methyl 2-chloro-5-nitroisonicotinate (10.0 g, 46.17 mmol, 1.0 eq) was added. The reaction endpoint was monitored by TLC (PE:EA=5:1). The reaction solution was poured into ice water (100 mL) and quenched. The aqueous phase was extracted with ethyl acetate (100 mL×2), and the organic phases were combined and dried over anhydrous sodium sulfate, filtered, and concentrated. The crude product was purified by silica gel column chromatography (PE:EA=5:1) to give a product as a pale yellow oil (1.8 g, yield: 15%).

Step 2: Synthesis of Methyl 5-amino-2-(2-methoxyethoxy)isonicotinate

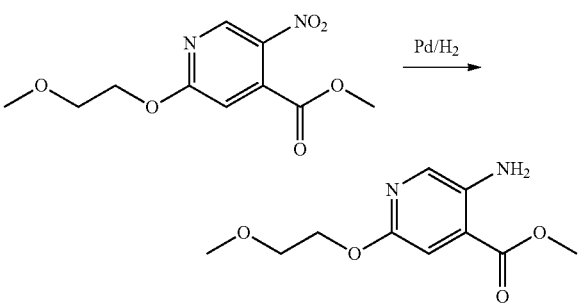

The intermediate methyl 2-(2-methoxyethoxy)-5-nitroisonicotinate (1.8 g, 7.02 mmol, 1.0 eq) was dissolved in methanol (10 mL), followed by addition of 10% palladium on carbon (500 mg), fed with hydrogen and reacted overnight at room temperature. The reaction endpoint was monitored by TLC (PE:EA=3:1). The reaction solution was filtered and concentrated, and the crude product was purified by silica gel column chromatography (PE:EA=5:1) to give a product as a pale yellow solid (1.2 g, yield: 75%).

Step 3: Synthesis of methyl 5-(2-cyanoacetamido)-2-(2-methoxyethoxy)isonicotinate

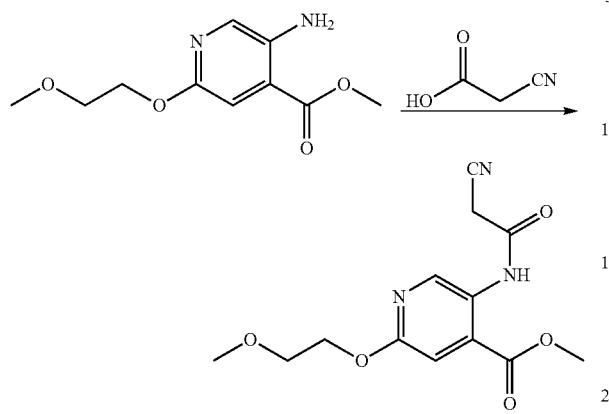

The intermediate methyl 5-amino-2-(2-methoxyethoxy)isonicotinate (1.2 g, 5.3 mmol, 1.0 eq) and cyanoacetic acid (901 mg, 10.6 mmol, 2.0 eq) were dissolved in dichloromethane (20 mL), followed by addition of EDCI (3.04 g, 15.9 mmol, 3.0 eq) and reacted at room temperature for 2 hours. The reaction endpoint was monitored by LC-MS. The reaction solution was poured into ice water (30 mL) and quenched. The aqueous phase was extracted with dichloromethane (30 mL×2), and the organic phases were combined and dried over anhydrous sodium sulfate, filtered, and concentrated. The crude product was slurried with methyl tert-butyl ether to give a product as a pale yellow solid (1.2 g, yield: 77%).

Step 4: Synthesis of 4-hydroxy-6-(2-methoxyethoxy)-2-oxo-1,2-dihydro-1,7-naphthyridin-3-carbonitrile

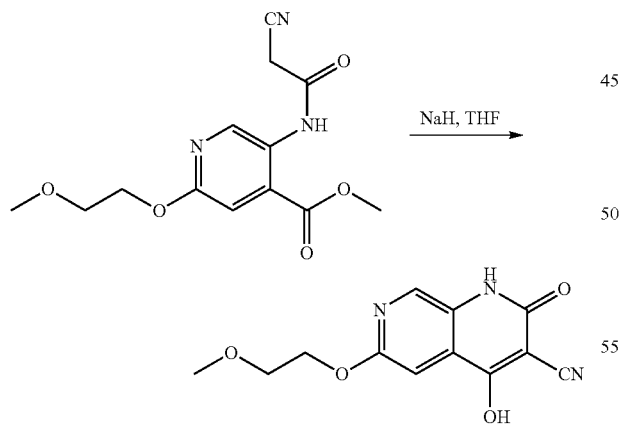

The intermediate methyl 5-(2-cyanoacetamido)-2-(2-methoxyethoxy)isonicotinate (1.2 g, 4.09 mmol, 1.0 eq) was dissolved in THF (20 mL), followed by addition of sodium hydride (327 mg, 8.18 mmol, 2.0 eq), then warmed to 80° C. and reacted for 4 hours. The reaction endpoint was monitored by LC-MS. The reaction solution was cooled to about 0° C., adjusted to a pH of 2 with 2 mol/L hydrochloric acid aqueous solution until solid was precipitated, and then filtered. The filter cake was dried at 50° C. under normal pressure to obtain a product as a yellow solid (800 mg, yield: 75%).

Step 5: Synthesis of 4-chloro-6-(2-methoxyethoxy)-2-oxo-1,2-dihydro-1,7-naphthyridin-3-carbonitrile

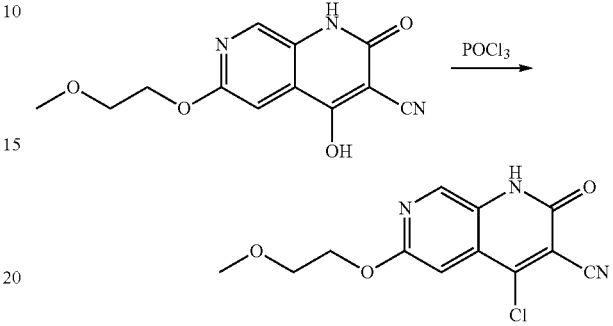

The intermediate 4-hydroxy-6-(2-methoxyethoxy)-2-oxo-1,2-dihydro-1,7-naphthyridin-3-carbonitrile (800 mg, 3.06 mmol, 1.0 eq) was dissolved in phosphorus oxychloride (8 mL), warmed to 100° C. and reacted for 1 h. The reaction endpoint was monitored by LC-MS. The reaction solution was poured into ice water (20 mL) and quenched. The aqueous phase was extracted with dichloromethane (30 mL×3), and the organic phases were combined and dried over anhydrous sodium sulfate, filtered, and concentrated. The crude product was slurried with methyl tert-butyl ether to give a product as a pale yellow solid (180 mg, yield: 21%).

Step 6: Synthesis of 4-(4-methoxy-4-methylpiperidin-1-yl)-6-(2-methoxyethoxy)-2-oxo-1,2-dihydro-1,7-naphthyridin-3-carbonitrile

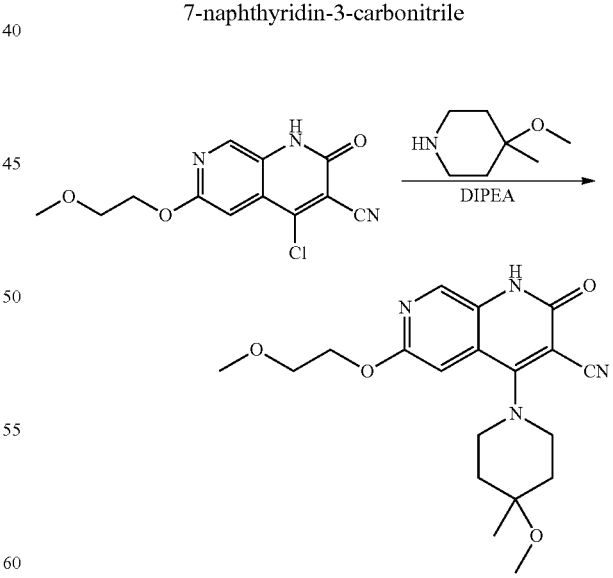

Compound 145

Intermediate 4-chloro-6-(2-methoxyethoxy)-2-oxo-1,2-dihydro-1,7-naphthyridin-3-carbonitrile (180 mg, 0.64 mmol, 1.0 eq) was dissolved in N,N-dimethylformamide (2 mL), followed by addition of N,N-diisopropylethylamine (332 mg, 2.58 mmol, 4.0 eq) and 4-methoxy-4 methylpiperidine (110 mg, 0.97 mmol, 1.0 eq), warmed to 80° C., and then reacted for two hours. The reaction endpoint was monitored by LC-MS. The reaction solution was poured into ice water (20 mL) and quenched. The aqueous phase was extracted with dichloromethane (30 mL×3), and the organic phases were combined, dried over anhydrous sodium sulfate, filtered, and concentrated. The crude product was purified by silica gel column chromatography (DCM:MeOH=15:1) to give a product as a pale yellow oil (60 mg, yield: 25%).

$^1$HNMR (400 MHz, DMSO-$d_6$) δ (ppm): 11.78 (s, 1H), 8.28 (s, 1H), 6.94 (s, 1H), 4.37 (m, 2H), 3.67 (m, 2H), 3.56-3.58 (m, 4H), 3.30 (s, 3H), 3.18 (s, 3H), 1.88-1.91 (m, 2H), 1.75-1.80 (m, 2H), 1.21 (s, 3H).

Molecular formula: $C_{19}H_{24}N_4O_4$ Molecular weight: 372.43 LC-MS (Pos, m/z)=373.3 [M+H]$^+$ Example 89: Synthesis of 3-cyano-N,N-dimethyl-2-oxo-4-(6-azaspiro[2.5]octane-6-yl)-1,2-dihydro-1,7-naphthyridin-6-carboxamide (Compound 149)

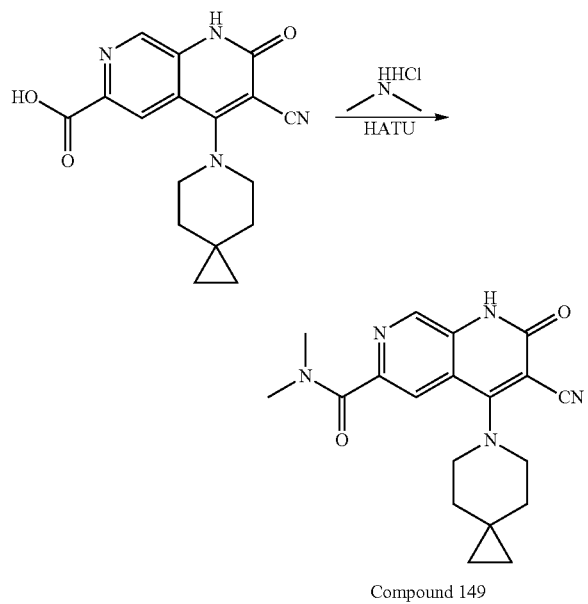

Compound 149

3-cyano-2-oxo-4-(6-azaspiro[2.5]octane-6-yl)-1,2-dihydro-1,7-naphthyridin-6-carboxylic acid (256.4 mg, 0.790 mmol, 1.0 eq) was dissolved in DMF (20 mL), cooled to 0° C. in ice bath, followed by addition of HATU (450.8 mg, 1.186 mmol, 1.5 eq) and then addition of DIPEA (613.0 mg, 4.743 mmol, 6.0 eq) and dimethylamine hydrochloride (193.3 mg, 2.371 mmol, 3.0 eq). After the addition, the mixture was stirred at room temperature for 30 min. The reaction endpoint was monitored by TLC. The mixture was followed by addition of water (100 mL) and extracted with ethyl acetate (20 mL×3). The organic phases were combined, washed with saturated brine (10 mL×4), dried over anhydrous sodium sulfate, filtered by suction, concentrated under reduced pressure, purified by preparative thin layer chromatography (DCM:MeOH=8:1) to give a product as a yellow solid (91.0 mg, yield: 32.8%).

$^1$H NMR (400 MHz, DMSO-$d_6$) δ (ppm): 12.19 (s, 1H), 8.61 (s, 1H), 7.89 (s, 1H), 3.68-3.65 (t, 4H), 3.06 (s, 3H), 3.02 (s, 3H), 1.61 (s, 4H), 0.44 (s, 4H).

Molecular formula: $C_{19}H_{21}N_5O_2$ Molecular weight: 351.41 LC-MS (Pos, m/z)=352.20 [M+H]$^+$.

Example 90: Synthesis of 4-(4-(2-hydroxyethyl)piperidin-1-yl)-2-oxo-1,2-dihydro-1,7-naphthyridin-3-carbonitrile (Compound 153)

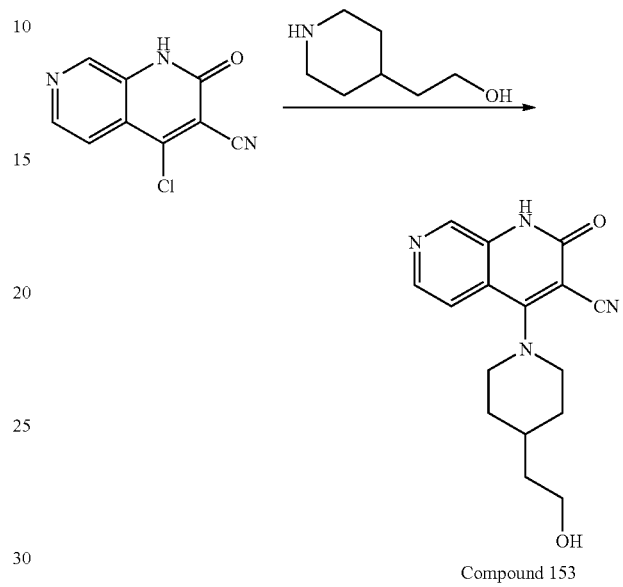

Compound 153

The intermediate 4-chloro-2-oxo-1,2-dihydro-1,7-naphthyridin-3-carbonitrile (60 mg, 0.29 mmol, 1.0 eq) was dissolved in N,N-dimethylformamide (1 mL), and N,N-diisopropylethylamine (112 mg, 0.87 mmol, 3.0 eq) was added to the reaction, then 2-(piperidin-4-yl)ethan-1-ol (38 mg, 0.29 mmol, 1.0 eq) was added. The temperature was raised to 80° C., and the reaction was carried out for 2 hours. The mixture was cooled to room temperature until solid was precipitated, and then filtered. The filter cake was rinsed with THF (1 mL) and petroleum ether (1 mL) sequentially, and dried at 45° C. to give a yellow solid product (16 mg, yield: 18%).

$^1$H NMR (400 MHz, DMSO-$d_6$) δ (ppm): 11.98 (s, 1H), 8.65 (s, 1H), 8.33-8.35 (d, 1H), 7.58-7.80 (d, 1H), 4.40-4.42 (m, 1H), 3.83-3.86 (m, 2H), 3.48-3.53 (m, 2H), 3.37-3.43 (m, 2H), 1.84-1.87 (m, 2H), 1.74-1.80 (m, 1H), 1.45-1.50 (m, 4H).

Molecular formula: $C_{16}H_{18}N_4O_2$ Molecular weight: 298.35 LC-MS (Neg, m/z)=297.15 [M−H]$^-$ Example 91: Synthesis of (R)-4-(3-(1H-1,2,4-triazol-1-yl)pyrrolidin-1-yl)-2-oxo-1,2-dihydro-1,7-naphthyridin-3-carbonitrile (Compound 154)

Step 1: Synthesis of Tert-Butyl (R)-3-(1H-1,2,4-triazol-1-yl)pyrrolidin-1-carboxylate

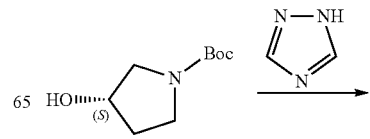

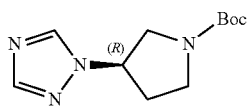

The starting material tert-butyl (S)-3-hydroxypyrrolidin-1-carboxylate (1.0 g, 5.34 mmol, 1.0 eq) was dissolved in anhydrous tetrahydrofuran (20 mL), and 1H-1,2,4-triazole (552.7 mg, 8.01 mmol, 1.5 eq) and triphenylphosphine (2.8 g, 10.68 mmol, 2.0 eq) were added to the reaction. After the addition, the temperature was reduced to 0° C. and diethyl azodicarboxylate (1.86 g, 10.68 mmol, 2.0 eq) was added dropwise. After completion of the addition, the reaction was carried out at room temperature for 12 h. The reaction endpoint was monitored by TLC. Saturated aqueous sodium carbonate solution (10 mL) was added to the solution mixture, and the solution mixture was extracted with ethyl acetate (50 mL×2), and separated. The organic phases were combined, dried with anhydrous sodium sulfate, filtered, and the filtrate was concentrated under reduced pressure. The crude product was purified by silica gel column chromatography (EA:PE=1:10-1:2) to give a product (1.05 g, yield: 83.3%).

Step 2: Synthesis of (R)-1-(pyrrolidin-3-yl)-1H-1,2,4-triazole Hydrochloride

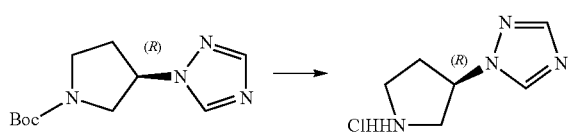

The intermediate tert-butyl (R)-3-(1H-1,2,4-triazol-1-yl)pyrrolidin-1-carboxylate (1.05 g, 4.41 mmol, 1.0 eq) was dissolved in anhydrous methanol (4 mL), followed by addition of 30% hydrogen chloride in ethanol solution (10 mL), and reacted at room temperature for 2 h to precipitate a white solid. The reaction endpoint was monitored by TLC. The reaction solution was filtered, and the filter cake was rinsed with ethyl acetate and dried to give a product (770 mg, yield: 100%).

Step 3: Synthesis of (R)-4-(3-(1H-1,2,4-triazol-1-yl)pyrrolidin-1-yl)-2-oxo-1,2-dihydro-1,7-naphthyridin-3-carbonitrile

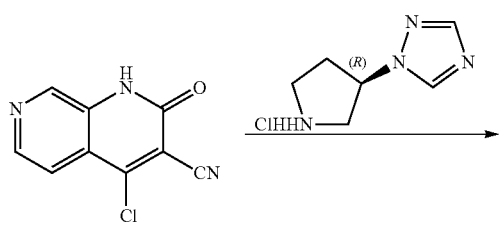

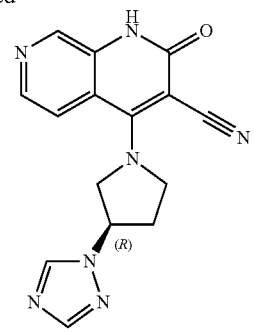

Compound 154

The intermediate 4-chloro-2-oxo-1,2-dihydro-1,7-naphthyridin-3-carbonitrile (200 mg, 0.97 mmol, 1.0 eq) was dissolved in DMF (2 mL), and (R)-1-(pyrrolidin-3-yl)-1H-1,2,4-triazole hydrochloride (238 mg, 1.36 mmol, 1.4 eq) and DIPEA (753.7 mg, 5.84 mmol, 6.0 eq) were added to the reaction. After the addition, the temperature was raised to 80° C., and the reaction was carried out for 2 h. The reaction endpoint was monitored by LC-MS. The reaction solution was cooled to room temperature and purified by preparative HPLC (0.1% aqueous trifluoroacetic acid:acetonitrile=70:30) to give a product (98.6 mg, yield: 33%).

$^1$HNMR (400 MHz, DMSO-$d_6$) δ (ppm): 11.67 (s, 1H), 8.69 (s, 1H), 8.62 (s, 1H), 8.28-8.27 (d, 1H), 8.03 (s, 1H), 7.98-7.96 (s, 1H), 5.33-5.28 (m, 1H), 4.61-4.57 (m, 1H), 4.35-4.29 (m, 2H), 4.23-4.17 (m, 1H), 2.56-2.53 (m, 1H), 2.48-2.47 (m, 1H).

Molecular formula: $C_{15}H_{13}N_7O$ Molecular weight: 307.21 LC-MS (Pos, m/z)=307.98 [M+H]$^+$.

Example 92: Synthesis of 4-(R)-3-(1H-pyrazol-1-yl)pyrrolidin-1-yl)-6-(1-hydroxyethyl)-2-oxo-1,2-dihydro-1,7-naphthyridin-3-carbonitrile (Compound 156)

Step 1: Synthesis of (R)-1-(pyrrolidin-3-yl)-1H-pyrazole Hydrochloride

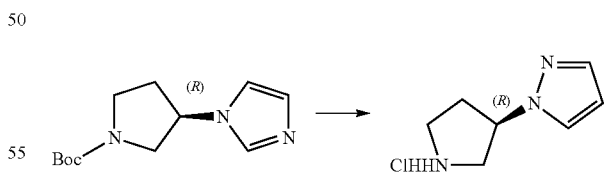

The starting material tert-butyl (R)-3-(1H-pyrazol-1-yl)pyrrolidin-1-carboxylate (2.7 g, 11.37 mmol) was dissolved in anhydrous methanol (4 mL), and 30% hydrogen chloride in ethanol solution (10 mL) was added to the reaction. After the addition, the reaction was carried out at room temperature for 2 h. The reaction endpoint was monitored by TLC. The mixture was concentrated under reduced pressure to give an oily product (3.29 g crude product).

Step 2: Synthesis of (R)-4-(3-(1H-pyrazol-1-yl)
pyrrolidin-1-yl)-6-chloro-2-oxo-1,2-dihydro-1,7-
naphthyridin-3-carbonitrile

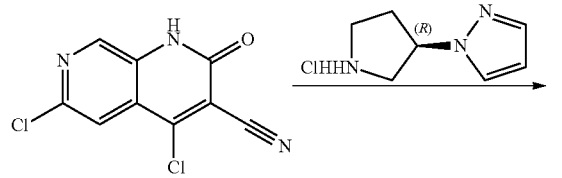

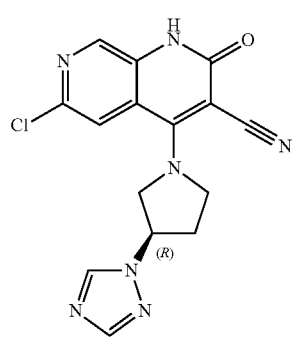

The intermediate 4-chloro-2-oxo-1,2-dihydro-1,7-naphthyridin-3-carbonitrile (2.27 g, 9.46 mmol, 1.0 eq) was dissolved in DMF (8 mL), and (R)-1-(pyrrolidin-3-yl)-1H-pyrazole hydrochloride (3.29 g crude product) and DIPEA (7.3 g, 56.76 mmol, 6.0 eq) were added to the reaction. After the addition, the temperature is raised to 80° C., and the reaction was carried out for 2 h. The reaction endpoint was monitored by LC-MS, and the temperature was reduced to room temperature. The reaction solution was poured into water (50 mL), stirred for 0.5 h, filtered. The filter cake was rinsed with water, then slurried with methyl tert-butyl ether, and filtered, and the filter cake was dried to give a product (2.35 g, yield after the two steps: 73.4%).

Step 3: Synthesis of (R)-4-(3-(1H-pyrazol-1-yl)
pyrrolidin-1-yl)-2-oxo-6-vinyl-1,2-dihydro-1,7-
naphthyridin-3-carbonitrile

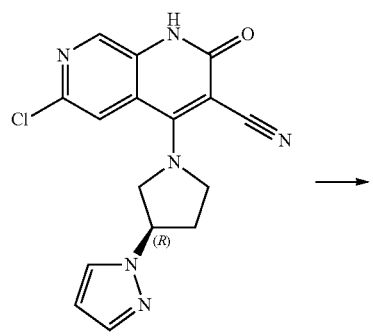

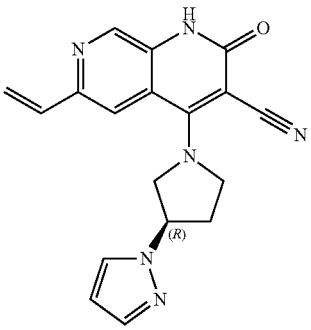

Intermediate (R)-4-(3-(1H-pyrazol-1-yl)pyrrolidin-1-yl)-6-chloro-2-oxo-1,2-dihydro-1,7-naphthyridin-3-carbonitrile (2.3 g, 6.75 mmol, 1.0 eq), cesium carbonate (6.6 g, 20.25 mmol, 3.0 eq) and vinyl potassium trifluoroborate (1.3 g, 10.12 mmol, 1.5 eq) were dissolved in a mixed solvent of 1,4-dioxane (50 mL) and water (50 mL). The air of the system was replaced by nitrogen for three times, and then [1,1'-bis(diphenylphosphino) ferrocene]palladium dichloride (493 mg, 0.68 mmol, 0.1 eq) was added to the reaction. The air of the system was replaced by nitrogen for three times, and the mixture was heated to reflux and reacted for 12 h. The reaction endpoint was monitored by TLC, and the temperature was reduced to room temperature. Ethyl acetate (50 mL) and water (10 mL) were added, stirred for 10 min, and filtered. The filter cake was rinsed with ethyl acetate, and the liquid was separated. The aqueous phase was extracted with dichloromethane (50 mL×3), and the organic phases were combined, dried over anhydrous sodium sulfate, and filtered. The mother liquor was concentrated under reduced pressure, slurried with methyl t-butyl ether to precipitate pale yellow solid, and then filtered. The filter cake was dried to give a product (1.45 g, yield: 65.9%).

Step 4: Synthesis of 4-((R)-3-(1H-pyrazol-1-yl)
pyrrolidin-1-yl)-6-(1,2-dihydroxyethyl)-2-oxo-1,2-
dihydro-1,7-naphthyridin-3-carbonitrile

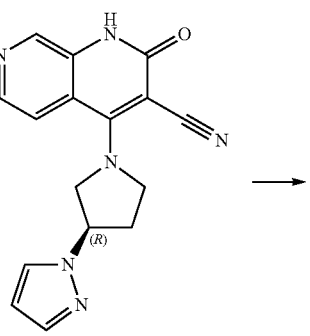

-continued

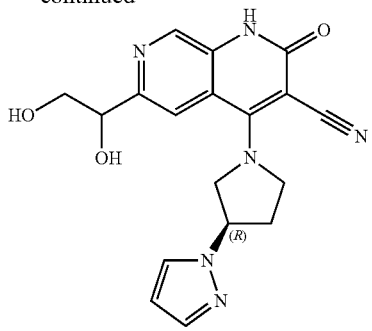

Intermediate (R)-4-(3-(1H-pyrazol-1-yl)pyrrolidin-1-yl)-2-oxo-6-vinyl-1,2-dihydro-1,7-naphthyridin-3-carbonitrile (453 mg, 1.36 mmol, 1.0 eq) was dissolved in a mixed solvent of tert-butanol (7 mL) and water (7 mL), followed by addition of methanesulfonamide (129.5 mg, 1.36 mmol, 1.0 eq) and AD-mix-β (5.4 g). After the addition, the mixture was reacted at room temperature for 12 h. The reaction endpoint was monitored by LC-MS. The reaction solution was directly subjected to the next step.

Step 5: Synthesis of (R)-4-(3-(1H-pyrazol-1-yl)pyrrolidin-1-yl)-6-formyl-2-oxo-1,2-dihydro-1,7-naphthyridin-3-carbonitrile

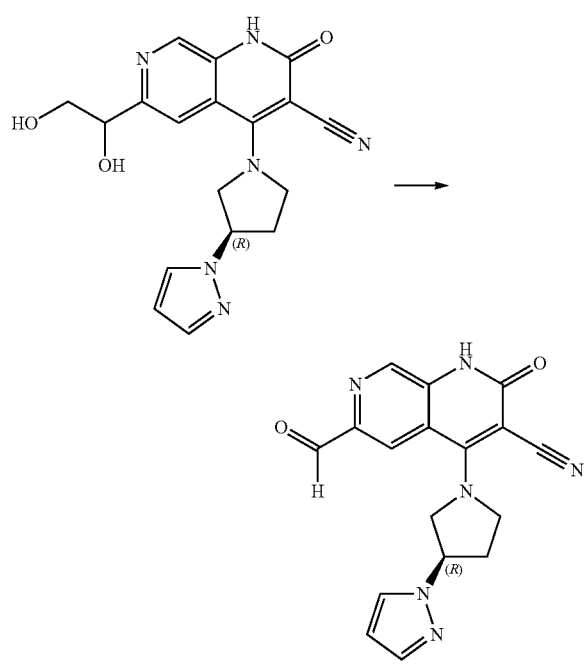

Sodium periodate (582.6 mg, 2.72 mmol, 2.0 eq) and tetrahydrofuran (5 mL) were added to the reaction solution obtained in the previous step. After the addition, the reaction was carried out for 4 h at room temperature, and the reaction endpoint was monitored by LC-MS. Water (20 mL) was added, and the liquid was separated. The aqueous phase was extracted with dichloromethane (50 mL×4), and the organic phases were combined, dried, and filtered. The filtrate was concentrated under reduced pressure to give a pale yellow solid. The solid was slurried with methyl tert-butyl ether, and filtered, and the filter cake was dried to give a product (215 mg, yield: 47.2%).

Step 6: Synthesis of 4-(R)-3-(1H-pyrazol-1-yl)pyrrolidin-1-yl)-6-(1-hydroxyethyl)-2-oxo-1,2-dihydro-1,7-naphthyridin-3-carbonitrile Compound 156

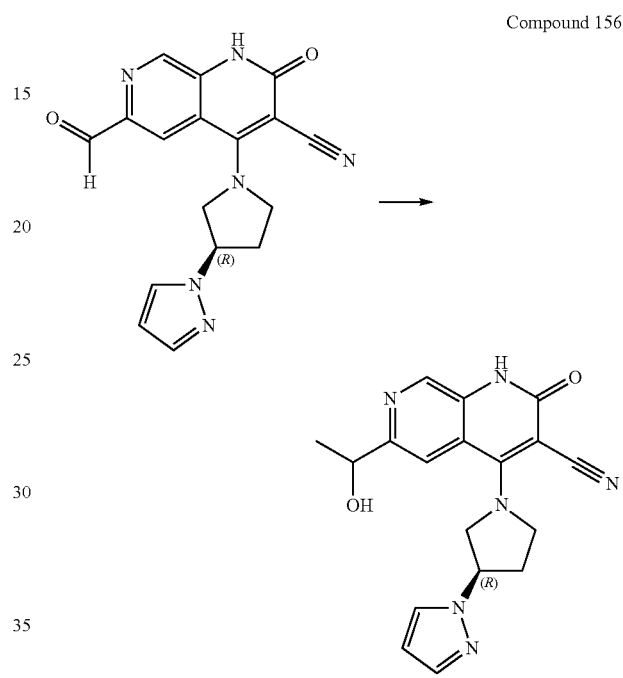

Intermediate (R)-4-(3-(1H-pyrazol-1-yl)pyrrolidin-1-yl)-6-formyl-2-oxo-1,2-dihydro-1,7-naphthyridin-3-carbonitrile (215 mg, 0.64 mmol, 1.0 eq) was dissolved in anhydrous tetrahydrofuran (3 mL), cooled to −10~0° C. under nitrogen protection, followed by a dropwise addition of a solution of methylmagnesium chloride in tetrahydrofuran (3 mol/L, 0.32 mL, 0.96 mmol, 1.5 eq). After the addition, the reaction was carried out for 12 h at room temperature. The reaction endpoint was monitored by LC-MS. The reaction solution was adjusted to a pH of about 8 by dropwise adding saturated aqueous ammonium chloride solution, and extracted with dichloromethane (50 mL×4). The organic phases were combined, dried, and filtered, and the filtrate was concentrated under reduced pressure. The crude product was purified by silica gel column chromatography (MeOH:DCM=1:100 to 1:40) to give a product (44.6 mg, yield: 19.8%).

$^1$H NMR (400 MHz, DMSO-$d_6$) δ (ppm): 11.59 (s, 1H), 8.54 (s, 1H), 8.00 (s, 1H), 7.90-7.89 (d, 1H), 7.58-7.56 (d, 1H), 7.51 (d, 1H), 6.31-6.30 (d, 1H), 6.29 (d, 1H), 5.46-5.45 (m, 1H), 5.20 (d, 1H), 4.79-4.73 (m, 1H), 4.57-4.50 (m, 1H), 4.37-4.20 (m, 1H), 2.48 (m, 2H), 1.38-1.37 (d, 3H).

Molecular formula: $C_{18}H_{18}N_6O_2$ Molecular weight: 350.38 LC-MS (Pos, m/z)=351.22 [M+H]$^+$.

Example 93: Synthesis of 4-(4-methoxy-4-methylpiperidin-1-yl)-6-methyl-2-oxo-1,2-dihydro-1,7-naphthyridin-3-carbonitrile (Compound 158)

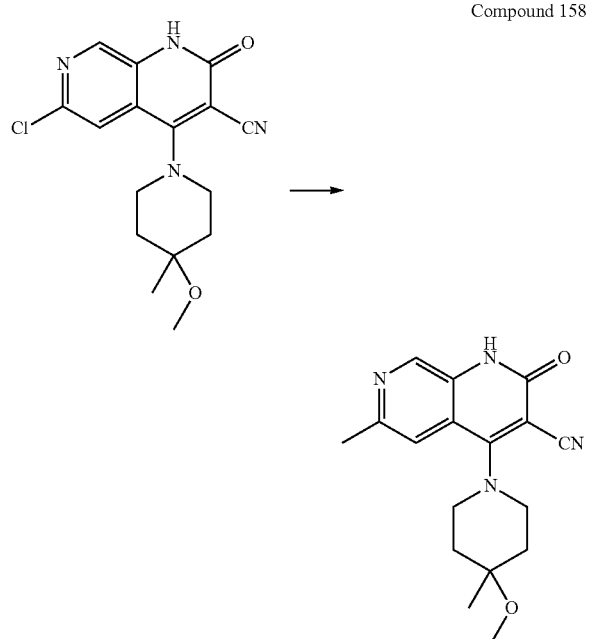

Compound 158

Intermediate 6-chloro-4-(4-methoxy-4-methylpiperidin-1-yl)-2-oxo-1,2-dihydro-1,7-naphthyridin-3-carbonitrile (1.3 g, 3.91 mmol, 1.0 eq), cesium carbonate (3.8 g, 11.73 mmol, 3.0 eq) and trimethylcyclotriborane (50% in THF, 3.9 g, 15.62 mmol, 4.0 eq) were dissolved in 1,4-dioxane (20 mL). After the addition, the air of the system was replaced by nitrogen for three times, and then [1,1'-bis(diphenylphosphino)ferrocene]palladium dichloride (286 mg, 0.39 mmol, 0.1 eq) was added to the reaction. After the addition, the air of the system was replaced by nitrogen for three times, and the mixture was heated to reflux for 12 hours. When the starting materials were still remained as monitored by TLC, additional trimethylcyclotriborane (50% THF solution, 3.9 g, 15.62 mmol, 4.0 eq) and [1,1'-bis(diphenylphosphino)ferrocene]palladium dichloride (286 mg, 0.39 mmol, 0.1 eq) were added and reflux was continued for 4 h. When there is no starting material remained as monitored by TLC, the system was cooled to room temperature, followed by addition of water (50 mL) and dichloromethane (100 mL), stirred for 5 min to precipitate solid, and filtered. The filter cake was rinsed with dichloromethane. The liquid was separated and the aqueous phase was extracted with dichloromethane (100 mL×3), and the organic phases were combined, dried over anhydrous sodium sulfate and filtered. The mother liquor was concentrated under reduced pressure, and the crude product was purified by silica gel column chromatography (MeOH:DCM=1:100-1:50) to give a product (309.9 mg, yield: 25.4%).

$^1$HNMR (400 MHz, DMSO-$d_6$) δ (ppm): 11.88 (s, 1H), 8.55 (s, 1H), 7.42 (s, 1H), 3.61-3.59 (m, 4H), 3.19 (s, 3H), 2.53 (s, 3H), 1.92-1.89 (m, 2H), 1.82-1.75 (m, 2H), 1.22 (s, 3H).

Molecular formula: $C_{17}H_{29}N_4O_2$ Molecular weight: 312.37 LC-MS (Pos, m/z)=313.25 [M+H]$^+$.

Example 94: Synthesis of 6-(cyclopropyl(hydroxy)methyl)-2-oxo-4-(7-azaspiro[3.5]nonane-7-yl)-1,2-dihydro-1,7-naphthyridin-3-carbonitrile (Compound 160)

Step 1: Synthesis of 6-chloro-2-oxo-4-(7-azaspiro[3.5]nonane-7-yl)-1,2-dihydro-1,7-naphthyridin-3-carbonitrile

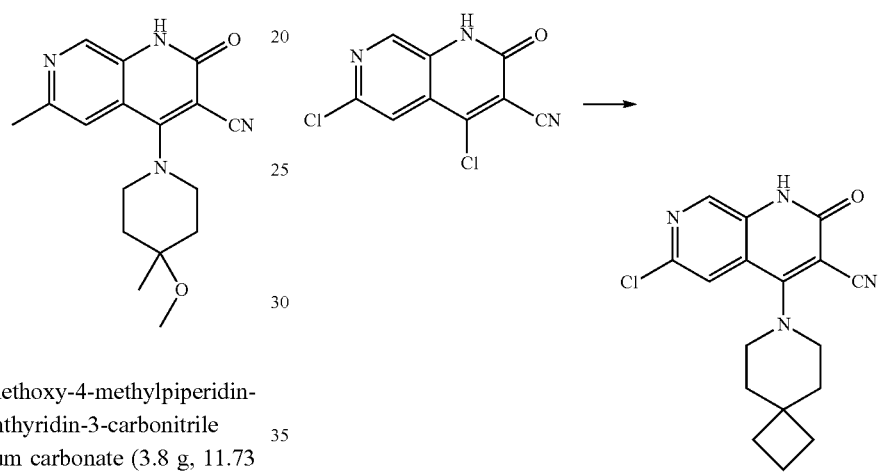

The intermediate 4,6-dichloro-2-oxo-1,2-dihydro-1,7-naphthyridin-3-carbonitrile (8.0 g, 33.3 mmol, 1.0 eq) was dissolved in DMF (100 mL), followed by addition of the starting material 7-azaspiro[3.5]nonane hydrochloride (6.5 g, 40.0 mmol, 1.2 eq) and DIPEA (17.2 g, 133.2 mmol, 4.0 eq) sequentially, and reacted at 80° C. for 0.5 h. The reaction endpoint was monitored by TLC. The reaction solution was concentrated, followed by addition of water and ethyl acetate (40 mL/40 mL), stirred overnight and filtered to give a yellow solid product (10.0 g, yield: 91.5%).

Step 2: Synthesis of 2-oxo-4-(7-azaspiro[3.5]nonane-7-yl)-6-vinyl-1,2-dihydro-1,7-naphthyridin-3-carbonitrile

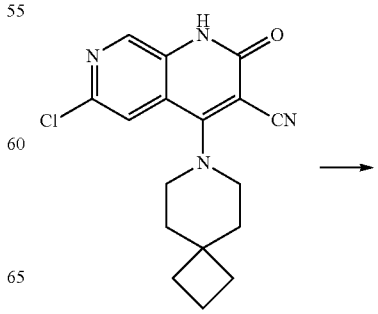

-continued

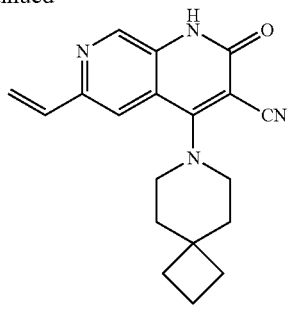

The intermediate 6-chloro-2-oxo-4-(7-azaspiro[3.5]nonane-7-yl)-1,2-dihydro-1,7-naphthyridin-3-carbo nitrile (5.0 g, 15.2 mmol, 1.0 eq) was dissolved in 1,4-dioxane (50 mL). The starting material vinyl potassium fluoroborate (6.1 g, 45.6 mmol, 3.0 eq), cesium carbonate (14.8 g, 45.6 mmol, 3.0 eq) and [1,1'-bis(diphenylphosphino)ferrocene]palladium dichloride (1.1 g, 15.2 mmol, 1.0 eq) were dissolved in water (10 mL) and added to the above reaction solution. The reaction was refluxed overnight under nitrogen protection. The reaction endpoint was monitored by LC-MS. The reaction solution was concentrated and extracted with EA (3×100 mL). The organic phase was dried over anhydrous sodium sulfate, filtered by suction, and concentrated under reduced pressure to give a product (4.5 g, yield: 92.5%).

Step 3: Synthesis of 6-formyl-2-oxo-4-(7-azaspiro[3.5]nonane-7-yl)-1,2-dihydro-1,7-naphthyridin-3-carbonitrile

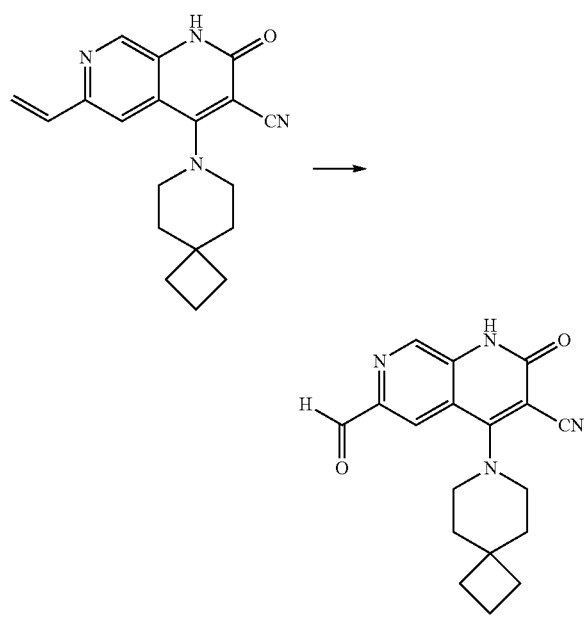

The intermediate 2-oxo-4-(7-azaspiro[3.5]nonane-7-yl)-6-vinyl-1,2-dihydro-1,7-naphthyridin-3-carbonitrile (2.0 g, 6.2 mmol, 1.0 eq) was dissolved in tert-butanol (50 mL) and water (40 mL), followed by addition of ad-mix-β (20 g, 10 eq) and methanesulfonamide (1.2 g, 12.5 mmol, 2.0 eq) sequentially at 0° C., and stirred at room temperature for 48 h. The reaction endpoint was monitored by LC-MS. Sodium periodate (4.0 g, 18.6 mmol, 3.0 eq) was dissolved in water (10 mL) at 0° C., and added dropwise to the above reaction solution. The reaction solution was stirred at room temperature for 12 h. The reaction endpoint was monitored by LC-MS. The reaction solution was extracted with EA (3×100 mL). The organic phase was dried over anhydrous sodium sulfate, and filtered by suction, and the filtrate was concentrated under reduced pressure. The crude product was purified by silica gel column chromatography (DCM:MeOH=40:1) to give a product as a yellow solid (1.0 g, yield: 50.4%).

Step 4: Synthesis of 6-(cyclopropyl(hydroxy)methyl)-2-oxo-4-(7-azaspiro[3.5]nonane-7-yl)-1,2-dihydro-1,7-naphthyridin-3-carbonitrile

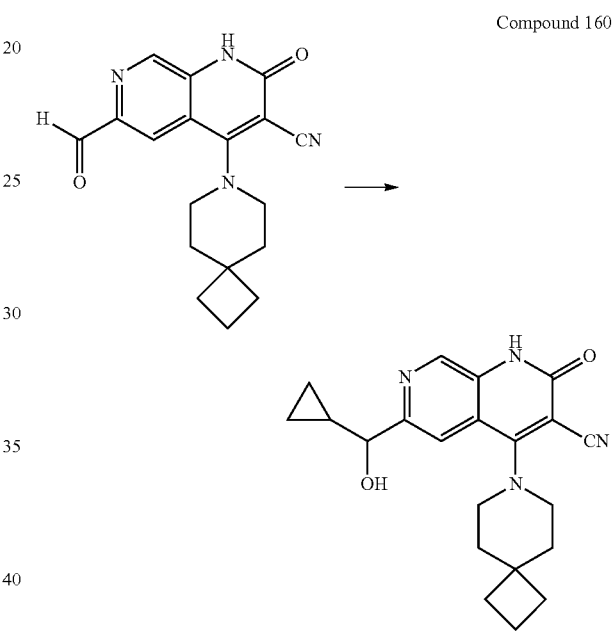

Compound 160

The intermediate 6-formyl-2-oxo-4-(7-azaspiro[3.5]nonane-7-yl)-1,2-dihydro-1,7-naphthyridin-3-carbo nitrile (500.0 mg, 1.6 mmol, 1.0 eq) was dissolved in 2-methyltetrahydrofuran (5 mL), followed by a slow addition of cyclopropylmagnesium bromide (7.5 mL, 7.75 mmol, 5 eq) under nitrogen protection at −20° C. and stirred at −10° C. for 12 h. The reaction endpoint was monitored by LC-MS. The reaction solution was quenched with saturated aqueous ammonium chloride solution at 0° C. and extracted with EA (3×30 mL). The organic phase was dried over anhydrous sodium sulfate, and filtered by suction, and the filtrate was concentrated under reduced pressure. The crude product was purified by silica gel column chromatography (DCM:MeOH=30:1-20:1) to give a product (80.0 mg, yield: 13.7%).

$^1$H NMR (400 MHz, DMSO-$d_6$) δ (ppm): 11.92 (br, 1H), 8.58 (s, 1H), 7.69 (s, 1H), 5.41 (d, 1H), 4.23-4.26 (m, 1H), 3.54 (s, 4H), 1.80-1.99 (m, 9H), 1.11-1.24 (m, 2H), 0.42 (s, 4H).

Molecular formula: $C_{21}H_{24}N_4O_2$ Molecular weight: 364.45 LC-MS (m/z)=365 [M+H]$^+$.

Example 95: Synthesis of 6-(1-hydroxy-2-methyl-propan-2-yl)-4-(4-methoxy-4-methylpiperidin-1-yl)-2-oxo-1,2-dihydro-1,7-naphthyridin-3-carbonitrile (Compound 161)

Step 1: Synthesis of ethyl 2-(3-cyano-4-(4-methoxy-4-methylpiperidin-1-yl)-2-oxo-1,2-dihydro-1,7-naphthyridin-6-yl)-2-methylpropionate

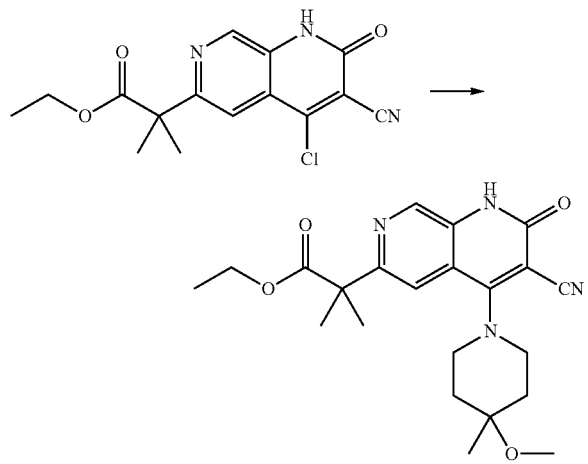

Intermediate ethyl 2-(4-chloro-3-cyano-2-oxo-1,2-dihydro-1,7-naphthyridin-6-yl)-2-methylpropionate (600.0 mg, 1.87 mmol, 1.0 eq) was dissolved in DMF (5 mL), followed by addition of the starting material 4-methyl-4-methoxypiperidine hydrochloride (339.4 mg, 2.05 mmol, 1.1 eq) and DIPEA (1.4 g, 11.2 mmol, 6.0 eq) sequentially, and reacted at 80° C. for 0.5 h. The reaction endpoint was monitored by TLC. The reaction solution was concentrated, followed by addition of water and extracted with EA (3×60 mL). The organic phases were combined, dried over anhydrous sodium sulfate, filtered, and concentrated, and the crude product was purified by silica gel column chromatography (PE:EA=3:2) to give a product (300.0 mg, yield: 38.9%).

Step 2: Synthesis of 6-(1-hydroxy-2-methylpropan-2-yl)-4-(4-methoxy-4-methylpiperidin-1-yl)-2-oxo-1,2-dihydro-1,7-naphthyridin-3-carbonitrile

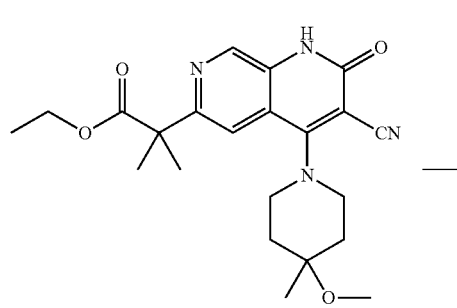

Compound 161

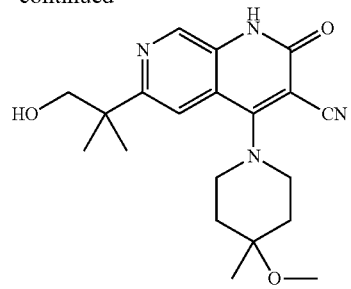

Intermediate ethyl 2-(3-cyano-4-(4-methoxy-4-methylpiperidin-1-yl)-2-oxo-1,2-dihydro-1,7-naphthyridin-6-yl)-2-methylpropionate (300.0 mg, 0.73 mmol, 1.0 eq) was dissolved in anhydrous 2-methyltetrahydrofuran (5 mL), followed by dropwise addition of DIBAL-H (1.5 mol/L toluene solution, 2.4 mL, 3.65 mmol, 5.0 eq) at −60° C. under nitrogen protection, and then was warmed to room temperature and stirred for 6 h. The reaction was quenched by dropwise adding water at 0° C., concentrated and extracted with EA (3×60 mL). The organic phases were combined, dried over anhydrous sodium sulfate, filtered and concentrated. The crude product was purified by silica gel column chromatography (PE:EA=3:2) to give a product (60.0 mg, yield: 22.2%).

$^1$H NMR (400 MHz, DMSO-$d_6$) δ (ppm): 11.88 (s, 1H), 8.63 (s, 1H), 7.53 (s, 1H), 4.65 (t, 1H), 3.59-3.62 (m, 4H), 3.54 (d, 2H), 3.19 (s, 3H), 1.91-1.95 (m, 2H), 1.73-1.78 (m, 2H), 1.28 (s, 6H), 1.23 (s, 3H).

Molecular formula: $C_{20}H_{26}N_4O_3$ Molecular weight: 370.45 LC-MS (Pos, m/z)=371 [M+H]$^+$.

Example 96: Synthesis of 3-cyano-4-(4-methoxy-4-methylpiperidin-1-yl)-N,N-dimethyl-2-oxo-1,2-dihydro-1,7-naphthyridin-6-carboxamide (Compound 162)

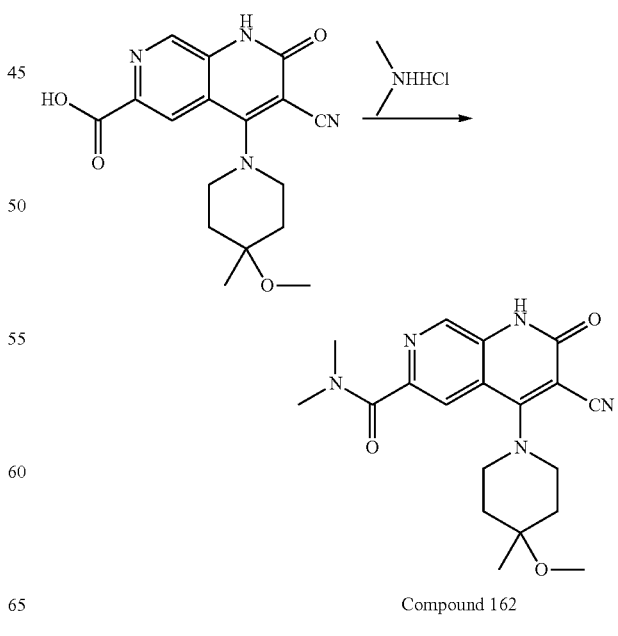

Compound 162

The intermediate 3-cyano-4-(4-methoxy-4-methylpiperidin-1-yl)-2-oxo-1,2-dihydro-1,7-naphthyridin-6-carboxylic acid (200 mg, 0.58 mmol, 1.0 eq), HATU (333 mg, 0.88 mmol, 1.5 eq) and DIPEA (376 mg, 1.76 mmol, 3.0 eq) were dissolved in DMAC (2 mL), stirred at room temperature for 30 min, followed by addition of dimethylamine hydrochloride (95 mg, 1.16 mmol, 2.0 eq), and was reacted at room temperature for 1 h. The reaction endpoint was monitored by LC-MS. Water (10 mL) was added and the mixture was extracted with dichloromethane (10 mL×3). The organic phase was washed with water (10 mL×3), dried over anhydrous sodium sulfate, filtered and concentrated under reduced pressure. The crude product was purified by silica gel column chromatography (DCM:MeOH=50:1) to give a product (120 mg, yield: 55%).

$^1$HNMR (400 MHz, DMSO-$d_6$) δ (ppm): 12.16 (s, 1H), 8.61 (s, 1H), 7.83 (s, 1H), 3.61-3.63 (m, 4H), 3.19 (s, 3H), 3.03-3.05 (d, 6H), 1.90-1.93 (d, 2H), 1.71-1.78 (m, 2H), 1.22 (s, 3H).

Molecular formula: $C_{19}H_{23}N_5O_3$ Molecular weight: 369.18 LC-MS (Pos, m/z)=370.43 $[M+H]^+$.

Other compounds can be obtained by referring to the above method. The characterization data of some other compounds of the present invention are shown in Table 2 below.

was diluted in 100 times with DMSO to obtain 100 μM compound working mother solution, and then the compound working mother solution was diluted in 3 times with DMSO to obtain 8-10 concentration gradients of diluted compound mother liquor (100×).

Incubation with the compounds: A very small amount of liquid pipetting system Echo was used to pipette the diluted compound mother liquor into a 384-well plate. 200 nL diluted compound mother liquor and 10 μL PDE9A2 enzyme solution were added to each compound well. After centrifugation at 1000 rpm for 1 min, the mixture was incubated for 15 min at the room temperature. Then the 10 μL substrate mixture was added. After centrifugation at 1000 rpm for 1 min, the mixture was incubated with shocking for 30 min at the room temperature. Finally, a stop solution was added to end the reaction system. The mixture was incubated with shocking for 60 min at the room temperature. In the maximum reading hole (Max), the compound was replaced by solvent. In the minimum reading hole (Min), the compound and enzyme solution were replaced by solvent.

Measurement: Fluorescence readings (F) at 480 nm/535 nm were measured using a microplate reader.

Calculation: The inhibition rate was calculated as follows, and $IC_{50}$ was fitted using GraphPad Prism 5.0:

TABLE 2

| Compound No. | Molecular formula | $^1$HNMR (400 MHz, DMSO-($d_6$) δ(ppm) | LC-MS (Pos, m/z) |
|---|---|---|---|
| 15 | $C_{18}H_{20}N_4O$ | 11.54(s, 1H), 8.58(s, 1H), 8.25-8.26(d, 1H), 8.00-8.01(d, 1H), 4.09-4.12(t, 2H), 3.82(s, 2H), 3.41-3.51(m, 2H), 1.42-1.46(t, 10H). | 309.04 $[M + H]^+$ |
| 29 | $C_{15}H_{16}N_4O$ | 11.98 (s, 1H), 8.65 (s, 1H), 8.33-8.35 (d, 1H), 7.57-7.59 (d, 1H), 3.86-3,89 (m, 2H), 3.35-3.37 (m, 4H), 1.84-1.87 (d, 2H), 1.71-1.75 (m, 1H), 1.40-1.50 (m, 2H), 1.24 (s, 2H). | |
| 36 | $C_{16}H_{16}N_4O$ | 11.55 (s, 1H), 8.58 (s, 1H), 8.25-8.26 (m, 1H), 7.99-8.00 (m, 1H), 4.02-4.06 (m, 2H), 4.00-4.02 (m, 2H), 1.96-2.08 (m, 4H), 1.84-1.95 (m, 4H). | 285.05 $[M + H]^+$ |
| 37 | $C_{18}H_{20}N_4O$ | 11.98 (s, 1H), (s, 1H), 8.32-834 (d, 1H), 7.58-7.60 (d, 1H), 3.55-3.58 (m, 2H), 3.47-3.50 (m, 2H), 2.34-2.43 (m, 1H), 2.03-2.09 (m, 2H), 1.81-1.84 (m, 2H), 1.72-1.75 (m, 2H), 1.42-1.45 (m, 2H), 1.05-1.10 (s, 3H) | 309.06 $[M + H]^+$ |
| 133 | $C_{17}H_{19}ClN_4O_2$ | 12.01 (s, 1H), 8.46 (s, 1H), 7.61 (s, 1H), 3.60-3.62 (m, 4H), 3.13 (s, 3H), 1.89-1.92 (m, 2H), 1.70-1.73 (m, 2H), 1.65-1.69 (m, 2H), 1.55-1.59 (m, 2H), 1.26-1.27 (m, 3H). | 347.17 $[M + H]^+$ |

The present invention can be better understood from the following experimental examples. However, those skilled in the art will readily understand that the contents of the experimental examples are merely illustrative of the invention, which should not and will not limit the invention as described in detail in the claims.

Experimental Example 1: PDE9 Enzymology Evaluation Method

Test substance: Compounds of the invention, prepared by the corresponding examples of the invention
1. Experimental materials and instruments
PDE9A2 Enzyme (BPS, Cat. No. 60090)
384-well plate (Perkin Elmer, Cat. No. 6007279)
2. Experimental procedure
Preparation of the compounds: the compounds were prepared into 10 mM compound stock solution in DMSO for long-term storage. The obtained compound stock solution $$\text{Inhibition rate (\%)} = \frac{FMax - Fcompound}{FMax - Fmin} \times 100\%$$

3. The test results are shown in Table 3:

TABLE 3

| Test compound | PDE9A2 $IC_{50}$ (nM) |
|---|---|
| Compound16 | 46 |
| Compound19 | 28 |
| Compound23 | 13 |
| Compound24 | 14 |
| Compound25 | 29 |
| Compound26 | 10 |
| Compound27 | 12 |
| Compound30 | 8 |
| Compound32 | 22 |
| Compound33 | 10 |

TABLE 3-continued

| Test compound | PDE9A2 IC$_{50}$ (nM) |
|---|---|
| Compound39 | 25 |
| Catnpound44 | 71 |
| Compound45 | 37 |
| Compound46 | 18 |
| Compound47 | 12 |
| Compound49 | 9 |
| Compound50 | 19 |
| Compound51 | 5 |
| Compound52 | 36 |
| Compound53 | 15 |
| Compound54 | 22 |
| Compound58 | 44 |
| Compolmd59 | 57 |
| Compound60 | 43 |
| Compound62 | 19 |
| Conmound63 | 9 |
| Cornpound64 | 14 |
| Compound65 | 13 |
| Compound66 | 21 |
| Compound76 | 16 |
| Compound77 | 33 |
| Compound78 | 33 |
| Compound79 | 12 |
| Compound80 | 20 |
| Compound81 | 42 |
| Compound82 | 29 |
| Compound83 | 8 |
| Compound84 | 78 |
| Compound85 | 8 |
| Compound87 | 13 |
| Compound90 | 17 |
| Compound91 | 47 |
| Compound92 | 83 |
| Compound93 | 86 |
| Compound94 | 12 |
| Compound95 | 91 |
| Compound96 | 11 |
| Compound97 | 27 |
| Compound107 | 15 |
| Compound108 | 4 |
| Compound109 | 38 |
| Compouud129 | 11 |
| Compound130 | 3 |
| Compound131 | 11 |
| Compound132 | 24 |
| Compound134 | 21 |
| Hydrochloride salt of compound 138 | 14 |
| Compound 139 | 69 |
| Compound140 | 61 |
| Trifluoroaectate salt of compound 141 | 52 |
| Trifluoroacetate salt of compound 142 | 85 |
| Compound144 | 25 |
| Compound145 | 31 |
| Compound149 | 60 |
| Compound151 | 38 |
| Compound154 | 8 |
| Compound156 | 22 |
| Compound158 | 9 |
| Compound160 | |
| Compound162 | 10 |

As can be seen from Table 3, the compounds of the present invention have a very good PDE9 enzymatic inhibition activity and have a potential clinical application value.

Experimental Example 2: Canine Pharmacokinetic Evaluation of Compounds of the Invention Test Compound: Compounds of the Invention, which was Prepared by the Corresponding Examples of the Invention
1. Animal Administration and Sample Collection The experimental compound 25 was dissolved in 2% DMSO+10% PEG400+88% (28% HP-β-CD) physiological saline to prepare a solution. The solution of compound 25 was intragastrically administered to Beagle dogs at a dose of 2.0 mg/kg.

The time of blood collection is 0 min, 15 min, 30 min, 1 h, 2 h, 4 h, 6 h, 8 h, 10 h, 24 h after administration.

The experimental compound 25 was dissolved in 2% DMSO+10% PEG400+88% (28% HP-β-CD) physiological saline to prepare a solution. The solution of compound 25 was administered to Beagle dogs at a dose of 1 mg/kg via intravenous bolus. The time of blood collection is 0 min, 5 min, 15 min, 30 min, 1 h, 2 h, 4 h, 6 h, 8 h, 10 h, 24 h after administration.

The experimental compound 65 was dissolved in 2% DMSO+10% PEG400+88% (28% HP-β-CD) physiological saline to prepare a solution. The solution of compound 65 was intragastrically administered to Beagle dogs at a dose of 2.0 mg/kg. The time of blood collection is 0 min, 15 min, 30 min, 1 h, 2 h, 4 h, 6 h, 8 h, 10 h, 24 h after administration.

The experimental compound 65 was dissolved in 2% DMSO+10% PEG400+88% (28% HP-β-CD) physiological saline to prepare a solution. The solution of compound 65 was administered to Beagle dogs at a dose of 1 mg/kg via intravenous bolus. The time of blood collection is 0 min, 5 min, 15 min, 30 min, 1 h, 2 h, 4 h, 6 h, 8 h, 10 h, 24 h after administration.

The experimental compound 107 was dissolved in 2% DMSO+10% PEG400+88% (28% HP-β-CD) physiological saline to prepare a solution. The solution of compound 107 was intragastrically administered to Beagle dogs at a dose of 1.0 mg/kg. The time of blood collection is 0 min, 15 min, 30 min, 1 h, 2 h, 4 h, 6 h, 8 h, 10 h, 24 h after administration.

The experimental compound 107 was dissolved in 2% DMSO+10% PEG400+88% (28% HP-β-CD) physiological saline to prepare a solution. The solution of compound 107 was administered to Beagle dogs at a dose of 1.0 mg/kg via intravenous bolus. The time of blood collection is 0 min, 5 min, 15 min, 30 min, 1 h, 2 h, 4 h, 6 h, 8 h, 10 h, 24 h after administration.

The experimental compound 158 was dissolved in 2% DMSO+10% PEG400+88% (28% HP-β-CD) physiological saline to prepare a solution. The solution of compound 158 was intragastrically administered to Beagle dogs at a dose of 1.0 mg/kg. The time of blood collection is 0 min, 15 min, 30 min, 1 h, 2 h, 4 h, 6 h, 8 h, 10 h, 24 h after administration.

The experimental compound 158 was dissolved in 2% DMSO+10% PEG400+88% (28% HP-β-CD) physiological saline to prepare a solution. The solution of compound 158 was administered to Beagle dogs at a dose of 1.0 mg/kg via intravenous bolus. The time of blood collection is 0 min, 5 min, 15 min, 30 min, 1 h, 2 h, 4 h, 6 h, 8 h, 10 h, 24 h after administration.

About 1 mL of blood from the upper extremity vein was collected. The blood collected was placed in an anti-coagulation tube containing EDTA-K2. Blood samples were centrifuged at 1800 g for 5 min at 4° C. to obtain plasma samples. Plasma was prepared within 30 min after blood collection, and placed in a −80° C. refrigerator before test.

2. Sample Analysis Method

The plasma sample to be tested was taken from the −80° C. refrigerator, thawed naturally at room temperature and vortexed for 5 min. 20 μL of plasma sample was accurately pipetted into a 1.5 mL centrifuge tube, followed by addition of 200 μL internal standard working solution (tolbutamide in methanol) at a concentration of 100 ng/mL, mixed, vortexed for 5 min, and then centrifuged at 12000 rpm for 5 min. 50

μL of supernatant was accurately pipetted into 96-well plates pre-filled with 150 μL/well of water; vortexed for 5 min, and measured by LC-MS/MS. Injection volume of compound 25, compound 65, compound 107, compound 158 was 20, 10, 20, 10 μL, respectively.

3. Data Processing Method

The concentration of compounds was output using Analyst 1.6.3 from AB SCIEX. Microsoft Excel was used to calculate the mean, standard deviation, coefficient of variation and other parameters (directly output by Analyst 1.6.3 and not calculated). Pharmacokinetic parameters were calculated using Pharsight Phoenix 6.1 software NCA ($T_{max}$ is the median).

4. Results

The experimental results are shown in Table 4:

TABLE 4

Pharmacokinetic parameters of compounds in Beagle dogs (n = 3)

| Compound | Dose iv/po mg/kg | $t_{z1/2}$ iv/po (h) | $V_{z\_obs}$iv (L/kg) | $Cl_{\_obs}$ iv (L/h/kg) | $T_{max}$ po (h) | $AUC_{inf}$iv/po ( h*ng/mL) | F % |
|---|---|---|---|---|---|---|---|
| Compound25 | 1/2 | 10.4/9.45 | 7.06 | 0.47 | 0.50 | 2244/4449 | 99.1 |
| Compound65 | 1/2 | 0.49/0.47 | 0.66 | 0.94 | 0.50 | 1065/543 | 25.5 |
| Compound107 | 1/1 | 1.64/2.56 | 2.05 | 0.96 | 0.50 | 1230/757 | 61.5 |
| Compound108 | 1/1 | 2.17/1.62 | 2.58 | 0.83 | 1.00 | 1337/1222 | 91.2 |

Note:
$t_{z1/2}$: Terminal elimination half-life, $Cl_{\_obs}$: Clearance rate, $V_{z\_obs}$: Apparent distribution volume, $T_{max}$: The time at which the concentration of the drug peaks in the blood, $AUC_{inf}$: The area under the medicine vs time curve, 0-∞.
As can be seen from the above table, the compounds of the invention have very good pharmacokinetic characteristics.

Experimental Example 3: Evaluation of Stability of the Compounds of the Invention in Human Liver Microsome Aim: Evaluation of stability of the compounds of the invention in human liver microsome.

Test substance: The compounds of the present invention and the compound I-8 of patent WO2017019723A1 having the following structural formula:

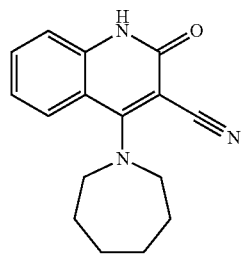

I-8

The composition of the incubation system is shown in Table 5:

TABLE 5

Composition of the incubation system

| Substance added | initial concentration | Percentage (%) | Final concentration |
|---|---|---|---|
| Phosphate buffer | 100 mM | 50 | 50 mM |
| MgCl₂ | 20 mM | 5 | 1 mM |
| Liver microsome | 20 mg protein/mL | 2.5 | 0.5 mg protein/mL |
| Additional water needed | — | 22.5 | — |
| Compound | 10 μM | 10 | 1 μM |
| β-NADPH | 10 mM | 10 | 1 mM |

Experimental Procedure (1). Liver microsomes (20 mg protein/mL) were removed from the −80° C. refrigerator, placed in a 37° C. water bath thermostat for pre-incubation for 3 min, and thawed for use.

(2). A mixed solution of the incubation system (without compound and β-NADPH) was prepared according to the ratio of "Composition of the incubation system" in Table 4, and pre-incubated for 2 min on a 37° C. water bath thermostat.

(3). Control group (without β-NADPH): 30 μL of water and 30 μL of compound working solution (10 μM, solvent: 1% DMSO aqueous solution) were added to 240 μL of mixed solution of the incubation system in step (2), vortexed for 30 s, mixed, and the total volume of the reaction was 300 μL. Sample was duplicated. The mixture was incubated in a 37° C. water bath thermostat and timing was started. The sampling time point is 0 min and 60 min.

(4). Sample group: 70 μL β-NADPH solution (10 mM) and 70 μL compound working solution (10 μM) were added to 560 μL mixed solution of the incubation system prepared in step (2). The total reaction volume was 700 μL. The mixture was vortexed for 30 s, and mixed, and the well was duplicated. The mixture was incubated in a 37° C. water bath thermostat and timing was started. The sampling time point is 0 min, 5 min, 10 min, 20 min, 30 min, 60 min after timing.

(5). After vortex for 3 min, the sample was centrifuged at 12000 rpm for 5 min.

(6). 50 μL of the supernatant was taken, followed by addition of 150 μL water, vortexed and mixed, and analyzed by LC/MS/MS.

Data Analysis:

The half-life ($t_{1/2}$) and clearance rate (Cl) were calculated using the following first-order dynamics formula:

$$Ct = C_0 * e^{-kt}$$

$$t_{1/2} = \ln 2/k = 0.693/k$$

$$Cl_{int} = V_d * k$$

Vd=1/protein content in liver microsome

Note: k is the slope of the logarithm of the remaining amount of the compound versus time, and Vd is the apparent distribution volume.

The results are shown in Table 6:

TABLE 6

| Compound | Original drug residual % at 60 min | k (min-1) | T1/2 (min) | CLint, (mL · min$^{-1}$ · mg$^{-1}$ proteins) |
|---|---|---|---|---|
| Compound 18 | 5.19% | 0.727 | 11.14 | 0.1244 |
| Compound 19 | 93.4% | 0.191 | 1155 | 0.00120 |
| Compound 25 | 87.5 | 0.0022 | 315 | 0.0044 |
| Compound 32 | 99.8% | −0.3760 | →∞ | →0 |
| Compound 51 | 74.1% | 0.9418 | 126 | 0.0110 |
| Compound 53 | 91.4% | 0.4821 | 630 | 0.0022 |
| Compound 66 | 101% | −0.515 | → | →0 |
| Compound 76 | 87.3 | 0.0015 | 462 | 0.0030 |
| Compound 80 | 41.7% | 0.9877 | 47.5 | 0.0292 |
| Compound 81 | 94.6 | 0.0012 | 578 | 0.0024 |
| Compound 82 | 72.4% | 0.9760 | 124 | 0.0112 |
| Compound 83 | 104.1% | 0.5421 | →∞ | →0 |
| Compound 90 | 80.5 | 0.0037 | 187 | 0.0074 |
| Compound 107 | 88.5 | 0.0023 | 301 | 0.0046 |
| Compound 109 | 91.9% | 0.4444 | 693 | 0.0020 |
| Compound 145 | 88.2 | 0.0019 | 365 | 0.0038 |
| Compound 158 | 92.6 | 0.0013 | 533 | 0.0026 |

From the above results, it can be seen that the compounds of the present invention have a lower clearance rate in human liver microsome than the prior art.

Experimental Example 4: Rat Pharmacokinetic Evaluation of the Compounds of the Invention Aim: The in vivo pharmacokinetic parameters of the compounds in SD male rats (purchased from Beijing Vital River Animal Technology Co., Ltd.) were evaluated and bioavailability of the compounds was examined.

Animal Administration and Sample Collection:

The experimental compounds 65, 90, 107, 158 were dissolved in 2% DMSO+10% PEG400+88% (28% HP-β-CD) physiological saline to prepare a solution. The solution of compounds 65, 90, 107, 158 was intragastrically administered to SD rat at a dose of 5.0 mg/kg. The time of blood collection is 15 min, 30 min, 1 h, 2 h, 4 h, 6 h, 8 h, 24 h after administration.

The experimental compounds 65, 90, 107, 158 were dissolved in 2% DMSO+10% PEG400+88% (28% HP-β-CD) physiological saline to prepare a solution. The solution of compounds 65, 90, 107, 158 was administered to SD rat at a dose of 1 mg/kg via intravenous bolus. The time of blood collection is 5 min, 15 min, 30 min, 1 h, 2 h, 4 h, 6 h, 8 h, 24 h after administration.

The experimental compound 76 was dissolved in 30% DMF+30% PEG400+40% saline to prepare a solution. The solution of compound 76 was intragastrically administered to SD rat at a dose of 5.0 mg/kg. The time of blood collection is 15 min, 30 min, 1 h, 2 h, 4 h, 6 h, 8 h, 24 h after administration.

The experimental compound 76 was dissolved in 30% DMF+30% PEG400+40% saline to prepare a solution. The solution of compound 76 was administered to SD rat at a dose of 1 mg/kg via intravenous bolus. The time of blood collection is 5 min, 15 min, 30 min, 1 h, 2 h, 4 h, 6 h, 8 h, 24 h after administration.

The experimental compound 25 was dissolved in 5% DMSO+20% (30% solutol)+2% 1M NaOH+73% saline to prepare a solution. The solution of compound 25 was intragastrically administered to SD rat at a dose of 5.0 mg/kg. The time of blood collection is 15 min, 30 min, 1 h, 2 h, 4 h, 6 h, 8 h, 24 h after administration.

The experimental compound 25 was dissolved in 5% DMSO+20% (30% solutol)+2% 1M NaOH+73% saline to prepare a solution. The solution of compound 25 was administered to SD rat at a dose of 1 mg/kg via intravenous bolus. The time of blood collection is 5 min, 15 min, 30 min, 1 h, 2 h, 4 h, 6 h, 8 h, 24 h after administration.

The experimental compounds 84 and 96 were dissolved in 5% DMSO+10% PEG400+85% (28% HP-β-CD) saline to prepare a solution. The solution of compounds 84 and 96 was intragastrically administered to SD rat at a dose of 5.0 mg/kg. The time of blood collection is 15 min, 30 min, 1 h, 2 h, 4 h, 6 h, 8 h, 24 h after administration.

The experimental compounds 84 and 96 were dissolved in 5% DMSO+10% PEG400+85% (28% HP-β-CD) saline to prepare a solution. The solution of compounds 84 and 96 was administered to SD rat at a dose of 1 mg/kg via intravenous bolus. The time of blood collection is 5 min, 15 min, 30 min, 1 h, 2 h, 4 h, 6 h, 8 h, 24 h after administration.

The animals were fixed. The tail was heated with a water bath at 10 min before each time point. About 100 μL of blood from tail vein was collected, and then placed in an anti-coagulation tube containing EDTA-K2 after collection. Blood samples were centrifuged at 8000 rpm at 4° C. for 6 min to obtain plasma samples. Plasma was prepared within 30 min after blood collection, and placed in a −80° C. refrigerator before test.

Sample Analysis Method

The plasma sample to be tested was taken from the −80° C. refrigerator, thawed naturally at room temperature and vortexed for 5 min. 20 μL of plasma sample was accurately pipetted into a 1.5 mL centrifuge tube, followed by addition of 200 μL of internal standard working solution (tolbutamide in methanol) at a concentration of 100 ng/mL, mixed, vortexed for 5 min, and then centrifuged at 12000 rpm for 5 min. 50 μL of supernatant was accurately pipetted into 96-well plates pre-filled with 150 μL/well of water; vortexed for 5 min, and measured by LC-MS/MS. Injection volume of compound 25, 65, 76, 84, 90, 96, 107, 154, and 158 was 20, 20, 5, 10 μL, respectively.

Data Processing Method

The concentration of test sample was output using Analyst 1.6.1 from AB SCIEX. Microsoft Excel was used to calculate the mean, standard deviation, coefficient of variation and other parameters (directly output by Analyst 1.6.1 and not calculated). Pharmacokinetic parameters were calculated using Pharsight Phoenix 6.1 software NCA ($T_{max}$ is the median).

The results are shown in Table 7:

TABLE 7

| Compound | Dose iv/po mg/kg | $t_{z1/2}$ iv/po (h) | $V_{z\_obs}$iv (L/kg) | $Cl_{\_obs}$ iv (L/h/kg) | $T_{max}$ po (h) | $AUC_{last}$ iv/po (h*ng/mL) | F % |
|---|---|---|---|---|---|---|---|
| Compound25 | 1/5 | 0.51/1.40 | 1.27 | 1.76 | 1.00 | 574/2050 | 74.2 |
| Compound65 | 1/5 | 1.47/2.25 | 1.75 | 0.83 | 0.50 | 1239/3003 | 51.8 |
| Compound76 | 1/5 | 0.89/9.60 | 1.25 | 1.04 | 1.00 | 1013/5748 | 113 |
| Compound84 | 1/5 | 1.89/3.24 | 1.16 | 0.49 | 1.00 | 2426/7575 | 62.5 |
| Compound90 | 1/5 | 1.48/4.49 | 1.38 | 0.63 | 1.00 | 1589/3704 | 47.4 |

TABLE 7-continued

| Compound | Dose iv/po mg/kg | $t_{z1/2}$ iv/po (h) | $V_{z\_obs}$ iv (L/kg) | $Cl_{obs}$ iv (L/h/kg) | $T_{max}$ po (h) | $AUC_{last}$ iv/po (h*ng/mL) | F % |
|---|---|---|---|---|---|---|---|
| Compound96 | 1/— | 0.30/ | 0.57 | 1.32 | — | 769/— | — |
| Compound107 | 1/5 | 1.25/2.68 | 2.13 | 1.45 | 0.50 | 748/1936 | 56.8 |
| Compound108 | 1/5 | 0.70/1.96 | 1.97 | 2.04 | 0.50 | 502/2023 | 84.9 |

Note:
$t_{z1/2}$: Terminal elimination half-life, $Cl_{obs}$: Clearance rate, $V_{z\_obs}$: Apparent distribution volume, $T_{max}$: The time at which the concentration of the drug peaks in the blood, $AUC_{inf}$: The area under the medicine vs time curve, 0-∞, F %: absolute bioavailability, —: not tested.

As can be seen from the above table, the compounds of the invention have very good pharmacokinetic characteristics.

Experimental Example 5: PDE Enzymology Evaluation Method

Test substance: Compounds of the invention, prepared by the corresponding examples of the invention 1. Experimental materials and instruments PDE1A1 Enzyme (BPS, Cat. No. 60010)
PDE3A Enzyme (BPS, Cat. No. 60030)
PDE5A1 Enzyme (BPS, Cat. No. 60050)
PDE8A1 Enzyme (BPS, Cat. No. 60080)
384-well plate (Perkin Elmer, Cat. No. 6007279)

2. Experimental procedure

Preparation of the compounds: the compounds were prepared into 10 mM compound stock solution in DMSO for long-term storage. The obtained compound stock solution was diluted in 100 times with DMSO to obtain 100 μM compound working mother solution, and then the compound working mother solution was diluted in 3 times with DMSO to obtain 10 concentration gradients of diluted compound mother liquor (100×).

Incubation with the compounds: A very small amount of liquid pipetting system Echo was used to pipette the diluted compound mother liquor into a 384-well plate. 200 nL diluted compound mother liquor and 10 μL PDE1A1, PDE3A, PDE5A1 and PDE8A1 enzyme solution were added to each compound well. After centrifugation at 1000 rpm for 1 min, the mixture was incubated for 15 min at the room temperature. Then the 10 μL substrate mixture was added. After centrifugation at 1000 rpm for 1 min, the mixture was incubated with shocking for 30 min at the room temperature. Finally, a stop solution was added to end the reaction system. The mixture was incubated with shocking for 60 min at the room temperature. In the maximum reading hole (Max), the compound was replaced by solvent. In the minimum reading hole (Min), the compound and enzyme solution were replaced by solvent.

Detection: Fluorescence readings (F) at 480 nm/535 nm were detected using a microplate reader.

Calculation: The inhibition rate was calculated as follows, and $IC_{50}$ was fitted using GraphPad Prism 5.0:

$$\text{Inhibition rate (\%)} = \frac{FMax - Fcompound}{FMax - Fmin} \times 100\%$$

4. The test results are shown in Table 8:

TABLE 8

| Test compound | $IC_{50}$ (nM) | | | |
|---|---|---|---|---|
| | PDE1A1 | PDE3A | PDE5A1 | PDE8A1 |
| Compound24 | 4916 | >10000 | >10000 | >10000 |
| Compound25 | >3000 | >3000 | >3000 | >3000 |

Experimental conclusions: The compounds of the present invention have no significant inhibitory activity against PDE1A1, PDE3A, PDE5A15 or PDE8A1 enzyme, and have relatively high selectivity for PDE9.

It should be noted that each of the above experimental examples can be implemented by a conventional method in the art, unless otherwise specified; and a third-party institution can also be entrusted to implement each experimental example; for example, experimental examples 1 and 5 herein are implemented by entrusting a third-party institution.

The above are only the preferred embodiments of the present invention, and are not intended to limit the present invention. Any modifications, equivalents, improvements and the like made within the spirit and principles of the present invention, should be included in the scope of the present invention.

The invention claimed is:

1. A compound represented by formula (II), or a pharmaceutically acceptable salt or a stereoisomer thereof,

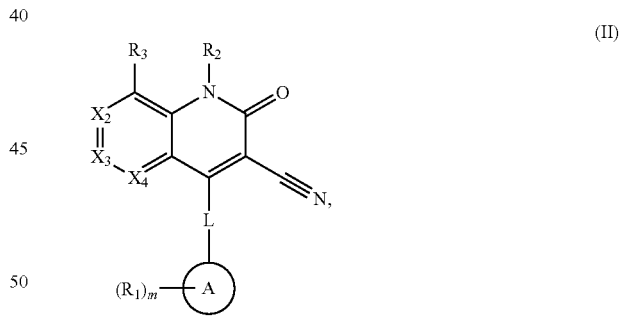

(II)

wherein,
$X_2$ is N;
$X_3$ is $CR_{3c}$, wherein $R_{3c}$ is selected from the group consisting of hydrogen, amino, cyano, halogen, carboxyl, $C_{1-4}$ alkyl, $C_{1-4}$ alkoxy, $C_{1-4}$ alkylamino, ($C_{1-4}$ alkyl)$_2$ amino, $C_{2-6}$ alkenyl, $C_{2-6}$ alkynyl, $C_{1-4}$ alkylcarbonyl, $C_{1-4}$ alkylaminocarbonyl,
($C_{1-6}$ alkyl)$_2$ aminocarbonyl, $C_{1-4}$ alkylsulfonyl, $C_{1-4}$ alkylthio, aminocarbonyl, cyclopropyl, azetidinyl, morpholinyl and piperazinyl, wherein $C_{1-4}$ alkyl, $C_{1-4}$ alkoxy, $C_{1-4}$ alkylamino, ($C_{1-4}$ alkyl)$_2$ amino, $C_{2-6}$ alkenyl, $C_{2-6}$ alkynyl, $C_{1-4}$ alkylcarbonyl, $C_{1-4}$ alkylaminocarbonyl, ($C_{1-6}$ alkyl)$_2$ aminocarbonyl, $C_{1-4}$ alkylsulfonyl, $C_{1-4}$ alkylthio, aminocarbonyl, cyclopropyl, azetidinyl, morpholinyl and piperazinyl are unsubstituted or optionally substituted with one or more groups independently selected from the group consisting of hydroxy, amino, cyano, halogen, $C_{1-4}$ alkyl, $C_{1-4}$ alkoxy, $C_{1-4}$ alkylamino, $(C_{1-4}$ alkyl$)_2$ amino, cyclopropyl, $C_{1-4}$ alkylcarbonyloxy, and unsubstituted or $C_{1-4}$ alkyl-substituted 4-6 membered heterocyclyl;

$X_4$ is $CR_{3d}$, wherein $R_{3d}$ is hydrogen;

$R_3$ is hydrogen;

L is a bond;

ring A is 4-12 membered heterocyclyl, wherein 4-12 membered heterocyclyl has one or two hetero atoms selected from the group consisting of O, S, and N, and contains at least one N, ring A is connected to L through N atom, and S atom can be optionally oxidized to $S(O)_2$;

each $R_1$ is independently selected from the group consisting of hydrogen, hydroxy, cyano, halogen, $C_{1-4}$ alkyl, $C_{1-4}$ alkoxy, pyrazolyl, thiazolyl and triazolyl, wherein $C_{1-4}$ alkyl, $C_{1-4}$ alkoxy, pyrazolyl, thiazolyl and triazolyl are unsubstituted or substituted with hydroxy;

m is 0, 1 or 2;

$R_2$ is hydrogen or $C_{1-6}$ alkyl.

2. The compound or a pharmaceutically acceptable salt or a stereoisomer thereof according to claim 1, wherein, $X_2$ is N;

$X_3$ is $CR_{3c}$, wherein $R_{3c}$ is selected from the group consisting of hydrogen, halogen, $C_{1-4}$ alkyl, $C_{1-4}$ alkoxy, $C_{2-6}$ alkenyl, $C_{1-4}$ alkylaminocarbonyl, and aminocarbonyl, wherein $C_{1-4}$ alkyl, $C_{1-4}$ alkoxy, $C_{2-6}$ alkenyl, $C_{1-4}$ alkylaminocarbonyl, and aminocarbonyl are unsubstituted or optionally substituted with one or more groups independently selected from the group consisting of hydroxy, amino, $C_{1-4}$ alkyl, $C_{1-4}$ alkoxy, cyclopropyl, $C_{1-4}$ alkylamino, $(C_{1-4}$ alkyl$)_2$ amino and unsubstituted or $C_{1-4}$ alkyl-substituted 4-6 membered heterocyclyl;

$X_4$ is $CR_{3d}$, wherein $R_{3d}$ is hydrogen;

$R_3$ is hydrogen;

L is a bond;

ring A is

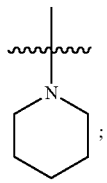

each $R_1$ is independently selected from the group consisting of hydrogen, $C_{1-4}$ alkyl, and $C_{1-4}$ alkoxy;

m is 0, 1 or 2;

$R_2$ is hydrogen or $C_{1-6}$ alkyl.

3. The compound or a pharmaceutically acceptable salt or a stereoisomer thereof according to claim 1, wherein, $X_2$ is N;

$X_3$ is $CR_{3c}$, wherein $R_{3c}$ is selected from the group consisting of hydrogen, cyano, amino, halogen, carboxyl, $C_{1-4}$ alkyl, $C_{1-4}$ alkoxy, $C_{2-6}$ alkenyl, $C_{1-4}$ alkylcarbonyl, $C_{2-6}$ alkynyl, $C_{1-4}$ alkylamino, $(C_{1-4}$ alkyl$)_2$ amino, $C_{1-4}$ alkylaminocarbonyl, $C_{1-4}$ alkylthio, $C_{1-4}$ alkylsulfonyl, cyclopropyl, azetidinyl, morpholinyl, and piperazinyl, wherein $C_{1-4}$ alkyl, $C_{1-4}$ alkoxy, $C_{2-6}$ alkenyl, $C_{1-4}$ alkylcarbonyl, $C_{2-6}$ alkynyl, $C_{1-4}$ alkylamino, $(C_{1-4}$ alkyl$)_2$ amino, $C_{1-4}$ alkylaminocarbonyl, $C_{1-4}$ alkylthio, $C_{1-4}$ alkylsulfonyl, cyclopropyl, azetidinyl, morpholinyl, and piperazinyl are unsubstituted or optionally substituted with one or more groups independently selected from the group consisting of hydroxy, amino, halogen, $C_{1-4}$ alkyl, $C_{1-4}$ alkylamino, $(C_{1-4}$ alkyl$)_2$ amino, cyclopropyl, and $C_{1-4}$ alkylcarbonyloxy;

$X_4$ is $CR_{3d}$, wherein $R_{3d}$ is hydrogen;

$R_3$ is hydrogen;

L is a bond;

ring A is

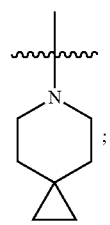

m is 0;

$R_2$ is hydrogen or $C_{1-6}$ alkyl.

4. A compound or a pharmaceutically acceptable salt or a stereoisomer thereof, wherein the compound is

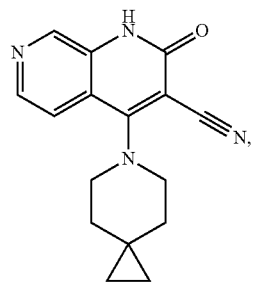

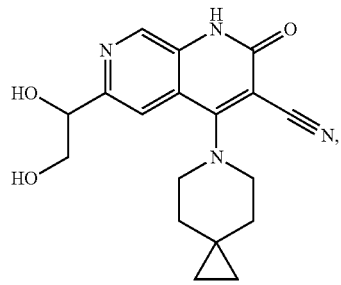

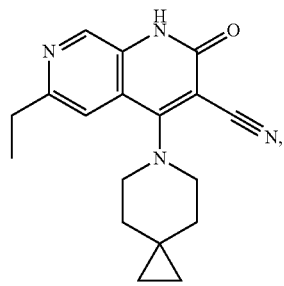

191

-continued

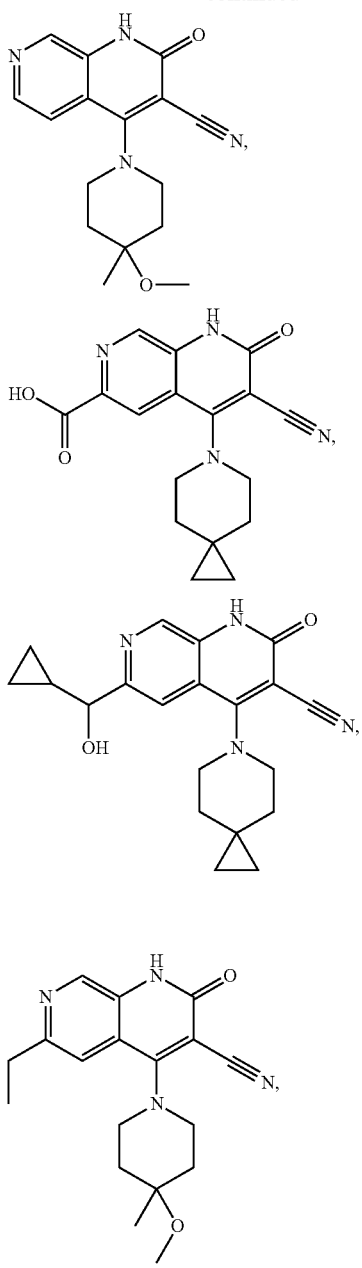

192

-continued

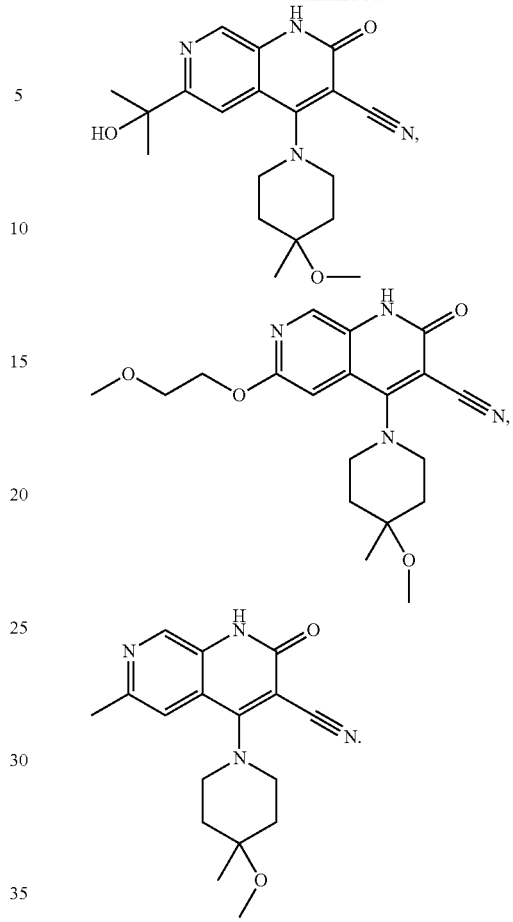

5. A pharmaceutical formulation comprising a compound or a pharmaceutically acceptable salt or a stereoisomer thereof according to claim 1.

6. The pharmaceutical formulation according to claim 5, wherein the pharmaceutical formulation comprises one or more pharmaceutically acceptable carriers.

7. A pharmaceutical formulation comprising a compound or a pharmaceutically acceptable salt or a stereoisomer thereof according to claim 4.

8. The pharmaceutical formulation according to claim 7, wherein the pharmaceutical formulation comprises one or more pharmaceutically acceptable carriers.

* * * * *

UNITED STATES PATENT AND TRADEMARK OFFICE
CERTIFICATE OF CORRECTION

PATENT NO. : 10,889,591 B2  
APPLICATION NO. : 16/702711  
DATED : January 12, 2021  
INVENTOR(S) : Frank Wu et al.

Page 1 of 1

It is certified that error appears in the above-identified patent and that said Letters Patent is hereby corrected as shown below:

In the Specification

At Column 83, Line numbers 5-20, please replace structural formula

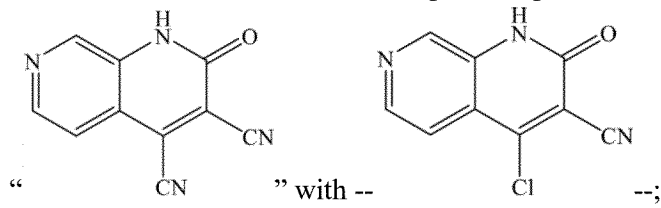

At Column 168, Line numbers 50-57, please replace structural formula

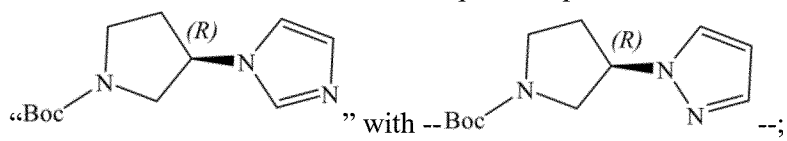

At Column 169, Line numbers 15-28, please replace structural formula

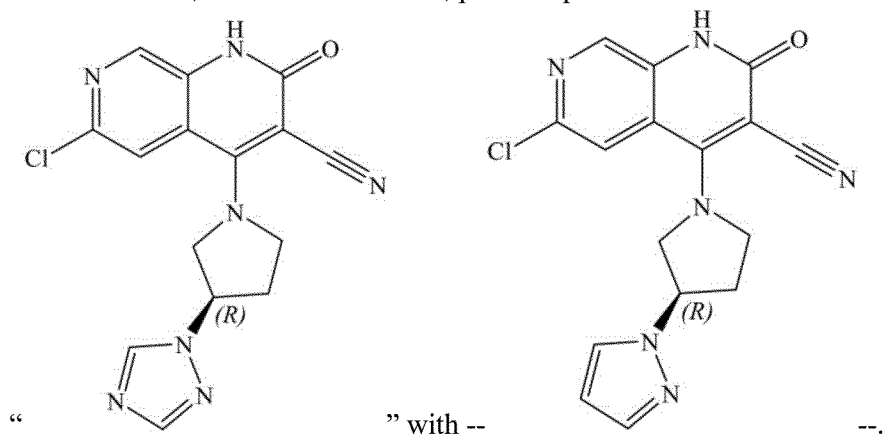

Signed and Sealed this  
Ninth Day of March, 2021

Drew Hirshfeld  
*Performing the Functions and Duties of the  
Under Secretary of Commerce for Intellectual Property and  
Director of the United States Patent and Trademark Office*